(12) United States Patent
Brahmbhatt et al.

(10) Patent No.: US 11,504,402 B2
(45) Date of Patent: Nov. 22, 2022

(54) COMPOSITIONS COMPRISING BACTERIALLY DERIVED MINICELLS AND METHODS OF USING THE SAME

(71) Applicant: EnGeneIC Molecular Delivery Pty Ltd, Sydney (AU)

(72) Inventors: Himanshu Brahmbhatt, Hunter Mill (AU); Jennifer MacDiarmid, Sydney (AU)

(73) Assignee: EnGeneIC Molecular Delivery Pty Ltd, Sydney (AU)

(*) Notice: Subject to any disclaimer, the term of this patent is extended or adjusted under 35 U.S.C. 154(b) by 116 days.

(21) Appl. No.: 16/518,833

(22) Filed: Jul. 22, 2019

(65) Prior Publication Data

US 2020/0054689 A1    Feb. 20, 2020

Related U.S. Application Data

(60) Provisional application No. 62/702,172, filed on Jul. 23, 2018, provisional application No. 62/788,265, filed on Jan. 4, 2019.

(51) Int. Cl.
| | |
|---|---|
| C07H 21/02 | (2006.01) |
| A61K 48/00 | (2006.01) |
| A61K 35/74 | (2015.01) |
| A61P 35/00 | (2006.01) |
| C12N 15/113 | (2010.01) |
| C12N 15/11 | (2006.01) |
| A61K 47/68 | (2017.01) |

(52) U.S. Cl.
CPC .............. *A61K 35/74* (2013.01); *A61P 35/00* (2018.01); *A61K 47/6807* (2017.08); *A61K 47/6879* (2017.08); *C12N 15/111* (2013.01); *C12N 15/113* (2013.01); *C12N 2310/14* (2013.01); *C12N 2310/141* (2013.01); *C12N 2310/17* (2013.01)

(58) Field of Classification Search
CPC ........................ C12N 15/113; C12N 2310/14
See application file for complete search history.

(56) References Cited

U.S. PATENT DOCUMENTS

| | | | |
|---|---|---|---|
| 7,183,105 B2 | 2/2007 | Sabbadini et al. | |
| 8,591,862 B2 | 11/2013 | Brahmbhatt et al. | |
| 9,220,724 B2* | 12/2015 | Reid ........................ | A61P 35/00 |
| 9,566,321 B2 | 2/2017 | Giacalone | |
| 9,730,897 B2 | 8/2017 | Brahmbhatt et al. | |
| 2008/0051469 A1 | 2/2008 | Brahmbhatt et al. | |
| 2015/0098897 A1 | 4/2015 | Brahmbhatt et al. | |
| 2017/0326235 A1 | 11/2017 | Brahmbhatt et al. | |
| 2018/0100159 A1 | 4/2018 | Brahmbhatt et al. | |

FOREIGN PATENT DOCUMENTS

| | | |
|---|---|---|
| WO | WO 2000/067776 | 11/2000 |
| WO | WO 2003/033519 A2 | 4/2003 |
| WO | WO 2004/113507 A1 | 12/2004 |
| WO | WO 2005/056749 A2 | 6/2005 |
| WO | WO 2005/079854 A1 | 9/2005 |
| WO | WO 2009/027830 A2 | 3/2009 |

OTHER PUBLICATIONS

Solomon et al. (PLOS ONE, 10(12), 2015, 1-17).*
Quintieri et al. (Clinical Cancer Research, 1608, 11, 2005, 1608-1617).*
Schneiders et al. (Clinical Immunology, 2011, 140, 130-141).*
Bograd et al. ( Cancer Immunol Immunother, 2011, 60, 1509-1527).*
Liang et al. (Molecular Cancer, 2015, 14:58, 1-13).*
Farkona, et al., "Cancer immunotherapy: the beginning of the end of cancer?," *BMC Medicine* 14, 73, 18 pages (2016).
Fang, et al., "NK cell-based immunotherapy for cancer," *Seminars in Immunology*, vol. 31, pp. 37-54 (2017).
Ferlazzo et al., "NK Cell Compartments and Their Activation by Dendritic Cells1," *The Journal of Immunology*, vol. 172, pp. 1333-1339 (2004).
Fernandes-Alnemri et al., "AIM2 activates the inflammasome and cell death in response to cytoplasmic DNA," Nature, vol. 458, pp. 509-513 (2009).
Field et al., "Inducers of Interferon and Host Resistance, II. Multistranded Synthetic Polynucleotide Comlexes," Proc. Natl Acad. Sci. USA, 58: pp. 1004-1010 (1967).
Fitzgerald-Bocarsly et al., "The role of type I Interferon Production by Dendritic Cells in Host Defense," *Biochimie* 89, pp. 843-855 (2007).
Fu, et al., "STING agonist formulated cancer vaccines can cure established tumors resistant to PD-1 blockade," *Sci Transl. Med.*, vol. 7, pp. 283, 24 pages (Apr. 2015).
Fukuda, "Chemical labeling of carbohydrates by oxidation and sodium borohydride reduction," Curr Protoc. Mol. Biol., pp. 17.5. 1-17.5.8: Supplement 26 (1994).
Gao et al., "In vivo Cancer Targeting and Imaging with Semiconductor Quantum Dots," *Nat Biotechnol.*, 22(8): pp. 969-976 (2004).
Gao et al., "Cyclic GMP-AMP Synthase is an Innate Immune Sensor of HIV and Other Retroviruses," *Science*, vol. 341: pp. 903-906 (2013).
Gao et al., "Cyclic [G(2',5')pA(3',5')p] is the Metazoan Second Messenger Produced by DNA-Activated Cyclic GMP-AMP Synthase," *Cell*, 153:1094-1107 (2013).
Gerard SK, Cavalieri RR. I-123 diagnostic thyroid tumor whole-body scanning with imaging at 6, 24, and 48 hours. Clin Nucl Med. 2002;27(1):1-8.
Ghosh A, Heston WDW. Tumor target prostate specific membrane antigen (PSMA) and its regulation in prostate cancer. *J Cell Biochem*. 2004;91(3):528-539.

(Continued)

Primary Examiner — Amy H Bowman
(74) *Attorney, Agent, or Firm* — Foley & Lardner LLP

(57) ABSTRACT

Compositions and methods for treating cancer are provided. In particular, the compositions comprise an anti-neoplastic agent and either an interferon type I agonist or an interferon type II agonist, or a combination of an interferon type I agonist and an interferon type II agonist.

17 Claims, 74 Drawing Sheets

(56) References Cited

OTHER PUBLICATIONS

Gitlin et al., "Essential role of mda-5 in type I IFN responses to polyriboinosinic:polyribocytidylic acid and encephalomyocarditis picornavirus," Proc. Natl. Acad. Sci. USA, 103: pp. 8459-8464 (2006).

Gray, et al., "Combinatorial Peptide Libraries: Mining for Cell-Binding Peptides," Chem. Rev., vol. 114, No. 2 pp. 1020-1081 (Jan. 2014).

Hobbs et al., "Regulation of Transport Pathways in Tumor Vessels: Role of Tumor Type and Microenvironment," Proc. Natl. Acad. Sci. USA, 95(8): pp. 4607-4612 (1998).

Hansen, et al., "Listeria monocytogenes induces IFNβ Expression through an IFI16-, CGAS- and STING-dependent Pathway," EMBO J., 33(15): 1654-66 (2014).

Holman, et al., "Single-photon emission computed tomography (SPECT): applications and potential," JAMA, vol. 263, No. 4, pp. 561-564 (1990).

Hornung et al., "AIM2 Recognizes Cytosolic dsDNA and forms a Caspase-1 Activating Inflammasome with ASC," Nature, 458, pp. 514-518 (2009).

Igarashi, et al., "Vasoactive intestinal peptide (VIP) and VIP receptors—elucidation of structure and function for therapeutic applications," Int J Clin Med., vol. 2, pp. 500-508 (2011).

Jarboe, et al., Expression of Interleukin-13 Receptor α2 in Glioblastoma Multiforme: Implications for Targeted Therapies, Cancer Res., vol. 67, pp. 7983-7986 (2007).

Jenkins et al., "Mechanisms of Resistance to Immune Checkpoint Inhibitors," British Journal of Cancer, vol. 118, pp. 9-16 (2018).

Jung et al., "Dendritic Cell-Based Immunotherapy for Solid Tumors," Translational oncology 11, pp. 686-690 (2018).

Kao et al., "A Significant Metabolic and Radiological Response after a Novel Targeted MicroRNA-based Treatment Approach in Malignant Pleural Mesothelioma," Am. J. Respir. Crit. Care Med., 191(12): pp. 1467-1469 (2015).

Kawai, et al., "The role of pattern-recognition receptors in innate immunity: update on Toll-like Receptors," Nat. Immunol., 11, pp. 373-384 (2010).

Kim, et al., "Aspartate-glutamate-alanine-histidine box motif (DEAH)/RNA helicase A helicases sense microbial DNA in human plasmacytoid dendritic cells," PNAS, vol. 107, No. 34, pp. 15181-15186 (Aug. 2010).

Kramer-Marek G, et al., "The role of nuclear medicine in modern therapy of cancer," Tumour Biol. 2012;33(3), pp. 629-640.

Xia et al., "Sox2 functions as a sequence-specific DNA sensor in neutrophils to initiate innate immunity against microbial infection," Nat. Immunol., 16, pp. 366-375 (2015).

Wu, et al., "Cyclic-GMP-AMP is an Endogenous Second Messenger in Innate Immune Signaling by Cytosolic DNA," Science, vol. 339, pp. 826-830 (2013).

Whittle, et al., "First in human nanotechnology doxorubicin delivery system to target epidermal growth factor receptors in recurrent glioblastoma," Journ. of Clinical Neuroscience, vol. 22, pp. 1889-1894 (2015).

White, et al., "Suppression of apoptosis: role in cell growth and neoplasia," Leukemia, 15: pp. 1011-1021 (2001).

Walrand, et al., "The impact of image reconstruction bias on PET/CT $^{90}$Y dosimetry after radioembolization," J Nucl Med., vol. 56(3):pp. 494-495 (2015).

Sharpe, "Introduction to Checkpoint Inhibitors and Cancer Immunotherapy," Immunological reviews vol. 276, pp. 5-8 (2017).

Kranzusch et al., "Structure of human cGAS reveals a conserved family of second-messenger enzymes in innate immunity," Cell Rep., vol. 3, pp. 1362-1368 (2013).

Krieg et al., "CpG Motifs in Bacterial DNA Trigger Direct B-cell Activation," Nature, vol. 374, pp. 546-549 (1995).

Kwekkeboom et al., "Treatment with the radiolabeled somatostatin analog [$^{177}$Lu-DOTA$^0$, Tyr$^3$] Octreotate: Toxicity, Efficacy, and Survival," J Clin Oncol., vol. 26, No. 13, pp. 2124-2130 (May 2008).

Landskron et al., "Chronic Inflammation and Cytokines in the Tumor Microenvironment," Journal of Immunology Research 2014, 149185, 20 pages (2014).

Lee et al., "Cytokines in Cancer Immunotherapy," Cancers 3, pp. 3856-3893 (2011).

Leung, et al., "When your cap matters: Structural insights into self vs non-self recognition of 5' RNA by immunomodulatory host proteins,", Curr. Opin. Struct. Biol., vol. 36 (2016), 30 pages.

Li et al., "Pivotal Roles of cGAS-cGAMP Signaling in Antiviral Defense and Immune Adjuvant Effects," Science, 341, pp. 1390-1394 (2013).

Liu et al., "Phosphorylation of innate immune adaptor proteins MAVS, STING, and TRIF induces IRF3 Activation," Science, vol. 347, 17 pages (2015).

Lu et al., "The Structural Basis of 50 Triphosphate Double-Stranded RNA Recognition by RIG-I C-Terminal Domain," Structure, vol. 18 , pp. 1032-1043 (2010).

Ma et al., "Positioning of the MinE binding site on the MinD surface suggests a plausible mechanism for activation of the Escherichia coli MinD ATPase during division site Selecti," Mol. Microbiol., 54, pp. 99-108 (2004).

MacDiarmid et al., "Targeted Doxorubicin Delivery to Brain Tumors viaMinicells: Proof of Principle Using Dogs with Spontaneously Occurring Tumors as a Model," PLoS One, 11(4), 13 pages (2016).

Majkowska et al., "Complexes of low energy beta emitters $^{47}$Sc and $^{177}$Lu with zoledronic acid for bone pain therapy," Appl. Radiat. Isot., vol. 67, No. 1, pp. 11-13 (2009).

McWhirter et al., "A Host Type I Interferon Response is Induced by Cytosolic Sensing of the Bacterial Second Messenger Cyclic-di-GMP,"J. Exp. Med., vol. 206, pp. 1899-1911 (2009).

Mellman et al., "Cancer Immunotherapy Comes of Age," Nature, vol. 480, pp. 480-489 (2011).

Morvan et al., "NK cells and cancer: you can teach innate cells new tricks," Nature reviews Cancer 16, pp. 7-19 (2016).

Muller, et al., "A Unique Matched Quadruplet of Terbium Radio-isotopes for PET and SPECT and for a-and b2-Radionuclide Therapy: An In Vivo Proof-of-Concept Study with a New Receptor—Targeted Folate Derivative," Matched Terbium Radionuclide Quadruplet, J. Nucl. Med., vol. 53, No. 12, pp. 1951-1959 (2012).

Oiseth et al., "Cancer immunotherapy: a brief review of the history, possibilities, and challenges ahead," Journal of Cancer Metastasis and Treatment 3, 250-261 (2017).

Orzalli et al., "Nuclear IFI16 induction of IRF-3 signaling during herpesviral infection and degradation of IFI16 by the viral ICP0 protein," Proc. Natl. Acad. Sci., vol. 109, pp. pp. E3008-E3017 (2012).

Reid et al., "Restoring expression of miR-16: a novel approach to therapy for malignant pleural mesothelioma," Annals of Oncology, Official Journal of the European Society for Medical Oncology, vol. 24, pp. 3128-3135 (2013).

Rezvani et al., "Engineering Natural Killer Cells for Cancer Immunotherapy," Molecular therapy: the Journ. of the American Society of Gene Therapy, vol. 25, pp. 1769-1781 (2017).

Sawa-Wejksza et al., "Tumor-Associated Macrophages as Target for Antitumor Therapy," Arch. Immunol. Ther. Exp., vol. 66, pp. 97-111 (2018).

Silver, et al., "Prostate-specific membrane antigen expression in normal and malignant human tissues," Clin Cancer Res., vol. 3, pp. 81-85 (1997).

Schoggins et al., "Pan-viral specificity of IFN-induced genes reveals new roles for cGAS in innate immunity," Nature, vol. 505, pp. 691-695 (2014).

Unterholzner et al., "IFI16 is an Innate Immune Sensor for Intracellular DNA," Nat. Immunol., vol. 11, pp. 997-1004 (2010).

Wang, et al., "Structural and functional insights into pattern recognition by the innate immune receptor RIG-1" Nat. Struct. Mol. Biol., vol. 17, No. 7, pp. 781-787 (2010).

Staudacher, et al., "Antibody drug corsjugates and bystander killing: is antigen-dependent internalisation required?," British Journ. of Cancer, vol. 117, pp. 1736-1742 (2017).

Wang et al., "The E3 Ubiquitin Ligase AMFR and INSIG1 Bridge the Activation of TBK1 Kinase by Modifying the Adaptor STING," Immunity, vol. 47(6), pp. 919-933 (2014).

(56) References Cited

OTHER PUBLICATIONS

Zhang et al., "The Cytosolic DNA Sensor cGAS Forms an Oligomeric Complex with DNA and Undergoes Switch-like Conformational Changes in the Activation Loop," *Cell Rep.*, vol. 6, pp. 421-430 (2014).
Nielsen et al, "Therapeutic efficacy of anti-ErbB2 Immunoliposomes targeted by a phage antibody selected for cellular endocytosis," *Biochim. Biophys. Acta.*, vol. 1591(1-3), pp. 109-118 (2002).
Ohki-Hamazaki, et al., "Development and Function of Bombesin-Like Peptides and Their Receptors," Int. J. Dev. Biol., vol. 49, pp. 293-300 (2005).
Sagnella et al., "Targeted Doxorubicin-Loaded Bacterially Derived Nano-Cells for the Treatment of Neuroblastoma," *Molecular Cancer Therapeutics*, vol. 17, pp. 1012-1023 (2018).
Sharma et al., "Primary, Adaptive, and Acquired Resistance to Cancer Immunotherapy," *Cell* 168, pp. 707-723 (2017).
Showalter, Cytokines in Immunogenic Cell Death: Applications for Cancer Immunotherapy, *Cytokine* vol. 97, pp. 123-132 (2017).
Sun, et al.,"Overexpression of Bcl2 Blocks TNF-Related Apoptosis-Inducing Ligand (TRAIL)—Induced Apoptosis in Human Lung Cancer Cells," Biochemical and Biophysical Research Communications, vol. 280, No. 3, pp. 788-797 (Jan. 2001).
Sun et al., "Cyclic GMP-AMP Synthase is a Cytosolic DNA Sensor that Activates the Type-I Interferon Pathway," *Science*, 339(6121), pp. 786-791 (2013).
Sun, et al., "Peptide based imaging agents for cancer detection," Adv. Drug Deliv. Rev., vol. 110-111, pp. 38-51 (2017).
Szkandera et al., "Validation of C-reactive protein levels as a prognostic indicator for survival in a large cohort of pancreatic cancer patients," British Journal of Cancer, vol. 110, pp. 183-188 (2014).
Takahashi, et al., "Imaging surface immobilization chemistry: correlation with cell patterning on non-adhesive hydrogel thin films," Adv Funct Mater, vol. 18, pp. 2079-2088 (2008).
Takaoka et al., "DAI (DLM-1/ZBP1) is a cytosollc DNA sensor and an activator of innate immune response," Nature, 448, pp. 501-505 (2007).
Takeshita et al., "Systemic Delivery of Synthetic MicroRNA-16 Inhibits the Growth of Metastatic Prostate Tumors via Downregulation of Multiple Cell-cycle Genes," Molec. Ther., vol. 18, pp. 181-187 (2010).
Tatemoto, et al., Neuropeptide Y: history and overview, Neuropeptide Y and Related Peptides. Springer; pp. 1-21 (2004).
Teunissen et al., "Peptide receptor radionuclide therapy," Best Pract Res Clin Gastroenterol., vol. 9(4), pp. 595-616 (2005).
Tyler-McMahon, et al., "Neurotensin: peptide for the next millennium," Regul. Pept., vol. 93, pp. 125-136 (2000).
Unterholzner, "The interferon response to intracellular DNA: why so many receptors?", Immunobiology, vol. 218(11), pp. 1312-1321 (Nov. 2013).
Van Zandwijk et al., "Safety and activity of microRNA-loaded minicells in patients with recurrent malignant pleural mesothelioma: a first-in-man, phase 1, open-label, dose-escalation study," Lancet Oncol., 18(10), pp. 1386-1396 (2017).
Ventola, "Cancer Immunotherapy, Part 2: Efficacy, Safety, and Other Clinical Consierations," Pharmacy and Therapeutics, vol. 42, pp. 452-463 (2017).
Ablasser, et al., "cGAS Produces a 2'-5'—linked cyclic dinucleotide second messenger that activates STING," *Nature*, vol. 498, No. 7454. pp. 380-384 (2013).
Frederick Allen and Juliana Bobanga, et al., "CCL3 augments tumor rejection and enhances CD8C T cell infiltration through NK and CD103C dendritic cell recruitment via IFNγ," *Oncommunology*, vol. 7, No. 3, e1393598 (11 pages).
Aduro Biotech Inc., Novartis Pharmaceuticals, *Study of the Safety and Efficacy of MIW815 (ADU-S100) in Patients with Advanced/Metastatic Solid Tumors or Lymphomas.* ClinicalTrials.gov [Internet]. Identifier: NCT02675439. Available from: https://ClinicalTrials.gov/show/NCT02675439 (Jul. 1, 2016).

Birkholz, et al., "The Alpha and Omega of Galactosylceramides in T Cell Immune Function," *The Journ. of Biological Chem.*, vol. 290, No. 25, pp. 15365-15370 (Jun. 2015).
Bredel, "Anticancer drug resistance in primary human brain tumors," brain Res. Rev., 35, pp. 161-204 (2001).
Brody et al., "In Situ Vaccination With a TLR9 Agonist Induces Systemic Lymphoma Regression: A Phase I/II Study." *J. Clin. Oncol.*, 28:4324-4332 (2010).
Bürckstümmer, et al., "An orthogonal proteomic-genomic screen identifies AIM2 as a cytoplasmic DNA sensor for the inflammasome," Nat. Immunol., vol. 10, pp. 266-272 (2009).
Burger, et al., "Small peptide inhibitors of the CXCR4 chemokine receptor (CD184) antagonize the activation, migration, and antiapoptotic responses of CXCL12 in chronic lymphocytic leukemia B cells," Blood, vol.106:1824-1830 (2005).
Carreno et al., "Synthetic Glycolipid Activators of Natural Killer T Cells as Immunotherapeutic Agents," *Clin Transl. Immunology*, 5(4): e69. 9 pages (2016).
Caskey, et al., "Synthetic double-stranded RNA induces innate immune responses similar to a live viral *vaccine* in humans," *J. Exp. Med.*, vol. 208, pp. 2357-2366 (2011).
Cauwels, et al., "*Delivering* Type I Interferon to Dendritic Cells Empowers Tumor Eradication and Immune Combination Treatments," *Cancer Research* 78, pp. 463-474 (2018).
Chatalic, et al., "Radiopeptides for imaging and therapy: a radiant future," J Nucl Med., vol. 56, pp. 1809-1812 (2015).
Chen et al., "Reversal of Drug Resistance Mediated by Multidrug Resistance Protein (MRP) 1 by Dual Effects of Agosterol A on MRP1 Function", Int. J. Cancer: 93, 107-113 (2001).
Chikuma et al., "Suppressors of cytokine signaling: Potential immune checkpoint molecules for cancer immunotherapy," *Cancer Sci.*, vol. 108, pp. 574-580 (2017).
Chiu et al., RNA Polymerase III Detects Cytosolic DNA and Induces Type-1 Interferons Through the RIG-I Pathway, *Cell*, vol. 138, pp. 576-591 (2009).
Civril et al., "Structural mechanism of cytosolic DNA sensing by cGAS," vol. 498, pp. 332-337 (2013).
Clark-Curtiss and Curtiss, "Analysis of Recombinant DNA Using *Escherichia coli* Minicells," Methods Enzymol., 101: 347-362 (1983).
Colonna, et al., "Plasmacytoid Dendritic Cells in Immunity," *Nature Immunology*, vol. 5, No. 12, pp. 1219-1226 (Dec. 2004).
Corrales, et al., "Direct Activation of STING in the Tumor Microenvironment Leads to Potent and Systemic Tumor Regression and Immunity," *Cell Reports*, vol. 11, pp. 1018-1030 (May 2015).
Cory, et al., "Use of an aqueous soluble tetrazolium/formazan assay for cell growth assays in culture," Cancer Commun., vol. 3, No. 7, pp. 207-212 (1991).
D'Aloia et al., "CAR-T Cells: The Long and Winding Road to Solid Tumors," *Cell death & disease* 9, 282 (2018), 12 pages.
D'Angiolella et al., "Cyclin F-Mediated Degradation of Ribonucleotide Reductase M2 Controls Genome Integrity and DNA Repair," Cell, 149:1023-34 (2012).
Deutscher, "Phage Display in Molecular Imaging and Diagnosis of Cancer," Chem Rev., vol. 110, pp. 3196-3211 (2010).
Dine et al., "Immune Checkpoint Inhibitors: An Innovation in Immunotherapy for the Treatment and Management of Patients with Cancer," *Asia-Pacific Journal of Oncology Nursing*, vol. 4, pp. 127-135 (2017).
Dobbs et al., "STING activation by translocation from the ER is associated with infection and autoinflammatory disease," Cell Host Microbe, 18(2): 15-24 (2015).
Dong et al., "CD86+ /CD206+, Diametrically Polarized Tumor-Associated Macrophages, Predict Hepatocellular Carcinoma Patient Prognosis," International journal of molecular sciences 17, 320 (2016), 12 pages.
Dowling et al., "The Ultra-Potent and Selective TLR8 Agonist VTX-294 Activates Human Newborn and Adult Leukocytes," PLoS One, 8:e58164 (2013), 11 pages.
Dredge et al., "Adjuvants and the promotion of Th1-type cytokines in Tumour immunotherapy," Cancer immunology, immunotherapy: CII 51, pp. 521-531 (2002).

(56) References Cited

OTHER PUBLICATIONS

Dynavax Technologies Corporation. Study of SD-101 in Combination with Localized Low-dose Radiation in Patients with Untreated Low-grade B-cell Lymphoma. 2016. ClinicalTrials.gov [Internet]. Bethesda (MD): National Library of Medicine (US). Identifier: NCT02266147. Available from: https://ClinicalTrials.gov/show/NCT02266147. (Jul. 1, 2016).

Zitvogel et al., "Type I IFNs and Anticancer Therapies," Nature reviews Immunology 15, pp. 405-414 (2015).

Ziegler-Heltbrock et al., "Toward a Refined Definition of Monocyte Subsets," Frontiers in Immunology 4, 23 (2013).

Zibert et al., CCL3/MIP-1α is a Potent Immunostimulator When Coexpressed with Interleukin-2 or Granulocyte-Macrophage Colony-Stimulating Factor in a Leukemia/Lymphoma Vaccine Human Gene Therapy 15, pp. 21-34 (2004).

Zhang et al., "The helicase DDX41 senses intracellular DNA mediated by the adaptor STING in dendritic cells," Nat. Immunol., 12, pp. 959-965 (2011b).

Zhang et al., "Cutting Edge: Ku70 is a Novel Cytosolic DNA Sensor That Induces Type III Rather Than Type I IFN," J. Immunol., 186:4541-4545 (2011a).

Yuan et al., "Opposite Effects of M1 and M2 Macrophage Subtypes on Lung Cancer Progression," Scientific reports 5, 14273 (2015).

Yi et al., Single Nucleotide Polymorphisms of Human STING Can Affect Innate Immune Response to Cyclic Dinucleotides PLoS One, 8(10):e77846 (2013), 16 pages.

Yang et al., "The cytosolic nucleic acid sensor LRRFIP1 mediates the production of type I interferon via a β-catenin-dependent pathway," Nat. Immunol., vol. 11, pp. 487-494 (2010).

Yang et al., "A Novel tumor-homing peptide specifically targeting metastasis," Clin Cancer Res., vol. 14, pp. 5494-5502 (2008).

Yague et al., "Complete reversal of multidrug resistance by stable expression of small interfering RNAs targeting MDR1," Gene Ther., 11, pp. 1170-1174 (2004).

Emens et al., "Cancer Immunotherapy: Opportunities and challenges in the rapidly evolving clinical landscape," European Journal of Cancer 81, pp. 116-129 (2017).

Erathodiyil N, Ying JY. Functionalization of inorganic nanoparticles for bioimaging applications. Acc Chem Res., vol. 44, pp. 925-935 (2011).

International Preliminary Report on Patentability issued in International Patent Application No. PCT/IB2019/056259, dated Jan. 26, 2021.

Ahmadzadehfar et al., "Radioembolization of liver tumors with yttrium-90 microspheres," Semin Nucl Med. 2010;40(2):105-121.

Ablasser et al., "RIG-I Dependent Sensing of Poly9dA-dT) via the Induction of an RNA Polymerase III Transcribed RNA Intermediate," Nat. Immunol., 10 (10):1065-72 (2009).

Ablasser et al., "Cell Intrinsic Immunity Spreads to Bystander Cells via the Intercellular Transfer of cGAMP," Nature, 503:530-534 (2013).

Adamus et al., "The Revival of CpG Oligonucleotide-based Cancer Immunotherapies," Contemp. Oncol (Ponzn), 22(1A):56-60 (Mar. 2018).

Ahmadzadehfar et al., "Therapeutic response and side effects of repeated radioligand therapy with 177Lu-PSMA-DKFZ-617 of castrate-resistant metastatic prostate cancer," Oncotarget. 2016;7(11):12477-12488.

Alexopoulou et al., "Recognition of Double-Stranted RNA and Activation of NF-kappaB by Toll-like Receptor 3," Nature, 413:732-738 (2001).

Anguille et al., "Dendritic Cells as Pharmacological Tools for Cancer Immunotherapy," Pharmacological Reviews 67, 731-753 (2015).

Barber et al., "Innate Immune DNA Sensing Pathways: STING, AIMII and the Regulation of Interferon Production and Inflammatory Responses," Curr. Opin. Immunol., 23(1): 10-20 (2011).

Bernardini et al., Dysregulation of Chemokine/Chemokine Receptor Axes and NK Cell Tissue Localization during Diseases, Frontiers in Immunology 7, 402, 9 pages (2016).

Alzahrani, et al., "Diagnostic value of recombinant human thyrotropin-stimulated 123I whole-body scintigraphy in the follow-up of patients with differentiated thyroid cancer," Clin Nucl Med. 2012;37(3):229-234.

Andersson, et al., "Large-scale synthesis of peptides," Biopolymers. vol. 55, pp. 227-250 (2000).

Belardelli et al., "Cytokines as a Link between Innate and Adaptive Antitumor Immunity," TRENDS in Immunology, vol. 23, pp. 201-208 (2002).

Debinski, et al., "Molecular Expression Analysis of Restrictive Receptor for Interleukin 13, a Brain Tumor-associated Cancer/Testis Antigen," Mol. Med., 6: 440-449 (2000).

Goh, et al., "Endocytosis of Receptor Tyrosine Kinases," Harb. Perspect., Biol., 5: a017459, 17 pages (2013).

Oh, et al., siRNA Delivery Systems for Cancer Treatment, Advanced Drug Delivery Rev., 61: 850-62 (2009).

Kota et al., "Therapeutic Delivery of miR-26a Inhibits Cancer Cell Proliferation and Induces Tumor-Specific Apoptosis," Cell, 137: 1005-1017 (2009).

Wykosky et al., "Interleukin-13 Receptor α2, EphA2, and Fos-Related Antigen 1 as Molecular Denominators of High-Grade Astrocytomas and Specific Targets for Combinatorial Therapy," Clin Cancer Res., 14: 199-208 (2008).

Lemmon, et al., "Cell Signaling by Receptor-Tyrosine Kinases," Cell, vol. 141, No. 7, pp. 1117-1134 (Jun. 2010).

Tanpure, et al., "Synthesis of Structurally Diverse Benzosuberene Analogues and their Biological Evaluation as Anti-Cancer Agents," Bioorg. Med. Chem., vol. 21, No. 24, pp. 8019-8032 (Dec. 2013).

MacDiarmid, et al., "Bacterially Derived 400 nm Particles for Encapsulation and Cancer Cell Targeting of Chemotherapeutics," Cancer Cell, No. 11. pp. 431-445 (May 2007).

MacDiarmid, et al., "Bacterially-Derived Nanocells for Tumor-Targeted Delivery of Chemotherapeutics and Cell Cycle Inhibitors," Cell Cycle, pp. 2099-2105 (2007).

Rice, et al., "The Next Generation of Positron Emission Tomography Radiopharmaceuticals in Oncology," Semin. Nucl. Med., vol. 41, No. 4, pp. 265-282 (2011).

Khalil, et al., "Many Human Large Intergenic Noncoding RNAs Associate with chromatin-modifying complexes and affect gene expression," PNAS, vol. 106, No. 28, pp. 11667-11672 (Jul. 2009).

Duxbury, et al., "Systemic siRNA-Mediated Gene Silencing a New Approach to Targeted Therapy of Cancer," Annals. of Surgery, vol. 240, No. 4, pp. 667-674 (Oct. 2004).

Debinski, et al., "Expression of a Restrictive Receptor for Interleukin 13 is Associated with Glial Transformation," J. Neurooncol., vol. 48, No. 2, pp. 103-111 (Jun. 2000)[Abstract].

DaSilva, et al., "HER3 and downstream pathways are involved in colonization of Brain Metastases from Breast Cancer," Breast Cancer Research, vol. 12, R46, pp. 1-13 (2010).

Chu et al., "Translation Repression in Human Cells by MicroRNA-Induced Gene Silencing Requires RCK/p54," PLOS Biology, vol. 4, No. 7, pp. 1122-1136 (Jul. 2006).

Caravella, et al., "Design of next-generation protein therapeutics," Curr. Opin. Chem. Biol., vol. 14, No. 4, (Aug. 2010).[Abstract].

MacDiarmid, et al., "Sequential Treatment of Drug-Resistant Tumors with Targeted Minicells containing SiRNA or a Cytotoxic Drug," Nature Biotechnology, vol. 27, No. 7, pp. 643-651 (2009).

Duan, et al., "Inhibition of ABCB1 (MDR1) and ABCB4 (MDR3) Expression by Small Interfering RNA and Reversal of Paclitaxel Resistance in Human Ovarian Cancer Cells," Molecular Cancer Therapies, vol. 3, No. 7, pp. 833-838 (Jul. 2004).

De Boer et al., "Roles of MinC and MinD in the Site-Specific Septation Block Mediated by the MinCDE System of Escherichia coli," vol. 174, No. 1, pp. 83-70 (Jan. 1992).

Okada, et al., "Cytoplasmic Axial Filaments in Escherichia coli Cells: Possible Function in the Mechanism of Chromosome Segregation and Cell Division," Journ. of Bacteriology, pp. 917-922 (Feb. 1994).

Nieth, et al., Modulation of the Classical Multidrug Resistance (MDR) Phenotype by RNA Interference (RNAi), FEBS Letters, vol. 545, pp. 144-150 (2003).

(56) References Cited

OTHER PUBLICATIONS

Reeve, et al., "bacteriophage SPO1-Induced Macromolecular Synthesis in Minicells of bacillus subtilis," *Journal of Virology*, pp. 1308-1316 (Jun. 1975).

Raskin, et al, "MinDE-Dependent Pole-to-Pole Oscillation of Division Inhibitor MinC in *Escherichia coli*," *Journ. of Bacteriology*, pp. 6419-6424 (Oct. 1999).

Caplen, et al., "Short Interfering RNA (siRNA)—Mediated RNA Interference (RNAi) in Human Cells," *Ann. N.Y. Acad. Sci.*, pp. 56-62 (2003).

Britton, et al., "Characterization of a prokaryotic SMC protein involved in chromosome partitioning," *Genes & Development*, pp. 1254-1259 (1998).

Caplen, "RNAi as Gene Therapy Approach," *Gene Therapy*, pp. 575-586 (2003).

Sioud, "Therapeutic siRNAs," *Trends in Pharm. Sciences*, vol. 25, No. 1, pp. 22-28 (Jan. 2004).

Stewart, et al., "Genetic and Morphological Characterization of an *Escherichia coli* Chromosome Segregation Mutant," *Journ. of Bact.*, pp. 4513-4516 (Jul. 1992).

Hiraga, et al., "Chromosome Partitioning in *Escherichia coli*: Novel Mutants Producing Anucleate Cells," *Journ. of Bacteriology*, pp. 1496-1505 (Mar. 1989).

Harry, "Bacterial Cell Divisional: Regulating Z-ring formation," *Molecular Microbiology*, vol. 40, No. 4, pp. 795-803 (2001).

Hu et al, "Topological Regulation of Cell Divisional in *Escherichia coli* involves rapid pole to pole oscillation of the divisional inhibitor MinC under the control of MinD and MinE," *Molecular Microbiologyi*, vol. 34, No. 1, 82-90 (1999).

Quintien, et al., "Formation and Antitumor Activity of PNU-159682, A Major Metabolite of Nemorubicin in Human Liver Microsomes," *American Associate of Cancer Research*, vol. 11, pp. 1608-1617 (Feb. 2005).

Iftode, et al, "Replication Protein A (RPA): the Eukaryolic SSB," *Crit Rev. Biochem. Mol. Biol.*, vol. 34, No. 3, pp. 141-180 (1999)[Abstract].

Gregory, et al., Methods in Molecular Biology, vol. 342, pp. 33-47 ( pril 2006).[Abstract].

Hershey, "IL-13 Receptors and Signaling Pathways: an Evolving web," *J. Allergy Clin. Immunol.*, vol. 111, No. 4, pp. 677 00 (2003).

Search Report issued in co-pending European Patent Application No. 19839892.7, dated Mar. 7, 2022.

International Search Report and Written Opinion issued in International Patent Application No. PCT/IB2019/056259, dated Dec. 24, 2019.

MacDiarmid, et al., "Minicells: Versatile Vectors for Targeted Drug or si/shRNA Cancer Therapy," *Current Opinion in Biotechnology*, vol. 22, pp. 909-916 (2011).

\* cited by examiner

Immunomodulatory 60-mer double-stranded DNA

O-polysaccharide

EDV

FIG. 3

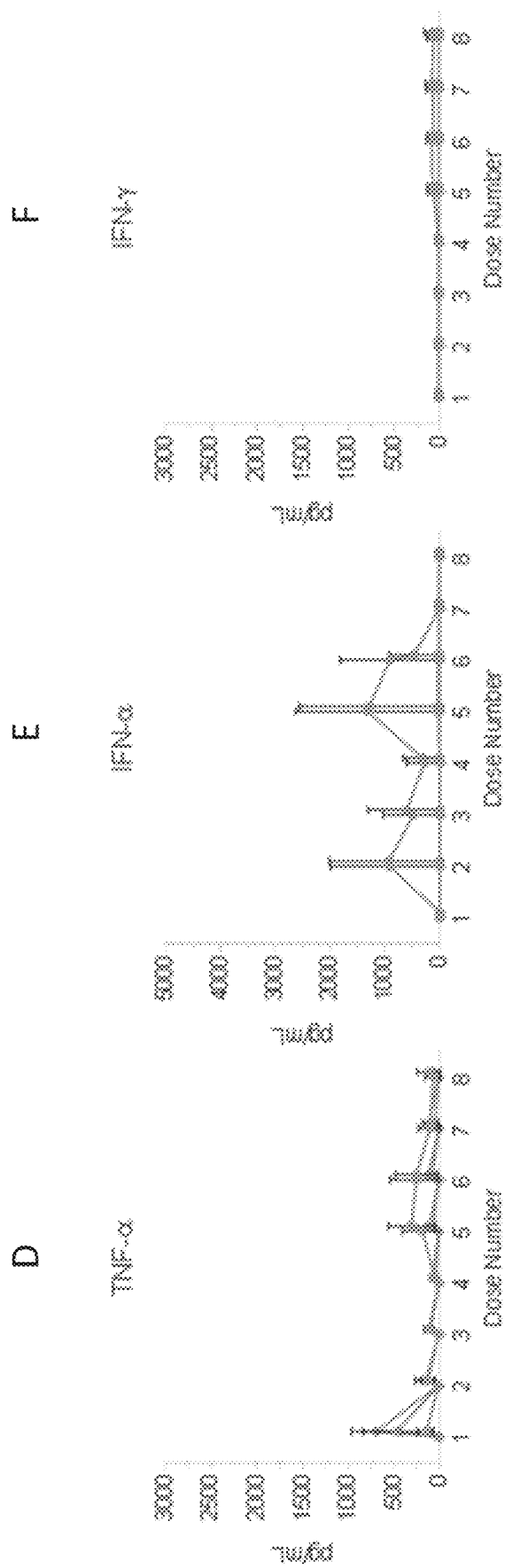

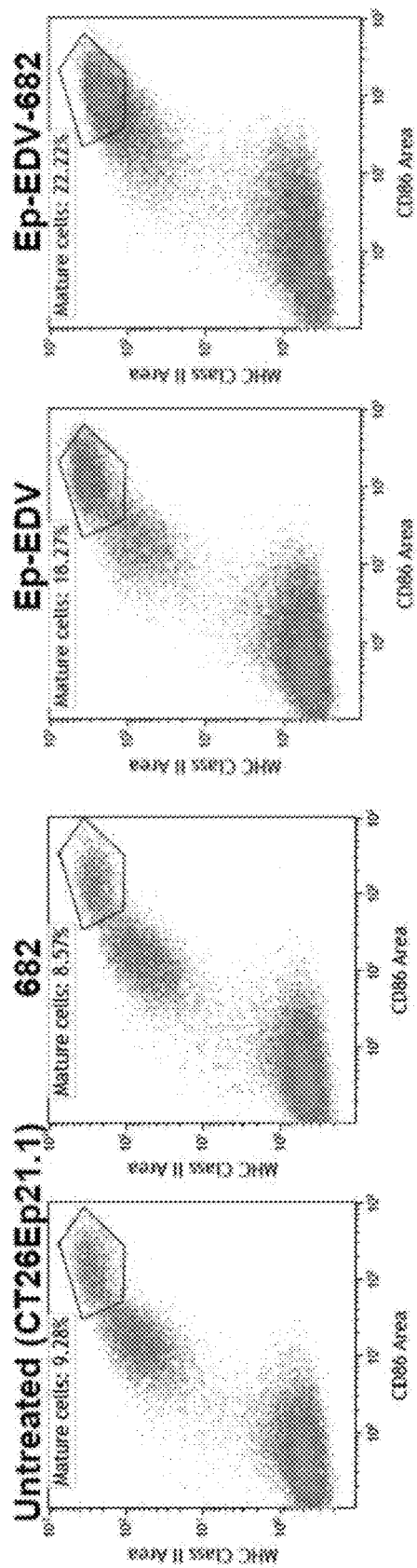

FIGS. 33A-33I
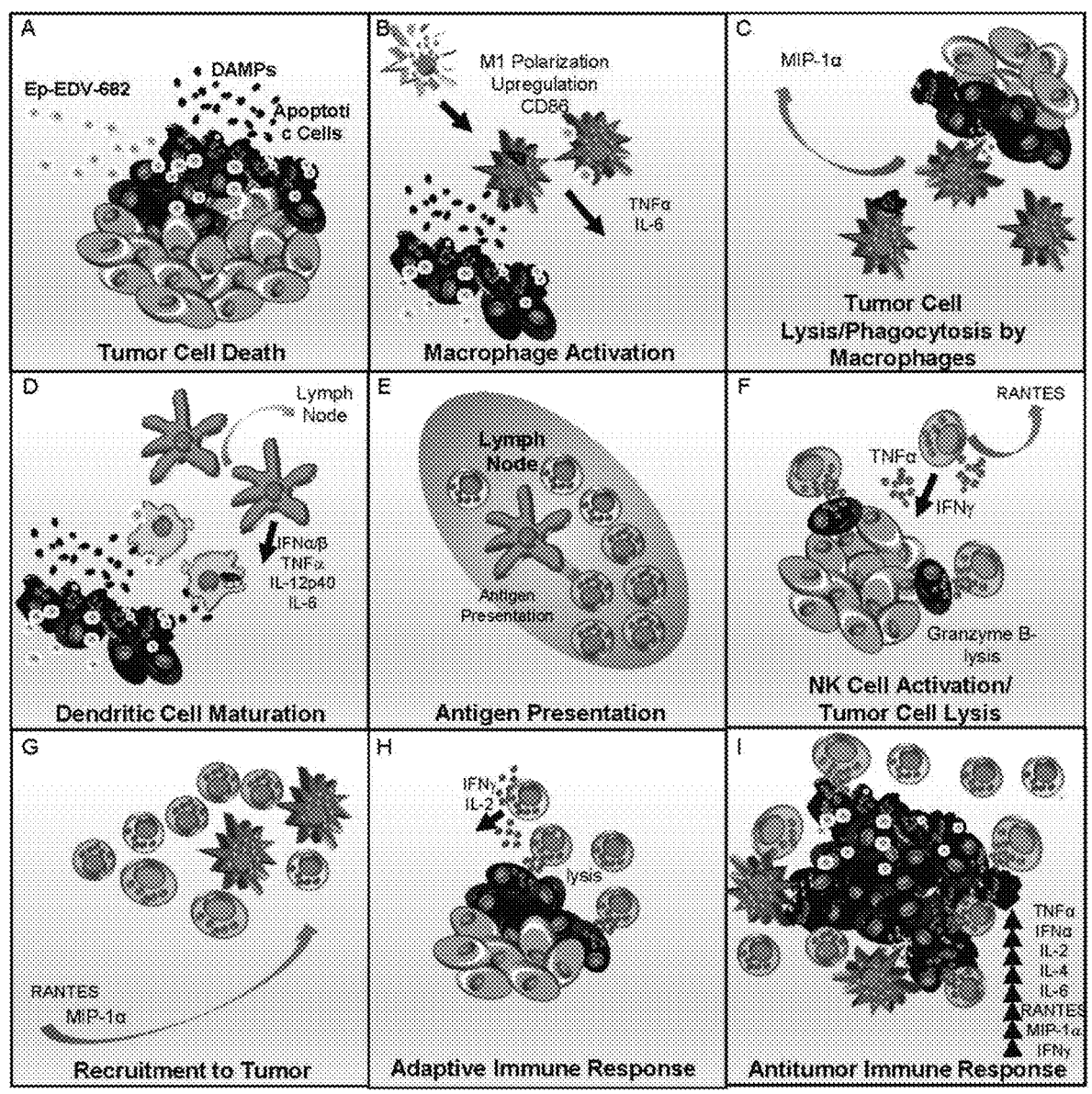
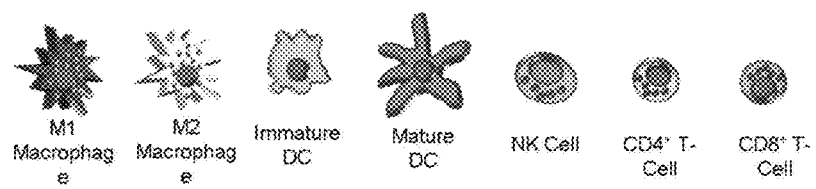

Head - 287,152 receptors/cell

Tail - 296,840 receptors/cell

FIGS. 43A-43F
CT26 (Epclone12.1) isograft; n=3; Tumor volume: 200-250mm³; Dose: 1; Sacrifice Time: 24 hr
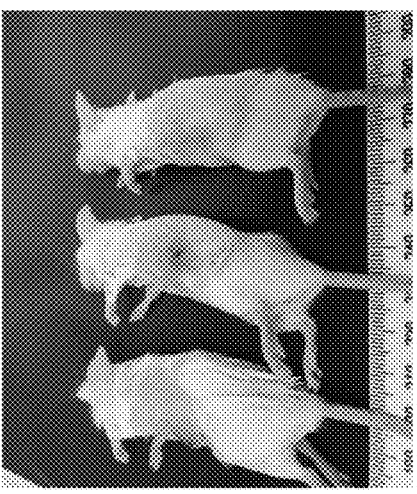
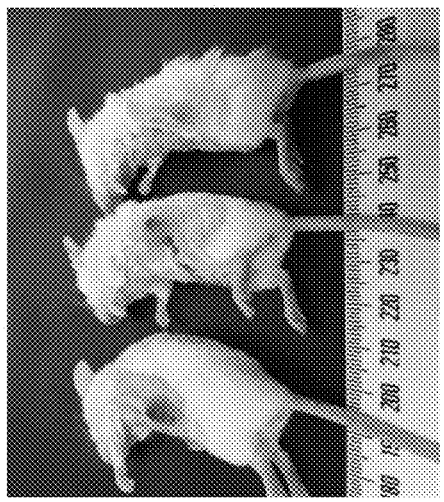
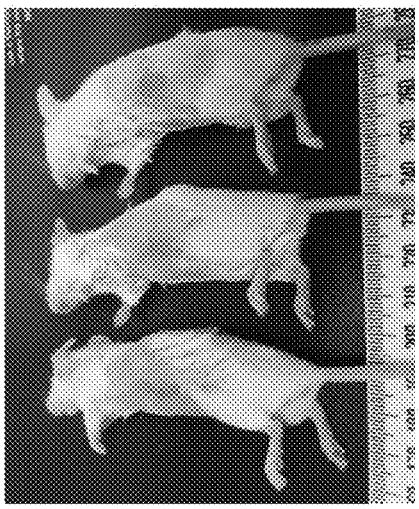

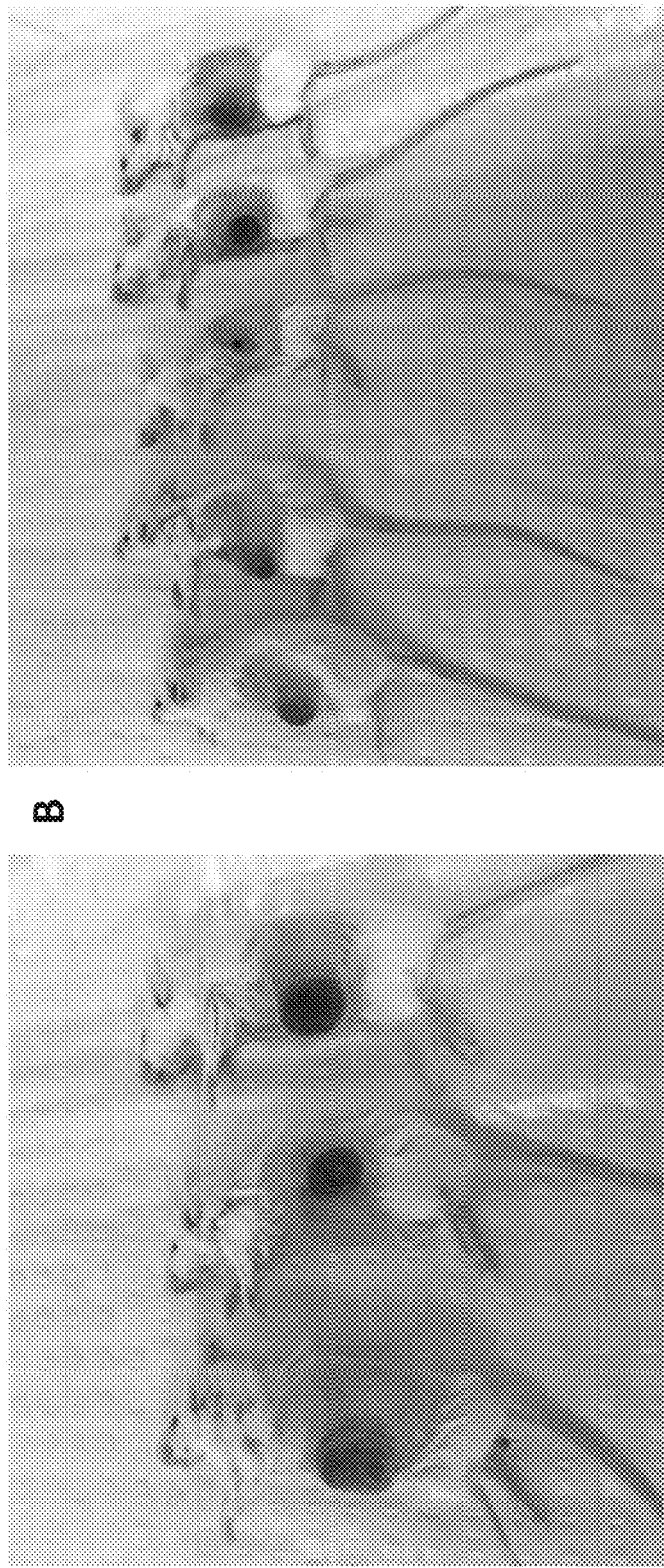
FIGS. 44-A-44B
CT26 (Epclone12.1) isograft, n=3; Tumor volume: 600-800mm³; Dose: 1; Sacrifice Time: 24 hr

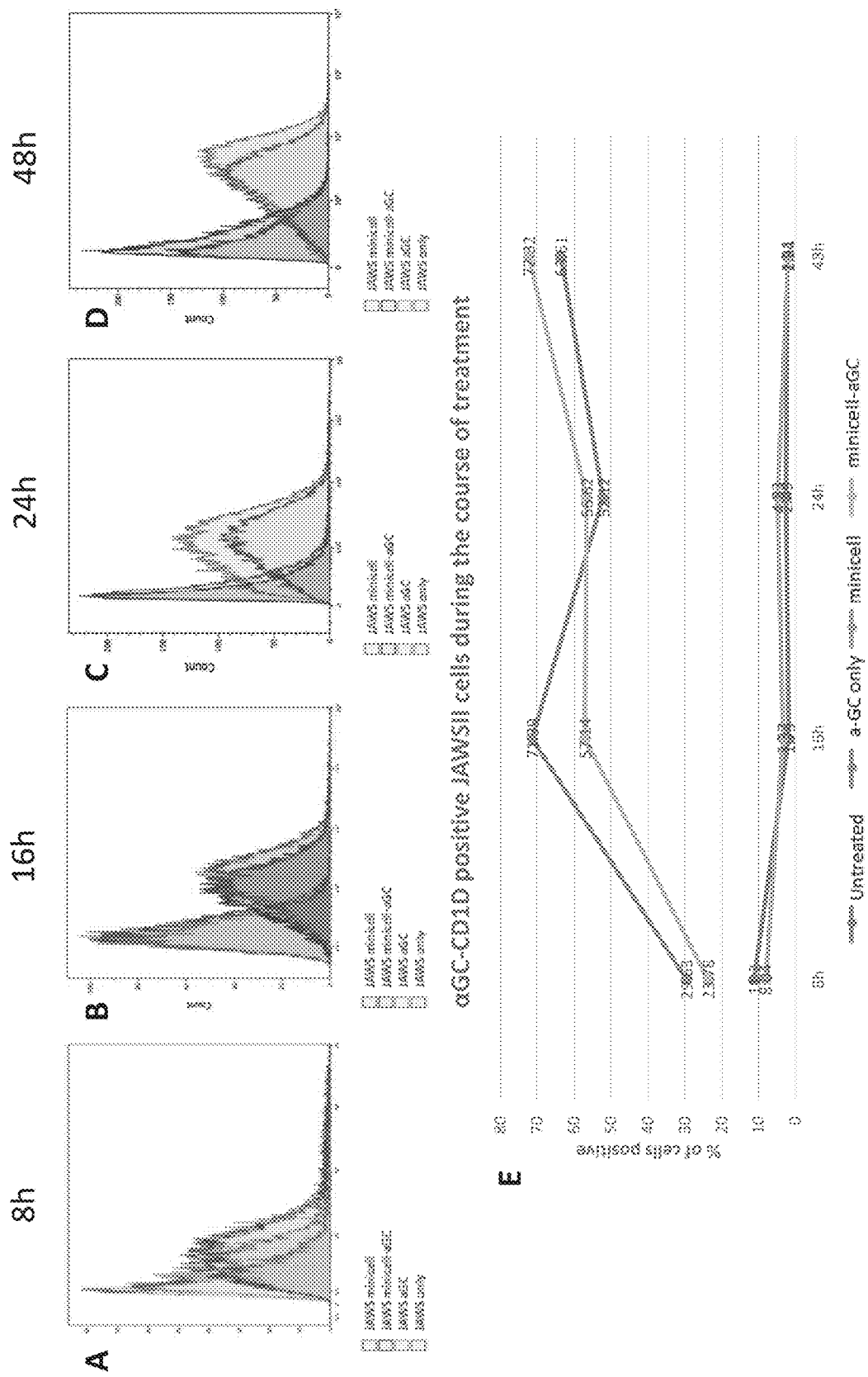

COMPOSITIONS COMPRISING BACTERIALLY DERIVED MINICELLS AND METHODS OF USING THE SAME

CROSS-REFERENCE TO RELATED APPLICATIONS

This application claims the priority benefits under 35 USC § 119 to U.S. provisional Application 62/702,172, filed Jul. 23, 2018, and U.S. provisional Application 62/788,265, filed Jan. 4, 2019, the entire contents of which are incorporated herein by reference in their entirety.

BACKGROUND

Currently, most drugs used for treating cancer are administered systemically. Although systemic delivery of cytotoxic anticancer drugs plays a crucial role in cancer therapeutics, it also engenders serious problems. For instance, systemic exposure of normal tissues/organs to the administered drug can cause severe toxicity. This is exacerbated by the fact that systemically delivered cancer chemotherapy drugs often must be delivered at very high dosages to overcome poor bioavailability of the drugs and the large volume of distribution within a patient. Also, systemic drug administration can be invasive, as it often requires the use of a secured catheter in a major blood vessel. Because systemic drug administration often requires the use of veins, either peripheral or central, it can cause local complications such as phlebitis. Extravasation of a drug also can lead to vesicant/tissue damage at the local site of administration, such as is commonly seen upon administration of vinca alkaloids and anthracyclines.

Another challenge in cancer therapy is intrinsic or acquired clinical tumor resistance to chemotherapy. Intrinsic resistance exists at the time of diagnosis in tumors that fail to respond to first-line chemotherapy. Acquired resistance occurs in tumors that may respond well to initial treatment, but exhibit a resistant phenotype upon recurrence. Such tumors gain resistance both to previously used drugs and to new drugs, including drugs with different structures and mechanisms of action. The term MDR (multidrug resistance) describes this phenomenon in which tumor cells become cross-resistant to several structurally unrelated drugs after exposure to a single drug. The mechanisms for multi-drug resistance are complex and multifactorial, owing largely to the high level of genomic instability and mutations in cancer cells. Exemplary mechanisms are drug inactivation, extrusion of drug by cell membrane pumps, decreased drug influx, mutations of drug targets and failure to initiate apoptosis. Bredel, 2001; Chen et al., 2001; Sun et al., 2001; and White & McCubrey, 2001.

Interactions between the immune system and malignant cells also play an important role in tumorigenesis. Failure of the immune system to detect and reject transformed cells may lead to cancer development. Tumors use multiple mechanisms to escape from immune-mediated rejection. Many of these mechanisms are now known on a cellular and molecular level. Despite this knowledge, cancer immunotherapy is still not an established treatment in the clinic.

Accordingly, there remains a great need for delivery systems that can provide targeted delivery of drugs that can reduce drug resistance, promote apoptosis, and induce immune responses while avoiding the problems associated with delivering these drugs systemically. The present invention satisfies these needs.

SUMMARY OF THE INVENTION

One embodiment of the invention relates to a composition comprising (a) a therapeutically effective dose of purified, intact bacterially derived minicells comprising an anti-neoplastic agent, and (b) an interferon type I agonist, an interferon type II agonist, or a combination of an interferon type I agonist and an interferon type II agonist. The interferon type I agonist and/or the interferon type II agonist can be optionally present within intact bacterially derived minicells.

In one embodiment, the composition comprises (a) a therapeutically effective dose of purified, intact bacterially derived minicells comprising an anti-neoplastic agent, and (b) a therapeutically effective dose of purified, intact bacterially derived minicells comprising an interferon type I agonist. In another embodiment, the composition comprises (a) a therapeutically effective dose of purified, intact bacterially derived minicells comprising an anti-neoplastic agent, and (b) a therapeutically effective dose of purified, intact bacterially derived minicells comprising an interferon type II agonist. In yet a further embodiment, the composition comprises (a) a therapeutically effective dose of purified, intact bacterially derived minicells comprising an anti-neoplastic agent; (b) a therapeutically effective dose of purified, intact bacterially derived minicells comprising an interferon type I agonist; and (c) a therapeutically effective dose of purified, intact bacterially derived minicells comprising an interferon type II agonist.

In one embodiment, the anti-neoplastic agent and the interferon type I agonist, the interferon type II agonist, or the combination of an interferon type I agonist and an interferon type II agonist, are packaged within two or more purified, intact bacterially derived minicells. In one embodiment, the anti-neoplastic agent and the interferon type I agonist, the interferon type II agonist, or the combination of an interferon type I agonist and an interferon type II agonist are packaged within three separate populations of purified, intact bacterially derived minicells.

In one embodiment, the composition comprises the anti-neoplastic agent, the interferon type I agonist, and the interferon type II agonist, wherein: (a) the anti-neoplastic agent, the interferon type I agonist, and the interferon type II agonist are comprised within the same minicell; (b) the anti-neoplastic agent and the interferon type I agonist are comprised within a first minicell, and the interferon type II agonist is comprised within a second minicell; (c) the anti-neoplastic agent and the interferon type II agonist are comprised within a first minicell, and the interferon type I agonist is comprised within a second minicell; (d) the anti-neoplastic agent is comprised within a first minicell, and the interferon type I agonist and the interferon type II agonist are comprised within a second minicell; or (e) the anti-neoplastic agent is comprised within a first minicell, the interferon type I agonist is comprised within a second minicell, and the interferon type II agonist is comprised within a third minicell.

In one embodiment, the composition does not comprise an interferon type I agonist.

In one embodiment, the anti-neoplastic agent is selected from the group consisting of a radionuclide, a chemotherapy drug, a functional nucleic acid, and a polynucleotide from which a functional nucleic acid can be transcribed. In one embodiment, the anti-neoplastic agent is a supertoxic chemotherapy drug. In one embodiment, the supertoxic chemotherapy drug is selected from the group consisting of morpholinyl anthracycline, a maytansinoid, ducarmycin, auristatins, calicheamicins (DNA damaging agents), α-amanitin (RNA polymerase II inhibitor), centanamycin, pyrrolobenzodiazepine, streptonigtin, nitrogen mustards, nitrosorueas, alkane sulfonates, pyrimidine analogs, purine analogs, antimetabolites, folate analogs, anthracyclines, taxanes, vinca alkaloids, topoisomerase inhibitors, hormonal agents, and a combination thereof. In one embodiment, the morpholinyl anthracycline is selected from the group consisting of nemorubicin, PNU-159682, idarubicin, daunorubicin; caminomycin, and oxorubicin. In one embodiment, the supertoxic chemotherapy drug is PNU-159682.

In one embodiment, the functional nucleic acid is selected from the group consisting of a siRNA, a miRNA, a shRNA, a lincRNA, an antisense RNA, and a ribozyme. In one embodiment, the functional nucleic acid inhibits a gene that promotes tumor cell proliferation, angiogenesis or resistance to chemotherapy and/or that inhibits apoptosis or cell cycle arrest. In some embodiments, the siRNA inhibits ribonucleotide reductase M1 (RRM1) expression. In some embodiments, the siRNA inhibits Polo like kinase 1 (Plk1) expression. In some embodiments, the miRNA is miRNA16a.

In one embodiment, the interferon type I agonist, the interferon type II agonist, or the combination of an interferon type I agonist and an interferon type II agonist is an oligonucleotide. In one embodiment, the oligonucleotide comprises a sequence of at least about 40 nucleotides, at least about 50 nucleotides, or at least about 60 nucleotides. In some embodiments, the oligonucleotide is a polynucleotide product of PNPase1, poly(I:C), poly-ICLC, imiquimod, imidazoquiolineresquimod, cGAMP or CpG-oligodeoxynucleotides.

In one embodiment, the interferon type I agonist is selected from the group consisting of double stranded RNA (dsRNA), poly(dA:dT) DNAs, double stranded Z-DNA and B-DNA, DNAs (dsDNAs) longer than 36 bp and DNA-RNA hybrids, bacterial second messenger cyclic-di-GMP, TLR3, TLR4, TLR7, TLR8 and TLR9 agonists, STING agonists, and a combination thereof.

In one embodiment, the interferon type II agonist is selected from the group consisting of C-glycosidific form of α-galactosylceramide (α-C-GalCer), α-galactosylceramide (α-GalCer), 12 carbon acyl form of galactosylceramide (β-GalCer), β-D-glucopyranosylceramide (β-GlcCer), 1,2-Diacyl-3-0-galactosyl-sn-glycerol (BbGL-II), diacylglycerol containing glycolipids (Glc-DAG-s2), ganglioside (GD3), gangliotriaosylceramide (Gg3Cer), glycosylphosphatidylinositol (GPI), α-glucuronosylceramide (GSL-1 or GSL-4), isoglobotrihexosylceramide (iGb3), lipophosphoglycan (LPG), lyosphosphatidylcholine (LPC), α-galactosylceramide analog (OCH), threitolceramide, and a combination thereof. In one embodiment, the interferon type II agonist is α-galactosylceramide (α-GalCer).

In one embodiment, the composition further comprises a bispecific ligand bound to the minicells comprising the anti-neoplastic agent. In one embodiment, the composition further comprises a bispecific ligand bound to the minicells comprising the type I interferon agonist. In one embodiment, the composition further comprises a bispecific ligand bound to the minicells comprising the type II interferon agonist.

In one embodiment, the bispecific ligand comprises a first arm that carries specificity for a minicell surface structure and a second arm that carries specificity for a non-phagocytotic mammalian cell surface receptor. In one embodiment, the minicell surface structure is an O-polysaccharide component of a lipopolysaccharide on the minicell surface.

In one embodiment, the non-phagocytotic mammalian cell surface receptor is capable of activating receptor-mediated endocytosis of the minicell.

In one embodiment, the bispecific ligand comprises a bispecific antibody or antibody fragment. In one embodiment, the antibody or antibody fragment comprises a first multivalent arm that carries specificity for a bacterially derived minicell surface structure and a second multivalent arm that carries specificity for a cancer cell surface receptor, wherein the cancer cell surface receptor is capable of activating receptor-mediated endocytosis of the minicell.

In one embodiment, the composition comprises fewer than about 1 contaminating parent bacterial cell per $10^7$ minicells, fewer than about 1 contaminating parent bacterial cell per 10 minicells, fewer than about 1 contaminating parent bacterial cell per $10^9$ minicells, fewer than about 1 contaminating parent bacterial cell per $10^{10}$ minicells, or fewer than about 1 contaminating parent bacterial cell per $10^{11}$ minicells.

In one embodiment, the composition further comprises a pharmaceutically acceptable carrier. In one embodiment, the minicells are approximately 400 nm in diameter. In one embodiment, the composition is free of parent bacterial cell contamination removable through 200 nm filtration.

In one embodiment, the composition comprises the following amount of minicells or killed bacterial cells (a) at least about $10^9$; (b) at least about $1 \times 10^9$; (c) at least about $2 \times 10^9$; (d) at least about $5 \times 10^9$; (e) at least $8 \times 10^9$; (f) no more than about $10^{11}$; (g) no more than about $1 \times 10^{11}$; (h) no more than about $9 \times 10^{10}$; or (i) no more than about $8 \times 10^{10}$.

One embodiment of the invention relates to a method of treating a subject in need, comprising administering to the subject an effective amount of a composition disclosed herein. In one embodiment, the subject is a human, a non-human primate, a dog, a cat, a cow, a sheep, a horse, a rabbit, a mouse, or a rat. In one embodiment, the subject is a human.

In one embodiment, the subject is suffering from a cancer. In one embodiment, the cancer is selected from the group consisting of lung cancer, breast cancer, brain cancer, liver cancer, colon cancer, pancreatic cancer, and bladder cancer. In one embodiment, the cancer is selected from the group consisting of an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor; breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonaryblastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymiccarcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; and Wilm's tumor.

In one embodiment, the brain cancer or tumor is selected from the group consisting of brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma.

In one embodiment, the composition is administered at least once a week over the course of several weeks. In one embodiment, the composition is administered at least once a week over several weeks to several months. In one embodiment, the composition is administered at least once a week for about 2, about 3, about 4, about 5, about 6, about 7, about 8, about 9, about 10, about 11, about 12, about 13, about 14, about 15, about 16, about 17, about 18, about 19 or about 20 weeks or more. In one embodiment, the composition is administered about twice every week. In one embodiment, the composition is administered twice a week for about 2, about 3, about 4, about 5, about 6, about 7, about 8, about 9, about 10, about 11, about 12, about 13, about 14, about 15, about 16, about 17, about 18, about 19 or about 20 weeks or more.

Both the foregoing summary and the following description of the drawings and detailed description are exemplary and explanatory. They are intended to provide further details of the invention, but are not to be construed as limiting. Other objects, advantages, and novel features will be readily apparent to those skilled in the art from the following detailed description of the invention.

BRIEF DESCRIPTION OF THE DRAWINGS

FIG. 1 is a graphical depiction of an EnGeneIC Dream Vehicle (EDV) (e.g., a bacterial minicell) comprising a bispecific antibody for O-polysaccharide and human epidermal growth factor receptor antigens and loaded with the anti-cancer drug PNU-159682 (an anthracycline analogue).

FIG. 2 is a graphical depiction of an EnGeneIC Dream Vehicle (EDV) comprising O-polysaccharides on the surface and loaded with immunomodulatory 60mer double stranded DNA.

FIG. 3 is a graphical depiction of an EnGeneIC Dream Vehicle (EDV) comprising O-polysaccharides on the surface and loaded with immunomodulatory alpha galactosylceramide (ctGC).

FIG. 5[ ]A compares the effect of the indicated chemotherapy drugs with the supertoxic drug PNU-159682. FIG. 5[ ]B compares the effect of doxorubicin and PNU-159682.

(FIG. 24A)=pg/mL of IL-6 measured for each of the 5 doses; (FIG. 24B)=pg/mL of IL-8 measured for each of the 5 doses; (FIG. 24C)=pg/mL of IL-10 measured for each of the 5 doses; (FIG. 24D)=pg/mL of TNF-α measured for each of the 5 doses; (FIG. 24E)=pg/mL of IFN-α measured for each of the 5 doses; (FIG. 24F)=pg/mL of IFN-γ measured for each of the 5 doses; (FIG. 24G)=pg/mL of IL-113 measured for each of the 5 doses; (FIG. 24H)=pg/mL of IL-2 measured for each of the 5 doses; (FIG. 24I)=pg/mL of IL-4 measured for each of the 5 doses; and (FIG. 24J)=pg/mL of IL-12 measured for each of the 5 doses. Finally, (FIG. 24K) shows the five doses tested.

FIGS. 25A-K show a cytokine profile of patients from a First-in-Man clinical study where different dosages of $^{EGFR}$EDVs™ loaded with doxorubicin were administered. (FIG. 25A)=pg/mL of IL-6 measured for each of the 8 doses; (FIG. 25B)=pg/mL of IL-8 measured for each of the 8 doses; (FIG. 25C)=pg/mL of IL-10 measured for each of the 8 doses; (FIG. 25D)=pg/mL of TNF-α measured for each of the 8 doses; (FIG. 25E)=pg/mL of IFN-α measured for each of the 8 doses; (FIG. 25F)=pg/mL of IFN-γ measured for each of the 8 doses; (FIG. 25G)=pg/mL of IL-113 measured for each of the 8 doses; (FIG. 25H)=pg/mL of IL-2 measured for each of the 8 doses; (FIG. 25I)=pg/mL of IL-4 measured for each of the 8 doses; and (FIG. 25J)=pg/mL of IL-12 measured for each of the 8 doses. Finally, (FIG. 25K) shows the additional three doses tested, with the first five doses being the same as those shown in (FIG. 24K).

FIGS. 27A-27L shows RAW264.7 cell and bone marrow derived dendritic cell (BMDC) activation in response to EDV treatment. (FIG. 27 A) CD86 expression in RAW cells incubated directly with 1 μg/ml LPS, Ep-EDV, Ep-EDV682, or 682. (FIG. 27 B) CD86 expression in RAW cells co-cultured with 4T1 or CT26Ep12.1 cells treated with Ep-EDV, Ep-EDV682, or 682. RAW cells co-cultured with Ep-EDV682 treated tumor cells resulted in a significant increase in CD86 expression. (FIG. 27 C) TNFα production in RAW cell/tumor cell co-cultures showing a significant increase in TNFα production by RAW cells incubated with EDV treated tumor cells. (FIG. 27 D) IL-6 production in RAW cell/tumor cell co-cultures showing a significant increase in IL-6 production by RAW cells incubated with EDV treated tumor cells. (FIG. 27 E) PCR quantitation of IFNα and IFNβ expression in BMDC/4T1 co-cultures. (FIG. 27 F) PCR quantitation of IFNα and IFNβ expression in BMDC/CT26Ep12.1 co-cultures. Quantitation of (FIG. 27 G) CD86$^{Hi}$ and MHC Class II$^{Hi}$ expression and (FIG. 27 H) CD80$^{Hi}$ expression in BMDC/tumor cell co-cultures. (FIG. 27 I) Flow cytometic density plots of MHC Class II vs CD86 expression in BMDC co-cultures with EDV and drug-treated CT26Ep12.1 cells. ELISA analysis of (FIG. 27 J) TNFα (FIG. 27 K) IL-12p40 and (FIG. 27 L) IL-6 from the supernatants of BMDC/tumor cell co-cultures. Data represents mean±s.e.m. and analyzed by one-way ANOVA and Tukey's multiple comparison test.

(FIG. 28 F) Ratio of M1 (CD86+): M2 (CD206$^+$) macrophages in 4T1 tumors of treated mice. (FIG. 28 G) xCELLigence RTCA of CD11b$^+$ isolated from CT26Ep12.1 tumors and co-cultured with CT26Ep12.1 cells at a 5:1 (E:T) ratio. (FIG. 28H) Ratio of M1 (CD86+): M2 (CD206$^+$) macrophages in CT26Ep12.1 tumors of treated mice. Data (FIGS. 28F and 28H) represents mean±s.e.m. and analyzed by one way ANOVA and Tukey's multiple comparison test.

(FIG. 29 A) xCELLigence RTCA of NK cells isolated from spleens of mice bearing 4T1 tumors co-cultured with 4T1 cells at a 20:1 (E:T) ratio. Plot represents cell viability, calculated from the normalized cell index, over time. (FIG. 29B) % viability of 4T1 cells co-cultured with NK cells from saline, Ep-EDV, or Ep-EDV-682 treated mice 70 h following the addition of NK. (FIG. 29C) xCELLigence RTCA of NK cells isolated from spleens of mice bearing CT26Ep12.1 tumors co-cultured with CT26Ep12.1 cells at a 20:1 (E:T) ratio. (FIG. 29D) % viability of CT26Ep12.1 cells co-cultured with NK cells from saline, Ep-EDV, or Ep-EDV-682 treated mice 50 h following the addition of NK cells (FIG. 29E) Expression of NKG2D in NK cells (CD45+, CD11b+, DX5+) within 4T1 tumors showing an increase in NKG2D expression in Ep-EDV-682 treated mice. Production of (FIG. 29F) RANTES and (FIG. 29G) TNFα in co-cultures of NK cells isolated from the spleens of EDV treated mice bearing 4T1 tumors with 4T1 cells. (FIG. 29H) Quantitation of NKG2D ligands RAE-1, H60a, and MULT-1 on the surface of 4 different mouse tumor cell lines. (FIG. 29I) xCELLigence RTCA of NK cells isolated from spleens of EpEDV-682 treated mice bearing 4T1 tumors co-cultured with 4T1 cells at a 20:1 (E:T) ratio in the presence of RAE-1 and/or H60a inhibiting antibodies demonstrating that both are important in NK tumor cell cytolysis. (FIG. 29J) Quantitation of NK cytolysis 80 h post NK cell addition showing significant inhibition of NK cytolysis with H60a antibody alone of in conjunction with RAE-1 inhibiting antibodies. Data (FIGS. 29B, 29D, 29E-G, and 29J) represents mean±s.e.m. and analyzed by one way ANOVA and Tukey's multiple comparison test.

(FIG. 31A) xCELLigence RTCA of CD8$^+$ T-cells isolated from the spleens of mice bearing 4T1 tumors co-cultured with 4T1 cells at a 30:1 (E:T) ratio. Plot represents normalized cell index which correlates to cell adhesion and growth/death vs time. (FIG. 31B) % viability of 4T1 cells co-cultured with CD8$^+$ T-cells from saline, Ep-EDV, or Ep-EDV-682 treated mice 30 h following the addition of CD8$^+$ T-cells. (FIG. 31C) xCELLigence RTCA of CD8$^+$ T-cells isolated from the spleens of mice bearing CT26Ep12.1 tumors co-cultured with CT26Ep12.1 cells at a 30:1 (E:T) ratio. Plot represents normalized cell index which correlates to cell adhesion and growth/death vs time. (FIG. 31D) % viability of CT26Ep12.1 cells co-cultured with CD8$^+$ T-cells from saline, Ep-EDV, or Ep-EDV-682 treated mice 20 h following the addition of CD8$^+$ T-cells. (FIG. 31E) Percentage of CD8$^+$ T-cells (defined as CD45$^+$, CD3$^+$, CD8$^+$) detected in 4T1 tumors. (FIG. 31F) Percentage of T-regs (defined as CD45$^+$, CD3$^+$, CD4$^+$, CD25$^+$) detected in 4T1 tumors. (FIG. 31G) Numbers of T-cells in tumor draining lymph nodes of mice bearing 4T1 tumors shown as % of total cells. (FIG. 31H) % CD80/MHC Class II expression in dendritic cells in the tumor draining lymph nodes of mice bearing 4T1 tumors. (FIG. 31I) Confocal image of the interaction between isolated CD8$^+$ T-cells from Ep-EDV-682 treated mice with 4T1 cells. Red—actin, green—perforin, blue (dark)—DAPI; scale bar 10 μm. Data (FIGS. 31B, 31D, and 31E-H) represents mean±s.e.m. and analyzed by one way ANOVA and Tukey's multiple comparison test (FIGS. 31B, 31D, and 31E-G) or t-test (FIG. 31H).

(FIG. 32G) CD8+ T cell subtypes. Cytotoxic CD8+ T cells include effectors and exhausted (PD1+) subtypes.

FIGS. 33A-33I shows a schematic of how the EDV first creates an immunogenic tumor microenvironment via the delivery of cytotoxic agents directly to the tumor, then stimulates the innate immune system either directly or indirectly towards an antitumor phenotype, and finally produces an adaptive response in which tumor specific cytotoxic T-cells arise. (FIG. 33A) Ep-EDV-682 enters the tumor microenvironment via the leaky vasculature resulting in tumor cell apoptosis and the release of immune activating DAMPs. (FIG. 33B) The interaction of macrophages within the tumor microenvironment via engulfment of apoptotic cells or even EDVs directly, results M1 macrophage polarization and release of inflammatory cytokines TNFα and IL-6 (FIG. 33C) M1 macrophages are capable of further lysing tumor cells and release MIP-1α which can recruit additional immune cells. (FIG. 33D) Immature dendritic cells engulf apoptotic cell bodies and released tumor antigens which occur in response to Ep-EDV-682 treatment and mature releasing type 1 interferons, TNFα, IL-12p40 and IL-6. (FIG. 33E) Mature DC then migrate to the lymph node for antigen presentation to T-cells. (FIG. 33F) NK cell activation also occurs in the tumor microenvironment resulting in release of IFNγ and TNFα as well as RANTES to attract additional immune cells. Further, activated NK cells effectively lyse tumor cells. (FIG. 33G) The release of RANTES and MIP-1α recruits additional T-cells, NK cells, and macrophages into the tumor where (FIG. 33H) tumor specific CD8$^+$ T-cells then contribute the response via tumor cell lysis. (FIG. 33I) All of these steps combine to create and effective antitumor immune response.

(FIG. 34A) TNFα production by RAW264.7 cells incubated directly with EDV formulations. (FIG. 34B) IL-6 productions by RAW264.7 cells incubated directly with EDV formulations. (FIG. 34 C) Flow cytometric histogram overlays of CD86 and MHC Class II expression in JAWS II cells co-cultures with untreated CT26Ep12.1 and 4T1 cells or those treated with Ep-EDV, Ep-EDV-682, or 682 alone. (FIG. 34D) Quantitation of CD86 expression as determined via flow cytometry on JAWS II cells co-cultured with treated tumor cells. (FIG. 34E) Quantitation of MHC Class II expression as determined via flow cytometry on JAWS II cells co-cultured with treated tumor cells. Data represent mean±s.e.m. and are analyzed by one-way ANOVA and Tukey's multiple comparison test.

(FIG. 35 G) xCELLigence RTCA of CD11b$^+$ isolated from A549/MDR tumors and co-cultured with A549/MDR cells at a 5:1 (E:T) ratio. Plot represents normalized cell index which correlates to cell adhesion and growth/death vs time. (FIG. 35H) % cytolysis of A549/MDR cells co-cultured with CD11b$^+$ cells from the tumors of saline or EGFR-EDV-682 treated mice 6.5 h following the addition of CD11b$^+$ cells. (FIG. 35I) Production of MIP-1α in co-cultures of CD11b$^+$ cells isolated from treated 4T1 tumors with 4T1 cells. Data (FIGS. 35E, 35F, 35H, and 35I) represents mean±s.e.m. and analyzed by one way ANOVA and Tukey's multiple comparison test (FIG. 35E, 35H, 35I) or t-test (FIG. 35F).

(FIG. 36A) xCELLigence RTCA of NK cells isolated from spleens of Balb/c nude mice bearing T84 tumors co-cultured with T84 cells at a 10:1 (E:T) ratio. Plot represents cell viability, calculated from the normalized cell index, over time. (FIG. 36B) Granzyme B production in co-cultures of NK cells isolated from spleens of saline and EGFR-EDV-682 treated mice and T84 cells. Data represents mean±s.e.m. and analyzed by t-test. (FIG. 36C) xCELLigence RTCA of NK cells isolated from spleens of Balb/c nude mice bearing A549/MDR tumors co-cultured with A549/MDR cells at a 10:1 (E:T) ratio. Plot represents cell viability, calculated from the normalized cell index, over time (Saline n=5; EGFR-EDV-682 n=4).

(FIG. 37A) EGFR surface receptor quantitation of cells from the head of the tumor. (FIG. 37B) EGFR surface receptor quantitation of cells from the tail of the tumor. (FIG. 37C) Drug sensitivity and IC50 of first and second line chemotherapy drugs/drug combinations as compared to 682 sensitivity.

(FIG. 39A) Isolation of CD11b$^+$ cells from mouse tumors. Density plots showing isotype control vs. FSC and CD11b vs. FSC. Samples had ~80% purity of CD11b$^+$ cells. (FIG. 39B) Isolation of NK cells from mouse spleens. Density plots show isotype control vs. FSC, NKp46 vs. FSC and CD11b vs. FSC. Samples had ~90% purity of NK cells. (FIG. 39C) CD8$^+$ T-cell isolation from mouse spleens. Density plots show isotype control vs. FSC, CD3e vs. FSC, and CD8 vs. FSC. Samples had ~90% purity of T-cells (CD3e$^+$) with over 98% of those T-cells being CD8$^+$.

FIGS. 43A-43F shows different sized CT26 isografts treated with (FIGS. 43A and 43B)$^{EP}$minicell$_{Dox}$ and minicell$_{\alpha\text{-}GC}$, (FIGS. 43D and 43E) minicell$_{\alpha\text{-}GC}$ only, (FIG. 43F) $^{EP}$minicell$_{Dox}$ only, and (FIG. 43C) saline.

FIGS. 44A-44B shows different sized CT26 isografts treated with $^{EP}$minicell$_{Dox}$ and minicell$_{\alpha\text{-}GC}$.

FIGS. 45A-45E shows aGC-CD1D presentation of JAWSII Cells Following minicell$_{\alpha\text{-}GC}$ treatment at various time points (FIGS. 45A-E)

DETAILED DESCRIPTION

I. Overview

Figure 4:
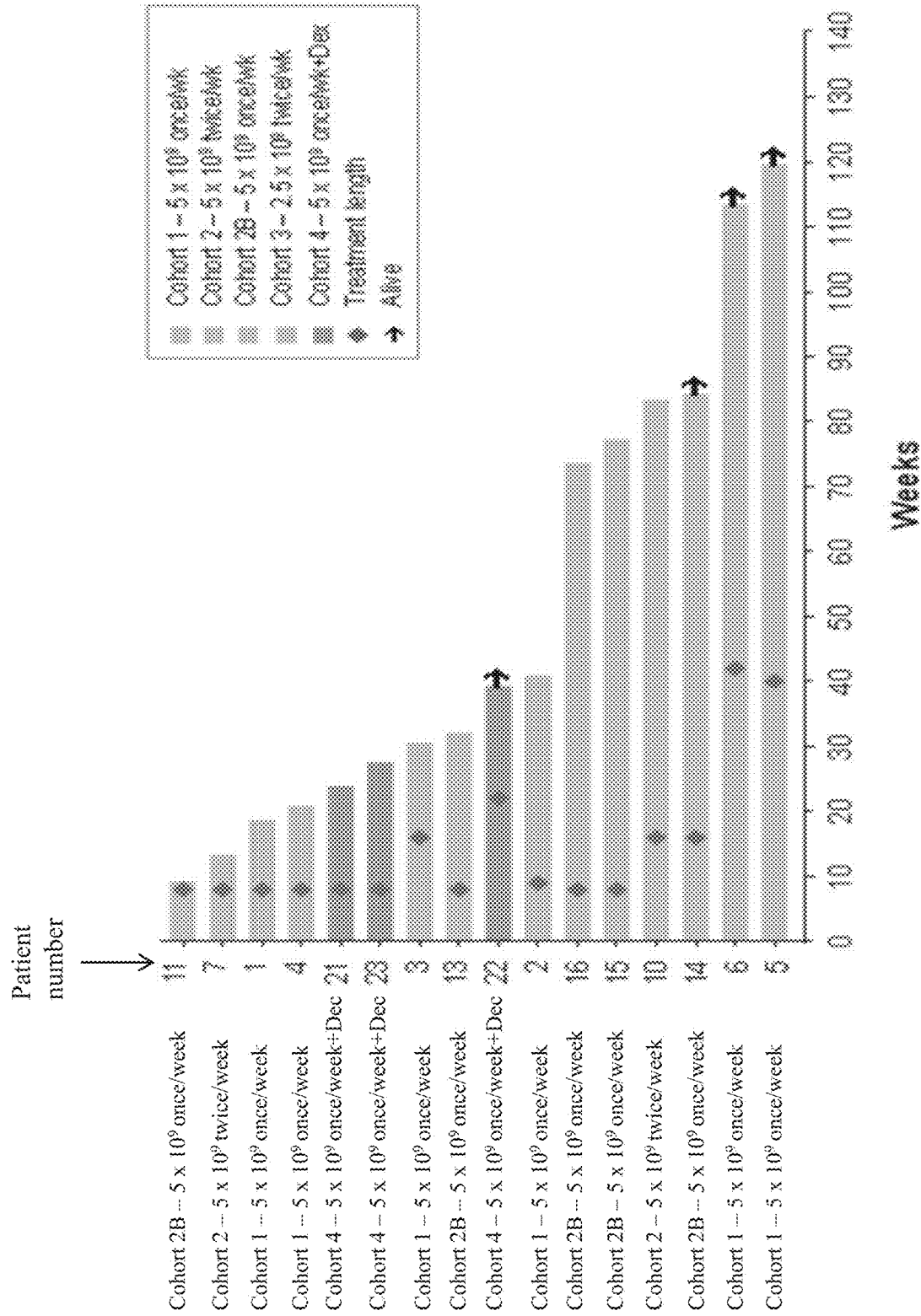
FIG. 4 is a graphical summary of a clinical trial evaluating EGFR-targeted and miRNA16a loaded EDVs for treating mesothelioma patients.

The present invention is based on the discovery that compositions comprising a combination of (i) an anti-neoplastic agent and a type I interferon agonist; (ii) an anti-neoplastic agent and a type II interferon agonist; or (iii) an anti-neoplastic agent, a type I interferon agonis, and a type II interferon agonist, wherein at least the anti-neoplastic agent is packaged within intact bacterially derived minicells, can synergistically improve cancer treatment strategies.

The combination of active agent and immunomodulatory agent(s), where at least the anti-neoplastic agent, and optionally the type I and/or type II interferon agonist is packaged within intact bacterially derived minicells, results in dramatic efficacy against cancerous cells, as well as surprising lack of drug-resistance development in subjects. The described compositions avoid the toxicity associated with systemic delivery of anti-neoplastic drugs combined with immunomodulatory drugs such as type I and/or type II interferon agonists to provide synergistically improved cancer treatment strategies.

Recent advances in cancer immunotherapy have resulted in unprecedented, durable clinical responses in specific cancers (Emens et al., 2017; Farkona et al., 2016; Oiseth and Aziz, 2017; Sharma et al., 2017; Ventola, 2017). However, current immunotherapeutic strategies have resulted in limited success rates across a variety of tumor types and a significant proportion of patients who initially demonstrate encouraging tumor regression relapse over time (Emens et al., 2017; Mellman et al., 2011; Oiseth and Aziz, 2017; Sharma et al., 2017; Ventola, 2017).

Described in Example 16 below is data elucidating the mechanism of the cyto-immuno-therapy function of a tumor-targeted nanocell therapeutic, where it launches a dual assault on the tumor via delivery of a super-cytotoxin combined with engagement of multiple arms of the immune system. This approach circumvents some of the current pitfalls with immunotherapies by creating an immunogenic tumor microenvironment and also acting on multiple immune cell subsets thereby avoiding primary and/or adaptive resistances that may arise in patients.

Further, a subset of patients lack tumor immunogenicity resulting from an absence of tumor cell antigens or lack of immune cell infiltration and therefore exhibit no initial response to the current strategies available (Emens et al., 2017; Oiseth and Aziz, 2017; Sharma et al., 2017). Thus, the identification of novel, robust immunotherapeutic approaches may result in significantly improved clinical outcomes and remains an area of high priority.

To mount an effective anti-tumor immune response, certain steps must be achieved either spontaneously or therapeutically. First, tumor cell antigens which may be derived in situ via tumor cell death, or delivered exogenously must be taken up by dendritic cells (DC) (Anguille et al., 2015; Emens et al., 2017; Jung et al., 2018; Mellman et al., 2011). In conjunction with antigen uptake, DCs need to receive a proper maturation signal prompting differentiation and enhanced processing and presentation of antigens such that antitumor function as opposed to tolerance is promoted (Anguille et al., 2015; Emens et al., 2017; Jung et al., 2018; Mellman et al., 2011; Simmons et al., 2012). These mature, tumor antigen loaded DCs must then effectively generate antitumor T-cell responses which can occur via production of tumor specific cytotoxic T-cells, triggering of NK and/or NKT cell responses, and enhancing T-helper type 1 responses, among others (Emens et al., 2017; Fang et al., 2017; Mellman et al., 2011; Sharma et al., 2017; Zitvogel et al., 2015). Antitumor T-cells must finally enter the tumor microenvironment, where immune suppressive signals may be present, and effectively perform their antitumor function (Emens et al., 2017; Mellman et al., 2011). Problems arising in any of these steps will impede efficacy of an immunotherapeutic, and can even result in total failure of the therapy (Emens et al., 2017; Mellman et al., 2011; Sharma et al., 2017).

Currently, the immunotherapeutic strategies which have received the most attention clinically include immunological checkpoint inhibitors and chimeric antigen receptor T-cell therapy (CAR-T) (Emens et al., 2017; Mellman et al., 2011; Oiseth and Aziz, 2017; Sharma et al., 2017; Ventola, 2017). Checkpoint inhibitors such as cytotoxic T lymphocyte antigen 4 (CTLA-4), and programmed cell death 1/programmed cell death 1 ligand (PD-1/PDL-1) function by blocking the transmission of immune-suppressive signals and direct stimulation to activate cytotoxic T lymphocytes within the tumor microenvironment (Dine et al., 2017; Jenkins et al., 2018; Sharpe, 2017). Inhibitors of these pathways have shown dramatic clinical results in specific cancers, but overall response rates across different cancers remains low (~15-25%) and immune related toxicities associated with these therapies can be high (Dine et al., 2017; Emens et al., 2017; Jenkins et al., 2018; Sharpe, 2017; Ventola, 2017). With new checkpoints continually being discovered as potential immune targets, it is apparent that tumors are capable of exploiting an elaborate and diverse set of immune-suppressive pathways (Dine et al., 2017; Emens et al., 2017; Farkona et al., 2016; Jenkins et al., 2018; Sharpe, 2017). Thus, development of resistance to checkpoint inhibitors continues to be a hurdle and attempts are being made to utilize combinations of more than one checkpoint inhibitors to overcome these issues, though this often exacerbates associated toxicities (Dine et al., 2017; Jenkins et al., 2018; Sharma et al., 2017; Ventola, 2017).

The second therapy receiving widespread attention is CAR-T cell therapy which entails the genetic engineering of a patient's T-cells to express membrane fusion receptors with defined tumor antigen specificities and capable of eliciting robust T-cell activation to initiate killing of the target tumor cells (D'Aloia et al., 2018'; Farkona et al., 2016; Mellman et al., 2011; Sharma et al., 2017). This therapeutic approach has produced unprecedented clinical outcomes in the treatment of "liquid" hematologic cancers, but to date has not produced comparable responses in targeting solid malignancies due to limitations associated with the lack of a good specific antigen target, poor homing to the tumor, poor extravasation into the tumor, and lack of persistence within a hostile tumor microenvironment (D'Aloia et al., 2018'; Sharma et al., 2017). Practical limitations relating to the availability of lymphocytes from heavily pre-treated patients and long manufacturing times and are not a feasible treatment option for patients with rapidly advancing disease are also present (Oiseth and Aziz, 2017; Rezvani et al., 2017).

The EnGeneIC Dream Vector (EDV) is a bacterially-derived delivery system consisting of nonviable nanocells that are 400±20 nm in diameter, generated by reactivating polar sites of cell division in bacteria (MacDiarmid et al., 2007b). It has been demonstrated that these nanocells can be packaged with a cytotoxic drug, siRNA, or miRNA and specifically targeted to tumor cell-surface receptors via attachment of bispecific antibodies to the surface polysaccharide of the nanocells (MacDiarmid et al., 2009; MacDiarmid et al., 2007b; Reid et al., 2013). Post-intravenous administration in mouse and dog studies has demonstrated that they are retained in the vascular system due to their size, but then rapidly extravasate into the tumor via the tumor-associated leaky vasculature (MacDiarmid et al., 2007b; Sagnella et al., 2018). Post-tumor cell-surface receptor engagement via the associated bispecific antibody results in macropinocytosis into endosomes and release of the payload via degredation intracellularly in the lysosomes (MacDiarmid et al., 2009; MacDiarmid et al., 2007b; Sagnella et al., 2018). The safety of these nanocell therapeutics has been demonstrated in three Phase I clinical trials with over a thousand doses administered in various end-stage cancer patients and 682 loaded EDVs are currently being delivered to patients in a phase I trial and to date have shown a promising safety profile (2017; Kao et al., 2015; Solomon et al., 2015; van Zandwijk et al., 2017; Whittle et al., 2015).

A. Overview of Bacterial Minicell Delivery Methods

The use of bacterial minicells to deliver chemotherapeutic agents to cancer cells has previously been described. This delivery method to treat cancer packages a toxic chemotherapy agent or drug, or functional nucleic acid, into a bacterially-derived minicell, which are typically about 400 nm in diameter. Typically, the minicell carries an antibody targeting specific cancer cells. The antibodies attach to the surface of cancer cells and the minicell is internalized by the cancer cell. In this way, the toxic chemotherapy agents are not widely distributed throughout the body, and therefore reduce the chance of side effects and intolerability as the toxic drug or compound is delivered inside the cancer cell. Using antibody-targeted minicells as a delivery vehicle for toxic chemotherapy agents results in much less drug needed to kill the cancer cell, thus improving the therapeutic index.

Indeed, the present inventors have shown that minicells (or EnGeneIC Dream Vehicles, EDVs) can deliver chemotherapy drugs, such as paclitaxel or doxorubicin, to xenograft tumors in mice (Example 1), dogs (Example 2), and monkeys (Example 3). The targeted delivery ensures that the cancer cells receive most of the chemotherapeutic agent, resulting in a low level of toxicity. See Examples 1-3; see also MacDiarmid et al., 2007b; MacDiarmid et al., 2007a; MacDiarmid et al., 2009; and MacDiarmid et al., 2016. Furthermore, the minicells do not induce a significant immune response in the xenograft models, and the minicells are well tolerated (Example 4). Thus, intact bacterially derived minicells are a well-tolerated vehicle for delivering anti-cancer drugs to patients, with examples including doxorubicin targeted to advanced solid tumors (Example 5), doxorubicin targeted to glioblastoma (Example 6), and MicroRNA-16a targeted to mesothelioma (Example 7).

These treatment strategies did not result in complete remission or cure of all cancers in all patients, however. Accordingly, there is a need for improved cancer treatment therapies. The present inventors discovered that using a combination of minicells having three different types of payloads produced surprisingly dramatic and effective clinical efficacy.

Specifically, the present inventors discovered that minicells comprising a chemotherapy agent (in the examples below, for instance, the agent is PNU-159682, a supertoxic chemotherapy drug) combined with minicells comprising an interferon type I agonist and/or an interferon type II agonist resulted in synergistic anti-tumor effects and was well-tolerated by a patient suffering from late stage pancreatic cancer. See Example 12. In fact, the late-stage pancreatic cancer patient exhibited markedly improved quality of life after this treatment, which is remarkable for a patient at that stage. This triple or duel combination strategy provides synergistically improved treatment of cancers, particularly late-stage terminal cancer. The inventors also discovered that minicells comprising a chemotherapy agent combined with minicells comprising an interferon type II agonist resulted in synergistic anti-tumor effects.

It was also surprisingly discovered that a dual combination of a minicell packaged antineoplastic agent, in combination with a type II interferon agonist, and in the absence of a type I interferon agonist, resulted in dramatic efficacy against large sized tumors. Such results have not previously been described. It is theorized that in some patients, combining a type I interferon agonist and type II interferon agonist may be counterproductive, as the two types of interferon agonists may compete rather than synergistically act. This data is described in more detailed below.

The following description outlines the invention related to these discoveries, without limiting the invention to the particular embodiments, methodology, protocols, or reagents described. Likewise, terminology used here describes particular embodiments only and does not limit the scope of the invention.

B. Summary of the Experimental Results (i) Minicell Packaged Antineoplastic Agent in Combination with Minicell Packaged Type I Interferon Agonist In a first embodiment, described are compositions and methods relating to a combination of a bacterial minicell packaged antineoplastic agent in combination with a type I interferon agonist packaged in a bacterial minicell.

Example 11 and FIG. 18 describe data showing the results in lung cancer xenograft models in mice treated with various minicell (EDVs) compositions, as summarized in the table below. The animals of Groups 1 and 5 were administered a combination of a chemotherapeutic agent (PNU 159682) packaged in an intact bacterially derived minicell and a type I interferon agonist (a 40mer double stranded DNA or a 50mer double-stranded DNA), also packaged in an intact bacterially derived minicell. All of the minicell compositions resulted in stabilization of tumor growth. However, the most dramatic results were obtained after treating the large tumor size that resulted from saline treatment in part 1 of the experiment. When the saline-treated control group was subsequently treated in part 2 of the experiment with a composition comprising a combination of minicell-packaged anti-neoplastic agent plus a minicell-packaged type I interferon agonist, the tumor size was reduced by 62% over a 5-day period.

TABLE 1

Figure 18:
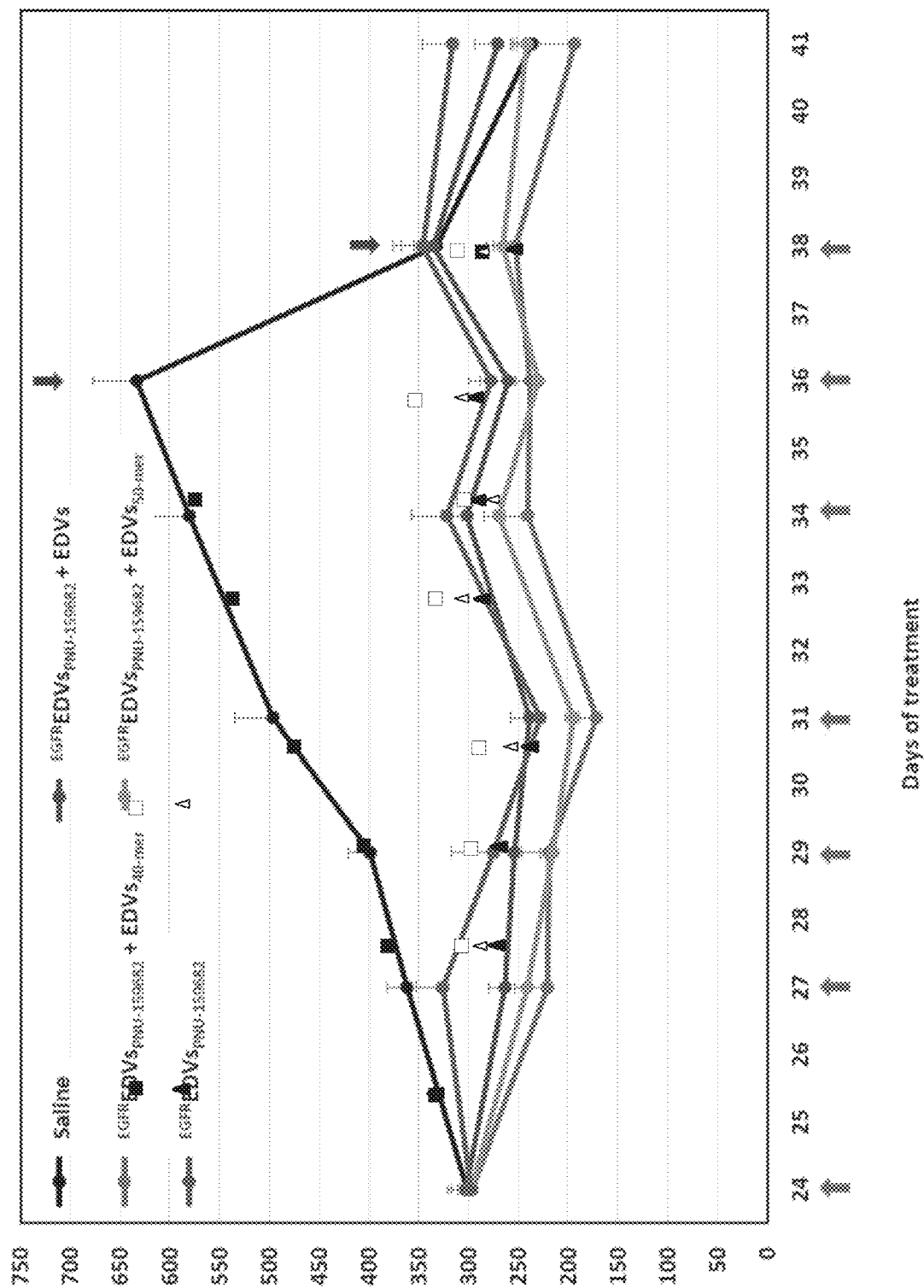
FIG. 18 shows the effect of A549 (lung cancer) xenograft tumor growth in Balb/c nu/nu mice treated with: (i) solid triangle=$^{EGFR}$EDVs$_{PNU-159682}$™+EDVs$_{40mer}$™, (ii) solid circle=$^{EGFR}$EDVs$_{PNU-59682}$™, (iii) open square=$^{EGFR}$EDVs$_{PNU-159682}$™+EDVs, (iv) open triangle=$^{EGFR}$EDVs$_{PNU-159682}$™+EDVs$_{50mer}$™, and (v) solid square=saline. The mice were treated with these EDVs combinations at day 24, 27, 29, 31, 34, 36, and 38 after the xenograft implantation as indicated with up arrows. On days 36 and 38, the saline group mice with tumor volume of ~650 mm$^3$ were treated with $^{EGFR}$EDVs$_{PNU-159682}$™+EDVs$_{50mer}$™ as indicated by the down arrows.

| Group | Treatment | FIG. | Phase I Results | Phase II Treatment Starting at days 36 and 38 | Results |
|---|---|---|---|---|---|
| 1 | $^{EGFR}$EDV$_{S_{PNU-159682}}$ + EDV$_{S_{40mer}}$ | FIG. 18, solid triangle | Tumor growth stabilization | | |
| 2 | $^{EGFR}$EDV$_{S_{PNU-159682}}$ | FIG. 18, solid circle | Tumor growth stabilization | | |
| 3 | $^{EGFR}$EDV$_{S_{PNU-159682}}$ + EDVs (no payload) | FIG. 18, open square | Tumor growth stabilization | | |
| 4 | $^{EGFR}$EDV$_{S_{PNU-159682}}$ + EDV$_{S_{50mer}}$ | FIG. 18, open triangle | Tumor growth stabilization | | |
| 5 | Saline | FIG. 18, solid square | tumor growth up to a volume of ~650 mm$^3$ | Treatment with $^{EGFR}$EDV$_{S_{PNU-159682}}$ + EDV$_{S_{40mer}}$ | In 5 days, tumors having a large volume of ~650 mm$^3$ decreased to ~250 mm$^3$ - or a 62% reduction in size in 5 days |

In a follow-up of Example 11 (results shown in FIG. 19), the addition of a type I interferon agonist packaged in a minicell resulted in dramatic tumor size reduction, which was not seen when an anti-neoplastic agent packaged in a minicell was used in the absence of the type I interferon agonist adjuvant. The results are summarized in the table below. These results clearly demonstrate the adjuvant effects on minicell-packaged anti-neoplastic agents with the addition of a minicell-packaged type I interferon agonist.

In particular, the human clinical data detailed in Example 12 demonstrate the safety profile of type I and type II IFN agonists used as adjuvants for minicell-packaged anti-neoplastic agents in human patients. See data in Table 3 below, in relation to which the type I interferon agonist packaged in intact, bacterially-derived minicells was 40mer double-stranded DNA (EDVs$_{40mer}$) or 60mer double-stranded DNA (EDVs$_{60mer}$).

TABLE 2

Figure 19:
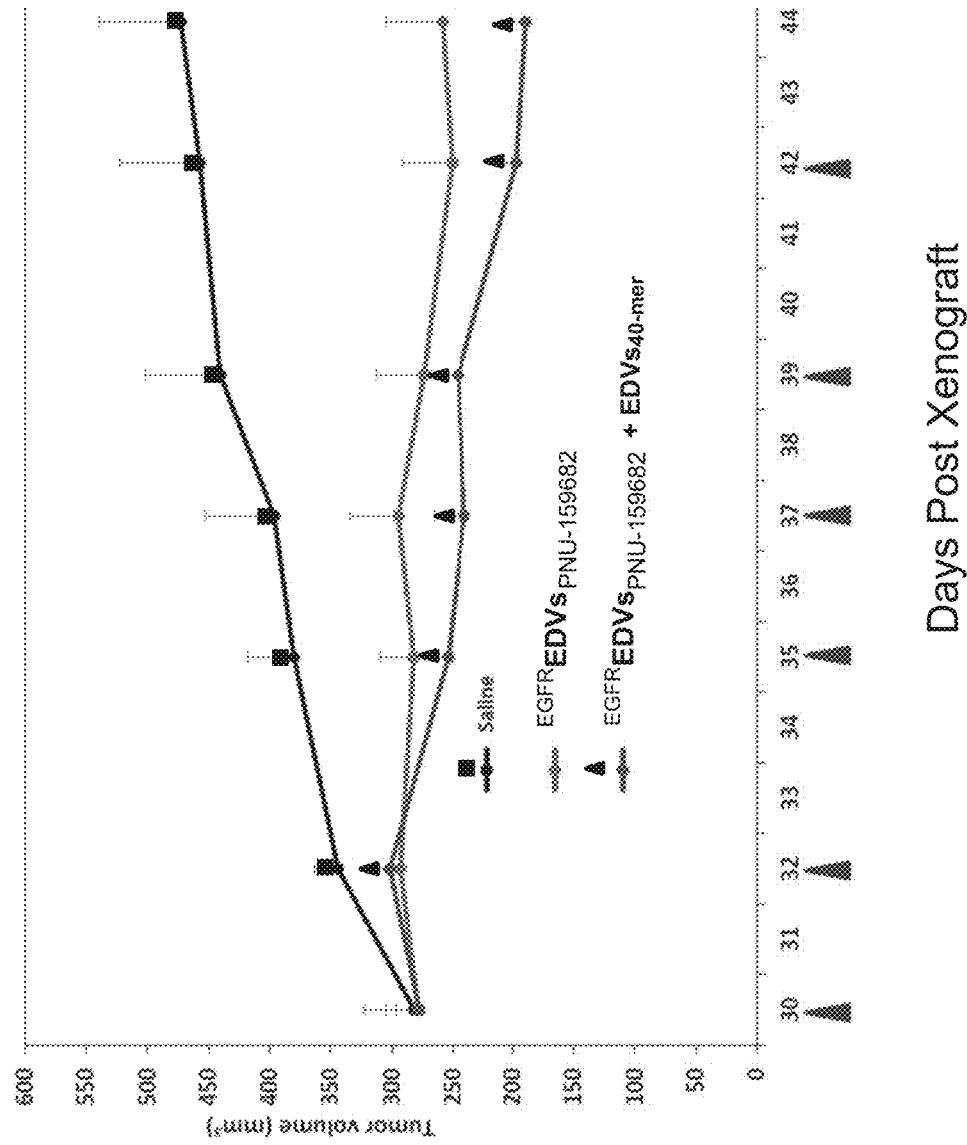
FIG. 19 shows the effect on A549 (lung cancer) xenograft tumor growth in Balb/c nu/nu mice treated with EDVs comprising 40mers ($^{EGFR}$EDVs$_{40mers}$™) in combination with EDVs comprising PNU-159682 ($^{EGFR}$EDVs$_{PNU}$™). The triangles indicate treatment days.

| Group | Treatment | FIG. | Results |
|---|---|---|---|
| 1 | $^{EGFR}$EDV$_{S_{PNU-159682}}$ | FIG. 19, solid circle | Slight tumor size reduction (from a tumor volume of about 275 mm$^3$ to 260 mm$^3$) |
| 2 | solid triangle = $^{EGFR}$EDV$_{S_{PNU-159682}}$ + EDV$_{S_{40mer}}$ | FIG. 19, solid triangle | Significant tumor reduction, from a tumor volume about 275 mm$^3$ to about 175 mm$^3$) |
| 3 | Saline | FIG. 19, solid square | Significant tumor growth. |

(ii) Minicell Packaged Antineoplastic Agent in Combination with Minicell Packaged Type I Interferon Agonist and Optionally a Type II Interferon Agonist (not Minicell Packaged)

A second embodiment is directed to methods and compositions utilizing a minicell packaged antineoplastic agent combined with a mincell-packaged type I interferon agonist or a minicell-packaged anti-neoplastic agent in combination with a mincell-packaged type I interferon agonist, and a type II interferon agonist (free from a bacterial minicell).

Further evidence of the dramatic and surprising effectiveness of the compositions of the invention is reflected in the clinical results shown in Example 12. Specifically, Example 12 relates what happened when patients suffering from advanced solid tumors were treated with compositions comprising (1) a combination of a minicell-packaged anti-neoplastic agent and a mincell-packaged type I interferon agonist; and (2) a combination of a minicell-packaged anti-neoplastic agent, a mincell-packaged type I interferon agonist, and a type II interferon agonist.

Moreover, the results obtained with a stage 4 pancreatic cancer patient, who had exhausted all other treatment options, were remarkable. The levels of the patient's tumor marker (CA 19-9) dropped by more than 90% after the initial three doses, equivalent to only 10 days of treatment. After ten doses this had dropped even further, with an almost 95% reduction in tumor marker levels. The patient also demonstrated significant weight gain, in contrast to the cachexic state experienced by most patients presenting with stage IV pancreatic cancer, and reported a marked improvement in quality of life. These results are dramatic, particularly given the poor prognosis associated with advanced pancreatic cancer.

In summary, five patients received a total of 69 doses of $^{EGFR(V)}$EDVs$_{PNU/Dox}$ or $^{EGFR(V)}$EDVs$_{PNU}$+ EDVs$_{40mer/60mer}$, (type I IFN agonist)±Imukin (type II IFN agonist). The treatments were well-tolerated, and the addition of immunomodulatory adjuvants did not seem to change the safety profile of single-agent-loaded and targeted EDVs.

TABLE 3

| Patient # | Treatment | Cancer | Comments |
|---|---|---|---|
| 3 patients | $^{EGFR(V)}$EDVs$_{PNU-159682}$ at $2.5 \times 10^9$ + EDVs$_{40mer}$ at $5 \times 10^8$ | advanced solid tumors | Treatment was well tolerated, no unexpected adverse reactions. One patient was ultimately withdrawn from the study due to dose-limiting toxicity. |
| 1 patient | $^{EGFR(V)}$EDVs$_{PNU-159682}$ and EDVs$_{40mer}$ or EDVs$_{60mer}$ And ITG-targeted EDVs loaded with PNU-159682 ($^{ITG(609)}$EDVs$_{PNU}$) | Stage IV pancreatic cancer | Treatment was well-tolerated; levels of the patient's tumor marker (CA 19-9) dropped by more than 90% after the first 3 doses, equivalent to only 10 days of treatment. After 10 doses this had dropped even further, with an almost 95% reduction in tumor marker levels. |
| 1 patient | $^{EGFR(V)}$EDVs$_{PNU}$ and EDVs$_{60mer}$ + Imukin (type II IFN agonist) | recurrent and end-stage adreno-cortical cancer with a very heavy tumor burden | Treatment was well tolerated. |

(iii) Minicell Packaged Antineoplastic Agent in Combination with Type II Interferon Agonist Example 13 describes the results of various studies conducted to evaluate the effectiveness of combining antineoplastic agents packaged in minicells with a type II interferon agonist, e.g., IFN-γ. The results show that the addition of a type II interferon agonist augments or enhances the anticancer effect of anti-neoplastic agents packaged in minicells in xenograft models of various cancers, including lung cancer and breast cancer. Further, the data set forth in Example 13 and excerpted in Table 4 below demonstrate that the addition of a type II interferon agonist to a composition comprising an antineoplastic agent packaged in a minicell in the treatment of tumors normally resistant to the antineoplastic agent alone is essential to achieve tumor stabilization. Thus, combining a minicell-packaged antineoplastic agent with a type II interferon agonist can overcome drug resistance.

(iv) Triple Combination of a Minicell-Packaged Antineoplastic Agent, a Minicell-Packaged Type I Interferon Agonist, and a Type II Interferon Agonist (Either Alone or Minicell-Packaged)

The present inventors also discovered that a triple combination of a minicell-packaged antineoplastic agent, a minicell-packaged type I interferon agonist, and a type II interferon agonist (either alone or minicell-packaged) can produce dramatic anticancer effects. Specifically, Example 14 details treatment of dogs with late stage endogenous tumors (brain cancer, sarcoma, or melanoma) with a combination of a minicell-packaged antineoplastic agent, a minicell-packaged type I interferon agonist, and a type II interferon agonist. The results show that the combination composition was well-tolerated. Moreover, in 6 of 7 evaluable animals (85.7%) the disease was stabilized, although one dog achieved a near partial response (29.8% reduction in tumor size).

TABLE 4

Figure 20:
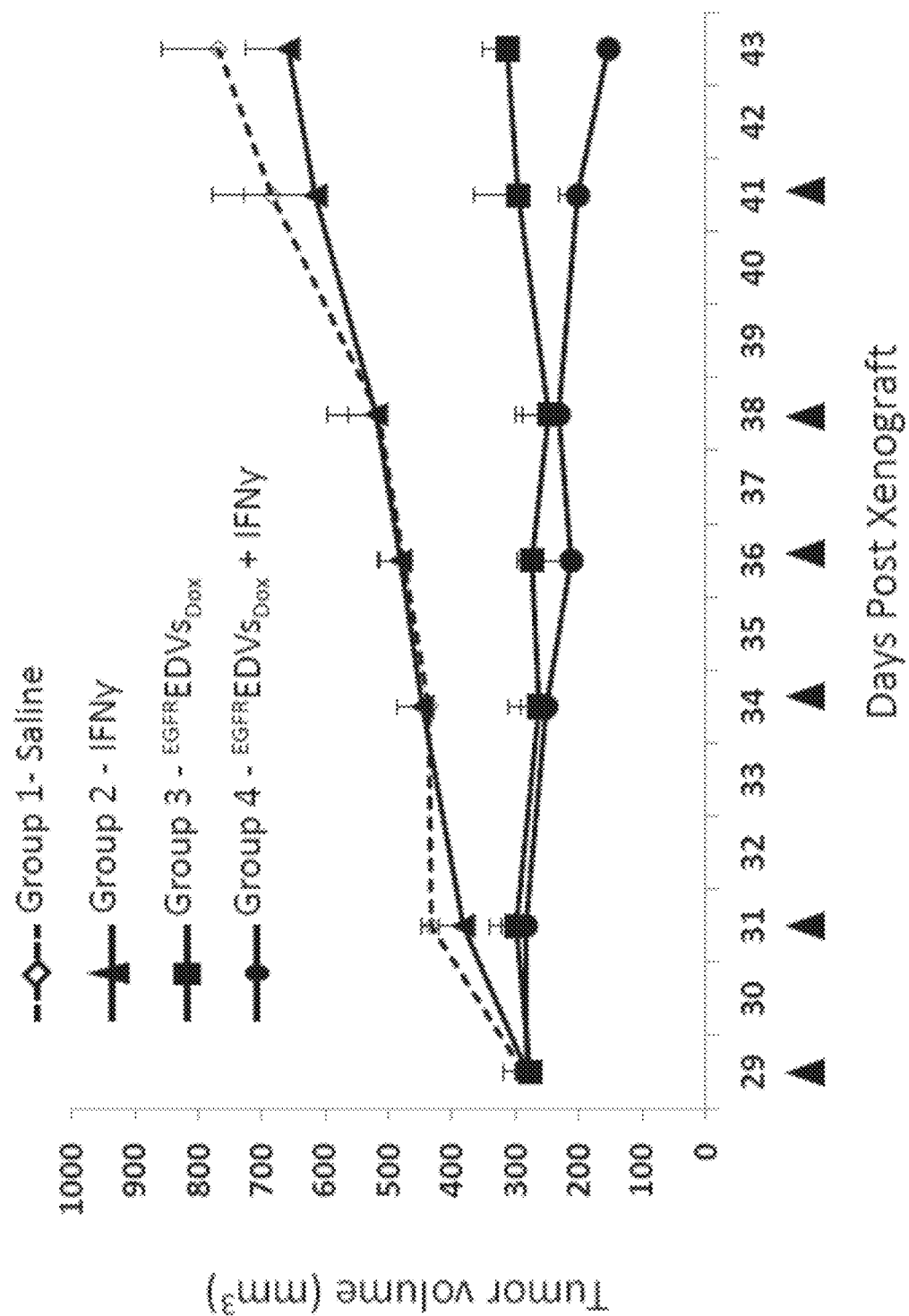
FIG. 20 shows the effect on A549 (lung cancer) xenograft tumor growth in Balb/c nu/nu mice treated with saline (negative control), IFN-γ (0.5×10$^4$ IU per dose), EGFR-targeted EDVs loaded with doxorubicine ($^{EGFR}$EDVs$_{Dox}$™), and $^{EGFR}$EDVs$_{Dox}$™+IFN-γ. The triangles indicate treatment days.
Figure 21:
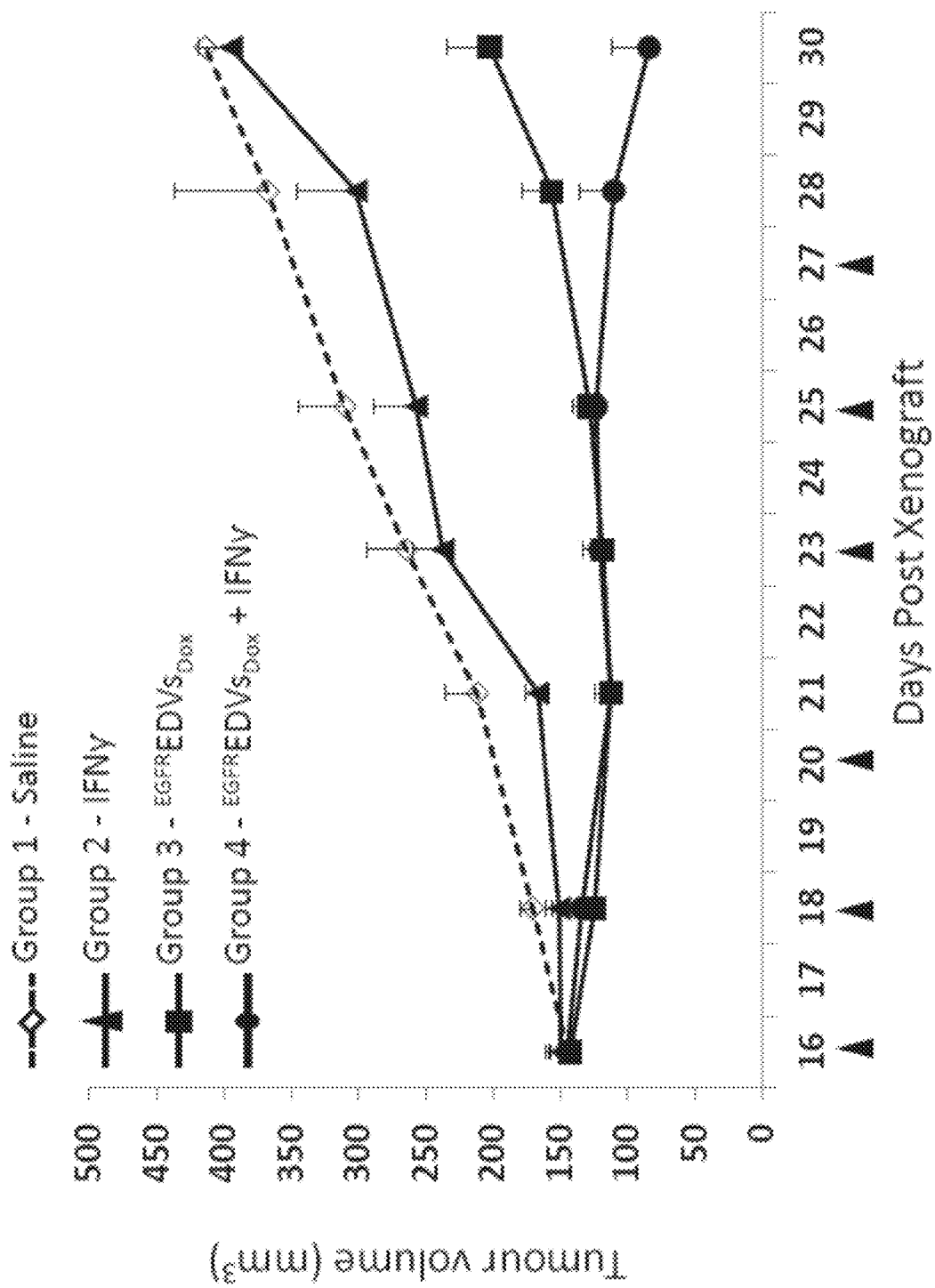
FIG. 21 shows the effect on MDA-MB 468 (breast cancer) xenograft tumor growth in Balb/c nu/nu mice treated with saline (negative control), IFN-γ (0.5×104 IU per dose), EGFR-targeted EDVs loaded with doxorubicine ($^{EGFR}$EDVs$_{Dox}$™), and $^{EGFR}$EDVs$_{Dox}$™+IFN-γ. The triangles indicate treatment days.

| Cancer | Treatment | FIG. | Results |
|---|---|---|---|
| Lung cancer | Group 1 = sterile physiological saline | FIG. 20, open diamonds | Significant tumor growth |
| | Group 2 = IFN-γ ($0.5 \times 10^4$ IU) per dose | FIG. 20, solid triangles | no anti-tumor efficacy |
| | Group 3 = $^{EGFR}$EDVs$_{Dox}$ | FIG. 20, solid squares | tumor stabilisation |
| | Group 4 = $^{EGFR}$EDVs$_{Dox}$ and IFN-γ ($0.5 \times 10^4$ IU) per dose | FIG. 20, solid circles | highly significant tumor regression by day 43 after a total of 6 doses |
| Breast cancer | Group 1 = sterile physiological saline | FIG. 21, open diamonds | Significant tumor growth |
| | Group 2 = IFN-γ ($0.5 \times 10^4$ IU) | FIG. 21, solid triangles | no anti-tumor efficacy |
| | Group 3 = $^{EGFR}$EDVs$_{Dox}$ | FIG. 21, solid squares | tumor stabilisation of breast cancer xenografts, but by ~day 25 the tumors began to grow again, likely due to development of resistance to doxorubicin |
| | Group 4 = $^{EGFR}$EDVs$_{Dox}$ and IFN-γ ($0.5 \times 10^4$ IU) per dose | FIG. 21, solid circles | highly significant tumor regression, and by day 30, after a total of 6 doses, these tumors were more like scar tissue |

(v) Duel Combination of a Minicell-Packaged Antineoplastic Agent in Combination with a Minicell-Packaged Type II Interferon Agonist, in the Absence of a Type I Interferon Agonist In another embodiment, this invention relates to the surprising discovery that compositions comprising a combination of a minicell-packaged antineoplastic agent and a minicell packaged type II interferon agonist, such as for example alpha-galactosyl ceramide (α-GC), and in the absence of a type I interferon agonist, demonstrates surprising anticancer efficacy.

Figure 40:
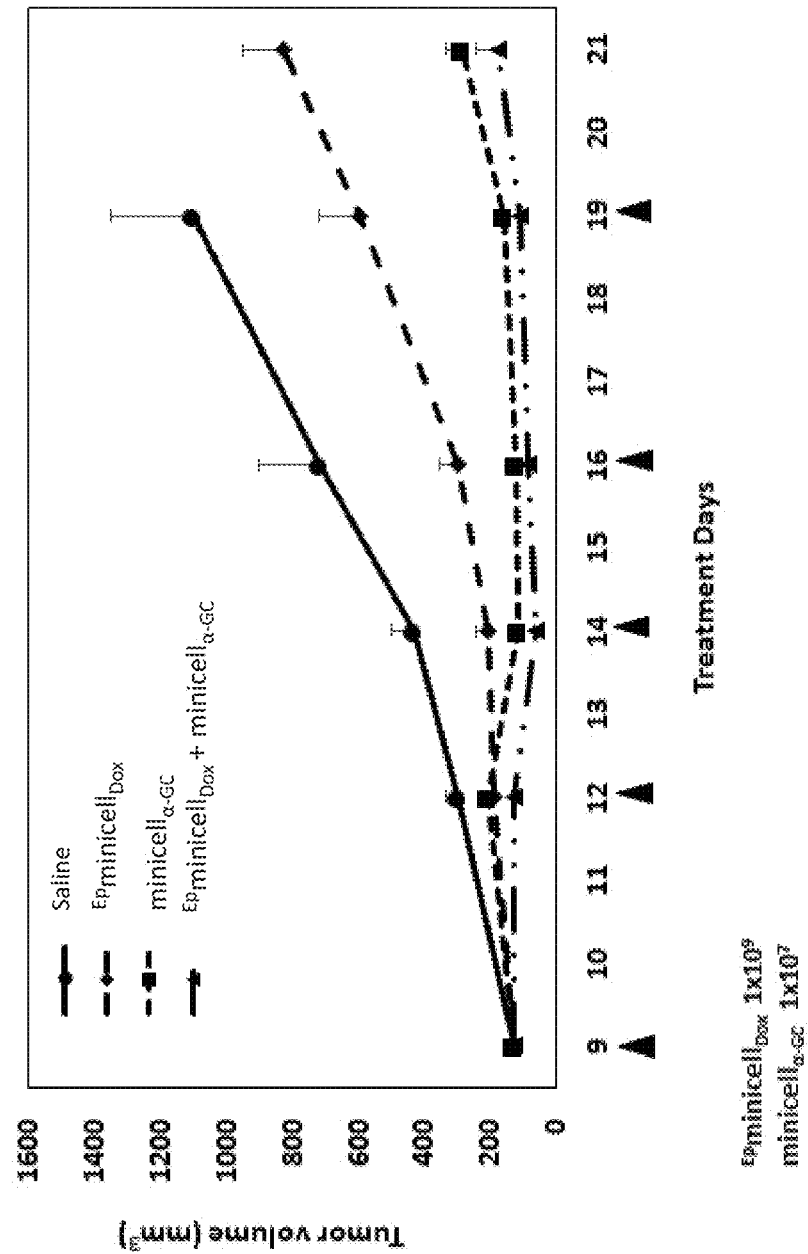
FIG. 40 shows combination treatment using $^{Ep}$minicell$_{Dox}$ and minicell$_{\alpha-GC}$ in a syngeneic mouse model ($^{Ep}$CT26 colon tumors in Balb/c mice).
Figure 42:
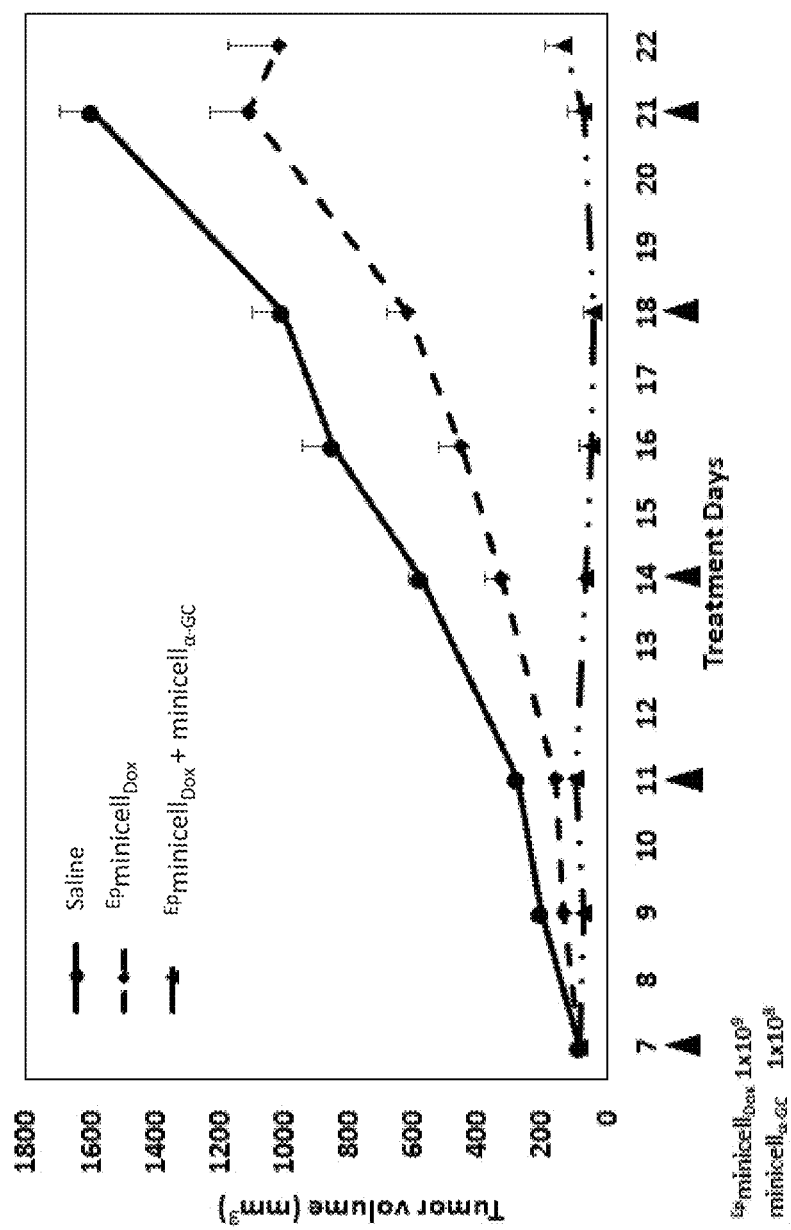
FIG. 42 shows effect of $^{EP}$minicell$_{Dox}$ and minicell$_{\alpha\text{-}GC}$ on tumor regression in Balb/c mice with CT26 isograft.

In particular, Example 23 describes data illustrating the efficacy of a dual combination of minicell contained therapeutic and minicell contained interferon type II agonist against tumors. This result demonstrates that compositions lacking interferon type I agonists can be used to effectively treat tumors. See also, FIGS. 40 and 42. The experimental results showed a marked halt in tumor progression for combination treatment groups receiving $^{EP}$minicell$_{Dox}$+ minicell$_{\alpha\text{-}GC}$ (interferon type II agonist) as compared to saline and $^{EP}$minicell$_{Dox}$ treatments. This result supports the theory of an immune adjuvant effect by the addition of minicell$_{\alpha\text{-}GC}$ treatment to $^{EP}$minicell$_{Dox}$.

Further data showed that saline treated control tumors demonstrated dramatic tumor regression following a treatment change to drug and α-GC EDV mediated dual combination therapy (FIG. 41); e.g., a combination of minicell packaged antineoplastic agent and minicell packaged type II interferon agonist. In particular, tumours that had reached 800 mm$^3$ dropped to below 600 mm$^3$ in 3 days before the experiment was terminated—a markedly dramatic tumor size reduction (~25%) in a short period of time. The ability for the dual combination composition to dramatically decrease large tumors in a short period of time was not known prior to the present invention.

In one embodiment of the invention, the dual combination composition (e.g., a minicell packaged antineoplastic agent in combination with a minicell packaged interferon type II agonist) can reduce a tumour's size, including the size of a large tumor, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The reduction in tumor size can be measured over any suitable time period, such as about 3 days, about 5 days, about 1 week, about 2 weeks, about 3 weeks, about 1, about 2, about 3, about 4, about 5, about 6, about 7, about 8, about 9, about 10, about 11, about 12 months, about 1.5 years, about 2 years or longer.

C. Immunotherapy Data

Example 16 details data demonstrating that minicell packaged antineoplastic agents targeted to a tumor cell surface receptor function as a cancer immunotherapy, e.g., as a cyto-immunotherapy. In particular, the example illustrates the ability of the bacterial minicell to activate cells of the innate immune system, including macrophages, NK cells and dendritic cells. This is followed by dendritic cell maturation and antigen presentation leading to an adaptive T-cell response in which tumor specific cytotoxic T-cells are produced and results in further recruitment of additional immune cells to the tumor microenvironment. This approach circumvents some of the current pitfalls with immunotherapies by creating an immunogenic tumor microenvironment and also acting on multiple immune cell subsets thereby avoiding primary and/or adaptive resistances that may arise in patients.

This example therefore shows the ability of the bacterial minicell to deliver a cytotoxic drug within tumor cells and to also simultaneously elicit an innate and adaptive immune response specifically targeting the tumor.

Further immunotherapy data is shown in Example 18, which describes data showing that NK cells adopt an antitumor phenotype in vivo following treatment with targeted minicells comprising an antineoplastic agent. This is significant as NK cells are the primary effector cell of the innate immune system and are tightly regulated by a balance of activating and inhibitory signals (Morvan and Lanier, 2016; Wallace and Smyth, 2005). Impairment of NK cell function has been associated with increased tumor incidence, growth, and metastasis, and thus its importance in contributing to an antitumor immune response is well documented (Fang et al., 2017; Morvan and Lanier, 2016; Rezvani et al., 2017; Wallace and Smyth, 2005).

Interesting, Example 19 details data showing that a predominantly Th1 cytokine response within a tumor microenvironment is exhibited following treatment with a minicell-encapsulated antineoplastic agent (e.g., PNU-159682). Cytokine and chemokine production within a tumor microenvironment allows immune cells to effectively communicate with each other to generate a coordinated response which can either be tumor promoting or suppressing (Belardelli and Ferrantini, 2002; Lee and Margolin, 2011). The effect of individual cytokines on immune response is dependent on a variety of factors including local concentration, cytokine receptor expression patterns and the activation state of surrounding cells (Lee and Margolin, 2011). Thus, many cytokines have been shown to be capable of eliciting opposing effects on tumor growth (Dredge et al., 2002; Landskron et al., 2014; Lee and Margolin, 2011).

Figure 31A:
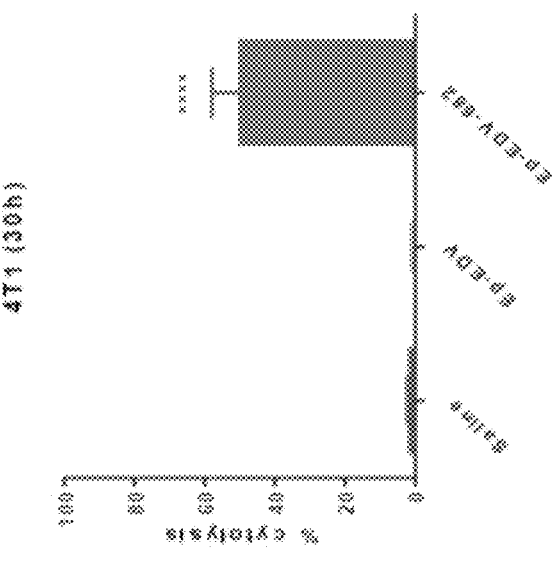
FIGS. 31A-31I shows T-cell function and phenotype in response to EDV treatment.
Figure 31B:
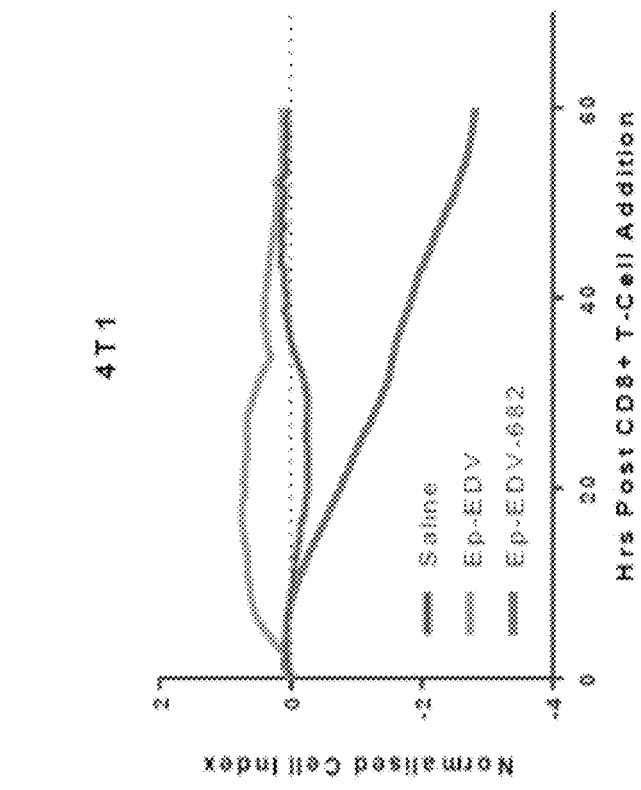
Figure 31C:
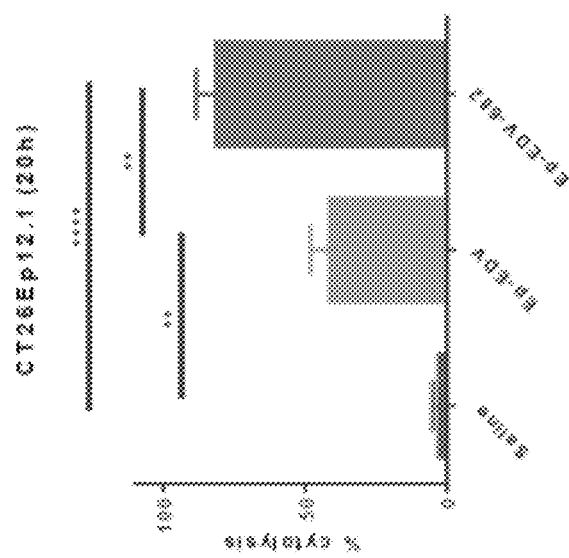

Further, Example 20 details data showing that treatment with a minicell-encapsulated antineoplastic agent (e.g., PNU-159682) results in the production of tumor specific CD8+ T-cells. Initial in vitro experiments indicated that EDV treatment can result in dendritic cell maturation either via direct interaction or as a result of cell death in response to a targeted EDV loaded with an effective chemotherapeutic. Thus, this experiment aimed to examine if this result could translate to DC maturation and antigen presentation in vivo resulting in the production of tumor specific CD8$^+$ cytotoxic T-cells. The resulting data demonstrated that minicell treatment successfully elicited the production of tumor specific CD8$^+$ T-cells. In addition, a significant increase in overall T-cell numbers (CD3+) as well as a significant increase in both CD4+ and CD8+ T-cells numbers were seen in the lymph nodes of mice treated with minicell encapsulated antineoplastic agent (e.g., PNU-159682) (FIG. 31G). A significant increase in mature dendritic cells in the lymph nodes of treated mice was also detected (FIG. 31H), and visualization of the interaction between isolated CD8$^+$ T-cells from treated mice with 4T1 cells shows that these T-cells are capable of attaching to and expelling perforin (green) into the tumor cell (FIG. 31I).

Example 21 demonstrates the ability of targeted bacterial minicells loaded with an antineoplastic agent (e.g., the super-cytotoxin PNU-159682) to not only effectively deliver this drug to the tumor site, but also behave as an immunotherapeutic by stimulating multiple immune cell subsets. The example demonstrates the ability of a minicell capsulated antineoplastic agent treatment to push immune cell subsets, including macrophages, NK cells and CD8$^+$ T-cells, towards an antitumor phenotype capable of effectively eliminating tumor cells. When combined with the effectiveness of an antineoplastic agent, this results in a dual assault on the tumor.

While the idea of cancer immunotherapy has been around for decades, it is only in recent times that its potential has begun to be realized with the approval of a number of immunotherapies (Farkona et al., 2016; Ventola, 2017). Bacterial minicells represent a unique, combined cyto-immunotherapy which first creates an immunogenic tumor microenvironment via the delivery of cytotoxic agents directly to the tumor, where it stimulates the innate immune system either directly or indirectly towards an antitumor phenotype. This innate immune activation then triggers an adaptive response in which tumor specific cytotoxic T-cells arise (FIG. 33).

Following intravenous administration, the minicell extravasates to a tumor via the tumor's leaky vasculature where ≥30% of the administered dose of targeted minicells carrying their toxic payload deposit directly into the tumor microenvironment within a 2 hr period (MacDiarmid et al., 2007b). Targeted bacterial minicells bind to receptors on the tumor cells (4T1 and CT26Ep12.1 in the case of Example 21), and are then internalized effectively delivering their payload (antineoplastic agent) directly within the tumor cells. PNU-159682 is a highly potent super cytotoxin resulting in rapid apoptosis within 24h of being delivered to the tumor cells (FIG. 33A). The apoptotic cells and DAMP signals produced by bacterial minicell (e.g., Ep-EDV-682) treatment can then interact with innate immune cells such as tumor associated macrophages (TAMs) and stimulate upregulation of CD86 and the production of Th1 pro-inflammatory cytokines such as TNFα and IL-6 (FIG. 33B). These changes are typical of M1 polarization of macrophages which are capable of lysing tumor cells and releasing cytokines to signal activation of other immune cell subsets, and have thus been shown to possess antitumor characteristics (Sawa-Wejksza and Kandefer-Szerszen, 2018; Yuan et al., 2015).

Furthermore, the bacterial minicell itself can also interact directly with TAMs producing a similar M1 polarization, albeit this would be expected to occur at very low levels in the current system. TAMs are generally the most abundant immune cell in the tumor microenvironment, and it has been demonstrated that increased numbers of TAMs are associated with poor prognosis and increased tumor growth (Sawa-Wejksza and Kandefer-Szerszen, 2018). This is due in large part to the fact that TAMs mostly consist of anti-inflammatory M2 macrophages which have been shown to possess tumor promoting characteristics, whereas inflammatory M1 macrophages exhibit antitumor characteristics (Sawa-Wejksza and Kandefer-Szerszen, 2018; Yuan et al., 2015). Example 21 demonstrates the ability of bacterial minicell treatment to shift the M1:M2 balance within the tumor microenvironment in 4 different tumor models. Despite differences in the degree of this shift in the different tumor models, it was shown that the increase in M1 polarization translated to increased tumor cell lysis by TAMs isolated from the tumors of mice which had been treated with bacterial minicells. In addition to the phenotypic shifts to M1, TAMs from tumors of bacterial minicell treated mice also secreted an increased amount of MIP-1 (FIG. 33C), a chemokine which has been established to play a role in promoting immune cell recruitment, and in particular tumor infiltration by NK cells, CD4$^+$ T-cells and CD8$^+$ T-cells (Allen et al., 2018).

In addition to TAM activation, immature dendritic cells (DC) interact either directly with bacterial minicells, or more likely, with the apoptotic cells and DAMP signals produced by bacterial minicell treated tumors resulting in dendritic cell maturation and migration to the lymph nodes for antigen presentation. DCs have been explored as a potential target in cancer immunotherapies as they are known to be the most effective antigen presenting cell and constitute the bridge between the innate and adaptive immune system (Allen et al., 2018).

Most current strategies for DC based immunotherapy involve ex vivo manipulation and priming of DCs or DC precursors, however success from this strategy has been limited due to a variety of factors including: development of immune tolerance, induction of insufficient numbers of CD8+ cytotoxic T-cells (CTL) or those with poor antitumor efficacy, and the suppressive nature of the tumor microenvironment (Anguille et al., 2015; Jung et al., 2018; Landskron et al., 2014; Oiseth and Aziz, 2017). Bacterial minicell treatment allows for in vivo priming and maturation of DCs within the tumor microenvironment in response to dying tumor cells (FIG. 33D). Immature DCs are capable of engulfing DAMPs and/or apoptotic tumor cell bodies produced in response to targeted, drug loaded bacterial minicells. These DAMPs and dying tumor cells are then processed for antigen presentation on the DC surface via MHC Class I and II molecules, with concomitant DC maturation. Upregulation of the co-stimulatory molecules CD86, CD80 and MHC Class II, which have been identified as markers of the DC maturation process, was shown to occur in DCs co-cultured with bacterial minicell treated tumor cells, along with an increase in the percentage of mature DCs detected in the tumor draining lymph nodes of bacterial minicell treated mice (Anguille et al., 2015; Cauwels et al., 2018; Simmons et al., 2012). During the maturation process, the DCs migrate to the tumor draining lymph nodes for antigen presentation to T-cells thereby increasing production of CD4$^+$ T-helper cells and tumor specific CD8$^+$ CTL initiating an adaptive immune response to the tumor (FIG. 33E). An increase in the production of IFNα/β, TNFα, IL-12p40, and IL-6 by DCs co-cultured with bacterial minicell treated tumor cells was subsequently detected, in addition to a significant increase in IFNα concentration in the tumor microenvironment observed in both the 4T1 and CT26Ep12.1 tumor models (Example 21). Expression levels of type 1 IFNs (IFNα/β) and IFN stimulated genes within the tumor microenvironment have been shown to correlate with favorable disease outcomes and may in fact even be necessary for the success of cancer therapies including immunotherapies (Cauwels et al., 2018; Fitzgerald-Bocarsly and Feng, 2007; Zitvogel et al., 2015). The antitumor activity of type 1 IFNs arise indirectly via immune cell activation of DCs, T and B lymphocytes, NK cells, and macrophages (Cauwels et al., 2018; Fitzgerald-Bocarsly and Feng, 2007; Showalter et al., 2017; Zitvogel et al., 2015).

In conjunction with enhancing macrophage and DC anti-tumor functions, treatment with bacterial minicells comprising an antineoplastic agent is capable of eliciting NK cell activation leading to increased cytotoxicity (FIG. 33F). NK cells possess the inherent ability to lyse malignant cells in an antigen independent manner, thus their activation and functional status must be tightly controlled in order to avoid potentially adverse effects on the host. The ability to attract NK cells to and activate NK cells within the tumor microenvironment is vital to their ability to exert their antitumor function. Cytokines including IL-2, IFNγ, and IFNα which are significantly increased in the microenvironment of Ep-EDV-682 treated tumors, are known to activate NK cells towards both increased cytokine production and enhanced cytolytic function (Fang et al., 2017; Ferlazzo and Munz, 2004; Lee and Margolin, 2011; Morvan and Lanier, 2016; Rezvani et al., 2017). In fact, evidence indicates that type 1 IFNs are required for the activation of NK cell cytotoxicity (Ferlazzo and Munz, 2004; Muller et al., 2017). Further, type 1 IFNs are capable of inducing cellular senescence followed by upregulation of NKG2D ligand expression in tumor cells thereby promoting their elimination by NK cells (Muller et al., 2017). Upregulation of the NKG2D receptor was observed on NK cells within the tumors of mice treated with Ep-EDV-682, and this receptor was demonstrated to contribute significantly to the cytolytic ability of NK cells isolated from Ep-EDV-682 treated mice. Moreover, immature, intermediate and mature mouse NK cells express both the CCR1 and CCR5 chemokine receptors that can bind the chemokines MIP1α and RANTES, both of which are upregulated in Ep-EDV-682 treated tumors as well as by macrophages and NK cells from Ep-EDV-682 treated mice (Bernardini et al., 2016).

Chemokines, such as MIP1α and RANTES, are responsible for the further recruitment of helper and effector immune cells including NK cells, macrophages, and T-cells to the tumor microenvironment (FIG. 33G) (Allen et al., 2018; Bernardini et al., 2016; Zibert et al., 2004). Following the initial innate immune response due to EDV treatment which encompasses macrophages, NK cells, and DCs, an adaptive immune response is mounted in which tumor specific CTLs and T-helper cells are produced and then recruited to the tumor site (FIG. 33H). Tumor specific CTLs then target and lyse tumor cells further contributing to the overriding antitumor environment which has been created by the other immune cell subsets in combination with the targeted, drug loaded EDVs. Targeted, drug loaded EDV treatment elicits a mainly Th1 response as evidenced by the increase of Th1 cytokines (TNFα, IFNα, IFNγ, IL-2, and IL-6) within the tumor microenvironment. As previously mentioned, innate immune cell subsets, when activated, become a primary source of one or more of these particular cytokines. T-cells are similarly capable of producing all of the aforementioned cytokines (Belardelli and Ferrantini, 2002; Lee and Margolin, 2011). Release of these cytokines by either innate immune cells or T-cells are responsible for co-stimulation, activation, growth, and increased antigen presentation of additional immune cells creating a feedback loop which further enhances the antitumor activity of the immune system FIG. 33I) (Lee and Margolin, 2011).

Bacterial minicell treatment represents a unique cancer therapeutic strategy capable of delivering conventional and novel drug therapies directly to the tumor site and subsequently eliciting an antitumor immune response. A dual assault on the tumor occurs, first through cell death in response to the delivered therapeutic and followed by innate immune cell activation leading to an adaptive immune response. This type of therapy has certain advantages over current immunotherapy strategies in that immune cell activation occurs both in vivo and primarily at the tumor site, which is a rapidly changing, dynamic environment. Further, it creates an immunogenic tumor environment and elicits effects on multiple immune cell subsets avoiding problems associated with patients who show little to no immune response to their tumors or adaptations to therapies which only target single immune cell subsets. The study described in Example 21 highlights the potential of bacterial minicells as a novel cancer immunotherapeutic, and future bacterial minicell formulations could further exploit its inherent immunogenic nature given the versatility of this technology with respect to both payload and targeting ability (MacDiarmid et al., 2007a).

D. Supertoxic Antineoplastic Agents

Example 17 details data demonstrating the effective delivery of a super toxic antineoplastic agent, e.g., PNU-159682, which is unable to be delivered using conventional means because of severe toxicity associated with the compound. Specifically, Example 17 details how PNU-159682 is a super cytotoxin with IC50s for even drug-resistant cancer cells in the pM range (Quintieri et al., 2005), which means that the compound is unable to be used clinically due to the severe systemic toxicity (Staudacher and Brown, 2017). However, when encapsulated in a bacterial minicell, super cytotoxins such as PNU-159682 can be effectively delivered to the tumor with few side effects.

II. Composition Components

As noted above, the compositions of the invention comprise at least two different active agents, an antineoplastic agent and a type I interferon agonist, a type II interferon agonist, or both a type I interferon agonist and a type II interferon agonist with the antineoplastic agent. The three different active agents can be packaged in one, two, or three different minicells. The type II interferon agonist also can be included in the methods and compositions of the invention without being packaged in a minicell.

A. Antineoplastic or Cytotoxic Active Agents Useful in Treating Cancer

The phrase "anti-neoplastic agent" denotes a drug, whether chemical or biological, that prevents or inhibits the growth, development, maturation, or spread of neoplastic cells. The term "antineoplastic agent" is used interchangeably with "anticancer agent" and "chemotherapy agent."

In the context of this disclosure, selecting an anti-neoplastic agent for treating a given brain tumor patient depends on several factors, in keeping with conventional medical practice. These factors include but are not limited to the patient's age, Karnofsky Score, and whatever previous therapy the patient may have received. See, generally, PRINCIPLES AND PRACTICE OF NEURO-ONCOLOGY, M. Mehta (Demos Medical Publishing 2011), and PRINCIPLES OF NEURO-ONCOLOGY, D. Schiff and P. O'Neill, eds. (McGraw-Hill 2005).

The composition can comprise at most about 1 mg of the antineoplastic or chemotherapeutic drug. Alternatively, the amount of the chemotherapeutic drug can be at most about 750 µg, about 500 µg, about 250 µg, about 100 µg, about 50 µg, about 10 µg, about 5 µg, about 1 µg, about 0.5 µg, or about 0.1 µg. In another aspect, the composition comprises a chemotherapeutic drug having an amount of less than about $1/1,000$, or alternatively less than about $1/2,000$, $1/5,000$, $1/10,000$, $1/20,000$, $1/50,000$, $1/100,000$, $1/200,000$ or $1/500,000$ of the therapeutically effective amount of the drug when used without being packaged into minicells. Pursuant to yet another aspect of the disclosure, the composition can comprise at least about 1 nmol of the chemotherapeutic drug. Accordingly, the disclosure also encompasses embodiments where the amount of the chemotherapeutic drug is at least about 2 nmol, about 3 nmol, about 4 nmol, about 5 nmol, about 10 nmol, about 20 nmol, about 50 nmol, about 100 nmol, or about 800 nmol, respectively.

In the context of this disclosure, selecting an anti-neoplastic agent for treating a given tumor depends on several factors. These factors include but are not limited to the patient's age, the stage of the tumor, and whatever previous therapy the patient may have received.

In accordance with the disclosure, a drug can be selected from one of the classes detailed below for packaging into intact, bacterially derived minicells. These drugs can also be synthetic analogs designed from drug design and discovery efforts. Any known chemotherapy agent can be utilized in the compositions of the invention. Examples of known chemotherapy agents include, but are not limited to:

(1) alkylating agents, such as mustard gas derivatives (Mechlorethamine, Cyclophosphamide (Cytoxan), Chlorambucil (Leukeran), Melphalan, and Ifosfamide), ethylenimines (Thiotepa (Thioplex) and Hexamethylmelamine), alkylsulfonates (Busulfan (Myleran)), hydrazines and triazines (Altretamine (Hexalen), Procarbazine (Matulane), Dacarbazine (DTIC) and Temozolomide), nitrosureas (Carmustine, Lomustine and Streptozocin), and metal salts (Carboplatin, Cisplatin (Platinol), and Oxaliplatin), Mechlorethamine, and Melphalan (Alkeran);

(2) Plant alkaloids, terpenoids and topoisomerase inhibitors, such as vinca alkaloids (Vincristine (Oncovin), Vinblastine (Velban), Vindesine, and Vinorelbine), taxanes (Paclitaxel (Taxol) and Docetaxel (Taxotere)), podophyllotoxins (Etoposide and Tenisopide), and camptothecan analogs (Irinotecan and Topotecan);

(3) antitumor antibiotics, such as anthracyclines (Doxorubicin (Adriamycin, Rubex, Doxil), Daunorubicin, Epirubicin, Mitoxantrone, Idarubicin, Duocarmycin, and Dactinomycin (Cosmegen)), chromomycins (Dactinomycin and Plicamycin (Mithramycin)), and miscellaneous (Mitomycin and Bleomycin (Blenoxane));

(4) antimetabolites, such as folic acid antagonists (Methotrexate), pyrimidine antagonists (5-Fluorouracil, Foxuridine, Cytarabine, Flurouracil (5-FU), Capecitabine, and Gemcitabine), purine antagonists (6-Mercaptopurine (Purinethol) and 6-Thioguanine), 6-Thiopurines, and adenosine deaminase inhibitor (Cladribine (Leustatin), Fludarabine, Nelarabine and Pentostatin), Azacitidine, Thioguanine, and Cytarabine (ara-C);

(5) topoisomerase Inhibitors, such as topoisomerase I inhibitors (Ironotecan, topotecan), and topoisomerase II inhibitors (Amsacrine, etoposide, etoposide phosphate, teniposide);

(6) hormonal agents, exemplified by Estrogen and Androgen Inhibitors (Tamoxifen and Flutamide), Gonadotropin-Releasing Hormone Agonists (Leuprolide and Goserelin (Zoladex)), Aromatase Inhibitors (Aminoglutethimide and Anastrozole (Arimidex));

(7) DNA hypomethylating agents, e.g., Azacitidine, Decitabine;

(8) Poly(adenosine diphosphate [ADP]-ribose) polymerase (PARP) pathway inhibitors, such as Iniparib, Olaparib, Veliparib;

(9) PI3K/Akt/mTOR pathway inhibitors, e.g., Everolimus;

(10) Histone deacetylase (HDAC) inhibitors, e.g., Vorinostat, Entinostat (SNDX-275), Mocetinostat (MGCD0103), Panobinostat (LBH589), Romidepsin, Valproic acid.

Cyclin-dependent kinase (CDK) inhibitors, e.g., Flavopiridol, Olomoucine, Roscovitine, Kenpaullone, AG-024322 (Pfizer), Fascaplysin, Ryuvidine, Purvalanol A, NU2058, BML-259, SU 9516, PD-0332991, P276-00. [0050] Heat shock protein (HSP90) inhibitors, e.g., Geldanamycin, Tanespimycin, Alvespimycin, Radicicol, Deguelin, and BIIB021;

(11) Murine double minute 2 (MDM2) inhibitors, e.g., Cis-imidazoline, Benzodiazepinedione, Spiro-oxindoles, Isoquinolinone, Thiophene, 5-Deazaflavin, Tryptamine;

(12) Anaplastic lymphoma kinase (ALK) inhibitors, e.g., Aminopyridine, Diaminopyrimidine, Pyridoisoquinoline, Pyrrolopyrazole, Indolocarbazole, Pyrrolopyrimidine, Dianilinopyrimidine;

(13) Poly [ADPribose] polymerase (PARP) inhibitors, illustrated by Benzamide, Phthalazinone, Tricyclic indole, Benzimidazole, Indazole, Pyrrolocarbazole, Phthalazinone, Isoindolinone; and

(14) miscellaneous anticancer drugs, exemplified by Amsacrine, Asparaginase (El-spar), Hydroxyurea, Mitoxantrone (Novantrone), Mitotane (Lysodren), Maytansinoid, Retinoic acid Derivatives, Bone Marrow Growth Factors (sargramostim and filgrastim), Amifostine, agents disrupting folate metabolism, e.g., Pemetrexed, ribonucleotide reductase inhibitors (Hydroxyurea), adrenocortical steroid inhibitors (Mitotane), enzymes (Asparaginase and Pegaspargase), antimicrotubule agents (Estramustine), and retinoids (Bexarotene, Isotretinoin, Tretinoin (ATRA)).

Chemotherapy drugs that are illustrative of the small molecule drug subcategory are Actinomycin-D, Alkeran, Ara-C, Anastrozole, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

Maytansinoids (molecular weight: ~738 Daltons) are a group of chemical derivatives of maytansine, having potent cytotoxicity. Although considered unsafe for human patient use, due to toxicity concerns, maytansinoids are suitable for delivery to brain tumor patients via minicells, pursuant to the present invention.

Duocarmycins (molecular weight: ~588 Daltons) are a series of related natural products, first isolated from *Streptomyces* bacteria. They also have potent cytotoxicity but are considered as unsafe for human use. Like maytansinoids, duocarmycins are suitable chemotherapy drugs for use in the invention.

The subcategory of biologic chemotherapy drugs includes, without limitation, Asparaginase, AIN-457, Bapineuzumab, Belimumab, Brentuximab, Briakinumab, Canakinumab, Cetuximab, Dalotuzumab, Denosumab, Epratuzumab, Estafenatox, Farletuzumab, Figitumumab, Galiximab, Gemtuzumab, Girentuximab (WX-G250), Herceptin, Ibritumomab, Inotuzumab, Ipilimumab, Mepolizumab, Muromonab-CD3, Naptumomab, Necitumumab, Nimotuzumab, Ocrelizumab, Ofatumumab, Otelixizumab, Ozogamicin, Pagibaximab, Panitumumab, Pertuzumab, Ramucirumab, Reslizumab, Rituximab, REGN88, Solanezumab, Tanezumab, Teplizumab, Tiuxetan, Tositumomab, Trastuzumab, Tremelimumab, Vedolizumab, Zalutumumab, and Zanolimumab.

In some embodiments, the anti-neoplastic agent comprises a compound selected from the group consisting of actinomycin-D, alkeran, ara-C, anastrozole, BiCNU, bicalutamide, bleomycin, busulfan, capecitabine, carboplatin, carboplatinum, carmustine, CCNU, chlorambucil, cisplatin, cladribine, CPT-11, cyclophosphamide, cytarabine, cytosine arabinoside, cytoxan, dacarbazine, dactinomycin, daunorubicin, dexrazoxane, docetaxel, doxorubicin, DTIC, epirubicin, ethyleneimine, etoposide, floxuridine, fludarabine, fluorouracil, flutamide, fotemustine, gemcitabine, hexamethylamine, hydroxyurea, idarubicin, ifosfamide, irinotecan, lomustine, mechlorethamine, melphalan, mercaptopurine, methotrexate, mitomycin, mitotane, mitoxantrone, oxaliplatin, paclitaxel, pamidronate, pentostatin, plicamycin, procarbazine, steroids, streptozocin, STI-571, tamoxifen, temozolomide, teniposide, tetrazine, thioguanine, thiotepa, tomudex, topotecan, treosulphan, trimetrexate, vinblastine, vincristine, vindesine, vinorelbine, VP-16, xeloda, asparaginase, AIN-457, bapineuzumab, belimumab, brentuximab, briakinumab, canakinumab, cetuximab, dalotuzumab, denosumab, epratuzumab, estafenatox, farletuzumab, figitumumab, galiximab, gemtuzumab, girentuximab (WX-G250), herceptin, ibritumomab, inotuzumab, ipilimumab, mepolizumab, muromonab-CD3, naptumomab, necitumumab, nimotuzumab, ocrelizumab, ofatumumab, otelixizumab, ozogamicin, pagibaximab, panitumumab, pertuzumab, ramucirumab, reslizumab, rituximab, REGN88, solanezumab, tanezumab, teplizumab, tiuxetan, tositumomab, trastuzumab, tremelimumab, vedolizumab, zalutumumab, zanolimumab, 5FC, accutane hoffmann-la roche, AEE788 novartis, AMG-102, anti neoplaston, AQ4N (Banoxantrone), AVANDIA (Rosiglitazone Maleate), avastin (Bevacizumab) genetech, BCNU, biCNU carmustine, CCI-779, CCNU, CCNU lomustine, celecoxib (Systemic), chloroquine, cilengitide (EMD 121974), CPT-11 (CAMP-TOSAR, Irinotecan), dasatinib (BMS-354825, Sprycel), dendritic cell therapy, etoposide (Eposin, Etopophos, Vepesid), GDC-0449, gleevec (imatinib mesylate), gliadel wafer, hydroxychloroquine, IL-13, IMC-3G3, immune therapy, iressa (ZD-1839), lapatinib (GW572016), methotrexate for cancer (Systemic), novocure, OSI-774, PCV, RAD001 novartis (mTOR inhibitor), rapamycin (Rapamune, Sirolimus), RMP-7, RTA 744, simvastatin, sirolimus, sorafenib, SU-101, SU5416 sugen, sulfasalazine (Azulfidine), sutent (Pfizer), TARCEVA (erlotinib HCl), taxol, TEMODAR schering-plough, TGF-B anti-sense, thalomid (thalidomide), topotecan (Systemic), VEGF trap, VEGF-trap, vorinostat (SAHA), XL 765, XL184, XL765, zarnestra (tipifarnib), ZOCOR (simvastatin), cyclophosphamide (Cytoxan), (Alkeran), chlorambucil (Leukeran), thiopeta (Thioplex), busulfan (Myleran), procarbazine (Matulane), dacarbazine (DTIC), altretamine (Hexalen), clorambucil, cisplatin (Platinol), ifosafamide, methotrexate (MTX), 6-thiopurines (Mercaptopurine [6-MP], Thioguanine [6-TG]), mercaptopurine (Purinethol), fludarabine phosphate, (Leustatin), flurouracil (5-FU), cytarabine (ara-C), azacitidine, vinblastine (Velban), vincristine (Oncovin), podophyllotoxins (etoposide {VP-16} and teniposide {VM-26}), camptothecins (topotecan and irinotecan), taxanes such as paclitaxel (Taxol) and docetaxel (Taxotere), (Adriamycin, Rubex, Doxil), dactinomycin (Cosmegen), plicamycin (Mithramycin), mitomycin: (Mutamycin), bleomycin (Blenoxane), estrogen and androgen inhibitors (Tamoxifen), gonadotropin-releasing hormone agonists (Leuprolide and Goserelin (Zoladex)), aromatase inhibitors (Aminoglutethimide and Anastrozole (Arimidex)), amsacrine, asparaginase (El-spar), mitoxantrone (Novantrone), mitotane (Lysodren), retinoic acid derivatives, bone marrow growth factors (sargramostim and filgrastim), amifostine, pemetrexed, decitabine, iniparib, olaparib, veliparib, everolimus, vorinostat, entinostat (SNDX-275), mocetinostat (MGCD0103), panobinostat (LBH589), romidepsin, valproic acid, flavopiridol, olomoucine, roscovitine, kenpaullone, AG-024322 (Pfizer), fascaplysin, ryuvidine, purvalanol A, NU2058, BML-259, SU 9516, PD-0332991, P276-00, geldanamycin, tanespimycin, alvespimycin, radicicol, deguelin, BIIB021, cis-imidazoline, benzodiazepinedione, spiro-oxindoles, isoquinolinone, thiophene, 5-deazaflavin, tryptamine, aminopyridine, diaminopyrimidine, pyridoisoquinoline, pyrrolopyrazole, indolocarbazole, pyrrolopyrimidine, dianilinopyrimidine, benzamide, phthalazinone, tricyclic indole, benzimidazole, indazole, pyrrolocarbazole, isoindolinone, morpholinyl anthracycline, a maytansinoid, ducarmycin, auristatins, calicheamicins (DNA damaging agents), α-amanitin (RNA polymerase II inhibitor), centanamycin, pyrrolobenzodiazepine, streptonigtin, nitrogen mustards, nitrosoruneas, alkane sulfonates, pyrimidine analogs, purine analogs, antimetabolites, folate analogs, anthracyclines, taxanes, *vinca* alkaloids, topoisomerase inhibitors, hormonal agents, and any combination thereof.

Active agents useable in accordance with the present disclosure are not limited to those drug classes or particular agents enumerated above. Different discovery platforms continue to yield new agents that are directed at unique molecular signatures of cancer cells; indeed, thousands of such chemical and biological drugs have been discovered, only some of which are listed here. Yet, the surprising capability of intact, bacterially derived minicells and killed bacterial cells to accommodate packaging of a diverse variety of active agents, hydrophilic or hydrophobic, means that essentially any such drug, when packaged in minicells, has the potential to treat a cancer, pursuant to the findings in the present disclosure.

Illustrative of the class of anti-neoplastic agents are radionuclides, chemotherapy drugs, and functional nucleic acids, including but not limited to regulatory RNAs. Members of the class are discussed further below.

i. Radionuclides

A "radionuclide" is an atom with an unstable nucleus, i.e., one characterized by excess energy available to be imparted either to a newly created radiation particle within the nucleus or to an atomic electron. Radionuclides herein may also be referred to as "radioisotopes," "radioimaging agents," or "radiolabels." Radionuclides can be used for imaging and/or therapeutic purposes. They can be contained within the minicell or attached to a ligand, peptide, or glycolipid on the minicell outer surface. Attachments may be directly or via a linker, a linker containing a chelating moiety comprising chelators such as mercaptoacetyltriglycine (MAG3), DOTA, EDTA, HYNIC, DTPA, or crown ethers may be used. The chelators may be attached directly the minicell surface component or attached to the minicell via a linker. Numerous radionuclides are known in the art, and a number of them are known to be suitable for medical use, such as yttrium-90, technetium-99m, iodine-123, iodine-124, iodine-125, iodine-131, rubidium-82, thallium-201, gallium-67, fluorine-18, xenon-133, and indium-111.

Thus, in some embodiments, the radioisotope comprises a radioisotope selected from the group consisting of yttrium-90, yttrium-86, terbium-152, terbium-155, terbium-149, terbium-161, technetium-99m, iodine-123, iodine-131, rubidium-82, thallium-201, gallium-67, fluorine-18, copper-64, gallium-68, xenon-133, indium-111, lutetium-177, and any combination thereof.

Radioisotopes useful for attaching to minicells for both imaging and therapeutic purposes include, for example, Iodine-131 and lutetium-177, which are gamma and beta emitters. Thus, these agents can be used for both imaging and therapy.

Different isotopes of the same element, for example, iodine-123 (gamma emitter) and iodine-131 (gamma and beta emitters), can also be used for both imaging and therapeutic purposes (Gerard and Cavalieri, 2002; Alzahrani et al., 2012).

Newer examples are yttrium-86/yttrium-90 or terbium isotopes (Tb): $^{152}$Tb (beta plus emitter), $^{155}$Tb (gamma emitter), $^{149}$Tb (alpha emitter), and $^{161}$Tb (beta minus particle) (Müller et al., 2012; Walrand et al., 2015).

Nuclear imaging utilizes gamma and positron emitters (β+). Gamma emitters, such as technetium-99m ($^{99m}$Tc) or iodine-123 ($^{123}$I), can be located using gamma cameras (planar imaging) or SPECT (single photon emission computed tomography) (Holman and Tumeh, 1990).

The tissue penetration of these particles is proportional to the energy of the radioisotopes (Kramer-Marek and Capala, 2012). Beta particles have a potential cytocidal effect, but they also spare the surrounding healthy tissue due to having a tissue penetration of only a few millimeters. Commonly used beta emitters in routine nuclear oncology practices include lutetium-177 ($^{177}$Lu, tissue penetration: 0.5-0.6 mm, maximum: 2 mm, 497 keV, half-life: 6.7 days) and yttrium-90 ($^{90}$Y, tissue penetration: mean 2.5 mm, maximum: 11 mm, 935 keV, half-life: 64 hours) (Teunissen et al., 2005; Kwekkeboom et al., 2008; Ahmadzadehfar et al., 2010; Pillai et al., 2013; Ahmadzadehfar et al., 2016).

Radionuclides have found extensive use in nuclear medicine, particularly as beta-ray emitters for damaging tumor cells. In some embodiments, radionuclides are suitably employed as the anti-neoplastic agents.

Radionuclides can be associated with intact, bacterially derived minicells by any known technique. Thus, a protein or other minicell-surface moiety (see below) can be labeled with a radionuclide, using a commercially available labeling means, such as use of Pierce Iodination reagent, a product of Pierce Biotechnology Inc. (Rockford, Ill.), detailed in Rice et al., Semin. Nucl. Med., 41, 265-282 (2011). Alternatively, radionuclides can be incorporated into proteins that are inside minicells.

In the latter situation, a minicell-producing bacterial strain is transformed with plasmid DNA encoding foreign protein. When minicells are formed during asymmetric cell division, several copies of the plasmid DNA segregate into the minicell cytoplasm. The resultant recombinant minicells are incubated in the presence of radiolabeled amino acids under conditions such that foreign protein expressed inside the minicell, from the plasmid DNA, incorporates into the radionuclide-carrying amino acids. Pursuant to the protocol of Clark-Curtiss and Curtiss, Methods Enzymol., 101: 347-362 (1983), for instance, recombinant minicells are incubated in minimal growth medium that contains $^{35S}$methionine, whereby newly expressed, plasmid-encoded proteins incorporate the $^{35S}$methionine. A similar approach can be used so that recombinant minicells become packaged with other radiolabels, as desired.

Oligosaccharides on the minicell surface also can be radiolabeled using, for example, well-established protocols described by Fukuda, Curr. Protocols Molec. Biol. (Suppl. 26), 17.5.1-17.5.8 (1994). Illustrative of such oligosaccharides that are endemic to minicells is the O-polysaccharide component of the lipopolysaccharide (LPS) found on the surface of minicells derived from Gram-negative bacteria (see below).

A preferred methodology in this regard is to radiolabel a bispecific antibody used as a tumor targeting ligand that is used to target minicells to specific tumors. See US Patent Publication 2007/0237744, the contents of which are incorporated herein by reference. That is, the bispecific antibody "coated" on a minicell exposes a significant amount of additional surface protein for radiolabeling. Accordingly, it is possible to achieve a higher specific activity of the radiolabel associated with the antibody-coated minicell. By contrast, the radiolabeling of non-coated minicells, i.e., when the radionuclide labels only endemic moieties, can result in weaker labeling (lower specific activity). In one embodiment, this weaker labeling is thought to occur because the outer membrane-associated proteins of minicells derived from Gram-negative bacteria are masked by LPS, which, as further discussed below, comprises long chains of O-polysaccharide covering the minicell surface.

For treating a tumor, a composition of the disclosure would be delivered in a dose or in multiple doses that affords a level of in-tumor irradiation that is sufficient at least to reduce tumor mass, if not eliminate the tumor altogether. The progress of treatment can be monitored along this line, on a case-by-case basis. In general terms, however, the amount of radioactivity packaged in the composition typically will be on the order of about 30 to about 50 Gy, although the invention also contemplates a higher amount of radioactivity, such as for example about 50 to about 200 Gy, which gives an overall range between about 30 Gy and about 200 Gy.

In some instances, the amount of radioactivity packaged in the composition can be even lower than mentioned above, given the highly efficient and specific delivery of the minicell-bourne radionuclides to a tumor. Accordingly, in one aspect the composition comprises from about 20 to about 40 Gy, or about 10 to about 30 Gy, or about 1 to about 20 Gy, or less than about 10 Gy.

Some tumor targeting ligands may include a radioisotope that functions to deliver radiation to the tumor while the ligand binds the tumor cell. In some embodiments, the ligand comprises Arg-Gly-Asp (RGD) peptide, bombesin (BBN)/gastrin-releasing peptide (GRP), cholecystokinin (CCK)/gastrin peptide, α-melanocyte-stimulating hormone (α-MSH), neuropeptide Y (NPY), neurotensin (NT), [$^{68}$Ga] Ga-PSMA-HBED-CC ([$^{68}$Ga]Ga-PSMA-11 [PET]), [$^{177}$Lu] Lu/[$^{90}$Y]Y-J591, [$^{123}$I]I-MIP-1072, [131I]I-MIP-1095, $^{68}$Ga or $^{177}$Lu labeled PSMA-I&T, $^{68}$Ga or $^{177}$Lu labeled DKFZ-PSMA-617 (PSMA-617), somatostatin (SST) peptide, substance P, T140, tumor molecular targeted peptide 1 (TMTP1), vasoactive intestinal peptide (VIP), or any combination thereof.

In some embodiments, the radioisotope is conjugated to the tumor targeting ligand. In some embodiments, the conjugation is via a linker. In some embodiments, the tumor targeting ligand comprises a peptide comprising functional group(s) for conjugation of a radioisotope or chelator moiety that chelates a radioisotope. The functional groups of peptides available for conjugation include but are not limited to the ε-amino group on lysine side chains, the guanidinium group on arginine side chains, the carboxyl groups on aspartic acid or glutamic acid, the cysteine thiol, and the phenol on tyrosine. The most common conjugation reactions are carbodiimide/N-hydroxysuccinimidyl (EDC/NHS) mediated carboxyl and amine coupling, maleimide conjugation to thiol groups, and diazonium modification of the phenol on tyrosine. The representative chemistries to couple peptides with imaging moieties can be found in a number of reviews (Erathodiyil and Ying, 2011; Takahashi et al., 2008).

In some embodiments, the radioisotope functions as a radioimaging agent. Several radioisotopes have been used for peptide labeling including $^{99}$mTc, $^{123}$I, and $^{111}$In for SPECT imaging and $^{18}$F, $^{64}$Cu and $^{68}$Ga for PET imaging (Chatalic et al., 2015). Generally, these radioisotopes are attached to the peptides via chelators. Some widely-used chelators are described in (Sun et al., 2017). Most therapeutic radiopharmaceuticals are labeled with beta-emitting isotopes (β-).

The minicells of the present invention, targeted to the tumor cells will also deliver targeted radiation from the radioisotope to the tumor cell to which the minicell is bound. In some embodiments, the radioisotope functions as a therapeutic radiation emitting agent, and wherein the amount of radiation provided by the radioisotope is sufficient to provide a therapeutic effect on the tumor. In some embodiments, the therapeutic effect is a reduction in tumor size. The tumor may be reduced in size by about 100%, about 90%, about 80%, about 70%, about 60%, about 50%, about 40%, about 30%, about 20%, about 10%, or about 5%.

Radiolabeled phosphonates have a high bone affinity and can be used for imaging and palliation of painful bone metastases. Depending on the degree of osseous metabolism, the tracer accumulates via adhesion to bones and, preferably, to osteoblastic bone metastases. Therapy planning requires a bone scintigraphy with technetium-99m-hydroxyethylidene diphosphonate (HEDP) to estimate the metabolism and the extent of the metastases involvement. Bisphosphonate HEDP can be labeled for therapy either with rhenium-186 (beta-emitter, half-life: 89 hours, 1.1 MeV maximal energy, maximal range: 4.6 mm) or rhenium-188 (beta-emitter [to 85%, 2.1 MeV] and gamma-emitter [to 15%, 155 keV], half-life: 16.8 hours, maximal range in soft tissue: 10 mm) (Palmedo, 2007). New promising radiopharmaceuticals for bone palliation therapy include radiolabeled complexes of zoledronic acid. Zoledronic acid belongs to a new, most potent generation of bisphosphonates with cyclic side chains. The bone affinity of zoledronic acid labeled with scandium-46 or lutetium-177 has shown excellent absorption (98% for [177Lu]Lu-zoledronate and 82% for [46Sc]Sc-zoledronate), which is much higher than of bisphosphonates labeled with samarium-153 (maximum: 67%) (Majkowska et al., 2009). These bisphosphonates can be conjugated to intact minicells for use as diagnostics or treatment for bone metastasis.

ii. Chemotherapy Drugs

An antineoplastic agent employed in the present disclosure can also be a chemotherapy drug. In this description, "chemotherapeutic drug," "chemotherapeutic agent," and "chemotherapy" are employed interchangeably to connote a drug that has the ability to kill or disrupt a neoplastic cell. A chemotherapeutic agent can be a small molecule drug or a biologic drug, as further detailed below.

The "small molecule drug" subcategory encompasses compounds characterized by having (i) an effect on a biological process and (ii) a low molecular weight as compared to a protein or polymeric macromolecule. Small molecule drugs typically are about 800 Daltons or less, with a lower limit of about 150 Daltons, as illustrated by Temodar® (temozolomide), at about 194 Daltons, which is used to treat glioblastoma and other types of brain cancer. In this context "about" indicates that the qualified molecular-weight value is subject to variances in measurement precision and to experimental error on the order of several Daltons or tens of Daltons. Thus, a small molecule drug can have a molecular weight of about 900 Daltons or less, about 800 or less, about 700 or less, about 600 or less, about 500 or less, or about 400 Daltons or less, e.g., in the range of about 150 to about 400 Daltons. More specifically, a small molecule drug can have a molecular weight of about 400 Daltons or more, about 450 Daltons or more, about 500 Daltons or more, about 550 Daltons or more, about 600 Daltons or more, about 650 Daltons or more, about 700 Daltons or more, or about 750 Daltons or more. In another embodiment, the small molecule drug packaged into the minicells has a molecular weight between about 400 and about 900 Daltons, between about 450 and about 900 Daltons, between about 450 and about 850 Daltons, between about 450 and about 800 Daltons, between about 500 and about 800 Daltons, or between about 550 and about 750 Daltons.

Specifically, suitable small molecule drugs include but are not limited to those listed above, such as nitrogen mustards, nitrosorueas, ethyleneimine, alkane sulfonates, tetrazine, platinum compounds, pyrimidine analogs, purine analogs, anti-metabolites, folate analogs, anthracyclines, taxanes, vinca alkaloids, and topoisomerase inhibitors, inter alia. Accordingly, a small molecule drug for use in the present invention can be selected from among any of the following, inter alia: enediynes, such as dynemicin A, unicalamycin, calicheamicin yl and calicheamicin-theta-1; meayamicin, a synthetic analog of FR901464; benzosuberene derivatives as described, for example, by Tanpure et al., Bioorg. Med. Chem., 21: 8019-32 (2013); auristatins, such as auristatin E, mono-methyl auristatin E (MMAE), and auristatin F, which are synthetic analogs of dolastatin; duocarmysins such as duocarmycin SA and CC-1065; maytansine and its derivatives (maytansinoids), such as DM1 and DM4; irinotecan (Camptosar®) and other topoisomerase inhibitors, such as topotecan, etoposide, mitoxantrone and teniposide; and yatakemycin, the synthesis of which is detailed by Okano et at, 2006.

More particularly, any one or more or all of the specific small molecule drugs detailed herein are illustrative of those suitable for use in this invention: actinomycin-D, alkeran, ara-C, anastrozole, BiCNU, bicalutamide, bisantrene, bleomycin, busulfan, capecitabine (Xeloda®), carboplatin, carboplatinum, carmustine, CCNU, chlorambucil, cisplatin, cladribine, CPT-11, cyclophosphamide, cytarabine, cytosine arabinoside, cytoxan, dacarbazine, dactinomycin, daunorubicin, dexrazoxane, docetaxel, doxorubicin, DTIC, epirubicin, ethyleneimine, etoposide, floxuridine, fludarabine, fluorouracil, flutamide, fotemustine, gemcitabine, hexamethylamine, hydroxyurea, idarubicin, ifosfamide, irinotecan, lomustine, mechlorethamine, melphalan, mercaptopurine, methotrexate, mitomycin, mitotane, mitoxantrone, oxaliplatin, paclitaxel, pamidronate, pentostatin, plicamycin, procarbazine, streptozocin, STI-571, tamoxifen, temozolomide, teniposide, tetrazine, thioguanine, thiotepa, tomudex, topotecan, treosulphan, trimetrexate, vinblastine, vincristine, vindesine, vinorelbine, and VP-16.

For purposes of this description a "biologic drug" is defined, by contrast, to denote any biologically active macromolecule that can be created by a biological process, exclusive of "functional nucleic acids," discussed below, and polypeptides that by size qualify as small molecule drugs, as defined above. The "biologic drug" subcategory thus is exclusive of and does not overlap with the small molecule drug and functional nucleic acid subcategories. Illustrative of biologic drugs are therapeutic proteins and antibodies, whether natural or recombinant or synthetically made, e.g., using the tools of medicinal chemistry and drug design.

iii. Supertoxic Chemotherapy Drugs

Certain molecules that are designed for chemotherapeutic purposes fail during pre-clinical or clinical trials due to unacceptable toxicity. The present inventors have shown that packaging a highly toxic or "supertoxic" chemotherapy drug in a minicell, followed by systemic delivery to a tumor patient, results in delivery of the drug to tumor cells. Further, even after the tumor cells are broken up and the drug-containing cytoplasm is released to the nearby normal tissue, the result is not toxicity to normal tissue. This is because the drug is already bound to the tumor cellular structures, such as DNA, and can no longer attack normal cells. Accordingly, the present invention is particularly useful for delivery of highly toxic ("supertoxic") chemotherapy drugs to a cancer patient.

When cancer subjects have exhausted all treatment options, the tumors are likely to have reached a stage of considerable heterogeneity with a high degree of resistance to conventional cytotoxic drugs. "Highly toxic chemotherapy drug" or "supertoxic chemotherapy drugs" in this description refer to chemotherapy drugs that can overcome the resistance to conventional drugs due to their relatively low lethal dose to normal cells as compared to their effective dose for cancer cells.

Thus, in one aspect a highly toxic chemotherapy drug has a median lethal dose ($LD_{50}$) that is lower than its median effective dose ($ED_{50}$) for a targeted cancer. For instance, a highly toxic or supertoxic chemotherapy drug can have an $LD_{50}$ that is lower than about 500%, 400%, 300%, 250%, 200%, 150%, 120%, or 100% of the $ED_{50}$ of the drug for a targeted cancer. In another aspect, a highly toxic or supertoxic chemotherapy drug has a maximum sub-lethal dose (i.e., the highest dose that does not cause serious or irreversible toxicity) that is lower than its minimum effective dose, e.g., about 500%, about 400%, about 300%, about 250%, about 200%, about 150%, about 120%, about 100%, about 90%, about 80%, about 70%, about 60% or about 50% of the minimum effective dose. In one embodiment, the targeted cancer can be, for example, (1) a cancer type for which the drug is designed, (2) the first cancer type in which a pre-clinical or clinical trial is run for that drug, or (3) a cancer type in which the drug shows the highest efficacy among all tested cancers.

Illustrative, non-limiting examples of supertoxic chemotherapy drugs include but are not limited to maytansinoids, duocarmycins, morpholinyl anthracycline, and their derivatives. Maytansinoids (molecular weight: about 738 Daltons) are a group of chemical derivatives of maytansine, having potent cytotoxicity. Although considered unsafe for human patient use, due to toxicity concerns, maytansinoids are suitable for delivery to tumor patients via minicells, pursuant to the present invention. Duocarmycins (molecular weight: about 588 Daltons) are a series of related natural products, first isolated from *Streptomyces* bacteria. They also have potent cytotoxicity but are considered as unsafe for human use. Like maytansinoids, duocarmycins are suitable chemotherapy drugs for use in the invention.

Illustrative as well are compounds in the class of morpholinyl anthracycline derivatives described in international patent application WO 1998/002446. Among such derivatives are nemorubicin (3'-deamino-3'-[2(S)-methoxy-4-morpholinyl]doxorubicin) (MMDX), and its major metabolite PNU-159682 (3'-deamino-3"-4'-anhydro-[2"(S)-methoxy-3"(R)-hydroxy-4"-morpholinyl-]doxorubicin), as well as four other such derivatives described in U.S. Pat. No. 8,470,984, the contents of which are incorporated here by reference: 3'-deamino-3"-4'-anhydro-[2"(S)-methoxy-3" (R)-hydroxy-4"-morpholinyl]-idarubicin; 3'-deamino-3"-4'-anhydro-[2"(S)-methoxy-3'(R)-hydroxy-4'-morpholinyl]-daunorubicin; 3'-deamino-3"-4'-anhydro-[2"(S)-methoxy-3' (R)-hydroxy-4'-morpholinyl]-caminomycin; and 3'-deamino-3"-4'-anhydro-[2"(S)-ethoxy-3(R)-hydroxy-4"-morpholinyl]d-oxorubicin.

In an exemplary embodiment of the present disclosure, the minicell comprises the supertoxic chemotherapy drug 3'-deamino-3",4'-anhydro-[2"(S)-methoxy-3'(R)-oxy-4-morpholinyl]doxorubicin (PNU-159682). The present inventors discovered that PNU-159682 is a potent drug that appears to overcome drug resistance in a number of different tumor cell lines and is much more potent than a range of conventional chemotherapeutics in cytotoxicity assays against many different tumor cell lines. See Examples 8 and 9. Further, it was shown in in vivo mouse xenograft experiments that human tumor xenografts resistant to doxorubicin can be treated effectively with IV administration of EGFR-targeted and PNU-159682-loaded EDVs. See Example 11. Remarkably, PNU-159682-loaded EDVs combined with type I interferon agonists was found to be well-tolerated and to provide synergistic and improved anti-cancer effect in a late-stage pancreatic cancer patient. See Example 12. Accordingly, in one embodiment of the present invention a composition comprises an EGFR-targeted minicell comprising PNU-159682 as an active anticancer drug.

Other suitable cancer chemotherapy drugs that may exhibit supertoxic chemotherapy properties include auristatins, calicheamicins (DNA damaging agents), α-amanitin (RNA polymerase II inhibitor), centanamycin, geldanamycin, pyrrolobenzodiazepine, streptonigtin, nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors, and hormonal agents, inter alia.

iv. Biologic Chemotherapy Drugs

In another aspect, the minicells may comprise a biologic chemotherapy drug. Examples of such drugs include but are not limited to asparaginase, AIN-457, bapineuzumab, belimumab, brentuximab, briakinumab, canakinumab, cetuximab, dalotuzumab, denosumab, epratuzumab, estafenatox, farletuzumab, figitumumab, galiximab, gemtuzumab, girentuximab (WX-G250), ibritumomab, inotuzumab, ipilimumab, mepolizumab, muromonab-CD3, naptumomab, necitumumab, nimotuzumab, ocrelizumab, ofatumumab, otelixizumab, ozogamicin, pagibaximab, panitumumab, pertuzumab, ramucirumab, reslizumab, rituximab, REGN88, solanezumab, tanezumab, teplizumab, tiuxetan, tositumomab, trastuzumab (Herceptin®), tremelimumab, vedolizumab, zalutumumab, and zanolimumab.

v. Functional Nucleic Acids

"Functional nucleic acid" refers to a nucleic acid molecule that, upon introduction into a host cell, specifically interferes with expression of a protein. With respect to treating cancer, in accordance with the disclosure, it is preferable that a functional nucleic acid payload delivered to cancer cells via intact, bacterially derived minicells inhibits a gene that promotes tumor cell proliferation, angiogenesis or resistance to chemotherapy and/or that inhibits apoptosis or cell-cycle arrest; i.e., a "cancer-promoting gene."

In general, functional nucleic acid molecules used in this disclosure have the capacity to reduce expression of a protein by interacting with a transcript for a protein. This category of minicell payload for the disclosure includes regulatory RNAs, such as siRNA, shRNA, short RNAs (typically less than 400 bases in length), micro-RNAs (miR- NAs), ribozymes and decoy RNA, antisense nucleic acids, and LincRNA, inter alia. In this regard, "ribozyme" refers to an RNA molecule having an enzymatic activity that can repeatedly cleave other RNA molecules in a nucleotide base sequence-specific manner. "Antisense oligonucleotide" denotes a nucleic acid molecule that is complementary to a portion of a particular gene transcript, such that the molecule can hybridize to the transcript and block its translation. An antisense oligonucleotide can comprise RNA or DNA. The "LincRNA" or "long intergenic non-coding RNA" rubric encompasses non-protein coding transcripts longer than 200 nucleotides. LincRNAs can regulate the transcription, splicing, and/or translation of genes, as discussed by Khalil et al., 2009.

Each of the types of regulatory RNA can be the source of functional nucleic acid molecule that inhibits a tumor-promoting gene as described above and, hence, that is suitable for use according to the present disclosure. Thus, in one embodiment of the disclosure the intact minicells carry siRNA molecules mediating a post-transcriptional, gene-silencing RNA interference (RNAi) mechanism, which can be exploited to target tumor-promoting genes. For example, see MacDiarmid et al., 2009 (antibody-presenting minicells deliver, with chemotherapy drug, siRNAs that counter developing resistance to drug), and Oh and Park, *Advanced Drug Delivery Rev.*, 61: 850-62 (2009) (delivery of therapeutic siRNAs to treat breast, ovarian, cervical, liver, lung and prostate cancer, respectively).

As noted, "siRNA" generally refers to double-stranded RNA molecules from about 10 to about 30 nucleotides long that are named for their ability specifically to interfere with protein expression. Preferably, siRNA molecules are about 12 to about 28 nucleotides long, more preferably about 15 to about 25 nucleotides long, still more preferably about 19 to about 23 nucleotides long and most preferably about 21 to about 23 nucleotides long. Therefore, siRNA molecules can be, for example, about 12, about 13, about 14, about 15, about 16, about 17, about 18, about 19, about 20, about 21, about 22, about 23, about 24, about 25, about 26, about 27, about 28, or about 29 nucleotides in length.

The length of one strand designates the length of an siRNA molecule. For instance, an siRNA that is described as 21 ribonucleotides long (a 21-mer) could comprise two opposing strands of RNA that anneal for 19 contiguous base pairings. The two remaining ribonucleotides on each strand would form an "overhang." When a siRNA contains two strands of different lengths, the longer of the strands designates the length of the siRNA. For instance, a dsRNA containing one strand that is 21 nucleotides long and a second strand that is 20 nucleotides long, constitutes a 21-mer.

Tools to assist the design of siRNA specifically and regulatory RNA generally are readily available. For instance, a computer-based siRNA design tool is available on the internet at www.dharmacon.com.

In another preferred embodiment, the intact minicells of the present disclosure carry miRNAs, which, like siRNA, are capable of mediating a post-transcriptional, gene-silencing RNA interference (RNAi) mechanism. Also like siRNA, the gene-silencing effect mediated by miRNA can be exploited to target tumor-promoting genes. For example, see Kota et al., 2009 (delivery of a miRNA via transfection resulted in inhibition of cancer cell proliferation, tumor-specific apoptosis and dramatic protection from disease progression without toxicity in murine liver cancer model), and Takeshita et al., 2010 (delivery of synthetic miRNA via transient transfection inhibited growth of metastatic prostate tumor cells on bone tissues).

Although both mediate RNA interference, miRNA and siRNA have noted differences. In this regard, "miRNA" generally refers to a class of about 17 to about 27-nucleotide single-stranded RNA molecules (instead of double-stranded as in the case of siRNA). Therefore, miRNA molecules can be, for example, about 17, about 18, about 19, about 20, about 21, about 22, about 23, about 24, about 25, about 26, or about 27 nucleotides in length. Preferably, miRNA molecules are about 21 to about 25 nucleotide long.

Another difference between miRNAs and siRNAs is that the former generally do not fully complement the mRNA target. In contrast, siRNA must be completely complementary to the mRNA target. Consequently, siRNA generally results in silencing of a single, specific target, while miRNA is promiscuous.

Additionally, although both are assembled into RISC (RNA-induced silencing complex), siRNA and miRNA differ in their respective initial processing before RISC assembly. These differences are described in detail in Chu et al., 2006; and Gregory et al., 2006. A number of databases serve as miRNA depositories. For example, see miRBase (www.mirbase.org) and tarbase (http://diana.cslab.ece.ntua.gr/DianaToolsNew/index.php?r=tarbase/index). In conventional usage, miRNAs typically are named with the prefix "-mir," combined with a sequential number. For instance, a new miRNA discovered after mouse mir-352 will be named mouse "mir-353." Again, tools to assist the design of regulatory RNA including miRNA are readily available. In this regard, a computer-based miRNA design tool is available on the internet at wmd2.weigelworld.org/cgi-bin/mirnatools.pl.

It is a discovery of the present inventors that miRNA16a can be administered by targeted minicell-mediated delivery to mesothelioma and Adreno-Cortical cancer cells. See Example 7. Once internalized by the cancer cells, the miRNA16a was found to potently inhibit cancer cell proliferation. Accordingly, in some embodiments the minicells of the present disclosure comprise miRNA16a. Other microRNAs useful in inhibiting the proliferation of neoplastic cells include mir-34 family and let-7 family.

As noted above, a functional nucleic acid employed in the compositions of the invention can inhibit a gene that promotes tumor cell proliferation, angiogenesis or resistance to chemotherapy. The inhibited gene also can itself inhibit apoptosis or cell cycle arrest. Examples of genes that can be targeted by a functional nucleic acid are provided below.

Functional nucleic acids of the disclosure preferably target the gene or transcript of a protein that promotes drug resistance, inhibits apoptosis or promotes a neoplastic phenotype. Successful application of functional nucleic acid strategies in these contexts have been achieved in the art, but without the benefits of minicell vectors. See, e.g., Sioud, *Trends Pharmacol. Sci.*, 2004; Caplen, *Expert Opin. Biol. Ther.*, 2003; Nieth et al., 2003; Caplen and Mousses, 2003; Duxbury et al., 2004; Yague et aL, 2004; and Duan et aL, 2004.

Proteins that contribute to drug resistance constitute preferred targets of functional nucleic acids. The proteins may contribute to acquired drug resistance or intrinsic drug resistance. When diseased cells, such as tumor cells, initially respond to drugs, but become refractory on subsequent treatment cycles, the resistant phenotype is acquired. Useful targets involved in acquired drug resistance include ATP binding cassette transporters such as P-glycoprotein (P-gp, P-170, PGY1, MDR1, ABCB 1, MDR-associated protein, Multidrug resistance protein 1), MDR-2 and MDR-3. MRP2 (multi-drug resistance associated protein), BCR-ABL (breakpoint cluster region—Abelson protooncogene), a STI-571 resistance-associated protein, lung resistance-related protein, cyclooxygenase-2, nuclear factor kappa, XRCC1 (X-ray cross-complementing group 1), ERCC1 (excision cross-complementing gene), GSTP1 (glutathione S-transferase), mutant .beta.-tubulin, and growth factors such as IL-6 are additional targets involved in acquired drug resistance.

Particularly useful targets that contribute to drug resistance include ATP binding cassette transporters such as P-glycoprotein, MDR-2, MDR-3, BCRP, APT11a, and LRP. Useful targets also include proteins that promote apoptosis resistance. These include Bcl-2 (B cell leukemia/lymphoma), Bcl-$X_L$, A1/Bfl 1, focal adhesion kinase, dihydrodiol dehydrogenase, and p53 mutant protein.

Useful targets further include oncogenic and mutant tumor suppressor proteins. Illustrative of these are .beta.-Catenin, PKC-.alpha. (protein kinase C), C-RAF, K-Ras (V12), DP97 Dead box RNA helicase, DNMT1 (DNA methyltransferase 1), FLIP (Flice-like inhibitory protein), C-Sfc, 53BPI, Polycomb group protein EZH2 (Enhancer of zeste homologue), ErbB1, HPV-16 E5 and E7 (human papillomavirus early 5 and early 7), Fortilin & MCI1P (Myeloid cell leukemia 1 protein), DIP13.alpha. (DDC interacting protein 13a), MBD2 (Methyl CpG binding domain), p21, KLF4 (Kruppel-like factor 4), tpt/TCTP (Translational controlled tumor protein), SPK1 and SPK2 (Sphingosine kinase), P300, PLK1 (Polo-like kinase-1), Trp53, Ras, ErbB1, VEGF (Vascular endothelial growth factor), BAG-1 (BCL2-associated athanogene 1), MRP2, BCR-ABL, STI-571 resistance-associated protein, lung resistance-related protein, cyclooxygenase-2, nuclear factor kappa, XRCC1, ERCC1, GSTP1, mutant—β-tubulin, and growth factors.

Also useful as targets are global regulatory elements exemplified by the cytoplasmic polyadenylation element binding proteins (CEPBs). For instance, CEPB4 is overexpressed in glioblastoma and pancreatic cancers, where the protein activates hundreds of genes associated with tumor growth, and it is not detected in healthy cells (Oritz-Zapater et aL, 2011). In accordance with the present description, therefore, treatment of a glioblastoma could be effected via administration of a composition containing intact, bacterially derived minicells that encompass an agent that counters overexpression of CEPB4, such as an siRNA or other functional nucleic acid molecule that disrupts CEPB4 expression by the tumor cells.

A further example of useful targets for functional nucleic acids include replication protein A (RPA), a trimeric complex composed of 70-kDa (RPA1), 32-kDa (RPA2), and 14-kDa (RPA3) subunits, which is essential for DNA replication in all organisms. Iftode et al., 1999.

Other useful targets are those important for mitosis and for the maintenance of genomic stability. Examples included the Polo-like kinase (PLK1), which was found to be overexpressed in a broad range of cancer cells. See Example 3, FIG. 12. The inventors of the present disclosure also found that siRNA inhibiting Plk1 (siPlk1) expression inhibits proliferation of mesothelioma and Adreno-Cortical cancer cells. See Example 10. Accordingly, in some embodiments, the minicells of the present disclosure comprise Plk1.

Other useful targets are those that are involved in DNA replication and repair. Examples include ribonucleotide reductase (RR), which is a potential therapeutic target for cancer because it catalyzes the conversion of ribonucleoside 5'-diphosphates into their corresponding 2'-deoxyribonucleoside 5'-triphosphates that are necessary for DNA replication and repair. See D'Angiolella et al., 2012. Human RR comprises two subunits, RRM1 and RRM2, and functional nucleic acids that target both subunits are useful in the present invention. The inventors of the present disclosure showed that siRNA targeting RRM1 (siRRM1) potently inhibited mesothelioma and Adreno-Cortical cancer cell proliferation upon delivery with minicells. See Example 10. Accordingly, in some embodiments the minicell comprises siRNA, which inhibits ribonucleotide reductase M1 (RRM1) expression.

B. Type I Interferon Agonists

The present compositions can comprise a type 1 interferon agonist, i.e., an agent that increases the level (e.g., the activity or expression level) of type 1 interferons. Human type I interferons (IFNs) are a large subgroup of interferon proteins that help regulate the activity of the immune system. Interferons bind to interferon receptors. All type I IFNs bind to a specific cell surface receptor complex known as the IFN-α receptor (IFNAR), which consists of IFNAR1 and IFNAR2 chains. Mammalian type I IFNs are designated IFN-α (alpha), IFN-β (beta), IFN-κ (kappa), IFN-δ (delta), IFN-ε (epsilon), IFN-τ (tau), IFN-ω (omega), and IFN-ξ, (zeta, also known as limitin).

i. Oligonucleotides

FIG. 2 shows a graphical depiction of an exemplary embodiment of a minicell comprising immunomodulatory, 60mer double-stranded DNA. The present inventors discovered that delivery of a type I interferon agonist, such as double-stranded DNA with EGFR-targeted minicells, acts as an adjuvant (i.e., it enhances) anti-tumor efficacy of minicells loaded with cytotoxic drugs. See Example 11. Thus, combining minicells packaged with the supertoxic drug PNU-159682 resulted in enhanced anti-tumor effects, and this treatment was well-tolerated by a late-stage pancreatic cancer patient. See Example 12.

Expression of type I interferons (IFN) can be induced by delivering double-stranded DNA to target cells. Specifically, innate immune activation by cytosolic DNA from microbial pathogens is a potent trigger of type I IFNs and pro-inflammatory cytokines mediated by cytosolic DNA sensors such as cGAMP, cyclic GMP-AMP synthetase (cGAS) and IFN gamma inducible factor 16 (IFI16). See, e.g., Hansen et al., 2014; and Unterholzner et al., 2013. Post-binding to double stranded DNA, cGAS has the enzymatic capacity to produce the second messenger cyclic GMP-AMP which docks onto the endoplasmic reticulum-bound protein stimulator of IFN genes (STING). Barber et al., 2011. This induces conformational changes that allow STING to homodimerize, migrate from the ER (Dobbs et al., 2015), and to recruit TANK-binding kinase 1 that phosphorylates STING, resulting in the transcription factor IFN regulatory factor 3 that initiates expression of IFN. See Dobbs et al., 2015; Wang et al., 2014; and Liu et al., 2015. Thus, expression of type I IFNs can be induced by delivering double-stranded DNA to target cells that can be recognized by cytosolic DNA sensors, as described above and in the cited references.

In some embodiments, the compositions disclosed herein include an intact minicell comprising an type I IFN agonist. In some embodiments, the type I IFN agonist is an oligonucleotide suitable for DNA sensor mediated induction of type I IFN, as described herein. In some embodiments the oligonucleotide comprises a sequence of at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, or at least about 200 nucleotides. In another embodiment, the oligonucleotide comprises a sequence of from about 10 up to about 200 nucleotides, or any amount in-between these two values. In some embodiments, the oligonucleotide comprises a sequence of at least about 40 nucleotides, at least about 50 nucleotides, or at least about 60 nucleotides.

In other embodiments, polynucleotide products of the enzyme polynucleotide phosphorylase (PNPase 1) may be used as synthetic inducers of IFN activity. Field et al., 1967. Similarly, the dsRNA mimetic polyinosinic:polycytidylic acid (poly(I:C)), was shown to function as an agonist for both TLR3 and MDA5. Alexopoulou et al., 2001; and Gitlin et al., 2006. Accordingly, in some embodiments, the oligonucleotide is a polynucleotide product of PNPase1, poly(I:C), poly-ICLC, imiquimod, imidazoquioline resquimod, or CpG-oligodeoxynucleotides.

Synthetic oligonucleotides can also be designed and used as agonists of nucleic acid sensors. For example, TLR9-stimulatory synthetic CpG oligodeoxynucleotides (CpG-ODNs) were designed based on the immune-stimulatory properties of bacterial DNA that, in contrast to human DNA, is rich in unmethylated CpG motifs. Krieg et al., 1995. Optimization of sequence features and backbone modifications led to CpG-ODN subtypes that preferentially activate either B cells or pDCs. Accordingly, it is contemplated herein that the CpG-ODN can be methylated or unmethylated, or a combination of both.

There are a number of molecules that are known to be stimulators of type I IFN secretion and these molecules along with their agonists are suitable for delivery via minicells to elicit type I IFN secretion. These molecules include but are not limited to, double stranded RNA (dsRNA), poly(dA:dT) DNAs, double stranded Z-DNA and B-DNA, DNAs (dsDNAs) longer than 36 bp and DNA-RNA hybrids, bacterial second messenger cyclic-di-GMP, TLR3, TLR4, TLR7, TLR8 and TLR9 agonists, and STING Agonists, which are more fully described below.

ii. Double-Stranded RNA (dsRNA)

Double-stranded RNA is an inducer of type I IFN. The RNA helicases retinoic acid-inducible gene I (RIG-I) and melanoma differentiation-associated gene 5 (MDA5) are cytoplasmic receptors that trigger type I IFN secretion. These receptors (RIG-I-like receptors) transmit signals through the mitochondria-localized adaptor molecule IPS-1 or MAVS and the kinases TBK1 and IKKi to activate IRF3 and induce transcription of the type I IFN genes (Kawai and Akira, 2010). RIG-I and MDA5 respond to viral RNAs tri-phosphorylated in their 5' ends (Leung and Amarasinghe, 2016; Lu et al., 2010; Marq et at, 2011; Wang et al., 2010).

iii. Poly(dA:dT) DNAs

RNA polymerase III is a cytosolic DNA sensor for poly(dA:dT) DNAs (Ablasser et al., 2009). In the cytosol, RNA polymerase III converts poly(dA:dT) to RNA with 5' tri-phosphorylation. The converted 5'-ppp RNA then initiates the RIG-I-MAVS pathway and NFκB activation to elicit type I IFN secretion.

iv. Double-Stranded Z-DNA and B-DNA

Figure 26:
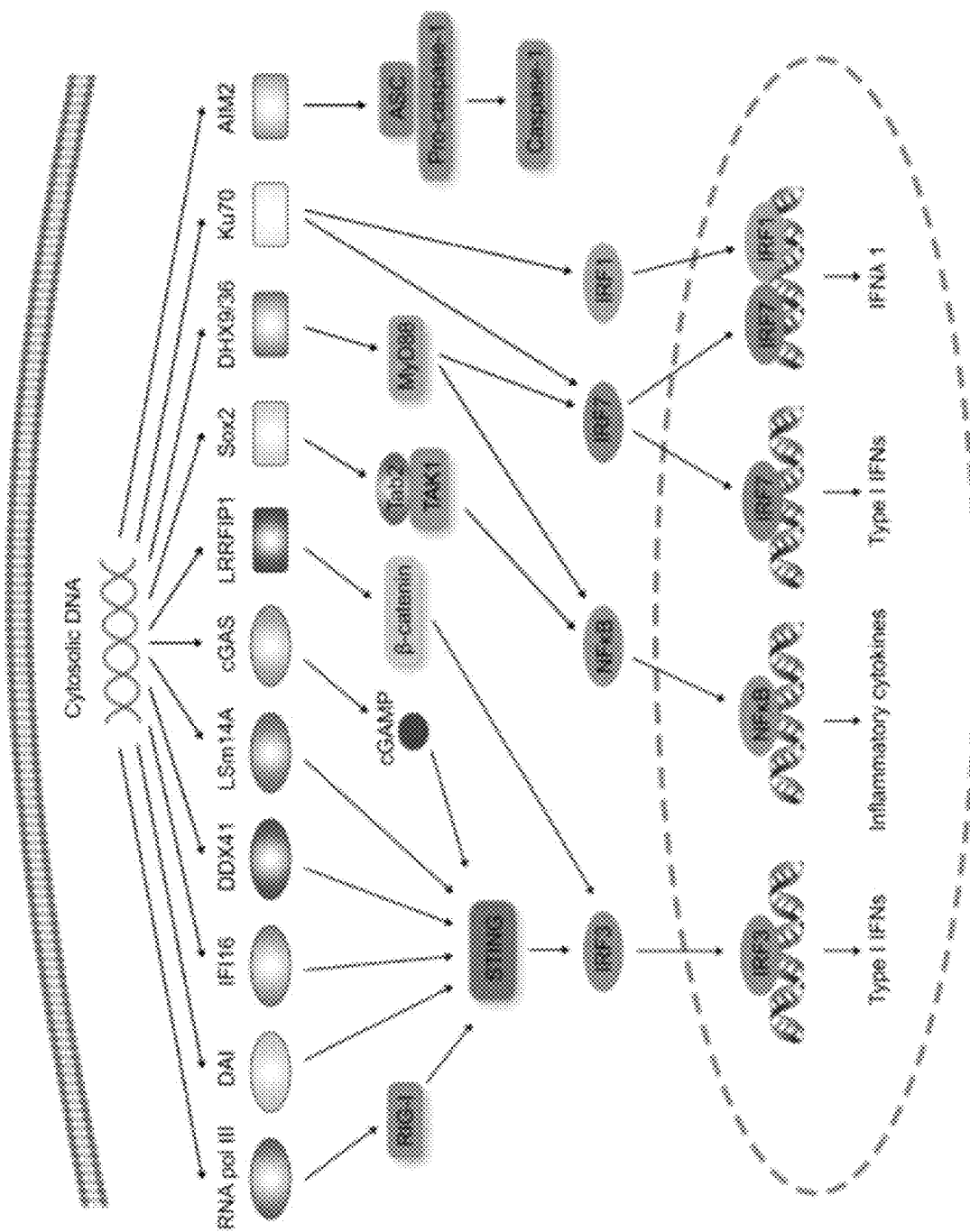
FIG. 26 shows signaling pathways of cytosolic DNA sensors with DNA challenge. Up to now, many cytosolic DNA sensors have been defined to detect intracellular double-stranded DNAs. RNA polymerase III transcribes AT-rich DNAs into RNAs that are recognized by RNA sensor RIG-I, followed by STING and IRF3 activation. DNA sensors DAI, IFI16, DDX41 and LSm14A sense dsDNA directly to activate STING for type I IFN production. In the presence of dsDNAs, cGAS catalyzes the synthesis of cGAMP, a strong activator of STING. With dsDNAs, LRRFIP1 initiates β-catenin and IRF3 activation in a STING-dependent manner. Other DNA sensors prime immune responses independently of STING. After recognition of dsDNAs, Sox2 triggers the activation of the Tab2/TAK1 complex in neutrophils. When detected by dsDNAs, DHX9/36 activates NFκB and IRF7 through MyD88. DNA sensor Ku70 triggers the activation of IRF1 and IRF7. AIM2 initiates the activation of inflammasome through ASC with DNA binding.

A cytosolic DNA sensor, DNA-dependent activator of IRFs (DAI) or Z-DNA binding protein 1, is known to induce type I IFN in response to the right-handed dsDNA conformation (B-DNA) in a TBK1- and IRF3-mediated mechanism (Kawai and Akira, 2010). RNA-polymerase III also transcribes B-DNA into 5'-ppp RNA, which then activates type I IFN transcription through RIG-I (Chiu et al., 2009). Once phosphorylated, these transcription factors help drive the expression of all genes of the type I IFN family, thereby amplifying type I IFN production. Many cytosolic DNA sensors have been reported to recognize intracellular pathogenic DNAs. See e.g. FIG. 26, excerpted from Xia et al., "DNA sensor cGAS-mediated immune recognition," *Protein Cell*, 7(11): 777-791 (2016)).

For example, DDX41 (Zhang et al., 2011b), IFI16 (Orzalli et al., 2012; Unterholzner et al., 2010) and DAI (Takaoka et al., 2007) detect double stranded DNAs (dsDNAs) and activate the STING-TBK1-IRF3 pathway. LRRFIP1 binds dsDNA and triggers IRF3 activation through β-catenin (Yang et al., 2010). DHX9 and DHX36 associate with dsDNA and lead to NFκB activation through MyD88 (Kim et al., 2010). Ku70 binds dsDNA to induce type I interferon (IFN) through activation of IRF1 and IRF7 (Zhang et al., 2011a). AIM2 interacts with dsDNA and activates inflammasomes by recruiting ASC and pro-caspase-1 (Burckstummer et al., 2009; Fernandes-Alnemri et al., 2009; Hornung et al., 2009). Of note, Sox2 is expressed in the cytosol of neutrophils and activates the Tab2/TAK1 complex upon binding to dsDNA in a sequence-dependent manner (Xia et al., 2015).

v. DNAs (dsDNAs) Longer than 36 bp and DNA-RNA Hybrids cGAS is a DNA sensor that recognizes cytoplasmic DNA (Ablasser et al., 2013a; Ablasser et al., 2013b; Gao et al., 2013a; Li et al., 2013b; Schoggins et al., 2014; Sun et al., 2013; Wu et al., 2013). Double stranded DNAs (dsDNAs) longer than 36 bp are optimal for cGAS activation (Gao et al., 2013b). Post-DNA binding, cGAS undergoes a conformational change that allows ATP and GTP to come into the catalytic pocket, leading to the synthesis of cGAMP a strong activator of the STING-TBK1 axis (Civril et al., 2013; Gao et al., 2013b; Kranzusch et al., 2013; Wu et al., 2013; Zhang et al., 2014). cGAS can be activated by dsDNAs and DNA-RNA hybrids (Mankan et al., 2014).

vi. Bacterial Second Messenger Cyclic-Di-GMP

Bacterial second messenger cyclic-di-GMP potently induces type I IFN via a mechanism that is independent of DAI or other known cytoplasmic receptors but requires TBK1 and IRF3 (McWhirter et al., 2009).

vii. TLR3, TLR4, TLR7, TLR8 and TLR9 Agonists

In some cell types, e.g., macrophages and DCs, type I IFN is produced in response to triggering of the transmembrane receptors Toll-like receptor 3 (TLR3) and TLR4 by dsRNA and lipopolysaccharide, respectively. TLR3 and TLR4 signal through the adaptor molecule TRIF, which associates with TBK1 and activates IRF3 (Kawai and Akira, 2010).

Natural IFN-producing cells, plasmacytoid DCs (pDCs) (Colonna et al., 2004) preferentially express the intracellular endosomal receptors TLR7 and TLR9, allowing them to respond to single-stranded RNA and DNA viruses, respectively, by triggering signal transduction through the adaptor protein MyD88 (Colonna et al., 2004). These receptors are efficient in inducing type I IFN only in pDCs because these cells constitutively express IRF7 and IRF8, and the MyD88-IRF7 complex undergoes a spatiotemporal regulation upon TLR ligation such that it is retained in the endosomal compartment, where it induces type I IFN production (Colonna et al., 2004).

The TLR4 agonist glucopyranosyl lipid adjuvant (GLA) is being tested alone or in combination with anti-PD-1 mAb [Immune Design 2016] (J. Meulen and S. Brady, "Immune Design," *Hum. Vaccin. Immunother.*, 13(1):15-16 (2017)). The TLR3 agonist Poly-ICLC (Hiltonol™) and the TLR7/8 agonist MEDI9197 also are being tested in patients with advanced accessible solid tumors (MedImmune 2016; Oncovir 201). ("Activating the Natural Host Defense; *Hiltonol (Poly-ICLC) and Malignant Brain Tumors*, A. Salzar, Oncovir, Inc., www.oncovir.com/id2 (accessed Jul. 11, 2018); and Gupta et al., "Abstract CT091: Safety and pharmacodynamic activity of MEDI9197, a TLR 7/8 agonist, administered intratumorally in subjects with solid tumors," *Cancer Research*, AACR Annual Meeting 2017; Apr. 1-5, 2017 (published July 2017)). Intratumoral injection of TLR agonists such as CpG-rich oligodeoxynucleotides (CpG ODN, PF-3512676) along with low-dose radiotherapy has shown clinical responses in patients with advanced non-Hodgkin's lymphoma in a phase I/II clinical study [Dynavax 2016]. (Adamus et al., 2018).

viii. STING Agonists

Cyclic dinucleotides (CDNs) [cyclic di-GMP (guanosine 5'-monophosphate), cyclic di-AMP (adenosine 5'-monophosphate), and cyclic GMP-AMP (cGAMP)] are a class of pathogen-associated molecular pattern molecules (PAMPs) that activate the TBK1/IRF3/type 1 interferon signaling axis via the cytoplasmic pattern recognition receptor stimulator of interferon genes (STING).

New STING agonists are being developed to elicit a type I interferon response. One major approach involves rational modifications of CDNs to improve efficiency, which led to the development of synthetic dithio-mixed linkage CDNs (Corrales et al., 2015). One compound (ML RR-S2 CDA or ADU-S100) binds both human and mouse STING, and showed a potent anti-tumor effect in multiple animal models (Corrales et al., 2015). A phase 1 clinical trial of ADU-S100 in patients with cutaneously accessible solid tumors and lymphomas is in progress (Aduro Biotech 2016).

An analysis of the 1000 Genome Project database (http://www.1000genomes.org/) identified five human STING variants including the WT allele, the reference (REF) allele (R232H), the HAQ allele (R71H, G230A, R293Q), the AQ allele (G230A, R293Q), and the Q allele (R293Q) (Yi et al., 2013).

A rationally designed synthetic CDN agonist, ML RR-S2 CDA, has been developed and exhibits enhanced stability, human STING activation, cellular uptake, and antitumor efficacy, as well as low reactogenicity compared with the natural STING ligands produced by bacteria or host cell cGAS (Corrales et al., 2015; Fu et al., 2015).

Rp, Rp (R,R) dithio-substituted diastereomer CDNs were resistant to digestion with phosphodiesterase, stimulated higher expression of IFN-3 in cultured human cells, and induced more potent antitumor immunity as compared with CDNs that did not contain a dithio modification (Corrales et al., 2015; Fu et al., 2015). To increase affinity for human STING, ML RR-S2 CDA contains a noncanonical structure defined by a phosphate bridge with one 2'-5' and one 3'-5' mixed phosphodiester linkages (2',3' CDNs). The 2',3' mixed linkage structure confers increased STING binding affinity (Gao et al., 2013b) and is also found in endogenous cGAMP produced by eukaryotic cGAS. ML RR-S2 CDA was shown to broadly activate all known human STING alleles in a HEK293T cellular STING signaling assay and induced dose-dependent expression of IFN-β in human peripheral blood monocytes (PBMCs) isolated from multiple donors with different STING genotypes, including a donor homozygous for the REF allele, which is known to be refractory to signaling induced by bacterial 3',3' CDNs (Corrales et al., 2015; Fu et al., 2015).

C. Type II Interferon Agonists

The present compositions and methods can include a type II IFN agonist, i.e., an agent that increases the level (e.g., the activity or expression level) of type II interferons. The class of type II interferons (IFNs) currently includes a member, called IFN-γ (gamma). Mature IFN-γ is an anti-parallel homodimer, which binds to the IFN-γ receptor (IFNGR) complex to elicit a signal within its target cell. IFNGR is made up of two subunits each of molecules designated IFNGR1 and IFNGR2. IFN-γ is involved in the regulation of the immune and inflammatory responses; in humans, there is only one type of interferon-gamma. It is produced in activated T cells and natural killer cells. IFN-γ potentiates the effects of type I IFNs. IFN-γ released by Th1 cells recruits leukocytes to a site of infection, resulting in increased inflammation. It also stimulates macrophages to kill bacteria that have been engulfed. IFN-γ released by Th1 cells also is important in regulating the Th2 response. As IFN-γ is vitally implicated in the regulation of immune response, and its production can lead to autoimmune disorders.

Thus, one embodiment of the invention encompasses compositions that comprise a minicell comprising a type II IFN agonist. Although minicells are derived from bacteria, the minicells by themselves do not activate type II interferon responses in human patients. See Example 15. The present inventors discovered that the addition of IFN gamma augmented the anti-tumor efficacy of EGFR-targeted EDVs loaded with doxorubicin and caused tumor regression in xenograft models. See Example 13. Furthermore, a composition comprising (i) EFGR targeted minicells loaded with the supertoxic chemotherapy drug PNU-159682, (ii) non-targeted minicells loaded with double stranded DNA comprising 60 nucleotides, and (iii) minicells comprising the IFN gamma product Imukin was well-tolerated and induced anti-cancer effects in dogs suffering from late-stage endogenous tumors. See Example 14.

Type II IFNs play an important role in anti-tumor immunity by activating cytotoxic T cells. See, e.g., Chikuma et al., 2017. IFN gamma cytokines are released by innate Natural Killer cells upon binding of natural antigen, but glycosphingolipid compounds can function as potent activators of both innate and acquired immune responses. The present inventors discovered that exposure to a glycosphingolipid induces a potent cytokine response by innate natural killer T (iNKT) cells, including the type II interferon, IFN-γ, and a number of Interleukins (Th1-, Th2-, and/or Th17-type cytokines). See, e.g., Carreno et al., 2016. iNKT cells then induce DC maturation and display T cell helper-like functions that result in the development of cytotoxic T cell responses.

Examples of glycosphingolips useful to induce a IFN type II response are described herein and include C-glycosidific form of α-galactosylceramide (α-C-GalCer), α-galactosylceramide (α-GalCer), 12 carbon acyl form of galactosylceramide (β-GalCer), β-D-glucopyranosylceramide (β-GlcCer), 1,2-Diacyl-3-0-galactosyl-sn-glycerol (BbGL-II), diacylglycerol containing glycolipids (Glc-DAG-s2), ganglioside (GD3), gangliotriaosylceramide (Gg3Cer), glycosylphosphatidylinositol (GPI), α-glucuronosylceramide (GSL-1 or GSL-4), isoglobotrihexosylceramide (iGb3), lipophosphoglycan (LPG), lyosphosphatidylcholine (LPC), α-galactosylceramide analog (OCH), and threitolceramide. In a particular embodiment the minicell disclosed herein comprises α-galactosylceramide (α-GalCer) as a type II IFN agonist.

α-GC, an INF type II agonist is known to stimulate the immune system through activation of a type of white blood cell known as natural killer T cell (NKT cell) (Birkholz et al 2015). Knowing that minicells were able to facilitate presentation of α-GC on target cells, as further discussed in Example 17, Applicant moved to investigate minicell facilitated immune activation using minicell$_{α-GC}$ could complement treatment consisting of minicell facilitated delivery of chemotherapeutic drug.

As shown in Example 18, Applicant discovered that tumor containing mice that were administered minicells containing the chemotherapeutic doxorubicin ($^{Ep}$minicell$_{Dox}$) and minicells containing α-GC (minicell$_{α-Gc}$) displayed a marked halt in tumor progression over mice administered only $^{Ep}$minicell$_{Dox}$. These observations indicated that minicell compositions excluding the INF type I agonist and instead incorporating an INF type II agonist, are effective at treating tumors in mice.

The minicell can deliver type II IFN agonists directly to cells of the immune system, with a view to enhancing iNKT cell activation and type II interferon IFN-γ production in vivo. Alternatively, non-targeted EDVs are taken up by phagocytic cells of the immune system, where they are broken down in endosomes, and aGC is presented to iNKT cells for immune activation. Accordingly, in some embodiments the minicell provides targeted delivery of type II interferon agonists. In other embodiments, the composition disclosed herein comprises a non-targeted minicell comprising a type II interferon agonist.

IFN-γ production is controlled by cytokines secreted by antigen presenting cells (APCs), most notably interleukin (IL)-12 and IL-18. These cytokines serve as a bridge to link infection with IFN-γ production in the innate immune response. Macrophage recognition of many pathogens induces secretion of IL-12 and chemokines. These chemokines attract NK cells to the site of inflammation, and IL-12 promotes IFN-γ synthesis in these cells. In macrophages, natural killer cells and T cells, the combination of IL-12 and IL-18 stimulation further increases IFN-γ production. Accordingly, any of these proteins or their combinations are suitable agents for the purpose of this disclosure.

Negative regulators of IFN-gamma production include IL-4, IL-10, transforming growth factor β and glucocorticoids. Proteins or nucleic acids that inhibit these factors will be able to stimulate the production of IFN-γ.

Also suitable for use in this context are polynucleotides that encode IFN-γ or genes that activate the production and/or the secretion of IFN-γ.

The agent that increases the level of IFN-γ may also be a viral vaccine. A number of viral vaccines are available that can induce IFN-γ production without causing infection or other types of adverse effects. Illustrative of this class of viral-vaccine agent is a flu (influenza) vaccine.

The data show that the serum concentration of IFN-γ required for effectively activating host immune response to tumor cells is low when the patient also receives administration of drug-loaded, bispecific antibody-targeted minicells or killed bacterial cells. Thus, in one aspect the inventive methodology results in increase of serum IFN-γ concentration that is not higher than about 30,000 pg/mL. In another aspect, the serum IFN-γ concentration is increased to not higher than about 5000 pg/mL, 1000 pg/mL, 900 pg/mL, 800 pg/mL, 700 pg/mL, 600 pg/mL, 500 pg/mL, 400 pg/mL, 300 pg/mL, 200 pg/mL, or 100 pg/mL. In a further aspect, the resulting serum IFN-gamma concentration is at least about 10 pg/mL, or at least about 20 pg/mL, 30 pg/mL, 40 pg/mL, 50 pg/mL, 60 pg/mL, 70 pg/mL, 80 pg/mL, 90 pg/mL, 100 pg/mL, 150 pg/mL, 200 pg/mL, 300 pg/mL, 400 pg/mL or 500 pg/mL.

Pursuant to some aspects, the agent is an IFN-γ protein or an engineered protein or analog. In some aspects, the administration achieves from about 0.02 ng to 1 microgram of IFN-γ per ml of host blood. In one aspect, the achieved IFN-gamma concentration in the host blood is from about 0.1 ng to about 500 ng per ml, from about 0.2 ng to about 200 ng per ml, from about 0.5 ng to about 100 ng per ml, from about 1 ng to about 50 ng per ml, or from about 2 ng to about 20 ng per ml.

III. Intact Bacterially-Derived Minicells

The term "minicell" is used here to denote a derivative of a bacterial cell that lacks chromosomes ("chromosome-free") and is engendered by a disturbance in the coordination, during binary fission, of cell division with DNA segregation. Minicells are distinct from other small vesicles, such as so-called "membrane blebs" (about 0.2 µm or less in size), which are generated and released spontaneously in certain situations but which are not due to specific genetic rearrangements or episomal gene expression. By the same token, intact minicells are distinct from bacterial ghosts, which are not generated due to specific genetic rearrangements or episomal gene expression. Bacterially derived minicells employed in this disclosure are fully intact and thus are distinguished from other chromosome-free forms of bacterial cellular derivatives characterized by an outer or defining membrane that is disrupted or degraded, even removed. See U.S. Pat. No. 7,183,105 at col. 111, lines 54 et seq. The intact membrane that characterizes the minicells of the present disclosure allows retention of the therapeutic payload within the minicell until the payload is released, post-uptake, within a tumor cell.

Minicell or EDVs are anucleate, non-living nanoparticles produced as a result of inactivating the genes that control normal bacterial cell division, thereby de-repressing polar sites of cell. Ma et al., 2004. The de-repression means that the bacteria divide in the centre as well as at the poles; the polar division resulting in minicells which the inventors of the present disclosure have shown can function as leak-resistant, micro-reservoir carriers that allow efficient packaging of a range of different chemotherapeutic drugs. Moreover, in contrast to current stealth liposomal drug carriers like DOXIL (liposomal doxorubicin), for example, that can package only ~14,000 molecules per particle (Park et al., *Breast Cancer Res.*, 4(3): 95-99 (2002), or "armed antibodies," which can carry fewer than 5 drug molecules, EDVs can readily accommodate payloads of up to 1 million drug molecules. Further, EDVs can be targeted to over-expressed receptors on the surface of cancer cells using bispecific antibodies, see section D infra, which allows highly significant tumor growth-inhibition and/or regression, both in vitro and in vivo.

The minicells employed in the present invention can be prepared from bacterial cells, such as *E. coli* and *S. typhymurium*. Prokaryotic chromosomal replication is linked to normal binary fission, which involves mid-cell septum formation. In *E. coli*, for example, mutation of min genes, such as minCD, can remove the inhibition of septum formation at the cell poles during cell division, resulting in production of a normal daughter cell and an chromosome-less minicell. See de Boer et al., *J. Bacteriol.*, 174: 63-70 (1992); Raskin & de Boer, *J. Bacteriol.*, 181: 6419-s24 (1999); Hu & Lutkenhaus, *Mol. Microbio.*, 34: 82-90 (1999); Harry, *Mol. Microbiol.*, 40: 795-803 (2001).

In addition to min operon mutations, chromosome-less minicells also are generated following a range of other genetic rearrangements or mutations that affect septum formation, for example, in the divIVB 1 in *B. subtilis*. See Reeve and Cornett, *J. Virol.*, 15: 1308-16 (1975). Minicells also can be formed following a perturbation in the levels of gene expression of proteins involved in cell division/chromosome segregation. For instance, over-expression of minE leads to polar division and production of minicells. Similarly, chromosome-less minicells can result from defects in chromosome segregation, e.g., the smc mutation in *Bacillus subtilis* (Britton et al., *Genes Dev.*, 12: 1254-9 (1998)), the spoOJ deletion in *B. subtilis* (Ireton et al., *J. Bacteriol.*, 176: 5320-29 (1994)), the mukB mutation in *E. coli* (Hiraga et aL, *J. Bacteriol.*, 171: 1496-1505 (1989)), and the parC mutation in *E. coli* (Stewart and D'Ari, *J. Bacteriol.*, 174: 4513-6 (1992)). Further, CafA can enhance the rate of cell division and/or inhibit chromosome partitioning after replication (Okada et al., *J. Bacteriol.*, 176: 917-22 (1994)), resulting in formation of chained cells and chromosome-less minicells.

Accordingly, minicells can be prepared for the present disclosure from any bacterial cell, be it of Gram-positive or Gram-negative origin due to the conserved nature of bacterial cell division in these bacteria. Furthermore, the minicells used in the disclosure should possess intact cell walls (i.e., are "intact minicells"), as noted above, and should be distinguished over and separated from other small vesicles, such as membrane blebs, which are not attributable to specific genetic rearrangements or episomal gene expression.

In a given embodiment, the parental (source) bacteria for the minicells can be Gram positive, or they can be Gram negative. In one aspect, the parental bacteria are one or more selected from Terra-/Glidobacteria (BV1), Proteobacteria (BV2), BV4 including Spirochaetes, Sphingobacteria, and Planctobacteria. Pursuant to another aspect, the bacteria are one or more selected from Firmicutes (BV3) such as Bacilli, Clostridia or Tenericutes/Mollicutes, or Actinobacteria (BV5) such as Actinomycetales or Bifidobacteriales.

Pursuant to the invention, killed bacterial cells are non-living prokaryotic cells of bacteria, cyanobateria, eubacteria and archaebacteria, as defined in the 2nd edition of *Bergey's Manual Of Systematic Biology*. Such cells are deemed to be "intact" if they possess an intact cell wall and/or cell membrane and contain genetic material (nucleic acid) that is endogenous to the bacterial species. Methods of preparing killed bacterial cells are described, for instance, in U.S. patent application publication No. 2008/0038296, the contents of which are incorporated herein by reference.

In yet a further aspect, the bacteria are one or more selected from Eobacteria (Chloroflexi, Deinococcus-Thermus), Cyanobacteria, Thermodesulfobacteria, thermophiles (Aquificae, Thermotogae), Alpha, Beta, Gamma (Enterobacteriaceae), Delta or Epsilon Proteobacteria, Spirochaetes, Fibrobacteres, Chlorobi/Bacteroidetes, Chlamydiae/Verrucomicrobia, Planctomycetes, Acidobacteria, Chrysiogenetes, Deferribacteres, Fusobacteria, Gemmatimonadetes, Nitrospirae, Synergistetes, Dictyoglomi, Lentisphaerae Bacillales, Bacillaceae, Listeriaceae, Staphylococcaceae, Lactobacillales, Enterococcaceae, Lactobacillaceae, Leuconostocaceae, Streptococcaceae, Clostridiales, Halanaerobiales, Thermoanaerobacterales, Mycoplasmatales, Entomoplasmatales, Anaeroplasmatales, Acholeplasmatales, Haloplasmatales, Actinomycineae, Actinomycetaceae, Corynebacterineae, Nocardiaceae, Corynebacteriaceae, Frankineae, Frankiaceae, Micrococcineae, Brevibacteriaceae, and Bifidobacteriaceae.

For pharmaceutical use, a composition of the disclosure should comprise minicells or killed bacterial cells that are isolated as thoroughly as possible from immunogenic components and other toxic contaminants. Methodology for purifying bacterially derived minicells to remove free endotoxin and parent bacterial cells are described, for example, in WO 2004/113507, which is incorporated by reference herein in its entirety. Briefly, the purification process achieves removal of (a) smaller vesicles, such as membrane blebs, which are generally smaller than 0.2 m in size, (b) free endotoxins released from cell membranes, and (c) parental bacteria, whether live or dead, and their debris, which also are sources of free endotoxins. Such removal can be implemented with, inter alia, a 0.2 m filter to remove smaller vesicles and cell debris, a 0.45 m filter to remove parental cells following induction of the parental cells to form filaments, antibiotics to kill live bacterial cells, and antibodies against free endotoxins.

Underlying the purification procedure is a discovery by the present inventors that, despite the difference of their bacterial sources, all intact minicells are approximately 400 nm in size, i.e., larger than membrane blebs and other smaller vesicles and yet smaller than parental bacteria. Size determination for minicells can be accomplished by using solid-state, such as electron microscopy, or by liquid-based techniques, e.g., dynamic light scattering. The size value yielded by each such technique can have an error range, and the values can differ somewhat between techniques. Thus, the size of minicells in a dried state can be measured via electron microscopy as approximately 400 nm±50 nm. Dynamic light scattering can measure the same minicells to be approximately 500 nm±50 nm in size. Also, drug-packaged, ligand-targeted minicells can be measured, again using dynamic light scattering, to be approximately 400 nm to 600 nm±50 nm.

This scatter of size values is readily accommodated in practice, e.g., for purposes of isolating minicells from immunogenic components and other toxic contaminants, as described above. That is, an intact, bacterially derived minicell is characterized by cytoplasm surrounded by a rigid membrane, which gives the minicell a rigid, spherical structure. This structure is evident in transmission-electron micrographs, in which minicell diameter is measured, across the minicell, between the outer limits of the rigid membrane. This measurement provides the above-mentioned size value of 400 nm±50 nm.

Another structural element of a killed bacterial cells or a minicell derived from Gram-negative bacteria is the O-polysaccharide component of lipopolysaccharide (LPS), which is embedded in the outer membrane via the lipid A anchor. The component is a chain of repeat carbohydrate-residue units, with as many as 70 to 100 repeat units of four to five sugars per repeat unit of the chain. Because these chains are not rigid, in a liquid environment, as in vivo, they can adopt a waving, flexible structure that gives the general appearance of seaweed in a coral sea environment; i.e., the chains move with the liquid while remaining anchored to the minicell membrane.

Influenced by the O-polysaccharide component, dynamic light scattering can provide a value for minicell size of about 500 nm to about 600 nm, as noted above. Nevertheless, minicells from Gram-negative and Gram-positive bacteria alike readily pass through a 0.45 µm filter, which substantiates an effective minicell size of 400 nm±50 nm. The above-mentioned scatter in sizes is encompassed by the present invention and, in particular, is denoted by the qualifier "approximately" in the phrase "approximately 400 nm in size" and the like.

In relation to toxic contaminants, a composition of the disclosure preferably comprises less than about 350 EU free endotoxin. Illustrative in this regard are levels of free endotoxin of about 250 EU or less, about 200 EU or less, about 150 EU or less, about 100 EU or less, about 90 EU or less, about 80 EU or less, about 70 EU or less, about 60 EU or less, about 50 EU or less, about 40 EU or less, about 30 EU or less, about 20 EU or less, about 15 EU or less, about 10 EU or less, about 9 EU or less, about 8 EU or less, about 7 EU or less, about 6 EU or less, about 5 EU or less, about 4 EU or less, about 3 EU or less, about 2 EU or less, about 1 EU or less, about 0.9 EU or less, about 0.8 EU or less, about 0.7 EU or less, about 0.6 EU or less, about 0.5 EU or less, about 0.4 EU or less, about 0.3 EU or less, about 0.2 EU or less, about 0.1 EU or less, about 0.05 EU or less, or about 0.01 EU or less.

A composition of the disclosure also can comprise at least about $10^9$ minicells or killed bacterial cells, e.g., at least about $1\times10^9$, at least about $2\times10^9$, at least about $5\times10^9$, or at least $8\times10^9$. In some embodiments, the composition comprises no more than about $10^{11}$ minicells or killed bacterial cells, e.g., no more than about $1\times10^{11}$ or no more than about $9\times10^{10}$, or no more than about $8\times10^{10}$.

IV. Loading Active Agents into Minicells or Killed Bacterial Cells

Active agents or anti-neoplastic agents, such as small molecular drugs, proteins and functional nucleic acids can be packaged into minicells directly by co-incubating a plurality of intact minicells with the active agent in a buffer. The buffer composition can be varied, as a function of conditions well known in this field, to optimize the loading of the active agent in the intact minicells. The buffer also may be varied in dependence on the agent (e.g., dependent upon the nucleotide sequence or the length of the nucleic acid to be loaded in the minicells in the case of a nucleic acid payload). An exemplary buffer suitable for loading includes, but is not limited to, phosphate buffered saline (PBS). Once packaged, the active agent remains inside the minicell and is protected from degradation. Prolonged incubation studies with siRNA-packaged minicells incubated in sterile saline have shown, for example, no leakage of siRNAs.

Active agents such as functional nucleic acids or proteins that can be encoded for by a nucleic acid, can be introduced into minicells by transforming into the parental bacterial cell a vector, such as a plasmid, that encodes the active agents. When a minicell is formed from the parental bacterial cell, the minicell retains certain copies of the plasmid and/or the expression product, the anti-neoplastic agent. More details of packaging and expression product into a minicell is provided in WO 03/033519, the contents of which are incorporated into the present disclosure in its entirety by reference.

Data presented in WO 03/033519 demonstrated, for example, that recombinant minicells carrying mammalian gene expression plasmids can be delivered to phagocytic cells and to non-phagocytic cells. WO 03/033519 also described the genetic transformation of minicell-producing parent bacterial strains with heterologous nucleic acids carried on episomally-replicating plasmid DNAs. Upon separation of parent bacteria and minicells, some of the episomal DNA segregated into the minicells. The resulting recombinant minicells were readily engulfed by mammalian phagocytic cells and became degraded within intracellular phagolysosomes. Moreover, some of the recombinant DNA escaped the phagolysosomal membrane and was transported to the mammalian cell nucleus, where the recombinant genes were expressed.

In other embodiments, multiple nucleic acids directed to different mRNA targets can be packaged in the same minicell. Such an approach can be used to combat drug resistance and apoptosis resistance. For instance, cancer patients routinely exhibit resistance to chemotherapeutic drugs. Such resistance can be mediated by over-expression of genes such as multi-drug resistance (MDR) pumps and anti-apoptotic genes, among others. To combat this resistance, minicells can be packaged with therapeutically significant concentrations of functional nucleic acid to MDR-associated genes and administered to a patient before chemotherapy. Furthermore, packaging into the same minicell multiple functional nucleic acid directed to different mRNA targets can enhance therapeutic success since most molecular targets are subject to mutations and have multiple alleles. More details of directly packaging a nucleic acid into a minicell is provided in WO 2009/027830, the contents of which are incorporated into the present disclosure in its entirety by reference.

Small molecule drugs, whether hydrophilic or hydrophobic, can be packaged in minicells by creating a concentration gradient of the drug between an extracellular medium comprising minicells and the minicell cytoplasm. When the extracellular medium comprises a higher drug concentration than the minicell cytoplasm, the drug naturally moves down this concentration gradient, into the minicell cytoplasm. When the concentration gradient is reversed, however, the drug does not move out of the minicells. More details of the drug loading process and its surprising nature are found, for instance, in U.S. Patent Application Publication No. 2008/0051469, the contents of which are specifically incorporated by reference.

To load minicells with drugs that normally are not water soluble, the drugs initially can be dissolved in an appropriate solvent. For example, paclitaxel can be dissolved in a 1:1 blend of ethanol and cremophore EL (polyethoxylated castor oil), followed by a dilution in PBS to achieve a solution of paclitaxel that is partly diluted in aqueous media and carries minimal amounts of the organic solvent to ensure that the drug remains in solution. Minicells can be incubated in this final medium for drug loading. Thus, the inventors discovered that even hydrophobic drugs can diffuse into the cytoplasm or the membrane of minicells to achieve a high and therapeutically significant cytoplasmic drug load. This is unexpected because the minicell membrane is composed of a hydrophobic phospholipid bilayer, which would be expected to prevent diffusion of hydrophobic molecules into the cytoplasm. The loading into minicells of a diversity of representative small molecule drugs has been shown, illustrating different sizes and chemical properties: doxorubicin, paclitaxel, fluoro-paclitaxel, cisplatin, vinblastine, monsatrol, thymidylate synthase (TS) inhibitor OSI-7904, irinotecan, 5-fluorouracil, gemcitabine, and carboplatin. Across the board, moreover, the resultant, small molecule drug-packaged minicells show significant anti-tumor efficacy, in vitro and in vivo.

V. Targeting Minicells to Specific Mammalian Cells and Tumors

The inventors discovered that blood vessels around tumor cells display a loss of integrity; that is, the vessels have large fenestrations and are "leaky," even in the blood brain barrier (BBB) environment. When cancer cells establish, they secrete substances that promote the formation of new blood vessels—a process called angiogenesis. These blood vessels grow quickly and, unlike normal blood vessels, they are leaky with "holes" (fenestrations) ranging from 50 nm to 1.2 m (hyperpermeable vasculature). Drug delivery particles such as liposomes are currently believed to effect tumor-targeting by a passive process involving extravasation from the leaky vasculature that supports the tumor microenvironment. Hobbs et al., 1998. Although it has been shown that the abnormal tumor microenvironment is characterised by interstitial hypertension, and that this phenomenon may limit access of anti-cancer antibody therapeutics, this does not appear to be an absolute barrier as is exemplified by immunoliposomes (Nielsen et al, 2002) and antibody conjugated to Quantum Dots (Gao et aL, 2004). This phenomenon also holds true for the EDV which has the added advantage of carrying a specifically directed tumor antibody. Following IV injection the EDV extravasates into the tumor microenvironment and this is followed by active targeting via cancer cell-surface receptor engagement and endocytosis. In contrast to conventional understanding, therefore, particles that are as large as minicells, i.e., much larger than the above-discussed consensus pore size limitations of the BBB, nevertheless are smaller than the fenestrations in the walls of the leaky blood vessel; hence, they can extravasate passively through these fenestrations and into the tumor microenvironment.

Upon entering the tumor microenvironment, minicells are able to trigger receptor-mediated internalization by the host tumor cells and to be taken up by them. Thus, a minicell that is packaged with an anti-neoplastic agent will release the agent into the cytoplasm of the tumor cell, killing it.

Pursuant to a further aspect of this disclosure, the minicells or killed bacterial cells of a composition, as described above, are directed to a target mammalian tumor cell via a ligand. In some embodiments the ligand is "bispecific." That is, the ligand displays a specificity for both minicell and mammalian (tumor) cell components, such that it causes a given vesicle to bind to the target cell, whereby the latter engulfs the former. Use of bispecific ligands to target a minicell to a tumor cell is further described in WO 05/056749 and WO 05/079854, and use of bispecific ligands to target a killed bacterial cell to a tumor cell is further described in U.S. Pat. No. 8,591,862, the respective contents of which are incorporated here by reference in its entirety. Once such a ligand is attached to a vesicle, the unoccupied specificity ("monospecificity") of the ligand pertains until it interacts with the target (tumor) mammalian cell. A number of tumor targeting ligands are known in the art (Hong et al., 2011; Hoelder et al., 2012; Galluzzi et al., 2013). Several peptides, such as somatostatin (SST) peptide, vasoactive intestinal peptide (VIP), Arg-Gly-Asp (RGD) peptide, and bombesin/gastrin-releasing peptide (BBN/GRP), have been successfully characterized for tumor receptor imaging (De Jong et al., 2009; Tweedle, 2009; Schottelius and Wester 2009; Igarashi et al., 2011; Laverman et al., 2012).

Tumor-targeting peptide sequences can be selected mainly in three different ways: (1) derivatization from natural proteins (Nagpal et al., 2011); (2) chemical synthesis and structure-based rational engineering (Andersson et al., 2000; Merrifield, 2006); and (3) screening of peptide libraries (Gray and Brown 2013). Among the methods, phage display technology is a conventional but most widely used method with many advantages such as ease of handling and large numbers of different peptides can be screened effectively (Deutscher, 2010).

Receptors that are overexpressed on tumor cells rather than on normal cells are excellent candidates for in vivo tumor imaging. To date, many tumor targeting peptides and their analogs have been identified as described below.

Arg-Gly-Asp (RGD) peptide—RGD specifically binds to integrin receptors (Ruoslahti, 1996). Integrins constitute two subunits ($\alpha$ and $\beta$ subunits). The integrin family, especially $\alpha_v\beta_3$, is associated with tumor angiogenesis and metastasis. They are overexpressed on endothelial cells during angiogenesis, but barely detectable in most normal organs. Therefore, they are widely used for diagnostic imaging.

Bombesin (BBN)/gastrin-releasing peptide (GRP)—Amphibian BBNs and their related peptides consist of a family of neuropeptides exhibiting various physiological effects such as exocrine and endocrine secretions, thermoregulation, sucrose regulations as well as cell growth (Ohki-Hamazaki et al., 2005). The bombesin-like peptide receptors have 4-subtypes: the neuromedin B receptor, the bombesin 3 receptor, the GRP receptor, and the bombesin 4 receptor. These receptors are overexpressed in many tumors such as breast cancer, ovarian cancer and gastrointestinal stromal tumors.

Cholecystokinin (CCK)/gastrin peptide—CCK and gastrin are structurally and functionally similar peptides that exert a variety of physiological actions in the gastrointestinal tract as well as the central nervous system (Matsuno et al., 1997). Three types of receptors for CCK (CCK1, CCK2 and CCK2i4sv have been identified, which all belong to the superfamily of GPCRs. Among them, CCK2/gastrin receptors have been frequently found in human cancers such as stromal ovarian cancers and astrocytomas.

$\alpha$-Melanocyte-stimulating hormone ($\alpha$-MSH)-$\alpha$-MSHs are linear tridecapeptides, mainly responsible for skin pigmentation regulation (Singh and Mukhopadhyay, 2014). $\alpha$-MSHs and their analogs exhibit binding affinities to melanocortin-1 receptors (MC-1r) which are expressed in over 80% of human melanoma metastases, and thus, are widely used as vehicles for melanoma-targeted imaging and radiotherapy.

Neuropeptide Y (NPY)—NPY is a 36 amino acid peptide and belongs to the pancreatic polypeptide family (Tatemoto, 2004). NPY receptors are overexpressed in various tumors including neuroblastomas, sarcomas, and breast cancers.

Neutrotensin (NT)—NT is a 13 amino acid peptide, targeting NT receptor which has been identified in various tumors such as ductal pancreatic adenocarcinomas, small cell lung cancer, and medullary thyroid cancer (Tyler-McMahon et al., 2000). Therefore, it is an attractive candidate for cancer imaging.

Prostate Specific Membrane Antigen (PSMA)—Prostate cancer cells overexpress PSMA on the cell surface (Silver et al., 2007; Ghosh and Heston, 2004; Mhawech-Fauceglia et al., 2007; Santoni et al., 2014). There are several available radiopharmaceuticals that target PSMA including [$^{68}$Ga]Ga-PSMA-HBED-CC (also known as [$^{68}$Ga]Ga-PSMA-11 [PET]), a monoclonal antibody (mAb) [$^{177}$Lu]Lu/[$^{90}$Y]Y-J591 (therapy), [$^{123}$I]I-MIP-1072 (planar/SPECT), [$^{131}$I]I-MIP-1095 (therapy), and the theranostic agents PSMA-I&T and DKFZ-PSMA-617 (PSMA-617), which are labeled with $^{68}$Ga for PET or with $^{177}$Lu for therapy.

Somatostatin (SST) peptide—SSTs are naturally occurring cyclopeptide hormones with either 14 or 28 amino acids (Weckbecker et al., 2003). They can inhibit the secretion of insulin, glucagon and some other hormones. Somatostatin receptors (SSTRs; five subtypes SSTR1-SSTR5) are overexpressed in many tumors including gliomas, neuroendocrine tumors and breast tumor. Neuroendocrine neoplasia (NEN) of the GEP system originates most frequently from the pancreas, jejunum, ileum, cecum, rectum, appendix, and colon. The common characteristic of all GEP-NEN is the compound features of endocrine and nerve cells. Well-differentiated NEN overexpresses somatostatin receptors (SSTRs), especially the SSTR-2 subtype.

Substance P—Substance P is an undecapeptide belonging to a family of neuropeptides known as tachykinins (Strand, 1999). Substance P is a specific endogenous ligand known for neurokinin 1 receptor (NKIR) which is found to be expressed on various cancer cells.

T140—T140 is a 14 amino acid peptide with one disulfide bridge and is an inverse agonist of chemokine receptor type 4 (CXCR4) (Burger et al., 2005). Its derivatives are widely used as CXCR4 imaging agents.

Tumor molecular targeted peptide 1 (TMTP1)—TMTP1 is a 5-amino acid peptide that has been found to specifically bind to highly metastatic cancer cells, especially those from a typical liver micrometastasis (Yang et al., 2008).

Vasoactive intestinal peptide (VIP)—VIP is a neuropeptide with 28 amino acids (Igarashi et al., 2011). It promotes vasodilation, cell growth and proliferation. Its action is mainly controlled by two receptor subtypes (VPAC1 and VPAC2). A large amount of VIP receptors are expressed on many tumors including adenocarcinomas of the pancreas and neuroendocrine tumors.

The ligand can be attached to the cell membrane of the vesicles by virtue of the interaction between the ligand and a component on the cell membrane, such as a polysaccharide, a glycoprotein, or a polypeptide. The expressed ligand is anchored on the surface of a vesicle such that the tumor surface component-binding portion of the ligand is exposed so that the portion can bind the target mammalian cell surface receptor when the vesicle and the mammalian tumor cell come into contact.

Alternatively, the ligand can be expressed and displayed by a living counterpart of a bacterially derived vesicle, e.g., by the parent cell of a minicell or by a bacterial cell before it becomes a killed cell. In this instance the ligand does not require a specificity to the vesicle and only displays a specificity to a component that is characteristic of mammalian cells. That is, such component need not be unique to tumor cells, per se, or even to the particular kind of tumor cells under treatment, so long as the tumor cells present the component on their surface.

Upon intravenous administration, vesicles accumulate rapidly in the tumor microenvironment. This accumulation, occurring as a function of the above-described leaky tumor vasculature, effects delivery of vesicle-packaged therapeutic payload to cells of the tumor, which then internalize packaged vesicles.

The inventors have found that this delivery approach is applicable to a range of mammalian tumor cells, including cells that normally are refractory to specific adhesion and endocytosis of minicells. For instance, ligands that comprise an antibody directed at an anti-HER2 receptor or anti-EGF receptor can bind minicells to the respective receptors on a range of targeted non-phagocytic cells, such as lung, ovarian, brain, breast, prostate, and skin cancer cells.

The binding thus achieved precedes uptake of the vesicles by each type of non-phagocytic cells. That is, in the context of the present invention a suitable target cell presents a cell surface receptor the binding of which, by a ligand on a vesicle, elicits endocytosis of that vesicle.

More specifically, the present inventors discovered that the interaction between (a) the ligand on a minicell or a killed bacterial cell and (b) a mammalian cell surface receptor can activate an uptake pathway, called here a "receptor-mediated endocytosis" (rME) pathway, into the late-endosomal/lysosomal compartment of the target host cell, such as a tumor cell. By this rME pathway, the inventors found, bacterially derived vesicles are processed through the early endosome, the late endosome and the lysosome, resulting in release of their payload into the cytoplasm of the mammalian host cell. Moreover, a payload that is a nucleic acid not only escapes complete degradation in the late-endosomal/lysosomal compartment but also is expressed by the host cell.

Figure 3:
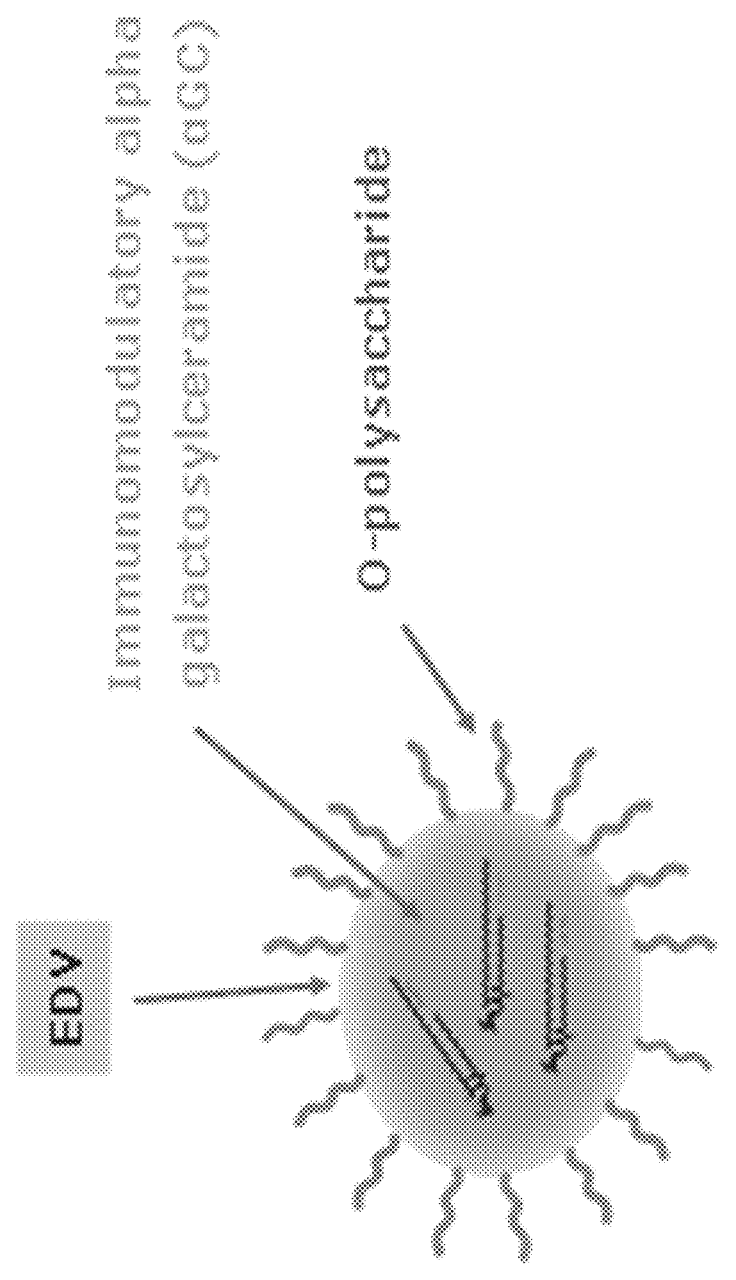

A tumor targeting ligand for this delivery approach can be "bispecific," as described above, because it binds to surface components on a payload-carrying vesicle and on a target cell, respectively, and its interaction with the latter component leads to uptake of the vesicle into the rME pathway. In any event, a given target cell surface receptor can be a candidate for binding by the ligand, pursuant to the invention, if interaction with the component in effect accesses an endocytic pathway that entails a cytosolic internalization from the target cell surface. Such candidates are readily assessed for suitability in the invention via an assay in which a cell type that presents on its surface a candidate component is co-incubated in vitro with minicells carrying a ligand that binds the candidate and that also is joined to a fluorescent dye or other marker amenable to detection, e.g., visually via confocal microscopy. (An in vitro assay of this sort is described by MacDiarmid et al., 2007b, in the legend to FIG. 3 at page 436.) Thus, an observed internalization of the marker constitutes a positive indication by such an assay that the tested target cell surface receptor is suitable for the present invention.

In accordance with the invention, the ligand can be any polypeptide or polysaccharide that exhibits the desired specificity or specificities. Preferred ligands are antibodies. In its present use the term "antibody" encompasses an immunoglobulin molecule obtained by in vitro or in vivo generation of an immunogenic response. Accordingly, the "antibody" category includes monoclonal antibodies and humanized antibodies, such as single-chain antibody fragments (scFv), bispecific antibodies, etc. A large number of different bispecific protein and antibody-based ligands are known, as evidenced by the review article of Caravella and Lugovskoy, Curr. Opin. Chem. Biol., 14: 520-28 (2010), which is incorporated here by reference in its entirety. Antibodies useful in accordance with the present disclosure can be obtained by known recombinant DNA techniques.

By way of non-limiting example, therefore, an antibody that carries specificity for a surface component, such as a tumor antigen, can be used to target minicells to cells in a tumor to be treated. Illustrative cell surface receptors in this regard include any of the RTKs epidermal growth factor receptor (EGFR), vascular endothelial growth factor receptor (VEGFR), platelet-derived growth factor receptor (PDGFR) and insulin-like growth factor receptor (IGFR), each of which is highly expressed in several solid tumors, including brain tumors, and folate receptor, which is overexpressed in some pituitary adenomas. Such a bispecific ligand can be targeted as well to mutant or variant receptors, e.g., the IL-13R$\alpha$2 receptor, which is expressed in 50% to 80% of human glioblastoma multiforme tumors, see Wykosky et al., 2008; Jarboe et al., 2007; Debinski et al, 2000; and Okada et al., 1994), but which differs from its physiological counterpart IL4R/IL13R, expressed in normal tissues. See Hershey, 2003. Thus, IL13R$\alpha$2 is virtually absent from normal brain cells. See Debinski and Gibo, 2000. Additionally, tumors that metastasize to the brain may overexpress certain receptors, which also can be suitable targets. For instance, Da Silva et at, 2010, showed that brain metastases of breast cancer expressed all members of the HER family of RTKs. HER2 was amplified and overexpressed in 20% of brain metastases, EGFR was overexpressed in 21% of brain metastases, HER3 was overexpressed in 60% of brain metastases and HER4 was overexpressed in 22% of brain metastases. Interestingly, HER3 expression was increased in breast cancer cells residing in the brain.

Illustrative of candidate target cell surface receptors are members of the receptor tyrosine kinases or "RKTs," a family of transmembrane proteins that undergo constitutive internalization (endocytosis) at a rate similar to that of other integral membrane proteins. See Goh and Sorkin, 2013. The family of RKTs is described by Lemmon and Schlessinger, *Cell,* 141(7): 1117-134 (2010). Exemplary RTKs are ErbB EGFR, ErbB2, ErbB3, ErbB4 Ins InsR, IGF1R, InsRR PDGF PDGFR.alpha., PDGFR.beta., CSF1R/Fms, Kit/SCFR, Fit3/Flk2 VEGF VEGFR1/Fit1, VEGFR2/KDR, VEGFR3/Fit4 FGF FGFR1, FGFR2, FGFR3, FGFR4 PTK7 PTK7/CCK4 Trk TrkA, TrkB, TrkC Ror Ror1, Ror2 MuSK Met, Ron Ax1, Mer, Tyro3 Tie Tie1, Tie2 Eph EphA1-8, EphA10, EphB1-4, EphB6 Ret Ryk DDR DDR1, DDR2 Ros LMR LMR1, LMR2, LMR3 ALK, LTK STYK1 SuRTK106/STYK1.

Another candidate for suitable target cell surface receptors are the family of membrane-associated, high-affinity folate binding proteins (folate receptor), which bind folate and reduced folic acid derivatives and which mediate delivery of tetrahydrofolate to the interior of cells; the family of membrane-bound cytokine receptors that play a role in the internalization of a cognate cytokine, such as IL13; the surface antigens such as CD20, CD33, mesothelin and HM1.24, that are expressed on certain cancer cells and that mediate the internalization of cognate monoclonal antibodies, e.g., rituximab in the instance of CD20; and the family of adhesion receptors (integrins), which are transmembrane glycoproteins that are trafficked through the endosomal pathway and are major mediators of cancer cell adhesion. In one embodiment of the invention, the tumor cell surface receptor comprises an integrin, neuromedin B receptor, bombesin 3 receptor, GRP receptor, bombesin 4 receptor, CCK2/gastrin, melanocortin-1 receptor (MC-1r), neuropeptide Y (NPY) receptor, neutrotensin (NT) receptor, prostate specific membrane antigen (PSMA), somatostatin (SST) receptor, neurokinin 1 receptor (NK1R), chemokine receptor type 4 (CXCR4), vasoactive intestinal peptide (VIP), epidermal growth factor receptor (EGFR), vascular endothelial growth factor receptor (VEGFR), platelet-derived growth factor receptor (PDGFR), insulin-like growth factor receptor (IGFR), or any combination thereof.

According to another embodiment of the invention, the cell surface receptor is an antigen which is uniquely expressed on a target cell in a disease condition, but which remains either non-expressed, expressed at a low level or non-accessible in a healthy condition. Examples of such target antigens which might be specifically bound by a targeting ligand of the invention may advantageously be selected from EpCAM, CCR5, CD19, HER-2 neu, HER-3, HER-4, EGFR, PSMA, CEA, MUC-1 (mucin), MUC2, MUC3, MUC4, MUC5, MUC5, MUC7, BhcG, Lewis-Y. CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, STEAP, mesothelin, A33 Antigen, Prostate Stem Cell Antigen (PSCA), Ly-6; desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGFRVIII, LG, SAS and CD63.

VI. Formulations

The invention includes within its scope compositions, or formulations, comprising minicells having as payloads a combination of one or more of (1) an anti-neoplastic agent, (2) a type I IFN agonist, and/or (3) a type II IFN agonist. In compositions comprising all three components, the anti-neoplastic agent, the type I IFN agonist, and the type II IFN agonist can be comprised in one or more minicells. For example: (a) the anti-neoplastic agent, the type I IFN agonist, and the type II IFN agonist can be comprised within the same minicell; (b) the anti-neoplastic agent and the type I IFN agonist can be comprised within a first minicell, and the type II IFN agonist can be comprised within a second minicell; (c) the anti-neoplastic agent and the type II IFN agonist can be comprised within a first minicell, and the type I IFN agonist can be comprised within a second minicell; or (d) the anti-neoplastic agent can be comprised within a first minicell and the type I IFN agonist and the type II IFN agonist can be comprised within a second minicell, or (e) the anti-neoplastic agent can be comprised within a first minicell, the type I IFN agonist can be comprised within a second minicell and the type II IFN agonist can be comprised within a third minicell.

The invention includes within its scope compositions, or formulations, comprising minicells having as payloads a combination of (1) an anti-neoplastic agent and (2) a type I IFN agonist or a type II IFN agonist. In some embodiments, the anti-neoplastic agent and the type I IFN agonist or the INF II agonist can be comprised in one or more minicells. For example: (a) the anti-neoplastic agent and the type I IFN agonist, can be comprised within the same minicell; (b) the anti-neoplastic agent can be comprised within a first minicell and the type I IFN agonist can be comprised within a second minicell; (c) the anti-neoplastic agent and the type II IFN agonist can be comprised within the same minicell; or (d) the anti-neoplastic agent can be comprised within a first minicell and the type II IFN agonist can be comprised within a second minicell.

In an exemplary embodiment, the compositions disclosed herein comprise the anti-neoplastic agent siPlk1, the interferon type I agonist 60mer double stranded DNA, and/or the interferon type II agonist α-galactosyl ceramide, wherein the siPlk1, the 60mer double stranded DNA, and the α-galactosyl ceramide are comprised within one or more minicells.

In another exemplary embodiment, the compositions disclosed herein comprise the anti-neoplastic agent siRRM1, the interferon type I agonist 60mer double stranded DNA, and/or the interferon type II agonist α-galactosyl ceramide, wherein the siRRM1, the 60mer double stranded DNA, and the α-galactosyl ceramide are comprised within one or more minicells.

In another exemplary embodiment, the compositions disclosed herein comprise the anti-neoplastic agent PNU-159682, the interferon type I agonist 60mer double stranded DNA, and/or the interferon type II agonist α-galactosyl ceramide, wherein the PNU-159682, the 60mer double stranded DNA, and/or the α-galactosyl ceramide are comprised within one or more minicells.

The formulations also optionally comprise a bispecific ligand for targeting the minicell to a target cell. The minicell and ligand may be any of those described herein. Thus, the bispecific ligand of the present invention is capable of binding to a surface component of the minicell and to a surface component of a target mammalian cell.

A formulation comprising minicells, drugs and optionally bispecific ligands of the present invention (that is, a formulation that includes such minicells, drugs and ligands with other constituents that do not interfere unduly with the drug or drug-delivering quality of the composition) can be formulated in conventional manner, using one or more pharmaceutically acceptable carriers or excipients.

Formulations or compositions of the disclosure can be presented in unit dosage form, e.g., in ampules or vials, or in multi-dose containers, with or without an added preservative. The formulation can be a solution, a suspension, or an emulsion in oily or aqueous vehicles, and can contain formulatory agents, such as suspending, stabilizing and/or dispersing agents. A suitable solution is isotonic with the blood of the recipient and is illustrated by saline, Ringer's solution, and dextrose solution. Alternatively, formulations can be in lyophilized powder form, for reconstitution with a suitable vehicle, e.g., sterile, pyrogen-free water or physiological saline. The formulations also can be in the form of a depot preparation. Such long-acting formulations can be administered by implantation (for instance, subcutaneously or intramuscularly) or by intramuscular injection. In some embodiments, administering comprises enteral or parenteral administration. In some embodiments administering comprises administration selected from oral, buccal, sublingual, intranasal, rectal, vaginal, intravenous, intramuscular, and subcutaneous injection.

In some aspects, a minicell-containing composition that includes a therapeutically effective amount of an anti-neoplastic agent is provided. A "therapeutically effective" amount of an anti-neoplastic agent is a dosage of the agent in question, e.g., a siRNA or a super-cytotoxic drug that invokes a pharmacological response when administered to a subject, in accordance with the present disclosure.

In the context of the present disclosure, therefore, a therapeutically effective amount can be gauged by reference to the prevention or amelioration of the tumor or a symptom of tumor, either in an animal model or in a human subject, when minicells carrying a therapeutic payload are administered, as further described below. An amount that proves "therapeutically effective amount" in a given instance, for a particular subject, may not be effective for 100% of subjects similarly treated for the tumor, even though such dosage is deemed a "therapeutically effective amount" by skilled practitioners. The appropriate dosage in this regard also will vary as a function, for example, of the type, stage, and severity of the tumor.

When "therapeutically effective" is used to refer to the number of minicells in a pharmaceutical composition, the number can be ascertained based on what anti-neoplastic agent is packaged into the minicells and the efficacy of that agent in treating a tumor. The therapeutic effect, in this regard, can be measured with a clinical or pathological parameter such as tumor mass. A reduction or reduced increase of tumor mass, accordingly, can be used to measure therapeutic effects.

A. Administration Routes

Formulations of the invention can be administered via various routes and to various sites in a mammalian body, to achieve the therapeutic effect(s) desired, either locally or systemically. Delivery may be accomplished, for example, by oral administration, by application of the formulation to a body cavity, by inhalation or insufflation, or by parenteral, intramuscular, intravenous, intraportal, intrahepatic, peritoneal, subcutaneous, intratumoral, or intradermal administration. The mode and site of administration is dependent on the location of the target cells. For example, tumor metastasis may be more efficiently treated via intravenous delivery of targeted minicells. Primary ovarian cancer may be treated via intraperitoneal delivery of targeted minicells. A combination of routes also may be employed. For example, in metastatic bladder cancer the cytotoxic drug-loaded and receptor-targeted minicells may be administered within the bladder as well as intravenously, and the adjuvant-packaged (receptor-targeted or non-targeted) minicells along with targeted-drug-packaged minicells may be administered intravenously. The in situ administration of targeted, drug-packaged minicells may target bladder surface-exposed tumors, while the full combination of minicells administered intravenously may target tissue-localized tumors and also elicit the anti-tumor immune response.

B. Purity

Minicells of the invention are substantially free from contaminating parent bacterial cells. Thus, minicell-comprising formulations preferably comprise fewer than about 1 contaminating parent bacterial cell per $10^7$ minicells, fewer than about 1 contaminating parent bacterial cell per $10^8$ minicells, fewer than about 1 contaminating parent bacterial cell per $10^9$ minicells, fewer than about 1 contaminating parent bacterial cell per $10^{10}$ minicells, or fewer than about 1 contaminating parent bacterial cell per $10^{11}$ minicells.

Methods of purifying minicells are known in the art and described in PCT/IB02/04632. One such method combines cross-flow filtration (feed flow is parallel to a membrane surface; Forbes, 1987) and dead-end filtration (feed flow is perpendicular to the membrane surface). Optionally, the filtration combination can be preceded by a differential centrifugation, at low centrifugal force, to remove some portion of the bacterial cells and thereby enrich the supernatant for minicells.

Another purification method employs density gradient centrifugation in a biologically compatible medium. After centrifugation, a minicell band is collected from the gradient, and, optionally, the minicells are subjected to further rounds of density gradient centrifugation to maximize purity. The method may further include a preliminary step of performing differential centrifugation on the minicell-containing sample. When performed at low centrifugal force, differential centrifugation will remove some portion of parent bacterial cells, thereby enriching the supernatant for minicells.

Particularly effective purification methods exploit bacterial filamentation to increase minicell purity. Thus a minicell purification method can include the steps of (a) subjecting a sample containing minicells to a condition that induces parent bacterial cells to adopt a filamentous form, followed by (b) filtering the sample to obtain a purified minicell preparation.

Known minicell purification methods also can be combined. One highly effective combination of methods is as follows:

Step A: Differential centrifugation of a minicell producing bacterial cell culture. This step, which may be performed at 2,000 g for about 20 minutes, removes most parent bacterial cells, while leaving minicells in the supernatant;

Step B: Density gradient centrifugation using an isotonic and non-toxic density gradient medium. This step separates minicells from many contaminants, including parent bacterial cells, with minimal loss of minicells. Preferably, this step is repeated within a purification method;

Step C: Cross-flow filtration through a 0.45 μm filter to further reduce parent bacterial cell contamination.

Step D: Stress-induced filamentation of residual parent bacterial cells. This may be accomplished by subjecting the minicell suspension to any of several stress-inducing environmental conditions;

Step E: Antibiotic treatment to kill parent bacterial cells;

Step F: Cross-flow filtration to remove small contaminants, such as membrane blebs, membrane fragments, bacterial debris, nucleic acids, media components and so forth, and to concentrate the minicells. A 0.2 µm filter may be employed to separate minicells from small contaminants, and a 0.1 µm filter may be employed to concentrate minicells;

Step G: Dead-end filtration to eliminate filamentous dead bacterial cells. A 0.45 um filter may be employed for this step; and Step H: Removal of endotoxin from the minicell preparation. Anti-Lipid A coated magnetic beads may be employed for this step.

C. Administration Schedules

In general, the formulations disclosed herein may be used at appropriate dosages defined by routine testing, to obtain optimal physiological effect, while minimizing any potential toxicity. The dosage regimen may be selected in accordance with a variety of factors including age, weight, sex, medical condition of the patient; the severity of the condition to be treated, the route of administration, and the renal and hepatic function of the patient.

Optimal precision in achieving concentrations of minicell and drug within the range that yields maximum efficacy with minimal side effects may require a regimen based on the kinetics of the minicell and drug availability to target sites and target cells. Distribution, equilibrium, and elimination of a minicell or drug may be considered when determining the optimal concentration for a treatment regimen. The dosages of the minicells and drugs may be adjusted when used in combination, to achieve desired effects.

Moreover, the dosage administration of the formulations may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See, e.g., WO 00/67776.

Specifically, the formulations may be administered at least once a week over the course of several weeks. In one embodiment, the formulations are administered at least once a week over several weeks to several months.

More specifically, the formulations may be administered at least once a day for about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or about 31 days. Alternatively, the formulations may be administered about once every day, about once every about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or about 31 days or more.

The formulations may alternatively be administered about once every week, about once every about 2, about 3, about 4, about 5, about 6, about 7, about 8, about 9, about 10, about 11, about 12, about 13, about 14, about 15, about 16, about 17, about 18, about 19 or about 20 weeks or more. Alternatively, the formulations may be administered at least once a week for about 2, about 3, about 4, about 5, about 6, about 7, about 8, about 9, about 10, about 11, about 12, about 13, about 14, about 15, about 16, about 17, about 18, about 19 or about 20 weeks or more.

The formulations may alternatively be administered about twice every week, about twice every about 2, about 3, about 4, about 5, about 6, about 7, about 8, about 9, about 10, about 11, about 12, about 13, about 14, about 15, about 16, about 17, about 18, about 19 or about 20 weeks or more. Alternatively, the formulations may be administered at least once a week for about 2, about 3, about 4, about 5, about 6, about 7, about 8, about 9, about 10, about 11, about 12, about 13, about 14, about 15, about 16, about 17, about 18, about 19 or about 20 weeks or more.

Alternatively, the formulations may be administered about once every month, about once every about 2, about 3, about 4, about 5, about 6, about 7, about 8, about 9, about 10, about 11 or about 12 months or more.

The formulations may be administered in a single daily dose, or the total daily dosage may be administered in divided doses of two, three, or four times daily.

In a method in which minicells are administered before a drug, administration of the drug may occur anytime from several minutes to several hours after administration of the minicells. The drug may alternatively be administered anytime from several hours to several days, possibly several weeks up to several months after the minicells.

More specifically, the minicells may be administered at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 hours before the drug. Moreover, the minicells may be administered at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or about 31 days before the administration of the drug. In yet another embodiment, the minicells may be administered at least about 1, about 2, about 3, about 4, about 5, about 6, about 7, about 8, about 9, about 10, about 11, about 12, about 13, about 14, about 15, about 16, about 17, about 18, about 19 or about 20 weeks or more before the drug.

In a further embodiment, the minicells may be administered at least about 1, about 2, about 3, about 4, about 5, about 6, about 7, about 8, about 9, about 10, about 11 or about 12 months before the drug.

In another embodiment, the minicell is administered after the drug. The administration of the minicell may occur anytime from several minutes to several hours after administration of the drug. The minicell may alternatively be administered anytime from several hours to several days, possibly several weeks up to several months after the drug.

VII. Methods of Treating Cancer

The compositions described herein may be used to treat a subject suffering from a cancer. The method disclosed herein comprises administering to the subject an effective amount of a composition according to the invention, comprising at least one anti-neoplastic agent, an interferon type I agonist, an interferon type II agonist, or a combination of an interferon type I agonist and an interferon type II agonist. The anti-neoplastic agent, the interferon type I agonist, the interferon type II agonist, or the combination of an interferon type I agonist and the interferon type II agonist are comprised in one or more minicells.

In another aspect, the composition used to treat a subject suffering from cancer further comprises a pharmaceutically acceptable carrier.

In another aspect, the methods disclosed herein are useful for treating a subject suffering from a cancer, wherein the subject is a human, a non-human primate, a dog, a cat, a cow, a sheep, a horse, a rabbit, a mouse, or a rat.

In another aspect, the methods disclosed herein are useful for treating a cancer disease. In some embodiment the cancer comprises a lung cancer, a breast cancer, a brain cancer, a liver cancer, a colon cancer, a pancreatic cancer, or a bladder cancer.

In some embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilm's tumor.

In some embodiments, the brain cancer or tumor is selected from the group consisting of brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma.

VIII. Definitions

Technical and scientific terms used herein have the meanings commonly understood by one of ordinary skill in the art to which the present invention pertains, unless otherwise defined. Materials, reagents and the like to which reference is made in the following description and examples are obtainable from commercial sources, unless otherwise noted.

For convenience, the meaning of certain terms and phrases employed in the specification, examples, and appended claims are provided below. Other terms and phrases are defined throughout the specification.

The singular forms "a," "an," and "the" include plural reference unless the context clearly dictates otherwise.

The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

"Individual," "subject," "host," and "patient," used interchangeably herein, refer to any mammalian subject for whom diagnosis, treatment, or therapy is desired. In one preferred embodiment, the individual, subject, host, or patient is a human. Other subjects may include, but are not limited to, cattle, horses, dogs, cats, guinea pigs, rabbits, rats, primates, and mice.

"Cancer," "neoplasm," "tumor," "malignancy" and "carcinoma," used interchangeably herein, refer to cells or tissues that exhibit an aberrant growth phenotype characterized by a significant loss of control of cell proliferation. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue, such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord. The methods and compositions of this invention particularly apply to precancerous, malignant, pre-metastatic, metastatic, and non-metastatic cells.

The terms "treatment," "treating," "treat," and the like refer to obtaining a desired pharmacological and/or physiologic effect in a tumor patient. The effect can be prophylactic in terms of completely or partially preventing tumor or symptom thereof and/or can be therapeutic in terms of a partial or complete stabilization or cure for tumor and/or adverse effect attributable to the tumor. Treatment covers any treatment of a tumor in a mammal, particularly a human. A desired effect, in particular, is tumor response, which can be measured as reduction of tumor mass or inhibition of tumor mass increase. In addition to tumor response, an increase of overall survival, progress-free survival, or time to tumor recurrence or a reduction of adverse effect also can be used clinically as a desired treatment effect.

As used herein, the term "administering" includes directly administering to another, self-administering, and prescribing or directing the administration of an agent as disclosed herein.

As used herein, the phrases "effective amount" and "therapeutically effective amount" mean that active agent dosage or plasma concentration in a subject, respectively, that provides the specific pharmacological effect for which the active agent is administered in a subject in need of such treatment. It is emphasized that an effective amount of an active agent will not always be effective in treating the conditions/diseases described herein, even though such dosage is deemed to be an effective amount by those of skill in the art.

As used herein, the term "active agent" is any small molecular drug, protein, functional nucleic acid, or polynucleic acid encoding a functional nucleic acid that is useful for treating a subject. The active agent can be any of the anti-neoplastic drugs, functional acids, interferon type I agonists or type II agonists described herein.

The phrase "pharmaceutically acceptable" is employed herein to refer to those compounds, materials, compositions, and/or dosage forms which are, within the scope of sound medical judgment, suitable for use in vivo without excessive toxicity, irritation, allergic response, or other problem or complication, commensurate with a reasonable benefit/risk ratio.

The term "endocytosis" encompasses (1) phagocytosis and (2) pinocytosis, itself a category inclusive of (2a) macropinocytosis, which does not require receptor binding, as well as of (2b) clathrin-mediated endocytosis, (2c) caveolae-mediated endocytosis and (2d) clathrin-/caveolae-independent endocytosis, all of which tend to access the late-endosome/lysosome pathway. The interaction between the ligand on a minicell and a mammalian cell surface receptor, the present inventors discovered, activates a particular endocytosis pathway, involving receptor mediated endocytosis (rME) to the late-endosomal/lysosomal compartment. By virtue of such an endocytosis pathway, the present inventors further discovered that the minicells were able to release their payload into the cytoplasm of the target mammalian cell. In the event the payload is an encoding nucleic acid, the nucleic acid not only is not completely degraded in the late-endosomal/lysosomal compartment, but also is expressed in the target mammalian cell.

The following examples are illustrative only, rather than limiting, and provide a more complete understanding of the invention. The examples demonstrate that drug resistant tumor cells can be effectively treated in-vivo by (1) administration of targeted recombinant minicells carrying RNAi sequences designed to reduce or eliminate expression of drug resistance encoding gene(s), and (2) administration of targeted, drug-packaged minicells carrying the drug to which the cancer cells are made sensitive.

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference.

WORKING EXAMPLES

Example 1: Pre-Clinical Studies in Mice

This example showed that minicells (EDVs) provided efficient delivery of chemotherapy drugs and inhibited tumor growth in mice xenograft models. The EDV targeted technology has been tested on mouse xenograft models of various cancers including colon cancer, breast cancer, ovarian cancer, leukaemia, lung cancer, mesothelioma, and uterine cancer. In addition, various targeting moieties were utilized, as EDVs were targeted to tumor cell surface receptors including EGFR, Human epidermal growth factor receptor 2 (HER2), Mesothelin (MSLN), and CD33. Finally, the tested targeted EDVs comprised a wide variety of cytotoxic drugs, including doxorubicin, paclitaxel, monastrol, irinotecan, super-cytotoxic drugs such as PNU-159682, and a novel thymidylate synthase inhibitor (OSI-7904). PNU-159682 is an anthracycline analogue which is thousands of times more cytotoxic than doxorubicin. OSI-7904 is a benzoquinazoline folate analog with antineoplastic activity. As a thymidylate synthase inhibitor, OSI-7904 noncompetitively binds to thymidylate synthase, resulting in inhibition of thymine nucleotide synthesis and DNA replication.

In all cases, tumor stabilisation or regression was observed when using specifically-targeted and drug-packaged EDVs, even with large (>1000 mm$^3$) tumors (see Table 5). Control mice treated with free drug (not packeged in an EDV) showed the expected toxicity of phlebitis and eventually lost weight and died. These toxicities were not observed following repeat administration of EDV-packaged drug.

Surprisingly, even though the concentration of cytotoxic drug delivered via EDVs was up to 8,000 times less than systemic delivery, the cytotoxic drug concentration delivered by EDVs was sufficient to maximise anti-tumor efficacy.

TABLE 5

Summaries of mouse xenograft studies

Figures 5A, 5B:
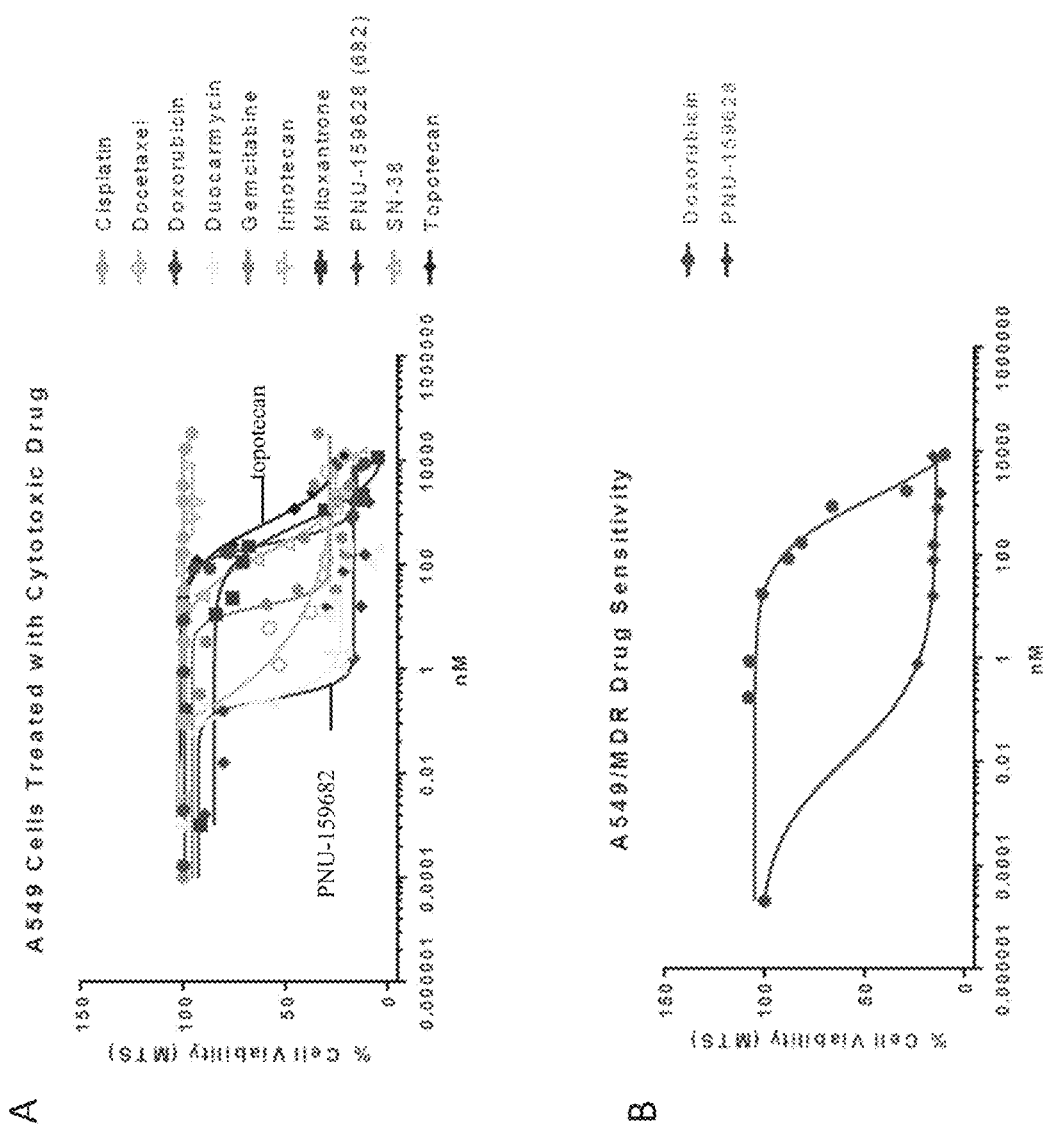
FIGS. 5A-5B shows the cytotoxic effect of the indicated chemotherapy drugs on an A549 lung cancer cell line.
Figures 6A, 6B:
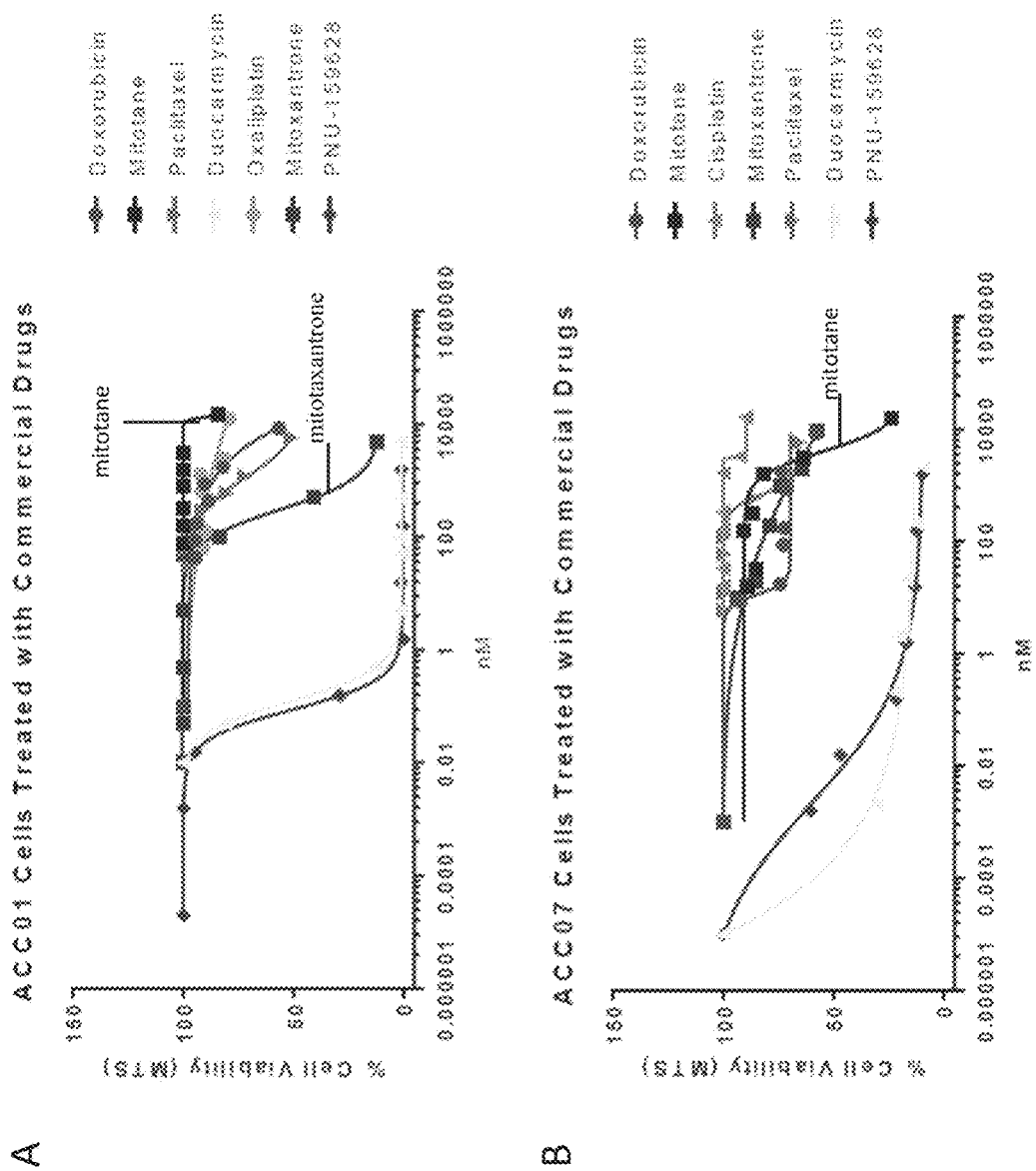
FIGS. 6A-6B shows the effect of the indicated chemotherapy drugs on adreno-cortical cancer cell lines ACC01 (FIG. 6A) and ACC07 (FIG. 6B).
Figure 7:
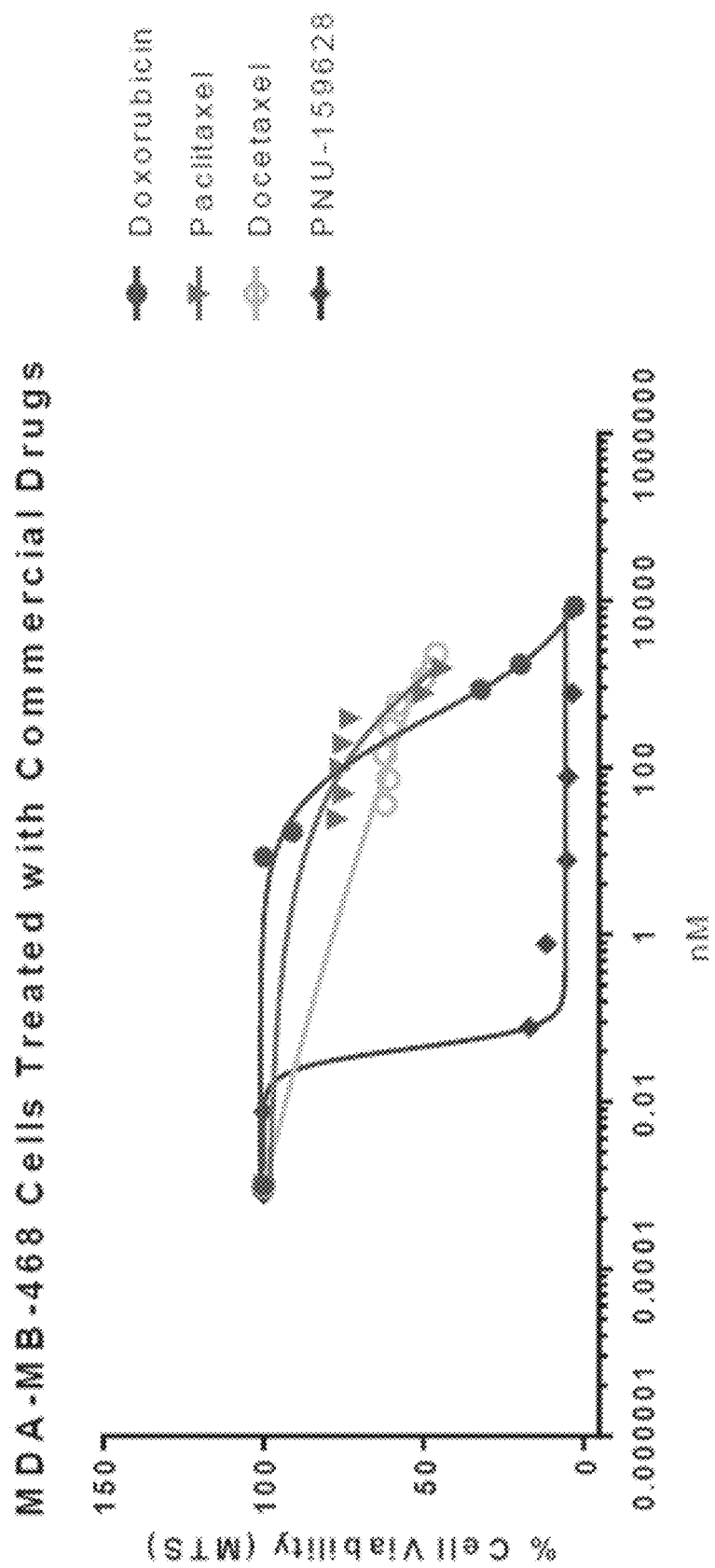
FIG. 7 shows the effect of the indicated chemotherapy drugs on the MDA-MB-468 breast cancer cell line.

| Type of EDV, Dose | Human cancer xenograft | Results | Reference |
|---|---|---|---|
| $^{EGFR}EDVs_{Dox/Pac}$, $1 \times 10^8$ per dose | Breast cancer MDA-MB-468 | Tumor stabilisation or regression | MacDiarmid et al., 2007b; FIG. 4A and 4B |
| $^{EGFR}EDVs_{Dox}$, $1 \times 10^8$ per dose | Lung cancer A549 | Tumor stabilisation or regression | MacDiarmid et al., 2007b; FIG. 4D |
| $^{CD33}EDVs_{Dox}$, $5 \times 10^8$ per dose | Promyelocytic leukaemia HL-60 | Tumor stabilisation or regression | MacDiarmid et al., 2007b; FIG. 5A |
| $^{HER2}EDVs_{Dox}$, $1 \times 10^8$ per dose | Ovarian cancer SKOV3 | Tumor stabilisation or regression | MacDiarmid et al., 2007b; FIG. 5B |
| $^{EGFR}EDVs_{Dox}$, $1 \times 10^8$ per dose (comparison with liposomal doxorubicin) | Breast cancer MDA-MB-468 | Tumor stabilisation or regression | MacDiarmid et al., 2007b; FIG. 5C |
| $^{EGFR}EDVs_{Dox}$, dose escalation | Breast cancer MDA-MB-468 | Tumor stabilisation or regression | MacDiarmid et al., 2007b; FIG. 5D |
| $^{EGFR}EDVs_{Dox}$, $1 \times 10^8$ per dose (stability comparison of fresh vs reconstituted EDVs) | Breast cancer MDA-MB-468 | Tumor stabilisation or regression | MacDiarmid et al., 2007b; FIG. 5E |
| $^{EGFR}EDVs_{Mon}$, $1 \times 10^8$ per dose | Breast cancer MDA-MB-468 | Tumor stabilisation or regression | MacDiarmid et al, 2007a; FIG. 1A |
| $^{EGFR}EDVs_{OSI-794}$, $1 \times 10^8$ per dose | Colon cancer HT29 | Tumor stabilisation or regression | MacDiarmid et al., 2007a; FIG. 1B |
| $^{EGFR}EDVs_{Dox/Pac}$, $1 \times 10^9$ per dose | Colon cancer HCT-116 | Tumor stabilisation or regression | MacDiarmid et al., 2007a; FIG. 4a |
| $^{EGFR}EDVs_{Irino}$, $1 \times 10^9$ per dose ($+/-^{EGFR}EDVs_{shMDR1}$)* | Colon cancer Caco-2 | Tumor growth slowed (stabilisation/regression with $^{EGFR}EDVs_{shMDR1}$) | MacDiarmid et al., 2009; FIG. 5a |
| $^{EGFR}EDVs_{Dox}$, $1 \times 10^9$ per dose ($+/-^{EGFR}EDVs_{shMDR1}$)* | Uterine cancer MES-SA | Tumor growth slowed (stabilisation/regression with $^{EGFR}EDVs_{shMDR1}$) | MacDiarmid et al., 2009; FIG. 6a |
| $^{EGFR}EDVs_{Dox}$, $1 \times 10^9$ per dose | Breast cancer MDA-MB-468 | Tumor stabilisation or regression | Taylor et al., *MAbs*, 7(1): 53-65 2015 (2015); FIG. 7 |
| $^{MSLN}EDVs_{Dox}$, $1 \times 10^9$ per dose | Mesothelioma H226 | Tumor stabilisation or regression | Alfaleh et al., *PLoS One*, 12: 1-21 (2017); FIG. 5a |

Example 2: Pre-Clinical Studies in Dogs

This example showed that minicells (EDVs) loaded with drugs could be safely administered to dogs.

Canine toxicology studies in dogs with a range of endogenous tumors (n=41) showed that up to 98 doses of targeted and drug-packaged EDVs could be safely administered to a single animal over the course of more than 2 years. There were mild spikes in temperature (increases of up to 1° C.) with concomitant elevation of Interleukin-6 (IL-6), Interleukin-10 (IL-10), and Tumor necrosis factor alpha (TNF-α), following doses in some dogs, however this was not associated with any significant adverse events.

Furthermore, pre-clinical studies in dogs showed that CD3-targeted, doxorubicin loaded EDVs can inhibit tumor growth. Two dogs with advanced non-Hodgkin's lymphoma were treated with CD3-targeted, doxorubicin-packaged EDVs, and both demonstrated marked tumor regression as was evident by highly significant reductions in lymph node size. MacDiarmid et aL, 2007b. Over 60% of dogs with hemangiosarcoma showed tumor stabilisation or regression when treated with CD33-targeted and doxorubicin-packaged EDVs.

In another study of dogs (n=17) with late-stage brain cancer, the animals were treated with EGFR-targeted EDVs loaded with doxorubicin. MacDiarmid et al., 2016. Up to 98 repeat doses were administered for a single dog (with 11 dogs receiving >20 doses) at a concentration of $1 \times 10^{10}$ $^{EGFR}$minicells$_{Dox}$ with no signs of toxicity observed.

The objective response rate was 23.53% (4 of 17 dogs; 95% confidence interval, 6.8-49.8%). Of the 15 dogs evaluated for tumor response, 2 had complete responses (CR) to therapy, 2 had partial responses (PR) to therapy (90-98.95% reduction in tumor volume), 10 had stable disease (SD), and 1 showed progressive disease (PD).

Bio-distribution studies using $^{123}$Iodine radio-labelled, EGFR-targeted EDVs in two dogs with brain cancer showed localisation of targeted EDVs to brain tumors, suggesting that EDVs can circumvent the blood-brain barrier to enter the tumor environment. Some localisation in the gastrointestinal track suggests excretion via the faeces.

Example 3: Pre-Clinical Studies in Monkeys

This example showed that minicell (EDV) technology is well tolerated by monkeys.

Three rhesus monkey trials were performed to assess the toxicity of empty EDVs (up to $2 \times 10^{10}$ per dose), EGFR-targeted, doxorubicin-loaded EDVs (up to $2 \times 10^{10}$ per dose), and EGFR-targeted, paclitaxel-loaded EDVs (up to $1 \times 10^{11}$ per dose). Monkeys were treated with EDVs once weekly for 5 weeks (35 day repeat dose testing).

As seen with dogs, there were transient spikes in temperature (increases of up to 1° C.) with concomitant elevation of IL-6 post-dose. The inflammatory marker C-reactive protein was also increased at these times, however no significant toxicities or adverse events were observed. A mild elevation of TNF-α was seen over the course of treatment with EGFR-targeted, doxorubicin-loaded EDVs only. A total of 72 monkeys have been safely administered with EDV technology.

Example 4: Inflammatory and Immunological Responses in the Pre-Clinical Studies This example showed that only minor inflammatory responses were observed in the pre-clinical mice studies (Example 1), the pre-clinical dog studies (Example 2), and the pre-clinical monkeys study (Example 3). These responses resolved as quickly as 4 hours post-dose. No other significant changes in haematological or biochemical parameters were observed. Animals remained healthy in appearance and behaviour throughout the course of treatments.

Formation of anti-product antibodies was evaluated in canine studies and in the monkey trials. The immune responses considered with respect to administration of targeted EDVs were:

Serum antibody responses to the EDV-surface exposed immunodominant antigen being the O-polysaccharide component of LPS (IgG or IgM responses). Anti-O-polysaccharide antibody responses are T-cell independent and do not exhibit memory responses.

Serum antibody responses to the mouse IgG monoclonal antibody used in construction of the BsAb to target the EDVs to tumor cell surface receptors (e.g., EGFR).

In dogs with hemangiosarcoma or brain cancer, the serum anti-LPS IgG titres rose to a mean of approximately 10,000 by Dose 3-4 of targeted and doxorubicin-packaged EDVs. Subsequent dosing did not result in any further elevation of titre. Anti-LPS IgG titres in the 3 monkey trials (healthy animals) generally showed a mild rise over the first 2-3 doses before plateauing. The response was largely dose-dependent, rising to a maximum titre of just over 100 for the highest dose levels of $^{EGFR}EDV_{Dox}$. These are considered weak antibody responses since anti-O-polysaccharide antibody titres expected in vaccines against Gram-negative bacteria are generally in the millions.

Anti-LPS IgM titre responses in monkey trials were also mild, rising to just over 100 on treatment with $^{EGFR}EDV_{Dox}$ and up to 1,000 on treatment with non-targeted EDVs. Titres were not augmented further after Doses 3-4.

Immunogenic responses to monoclonal antibodies used in construction of the BsAbs were also measured in monkey studies, with a mild rise in titre observed in response to the EGFR antibody in monkeys treated with EGFR-targeted EDVs (mouse IgG). These results suggest that administration of BsAb-targeted, drug-packaged EDVs may not elicit significant anti-LPS immune responses that could prevent the effectiveness of subsequent doses. This is particularly relevant for cancer patients, whose immune system is likely to be compromised, as it suggests that repeat dosing is likely to be a viable treatment option.

Example 5: First-in-Man, Phase 1 Clinical Trial Evaluating Erbitux-Targeted, Paclitaxel-Packaged EDVs ($^{EGFR(Erb)}EDVs_{Pac}$) in Advanced Solid Tumors This example showed the promising result of using minicells (EDVs) to deliver Paclitaxel (Taxol®) to advanced solid tumors.

In this trial, it was shown that ERBITUX (cetuximab)-Targeted, Paclitaxel-Packaged EDVs are well tolerated in human patients, but a significant number of the patients had to end the study because of adverse events or dose-limiting toxicity in a clinical trial. Furthermore, although this treatment strategy achieved stabilization of the disease, none of the patients in this study exhibited a partial or complete response to the treatment. The results of this trial data are published in Solomon et al., 2015.

The First-in-Man trial was designed as a dose escalation study to determine the safety, tolerability and maximum tolerated dose or recommended phase 2 dose of EGFR-targeted, paclitaxel-loaded EDVs ($^{EGFR(Erb)}EDVs_{Pac}$). Note that the antibody used for targeting EDVs to EGFR is based on the Erbitux sequence. Other objectives were to assess immune and inflammatory responses to IV administered $^{EGFR(Erb)}EDVs_{Pac}$, and to assess response to therapy according to RECIST criteria.

The study was conducted at 3 oncology clinics in Melbourne, Australia, and was registered with the Australian New Zealand Clinical Trials Registry (number ACTRN12609000672257). The final study report is available and the study has been published in Solomon et al, 2015.

Patients were adults of at least 18 years of age with advanced epithelial malignancies for which standard curative treatment was not available.

$^{EGFR(Erb)}EDVs_{Pac}$ was administered weekly as a 20-minute IV infusion in cycles consisting of 5 weeks of treatment. This was followed by a treatment-free week in which patients underwent radiological assessment of their tumors with MRI, CT, and or FDG-PET. Patients could continue to receive further cycles of treatment if the tumor remained stable or was responding to treatment, or if they were deriving clinical benefit from the therapy, and they did not experience any dose limiting toxicities (DLTs) or other adverse events (AEs) requiring discontinuation of treatment.

A total of 236 doses were delivered over 7 dose levels: $1 \times 10^8$, $1 \times 10^9$, $3 \times 10^9$, $1 \times 10^{10}$, $1.5 \times 10^{10}$, $2 \times 10^{10}$ and $5 \times 10^{10}$ EGFR(Erb) targeted EDVs comprising Paclitaxel per dose. Twenty-two of the 28 patients completed at least 1 full cycle of treatment (5 weekly doses), with one patient receiving 45 doses over 9 complete cycles (approximately 14 months). No treatment-related deaths occurred. The maximum tolerated dose was identified as $1 \times 10^{10}$ $^{EGFR(Erb)}EDVs_{Pac}$, with significant toxicities observed above this dose level, particularly in the form of prolonged fever and transient elevation of liver function tests (LFT). The treatment was generally well tolerated with acceptable safety findings in the indicated population.

A summary of the clinical study and findings is presented in Table 6 below.

TABLE 6

Summary of clinical data - $^{EGFR(Erb)}EDVs_{Pac}$

| | | Number of Patients | Percent |
|---|---|---|---|
| Dose levels | $1 \times 10^8$ | 6/28 | 21.4% |
| | $1 \times 10^9$ | 6/28 | 21.4% |
| | $3 \times 10^9$ | 4/28 | 14.3% |
| | $1 \times 10^{10}$ | 6/28 | 21.4% |
| | $1.5 \times 10^{10}$ | 3/28 | 10.7% |
| | $2 \times 10^{10}$ | 1/28 | 3.6% |
| | $5 \times 10^{10}$ | 2/28 | 7.1% |
| Length of treatment[1] | At least 1 full cycle | 22/28 | 78.6% |
| | <1 complete cycle | 6/28 | 21.4% |

TABLE 6-continued

Summary of clinical data - $^{EGFR(Erb)}$EDVs$_{Pac}$

|  |  | Number of Patients | Percent |
|---|---|---|---|
| Adverse events | All treatment-related | 24/28 | 85.7% |
|  | Rigors | 16/28 | 57.1% |
|  | Pyrexia | 13/28 | 46.4% |
|  | Serious adverse events | 5/28 | 17.9% |
|  | Dose limiting toxicities | 8/28 | 28.6% |
|  | Withdrawal due to AE | 4/28 | 14.3% |
| Response[2] | Stable disease | 10/22 | 45.5% |
|  | Progressive disease | 12/22 | 55.5% |

[1]One full cycle consisted of 5 weekly doses.
[2]Response was evaluated at completion of 1 full cycle of treatment.

The most common adverse events that were at least probably related to study treatment were low-grade pyrexia (fever) and rigor (chills), experienced in up to 60% of patients (Grade 1-2 severity). Most patients experienced mild transient elevations of the cytokines IL-6, IL-8 and IL-10 at 4 hours post-dose. Levels generally returned to baseline within 24 hours of receiving the dose. This is consistent with a minor inflammatory response to treatment.

Five patients experienced treatment-related adverse events that were considered serious, and 8 patients experienced dose limiting toxicity or adverse events that that required dose reduction. These events are summarised in Table 7 and described in the narrative below.

TABLE 7

Serious adverse events or dose limiting toxicities

| Adverse events | Number of patients | Percent | Serious | DLT |
|---|---|---|---|---|
| Musculoskeletal and connective tissue disorders | | | | |
| Arthritis reactive | 1/28 | 3.6% | Y | Y |
| Nervous system disorders | | | | |
| Syncope | 1/28 | 3.6% | Y | N |
| Metabolism and nutrition disorders | | | | |
| Hypophosphatemia | 1/28 | 3.6% | N | Y |
| Immune system disorders | | | | |
| Cytokine release syndrome[1] | 1/28 | 3.6% | Y | N |
| Investigations | | | | |
| Elevated liver function tests (ALT, AST) | 5/28 | 17.9% | 2* | 2* |
| General disorders and administration site conditions | | | | |
| Pyrexia | 2/28 | 7.1% | Y | N |
| Vascular disorders | | | | |
| Hypotension | 1/28 | 3.6% | Y | Y |

One patient at the $1 \times 10^8$ dose level experienced elevated LFTs meeting the DLT criteria. This event was not considered serious, and the definition of DLT was amended for subsequent dose levels. Four patients at dose levels above the MTD experienced elevated LFTs not meeting the amended DLT criteria, however these patients also experienced serious treatment-associated clinical symptoms (pyrexia, rigors, nausea, vomiting) and the safety committee decided on dose reduction.

Three patients were recruited into the first dose level, $1 \times 10^8$ $^{EGFR(Erb)}$EDVs$_{Pac}$. One patient experienced a grade 3 drop in phosphate levels after 3 of his 5 doses. In each case the levels returned to normal by 24 hours post-dose, and there were no clinical symptoms. Another patient experienced asymptomatic grade 3 elevations in the liver enzymes alanine transaminase (ALT) and aspartate transaminase (AST) at 4 hours post-Dose 3, which returned to baseline by the next dose. These events met the protocol's original definition of dose limiting toxicity (DLT), and the ongoing patients' doses were reduced to $5 \times 10^7$ $^{EGFR(Erb)}$EDVs$_{Pac}$, with one patient receiving a total of 45 doses over the study duration. A further 3 patients were recruited to receive $1 \times 10^8$ $^{EGFR(Erb)}$EDVs$_{Pac}$, and no drug related adverse events were reported by these 3 individuals. The protocol's definition of DLT was amended to exclude biochemical abnormalities that resolved within 7 days of treatment.

The dose was escalated to $1 \times 10^9$ $^{EGFR(Erb)}$EDVs$_{Pac}$. Two days after the second dose one patient experienced severe joint pain. This was accompanied by a significant rise in the cytokine interferon-suggesting a viral infection. The patient was admitted for observation and was later diagnosed with reactive arthritis, which was classed as a serious adverse event (SAE). After some consideration the safety committee decided to proceed cautiously and defined this event as a DLT. Therefore, this cohort was also extended to 6 patients. No other patients on the trial experienced similar events. At the completion of the first cycle the safety data supported escalating the dose further.

A cohort of three patients was recruited to the next dose level, $3 \times 10^9$ $^{EGFR(Erb)}$EDVs$_{Pac}$. One patient was withdrawn after receiving only 1 dose due to rapidly progressive disease, and subsequently died as a result of disease. A fourth patient was recruited at the same dose level. The patients all tolerated this dose without any major concerns and the safety data supported escalating the dose further. One patient in this cohort achieved stabilized disease after the first cycle and completed two cycles with 10 doses in total. One patient received only 4 of 5 doses due to disease infiltration of his bone marrow.

A cohort of three patients was recruited to the next dose level, $1 \times 10^{10}$ $^{EGFR(Erb)}$EDVs$_{Pac}$. The patients tolerated this dose level without any major concerns and at the completion of cycle 1 the safety data supported escalating the dose further. Two of the three patients achieved stabilized disease and completed three and five cycles of 15 and 25 doses respectively.

Two patients were recruited to the next dose level, $5 \times 10^{10}$ $^{EGFR(Erb)}$EDVs$_{Pac}$. They received one dose at this level and both experienced a grade 3-4 rise in the liver enzymes ALT and AST. These changes were transient and as such did not meet the protocol's amended definition of a DLT, however, as the patients experienced other AEs such as fever, rigors, and nausea (in one case resulting in hospitalisation for a SAE), the decision was made to reduce the dose level to $1 \times 10^{10}$ $^{EGFR(Erb)}$EDVs$_{Pac}$. These patients also experienced considerable elevation of the inflammatory markers IL-6, IL-8, IL-10 and TNF-α. One of these two patients went on to achieve stabilized disease and completed two full cycles following dose reduction.

To identify the maximum tolerate dose (MTD) one patient was recruited to the intermediate dose level of $2 \times 10^{10}$ $^{EGFR(Erb)}$EDVs$_{Pac}$. The patient received one dose at this level and similarly experienced grade 3-4 transient elevations in ALT and AST, with fever, rigors, nausea and vomiting, and elevation of inflammatory markers. Clinically significant elevations in lactate dehydrogenase (LDH) and gamma glutamyltransferase (GGT) were also observed. Again, though these parameters did not meet the protocol's amended definition of a DLT, the elevated liver enzymes were considered to be SAEs, and it was judged clinically appropriate to reduce the dose to $1 \times 10^{10}$ $^{EGFR(Erb)}EDVs_{Pac}$. This patient achieved stabilized disease and completed four cycles receiving 19 doses.

In a further attempt to identify the MTD, three patients were recruited to the intermediate dose level of $1.5 \times 10^{10}$ $^{EGFR(Erb)}EDVs_{Pac}$. One of these patients received their first dose without any adverse reaction however they did not continue treatment due to rapidly progressive disease. Another patient experienced grade 3 hypotension, which was considered a dose limiting serious adverse event, and hence their dose level was reduced to $5 \times 10^9$ $^{EGFR(Erb)}EDVs_{Pac}$. The final patient in this cohort experienced a grade 3 rise in AST with treatment-associated symptoms (fever, rigors, vomiting) after their first dose, as well as elevation of inflammatory markers, and subsequent doses were reduced to $1 \times 10^{10}$ $^{EGFR(Erb)}EDVs_{Pac}$.

It was concluded, therefore, that the MTD for $^{EGFR(Erb)}EDVs_{Pac}$ was a dose level of $1 \times 10^{10}$ and a further 3 patients were recruited to this dose level. One patient was withdrawn from the study after one dose due to presumed cytokine release syndrome. The patient had a pre-existing cough and experienced occasional episodes of syncope due to a supraclavicular mass pressing on the brachiocephalic veins. Between 2-4 hours post-dose the patient became febrile, began coughing, and experienced 3-4 episodes of syncope witnessed by staff. The patient was admitted for observation and diagnosed with cytokine release syndrome, although no increase in IFN-γ was detected. The patient experienced elevation of IL-6, IL-8 and IL-10, similar to that observed in other patients at or above this dose level, which likely represents an inflammatory response to the bacterial component of the drug product rather than typical cytokine release syndrome. While this incident did represent an SAE, the safety committee decided this did not meet the DLT criteria due to pre-existing disease involvement. The remaining two patients completed the first cycle of treatment without any major concerns.

No deaths resulted from treatment-emergent adverse events. Overall the treatment was well tolerated and there are no particular safety concerns for the intended target population.

Antibodies to *Salmonella typhimurium* (anti-LPS) and Erbitux at screening were negative in all patients. All patients, with the exception of one, developed positive *Salmonella* antibody titres following treatment with the $^{EGFR(Erb)}EDVs_{Pac}$ (27/28=96%). Anti-LPS antibody titres reached a peak by Dose 3 (Day 15) and were maintained at that level despite repeat dosing. No patients developed positive Erbitux antibody titres.

The 22 patients who completed cycle 1 were evaluated for tumor response. The best response observed was stable disease (SD) (no patients achieved a partial or complete response according to RECIST criteria). Stable disease was observed in 10/22 (45.5%) of patients at the end of cycle 1, with 12/22 (55.5%) demonstrating progressive disease (PD). One patient in dose level 1 completed nine full treatment cycles, her disease being alternately stable and progressive from the end of Cycle 4. Hers was the longest time to development of PD, 197 days.

In conclusion, the first in man study demonstrated that EDVs packaged with paclitaxel are well tolerated and 45.5% of the patients exhibit disease stabilization. This example also demonstrates that it is desirable to improve cancer treatment strategies to improve survival and disease response.

Example 6: Phase 1 Clinical Trial Evaluating EGFR-Targeted, Doxorubicin-Packaged EDVs ($^{EGFR(V)}EDVs_{Dox}$) in Recurrent Glioblastoma This is example showed that treatment with EGFR-Targeted, Doxorubicin-Packaged minicells (EDVs) was well tolerated in patients suffering from Recurrent Glioblastoma. 50% of the patients exhibited stabilization of the disease, but no patients experienced partial or complete response. Whittle et al., *J. Clin. Neurosci.*, 22(12): 1889-1894 (2015).

The Recurrent glioblastoma trial was designed as a dose escalation study to determine the safety, tolerability and maximum tolerated dose or recommended phase 2 dose of EGFR-targeted, doxorubicin-loaded EDVs ($^{V}EDVs_{Dox}$). Note that the antibody used for targeting EDVs to EGFR is the same as the antibody for the current protocol (Vectibix-based sequence). Other objectives were to assess immune and inflammatory responses to IV administered $^{V}EDVs_{Dox}$, and to assess response to therapy according to Response Assessment in Neuro-Oncology (RANO) criteria.

The study began on 5 Feb. 2013 and was concluded on 26 Jun. 2014. It was conducted at 4 oncology clinics in Sydney and Melbourne, Australia, and was registered with the Australian New Zealand Clinical Trials Registry (number ACTRN12613000297729). A final clinical study report is available. The study has been published based on draft listings in Whittle et al., *J. Clin. Neurosci.*, 22(12): 1889-1894 (2015).

Patients were adults of at least 18 years of age with pathologically documented and definitively diagnosed recurrent World Health Organization (WHO) Grade IV glioblastoma, who had experienced disease recurrence or progression following receipt of standard of care therapy (including maximum safe surgical resection, standard adjuvant radiation/temozolomide, and maintenance temozolomide treatment).

$^{V}EDVs_{Dox}$ was administered weekly as a 20-minute IV infusion in cycles consisting of 8 weeks of treatment. At the end of each cycle, patients underwent radiological assessment of their tumors with magnetic resonance imaging (MRI). Patients could continue to receive further cycles of treatment if the tumor remained stable or was responding to treatment, or if they were deriving clinical benefit from the therapy, and they did not experience any DLTs or other AEs requiring discontinuation of treatment.

A total of 197 doses were delivered over 3 dose levels: $2 \times 10^9$, $5 \times 10^9$ and $8 \times 10^9$ $^{V}EDVs_{Dox}$ per dose. Eight of the 14 patients completed at least 1 full cycle of treatment (8 weekly doses), with one patient receiving 47 doses over almost 6 complete cycles (approximately 12 months). No treatment-related deaths occurred, and no patients experienced a dose limiting toxicity or other adverse events requiring discontinuation of treatment. A summary of the clinical study and findings is presented in Table 8 below.

TABLE 8

Summary of clinical data - $^{EGFR(V)}EDVs_{Dox}$

|  |  | Number of Patients | Percent |
|---|---|---|---|
| Dose levels | $2 \times 10^9$ | 3/14 | 21.4% |
|  | $5 \times 10^9$ | 3/14 | 21.4% |
|  | $8 \times 10^9$ | 8/14 | 57.1% |
| Length of treatment[1] | At least 1 full cycle | 8/14 | 57.1% |
|  | <1 complete cycle | 6/14 | 42.9% |

TABLE 8-continued

Summary of clinical data - $^{EGFR(V)}EDVs_{Dox}$

| | | Number of Patients | Percent |
|---|---|---|---|
| Adverse events | All treatment-related | 13/14 | 92.9% |
| | Pyrexia | 7/14 | 50.0% |
| | Nausea | 6/14 | 42.9% |
| | Rigor | 6/14 | 42.9% |
| | Serious adverse events | 2/14 | 14.3% |
| | Dose limiting toxicities | 0/14 | 0.0% |
| | Withdrawals due to AEs | 0/14 | 0.0% |
| Best response[2] | Stable disease | 3/6 | 50.0% |
| | Progressive disease | 3/6 | 50.0% |
| Survival[3] | >5 months | 8/8 | 100.0% |
| | ≤5 months | 0/8 | 0.0% |
| | Percentage survival[4] | 3/8 | 37.5% |

[1]One full cycle consisted of 8 weekly doses.
[2]For patients who completed at least 1 cycle of treatment.
[3]Median historical survival for recurrent glioblastoma is approximately 5 months.
[4]Number and percentage of patients alive at 2 years.

The most common adverse events that were at least probably related to the study treatment were low-grade pyrexia (fever), nausea, and rigor (chills), experienced in up to 50% of patients (generally Grade 1-2 severity). Most patients experienced mild transient elevations of the cytokines IL-6, IL-8, IL-10, and TNF-α at 3 hours post-dose. Levels generally returned to baseline within 24 hours of receiving the dose. This is consistent with a minor inflammatory response to treatment.

Five patients experienced treatment-related AEs of Grade 3 or higher severity according to the National Cancer Institute's Common Terminology Criteria for Adverse Events (NCI-CTCAE). These events are summarised in Table 9 below and described in the narrative below.

TABLE 9

Grade 3 or higher treatment-related adverse events (AE) to $^{V}EDVs_{Dox}$

| Adverse events | Number of patients (N = 14) | Percent | Serious |
|---|---|---|---|
| Total patients with ≥Grade 3 severity AEs | 5 | 35.7 | |
| Blood and lymphatic system disorders | 1 | 7.1 | |
| Lymphopenia | 1 | 7.1 | |
| Metabolism and nutrition disorders | 2 | 14.3 | |
| Hypophosphatemia | 2 | 14.3 | |
| Investigations | 1 | 7.1 | |
| Alanine aminotransferase increased | 1 | 7.1 | |
| Aspartate aminotransferase increased | 1 | 7.1 | |
| Gamma-glutamyltransferase increased | 1 | 7.1 | |
| Musculoskeletal and connective tissue disorders | 1 | 7.1 | |
| Generalised muscle weakness | 1 | 7.1 | Yes |
| Vascular disorders | 1 | 7.1 | |
| Hypotension | 1 | 7.1 | Yes |

Two patients experienced adverse events of ≥Grade 3 severity that were considered serious. One patient at the $5 \times 10^9$ dose level was hospitalised in the evening following Dose 2 of Cycle 1 for a serious adverse event of Grade 3 body weakness accompanied by Grade 1 fever. This was not considered a dose limiting toxicity as the patient was positive for anti-product antibodies (antibodies to the Salmonella LPS component of the EDV) at study enrollment. This patient went on to receive 2 further doses of treatment with no repetition of the event.

Another patient at the $8 \times 10^9$ dose level experienced a serious adverse event of Grade 3 symptomatic hypotension 4 hours post-Dose 1 of Cycle 1, which resulted in hospitalisation for IV hydration. This was not considered a DLT as it was likely attributable to an E. Coli urinary tract infection, for which the patient was treated. The patient received 3 subsequent additional doses of study drug.

Three patients experienced an adverse event of ≥Grade 3 severity that were not considered serious. One patient experienced Grade 3 increases in liver enzymes after some doses. These were not considered dose limiting toxicity or serious adverse events as they were asymptomatic and transient, returning to baseline in between doses. Two patients experienced Grade 3 hypophosphatemia, and in one instance this was accompanied by Grade 4 lymphopenia. These were also not considered dose limiting toxicity or serious adverse events as they were transient and did not require therapeutic intervention.

Overall the treatment was well tolerated and there are no particular safety concerns for the intended target population.

To evaluate immune response to the EDV treatment, antibodies to Salmonella were assessed at screening. Thirteen of 14 patients (93%) were negative for Salmonella antibodies at screening. One patient assigned to dose Level 2 was positive at screening. All patients showed an initial rise in antibody titre through to dose 3. The titres were maintained with no further augmentation over subsequent doses, despite one patient receiving a total of 47 doses. No patient developed antibodies to Vectibix.

To evaluate efficacy, eight patients who completed Cycle 1 were evaluated for tumor response. No patient experienced complete or partial remission, however 50% demonstrated stable disease and no patient experience disease progression. One patient was reported to have stable disease for the whole duration of study, receiving almost 6 full cycles of treatment (approximately 12 months).

The eight patients who completed at least 1 full cycle of treatment were followed for survival. All 8 patients survived beyond the median historical survival of 5-7 months, with a median OS of 15.1 months (range 9.1 to >18.4). Four subjects were alive at last contact and were censored at this time. Two of these (14.3%) who completed at least 1 cycle of treatment survived for >18 months.

In conclusion, the treatment for recurrent glioblastoma with EGFR-Targeted, Doxorubicin-Packaged EDVs showed promising results with few adverse events and 50% of the patients experienced stabilization of the disease. However, there is a need for improved treatment strategies.

Example 7: Phase 1 Clinical Trial Evaluating EGFR-Targeted EDVs Packaged with a MicroRNA-16 Mimic ($^{EGFR(V)}EDVs_{miRNA16a}$) in Mesothelioma This example showed that EGFR-Targeted EDVs Packaged with a MicroRNA-16 gave partial response in one mesothelioma patient out of 16 patients tested for efficacy; whereas 62.5% of the patients experienced stabilized disease, and 31.3% of the patients experienced progressive disease. The trial data are published in van Zandwijk et al., Lancet Oncol., 18(10): 1386-1396 (2017) and Kao et al., Am. J. Respir. Crit. Care Med., 191(12): 1467-1469 (2015). This treatment strategy was generally well tolerated.

$^V$EDVs$_{miRNA16a}$ was evaluated in an open-label, multi-centre, exploratory Phase 1 study in subjects with recurrent malignant pleural mesothelioma (MPM). The primary end points of the trial were to establish the maximum tolerated dose and DLTs of $^V$EDVs$_{miRNA16a}$, to evaluate the effect of multiple dosing, and to detect early signs of efficacy with $^V$EDVs$_{miRNA16a}$. Note that the antibody used for targeting EDVs to EGFR was the same as the antibody for the current protocol (Vectibix-based sequence). Secondary endpoints of the trial were to assess the quality of life in patients receiving $^V$EDVs$_{miRNA16a}$ and to monitor changes in Eastern Cooperative Oncology Group (ECOG) performance status and pulmonary function parameters during treatment. Exploratory endpoints evaluated changes in immune and cytokine markers during treatment.

To be eligible, patients must have had histological or cytological documentation of MPM with evidence of EGFR expression in their tumor tissue. Patients included men and women aged 18 years or older with an ECOG performance status of 0 or 1 and a life expectancy of at least 3 months. Patients must have displayed disease progression during or following the administration of standard $1^{st}$ or $2^{nd}$ line therapy regimens and were required have adequate bone marrow, liver and renal function.

$^V$EDVs$_{miRNA16a}$ was administered weekly or twice weekly as a 20-minute IV infusion in cycles consisting of 8 weeks of treatment. At the end of each cycle, patients underwent radiological assessment of their tumors. Tumor response was assessed according to the modified response evaluation criteria in solid tumors (RECIST) criteria. Spirometry, FDG-PET scan and CT scans were used to assess disease extent.

The trial was initiated on 2 Oct. 2014 at three oncology clinics in Sydney, Australia, and was concluded on 24 Nov. 2016. The study was registered with the Australian New Zealand Clinical Trials Registry (number ACTRN 12614001248651) and on ClinicalTrials.gov (number NCT02369198). A total of 27 patients were recruited over 5 cohorts, with 26 patients receiving a total of 316 doses of $^V$EDVs$_{miRNA16a}$ (one subject died before receiving any treatment and was excluded from further analysis). This study has been published in Kao et al, 2015 and van Zandwijk et al, 2017.

The dose levels evaluated were $5 \times 10^9$ once or twice weekly, and $2.5 \times 10^9$ twice weekly. To avoid increased cytokine reactions, dose adaptation whereby the dose was gradually increased from $1 \times 10^9$ to the Phase 1 equivalent dose was also evaluated. A dexamethasone (dex) adaptation whereby dex was gradually decreased for pre-medication of subsequent doses was also evaluated. The MTD was identified as $5 \times 10^9$ $^V$EDVs$_{miR16a}$ once weekly. The treatment was generally well tolerated with acceptable safety findings in the indicated population.

A summary of the clinical study and findings is presented in Table 10 below.

TABLE 10

Summary of clinical data - $^{EGFR(V)}$EDVs$_{miRNA16a}$

| | | # of Patients[1] | Percent |
|---|---|---|---|
| Dose levels | $5 \times 10^9$ weekly | 6/26 | 23.1% |
| | $5 \times 10^9$ twice weekly | 4/26 | 15.4% |
| | $5 \times 10^9$ weekly + dose escalation | 6/26 | 23.1% |
| | $2.5 \times 10^9$ twice weekly + dose escalation | 2/26 | 7.7% |
| | $5 \times 10^9$ weekly + dose escalation + dex adaptation | 8/26 | 30.8% |

TABLE 10-continued

Summary of clinical data - $^{EGFR(V)}$EDVs$_{miRNA16a}$

| | | # of Patients[1] | Percent |
|---|---|---|---|
| Length of treatment[2] | At least 1 full cycle | 16/26 | 61.5% |
| | <1 complete cycle | 10/26 | 38.5% |
| Adverse events | All treatment-related | 26/26 | 100.0% |
| | Infusion-related reactions[4] | 25/26 | 50.0% |
| | Non-cardiac chest pain (tumor pain) | 14/26 | 42.9% |
| | Serious adverse events | 8/26 | 30.8% |
| | Dose limiting toxicities | 3/26 | 11.5% |
| | Withdrawals due to AEs | 2/26 | 7.7% |
| Best response[3] | Partial response | 1/16 | 6.3% |
| | Stable disease | 10/16 | 62.5% |
| | Progressive disease | 5/16 | 31.3% |

[1]One of 27 patients enrolled died before receiving treatment and was excluded from further analyses.
[2]One full cycle consisted of 8 weeks of treatment (8 weekly doses or 16 bi-weekly doses).
[3]For patients who completed at least 1 cycle of treatment.
[4]Infusion-related reactions included any of the following: chills, rigors, pyrexia, tachycardia, night sweats, or hypertension.

16 of the 24 patients completed at least 1 full cycle of treatment, with 2 patients receiving at least 40 doses in total (≥5 full cycles of treatment). The best response observed was a partial response in 1 patient. This patient demonstrated a near complete remission in response to treatment with $^V$EDVs$_{miR16a}$, as described below. Ten patients (62.5%) demonstrated stabilized disease and 5 patients (31.3%) demonstrated progressive disease. The median survival was 36.5 weeks, or 8.4 months (range 9.3→119.6 weeks), with 9 patients (60.0%) surviving for ≥6 months and 5 of these alive and well at >12 months from the start of treatment. See FIG. 4.

Of particular note, one patient (patient #5 from Cohort 1) displayed a dramatic clinical response at the end of the first cycle (see Kao et al., Am. J. Respir. Crit. Care Med., 191(12): 1467-1469 (2015)). At the end of the 8-week period, a "complete" metabolic response was evident on his PET-CT scan, and a partial response was noted on the chest CT scan and confirmed 4 weeks later. The objective imaging response was accompanied by a marked improvement in respiratory function test parameters.

The most common treatment-related adverse events were infusion-related reactions (96.2%) which included chills, rigors, pyrexia, tachycardia, or hypertension (night sweats were also included in this category). The majority of these were mild to moderate in severity. Non-cardiac chest pain at the tumor site was also experienced by 14 patients (53.8%) after infusion. These reactions were addressed by an amendment to the protocol in which all subjects received an adapted escalating dose schedule in Cycle 1, resulting in fewer infusion-related reactions and of lesser severity. Laboratory examination revealed a transitory rise in inflammatory cytokines and neutrophils, and a transient decrease in lymphocytes shortly after $^V$EDVs$_{miRNA16a}$ infusion in the majority of patients, consistent with a mild inflammatory response.

8 patients experienced 9 serious adverse events that were at least possibly related to treatment. Non-cardiac chest pain and infusion-related reactions both occurred in 2 patients. Three patients experienced dose limiting toxicities and an additional 2 subjects experienced toxicities that were considered dose-limiting but did not fit the criteria for a dose limiting toxicity as they occurred outside of the dose limiting toxicity window. No treatment-related deaths occurred.

These events are summarized in Table 11 below and described in the narrative below.

TABLE 11

Treatment-related SAEs or dose limiting toxicities

| Adverse events | Number of patients | Percent | DLT | Dose reduction/ withdrawal |
|---|---|---|---|---|
| General disorders | | | | |
| Non-cardiac chest pain (tumor-related) | 2/26 | 7.7% | Y (1) | Y (1) |
| Infusion-related reaction | 2/26 | 7.7% | Y (1) | Y (1) |
| Dizziness, confusion, cold sweat | 1/26 | 3.8% | N | N |
| Cardiac events | | | | |
| Ischaemia (with ECG changes) | 1/26 | 3.8% | N | Y |
| Cardiomyopathy (post-infusion reaction) | 1/26 | 3.8% | Y | Y |
| Other events | | | | |
| Dysphagia | 1/26 | 3.8% | N | N |
| Anaphylactoid reaction | 1/26 | 3.8% | N | Y |

Three patients were recruited into Cohort 1 ($5 \times 10^9$ weekly). One of these experienced a dose limiting toxicity of non-cardiac chest pain around the tumor site. This subject went on to a reduced dose, with subsequent escalation back to full strength. This cohort was expanded to enroll a total of 6 subjects, with no further DLTs.

Two of 2 subjects in Cohort 2 ($5 \times 10^9$ twice weekly) experienced toxicities leading to dose reduction or study withdrawal. The first was an infusion-related reaction which was classified as a dose limiting toxicity. This subject went on to a reduced dose, with subsequent escalation back to full strength. The second event was persistent ECG changes with concurrent coronary ischaemia, which was not classified as a dose limiting toxicity as it occurred in the $4^{th}$ week of dosing (discussed further below). This subject was removed from study and no further subjects were enrolled to this cohort (maximum administered dose).

Six subjects were enrolled to an additional cohort (Cohort 3, $5 \times 10^9$ weekly+dose escalation) where all subjects began on a reduced dose with subsequent escalation to full strength to minimise infusion reactions to study medication. No subjects experienced a dose limiting toxicity in this cohort.

Two subjects were enrolled to Cohort 4 ($2.5 \times 10^9$ twice weekly+dose escalation) and no dose limiting toxicities were experienced. However due to the substantial clinical burden associated with twice weekly dosing it was decided to discontinue recruitment to this cohort.

Nine subjects were enrolled to an additional cohort (Cohort 5, $5 \times 10^9$ weekly+dose escalation+dex adaptation) to evaluate a dosing regimen which included dose escalation and also gradual reduction of dexamethasone premedication. See FIG. 4. One subject did not receive any treatment in this cohort. Of the 8 remaining subjects, 2 experienced toxicities leading to dose reduction or study withdrawal. The first was Takotsubo (stress-related) cardiomyopathy, which was classified as a dose limiting toxicity (discussed further below). This subject was withdrawn from study. The second was an anaphylactoid reaction, which was not classified as a dose limiting toxicity as it occurred in the $7^{th}$ week of dosing. This subject was, however, removed from the study, and recruitment to this cohort was halted. The maximum tolerated dose was determined to be $5 \times 10^9$ $^VEDVs_{miRNA16a}$ once weekly.

A number of cardiac events were noted in this study which had not previously been observed in trials of different EDV products for other indications. Two subjects experienced serious adverse events of cardiac events resulting in dose reduction or withdrawal (ischaemia and Takotsubo cardiomyopathy). The ischaemia was considered unlikely to be due to study treatment, as the event occurred 7 days post-dose and the subject had a previous history of coronary artery disease. This subject experienced ECG changes during earlier doses. The cardiomyopathy event was preceded by an infusion reaction, possibly as a consequence of dex tapering. This subject also had a history of coronary artery disease. Three additional subjects experienced transient ECG changes (T-wave abnormalities) post-dose, which were not classified as serious. These were not associated with elevated troponin, ischaemia or LVEF changes. All events resolved and subjects went on to receive additional doses with no further ECG abnormalities. Nevertheless, in view of the advanced age of patients with malignant pleural mesothelioma, and the morbidities associated with the disease, these observations collectively led the safety committee to recommend more stringent cardiac exclusion criteria and additional cardiac monitoring for the remainder of the study and for any future trials.

Overall treatment with $^VEDVs_{miRNA16a}$ was generally well tolerated up to the maximum tolerated dose of $5 \times 10^9$ EDVs, with no significant concerns in this particular patient population given adequate monitoring and an adapted escalating dose schedule.

Thus, this example showed promising results in treating mesothelioma by using EDVs targeting EGFR to deliver miRNA16a to the cancer cells. However, the example results also demonstrate a need for improved treatment strategies for mesothelioma.

Example 8: In Vitro Cytotoxicity Assays Revealed that the Supertoxic Drug PNU-159682 Inhibits Proliferation of Tumor Cell Lines to a Greater Extent than Other Chemotherapy Agents This example showed that PNU-159682, which is a supertoxic cytotoxic chemotherapy agent, was a more potent inhibitor of cancer cell growth than a wide range of other chemotherapy drugs.

PNU-159682 is a highly potent metabolite of the anthracycline nemorubicin (MMDX) and is more than 3,000-times more cytotoxic than its parent compound (MMDX and doxorubicin); thus, PNU-159682 is considered a "supertoxic" chemotherapy drug. Use of such drugs is generally not possible with typical chemotherapy treatments as the toxicity levels of supertoxic drugs result in severe adverse events, including death.

PNU-159682 and the other indicated chemotherapeutic agents were added to tumor cell lines at the concentrations indicated in FIGS. 5A-5B-10A-10B.

All cells were incubated for a further 72 hrs followed by the colorimetric MTS cell proliferation assay (Cory et al., Cancer Commun., 3(7): 207-12 (1991)) using the CellTiter 96 AQu$_{eous}$ One Solution Cell Proliferation Assay (Promega Corp., Madison, Wis., USA), according to the manufacturer's instructions. The colorimetric measurements were read at 490 nm.

Greater Cytotoxicity:

The results of these in vitro cytotoxicity assays showed that PNU-159682 exhibited greater cytotoxicity against the human lung cancer cell line A549 as compared to the cytotoxicity observed by a range of known chemotherapeutic agents as shown in FIG. 5A. In particular, PNU-159682 inhibited A549 cells to a much greater degree than doxorubicin. FIG. 5B.

Figures 8A, 8B:
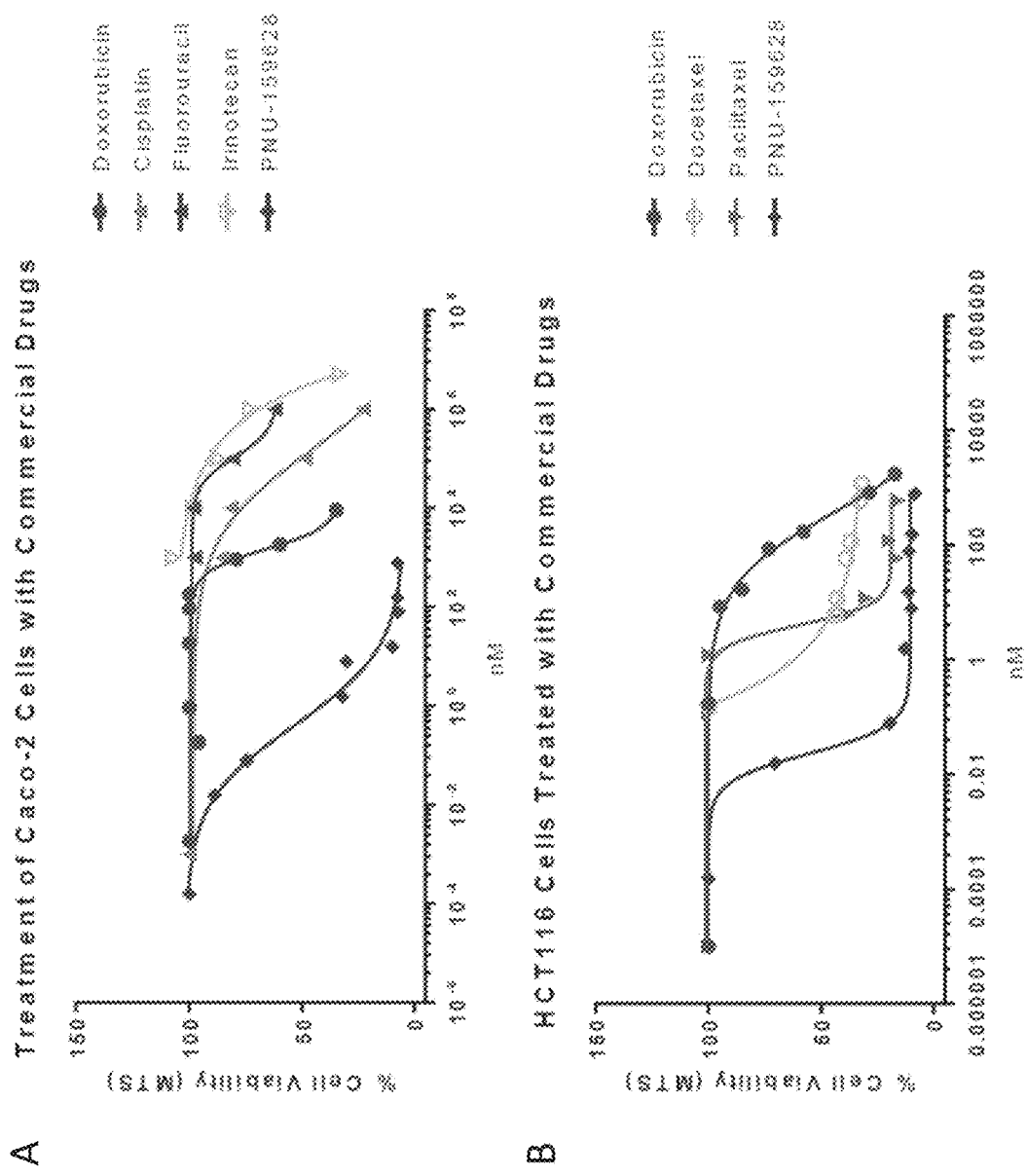
FIGS. 8A-8B shows the effect of the indicated chemotherapy drugs on the human colorectal cancer cell lines Caco-2 (FIG. 8A) and HCT116 (FIG. 8B).
Figure 9:
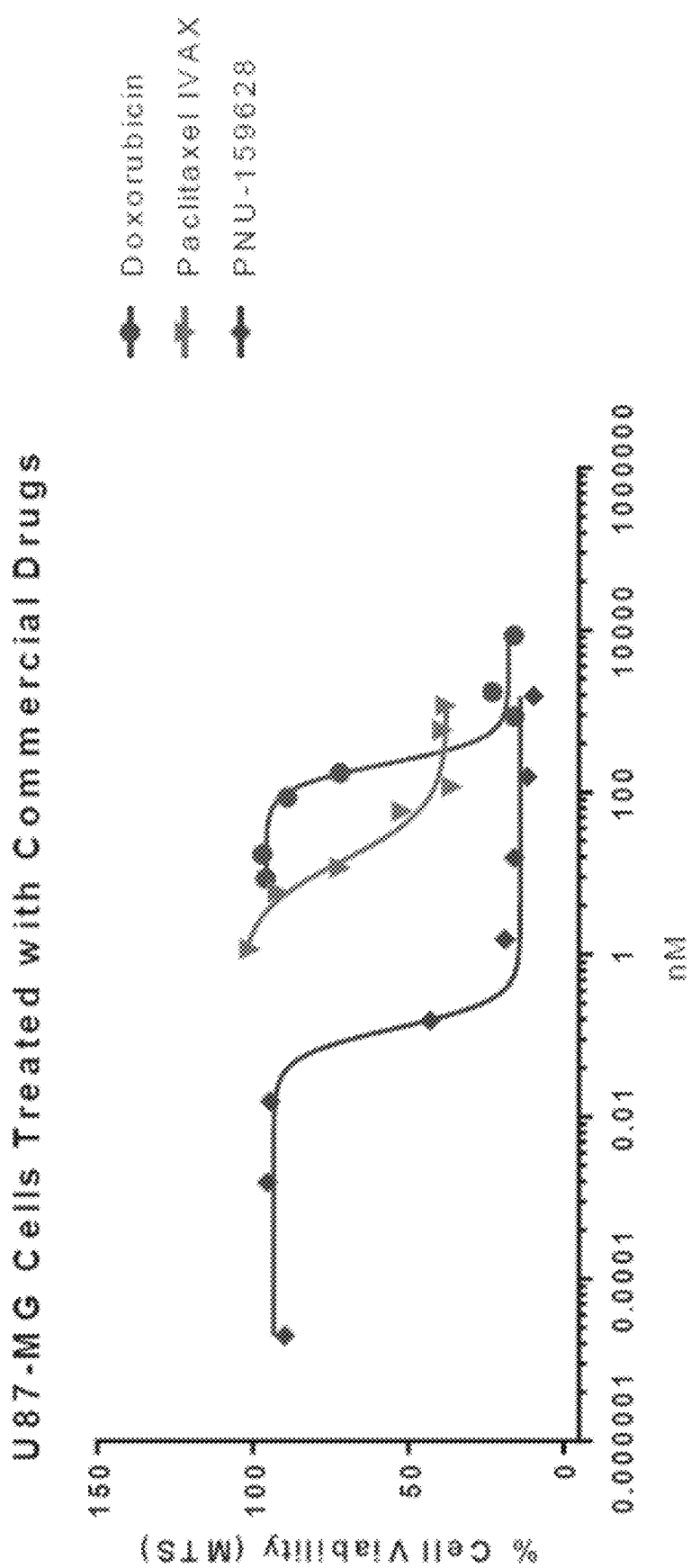
FIG. 9 shows the effect of the indicated chemotherapy drugs on the glioblastoma cell line U87-MG.
Figures 10A, 10B:
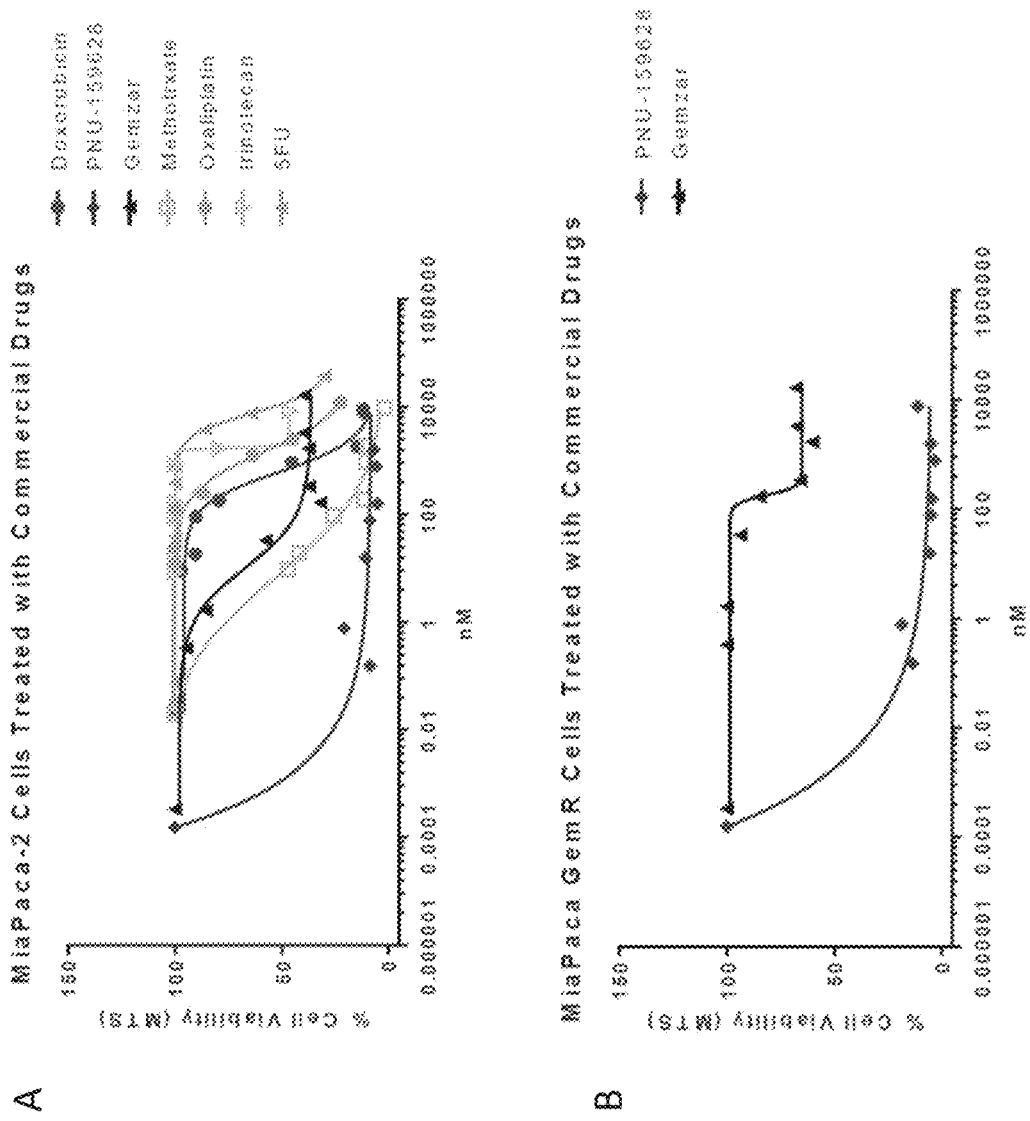
FIGS. 10A-10B shows the effect of the indicated chemotherapy drugs on the human pancreatic cell lines MiaPaca-2 (FIG. 10A) and gemcitabine-resistant MiaPaca-2 GemR cells (FIG. 10B).

Effectiveness against cancer cells known to exhibit resistance to conventional chemotherapy agents: Further, FIGS. 6A-6B shows that PNU-159682 and duocarmycin exhibited potent cytotoxic effects against two Adreno-cortical cancer cell lines derived from Stage IV patients that were highly resistant to doxorubicin, mitotane, paclitaxel, oxaliplatin, and mitoxantrone. Moreover, FIG. 7 shows that PNU-159682 inhibited proliferation of the human breast cancer cell line MDA-MB-468 that was resistant to doxorubicin, paclitaxel, and docetaxel. FIGS. 8A-8B shows that PNU-159682 inhibited proliferation of the human colorectal cancer cell lines Caco-2 (FIG. 8A) and HCT116 (FIG. 8B) that were resistant to doxorubicin, cisplatin. FIG. 9 shows that PNU-159682 could inhibit proliferation the Glioblastoma cell line U87-MG that was resistant to doxorubicin and paclitaxel IVAX. FIG. 10A shows that PNU-159682 could inhibit proliferation of human pancreatic cell lines that were gemicitabine sensitive (MiaPaca-2 cells, FIG. 10A) even though these cells were resistant to doxorubicin, gemzar, mathotrxate, oxaliplatin, irinotecan, and 5-Fluoro Uracil (5-FU). FIG. 10B shows that PNU-159682 could inhibit proliferation of human pancreatic cell lines that were gemicitabine-resistant cells (MiaPaca-2 GemR cells, FIG. 10B) even though these cells were resistant to gemzar.

These data demonstrate that it would be highly desirable to use supertoxic chemotherapy agents such as PNU-159682 in cancer therapies as the drug can be useful in treating cancers that demonstrate resistance to conventional, non-supertoxic chemotherapy drugs.

Example 9: PNU-159682 Delivered with EGFR Targeted EDVs can Overcome Drug Resistance in Human Lung Cancer Cells in a Mouse Xenograft Model This example showed that using minicells (EDVs) to deliver a supertoxic chemotherapy agent, such as PNU-159682, effectively inhibits tumor growth in a lung cancer xenograft model.

Figure 1:
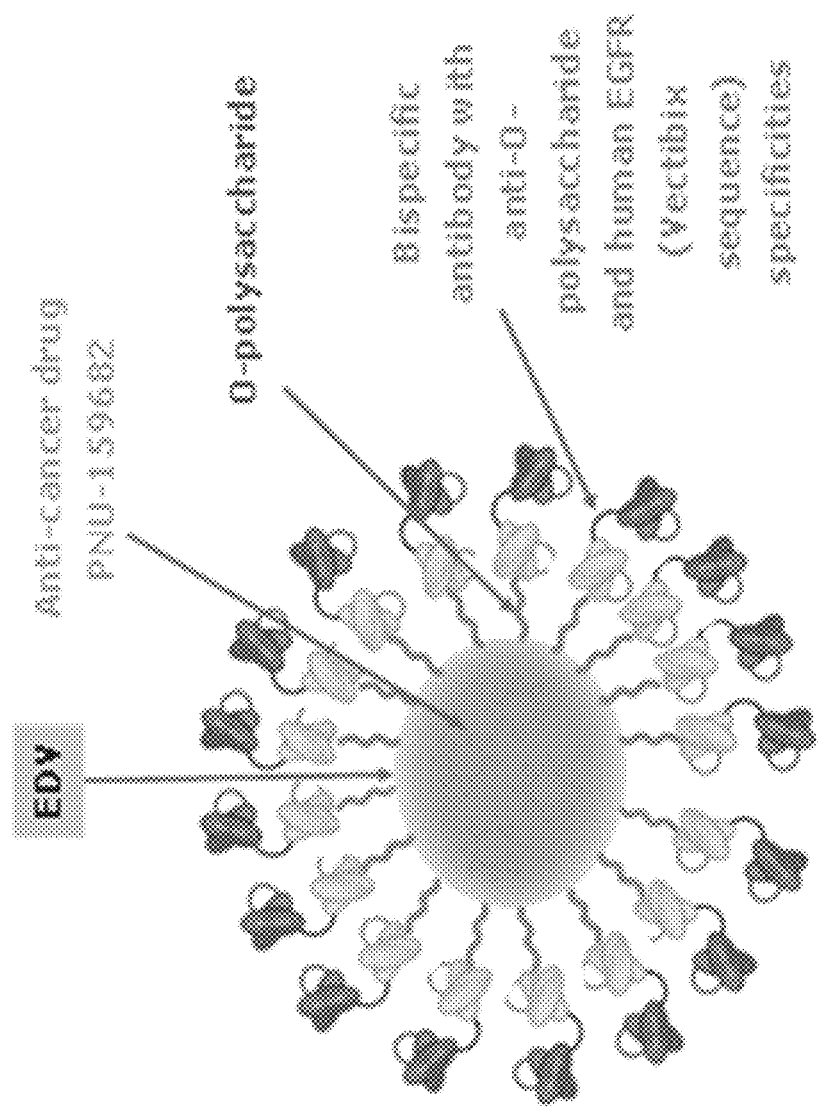

A549 (lung cancer) cells were made doxorubicin-resistant by continuous culture in the presence of doxorubicin (dox) and selecting dox-resistant clones. These cells were then implanted as xenografts in Balb/c nu/nu mice. When the tumor volumes reached ~150 mm$^3$, 4 different groups of mice (n=7 per group) were treated intravenously (IV) with (i) saline, (ii) epidermal growth factor receptor (EGFR) targeting EDVs loaded with doxorubicin ($^{EGFR}$EDVs™$_{Dox}$), (iii) EGFR targeting EDVs loaded with PNU-159682 ($^{EGFR}$EDVs™$_{682}$), and (iv) non targeted EDVs loaded with PNU-159682 (EDVs™$_{682}$) at the time points indicated with solid arrows in FIG. 11. The composition of an EDV targeting EGFR and loaded with PNU-159682 is depicted graphically in FIG. 1.

Figure 11:
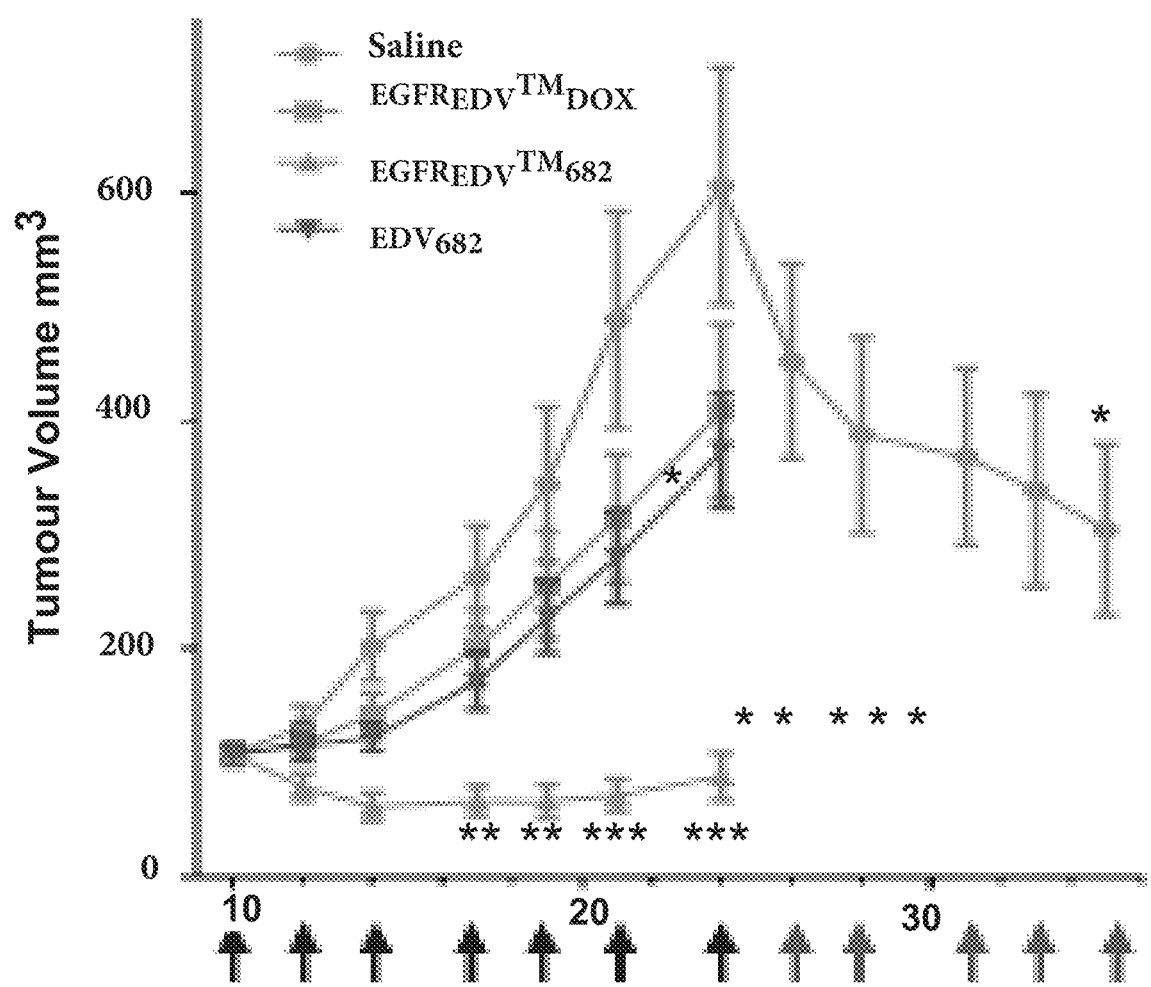
FIG. 11 shows the effect of EDVs targeted to EGFR and loaded with PNU-159682 ($^{EGFR}$EDVs$_{682}$™) or doxorubicine ($^{EGFR}$EDVs$_{Dox}$™) on A549 xenograft tumor growth in mice. Negative controls are saline only or untargeted EDVs loaded with PNU-159682 (EDVs$_{682}$™). Arrows indicated when the mice were treated with the indicated saline or EDV compositions. Asterisks indicate when the mice initially treated with saline were administered the $^{EGFR}$EDVs$_{682}$™ composition.

The results depicted in FIG. 11 show that $^{EGFR}$EDVs™$_{Dox}$ had no anti-tumor efficacy, and therefore, the tumors exhibited dox resistance. In contrast, mice treated with $^{EGFR}$EDVs™$_{682}$ showed complete tumor stabilisation. When the saline treated tumors reached tumor volumes in the range of 500 mm$^3$ to 700 mm$^3$, the treatment was changed to $^{EGFR}$EDVs™$_{682}$ at the time points indicated with asterisks (*) in FIG. 11. Surprisingly, the results showed a highly significant anti-tumor efficacy, even in tumors having reached a volume in the range of 500 mm$^3$ to 700 mm$^3$.

Example 10: Delivering Functional DNA Agents with EGFR Targeted EDVs Effectively Inhibits Mesothelioma (MSTO) and Adreno-Cortical Cancer (ACC) Cancer Cell Growth This example showed that using minicells (EDVs) to deliver siRNA targeting Polo like kinase 1 (Plk1), siRNA targeting ribonucleotide e reductase enzyme 1 (RRM1), or miRNA16a can effectively inhibit growth of cancer cells.

Figure 12:
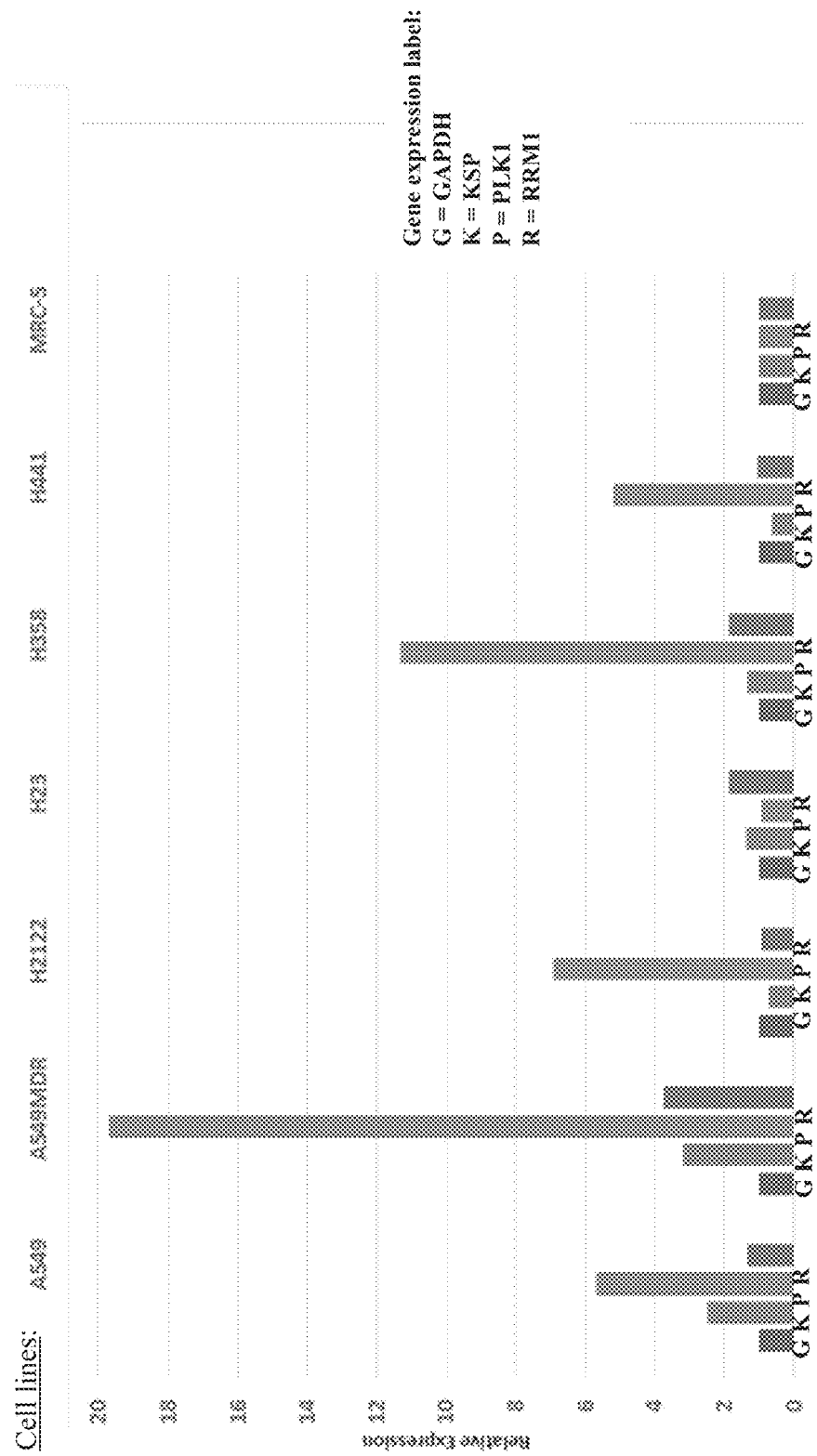
FIG. 12 shows expression of GAPDH (glyceraldehyde 3-phosphate dehydrogenase) (G), KSP (Kinesin Spindle Protein), Plk1 (Polo like kinase 1) (P), and RRM1 (ribonucleotide reductase enzyme 1) (R) relative to GAPDH expression in the indicated NSCLC cell lines.

Polo like kinase 1 (Plk1) and ribonucleotide reductase enzyme 1 (RRM1) were shown to be over-expressed in several non-small cell lung carcinoma (NSCLC) cell lines including A549, A549MDR (dox resistant A549 cell line, over-expressing the multi-drug resistance membrane pump, MDR), H2122, H358 and H441. FIG. 12 shows expression of GAPDH (G), KSP (K), Plk1 (P), and RRM1(R) and the expression is shown relative to the GAPDH expression in the indicated NSCLC cell lines.

Figures 13A, 13B:
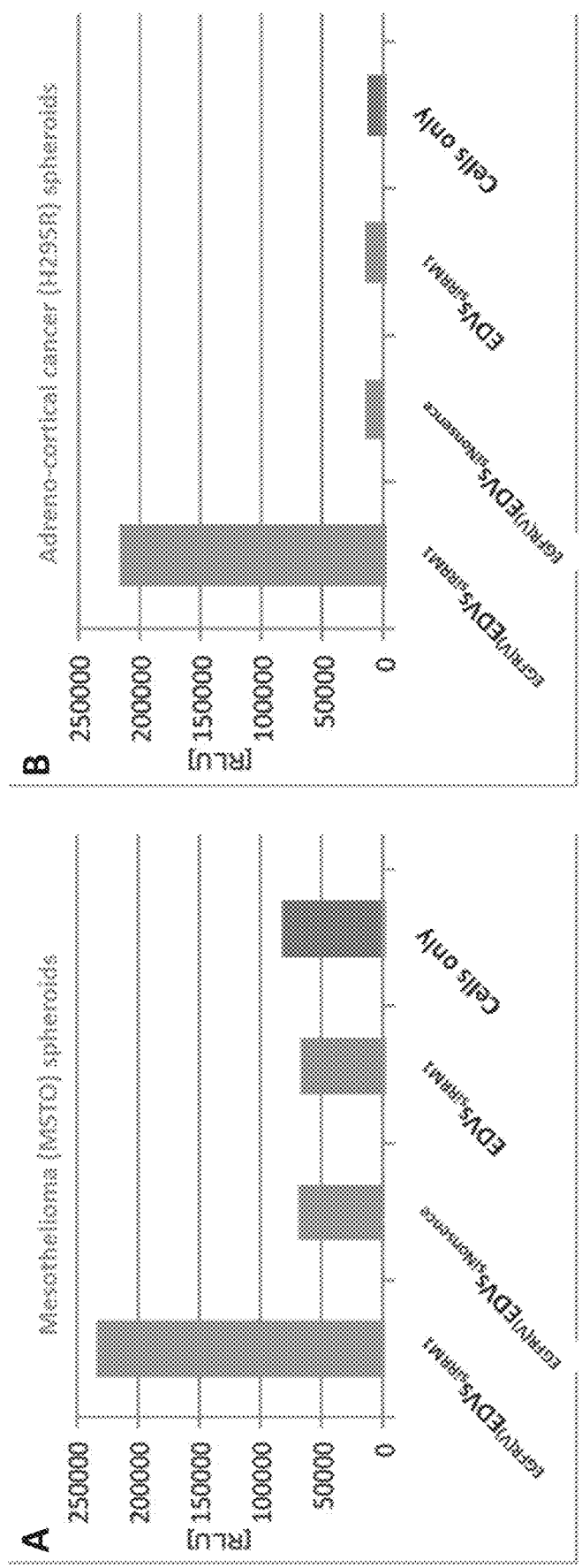
FIGS. 13A-13B shows the effect of delivering EGFR-targeted, siRRM1-packaged EDVs to a mesothelioma cell line (MSTO, FIG. 13A) or an adreno-cortical cancer cell line (H295R, FIG. 13B).

To test if the Plk1 or RRM1 are useful targets for cancer treatment, inhibiting non-coding small interfering RNAs (siRNAs) targeting RRM1 (siRRM1) and Plk1 (siPlk1) were synthesized and packaged in EDVs for delivery to cancer cell lines.

siRNA targeting RRM1 was found to inhibit proliferation of mesothelioma and adreno-cortical cancer cells. The EGFR-targeted, siRRM1-packaged EDVs were transfected into MSTO (mesothelioma cell line) or H295R (adreno-cortical cancer cell line). Five days post-transfection, cell proliferation was measured and the results are depicted in FIGS. 13A-13B and showed highly significant inhibition of cell proliferation as compared to control transfections with non-targeted, siRRM1-packaged EDVs or EGFR-targeted, siNonsense-packaged EDVs.

Figure 14:
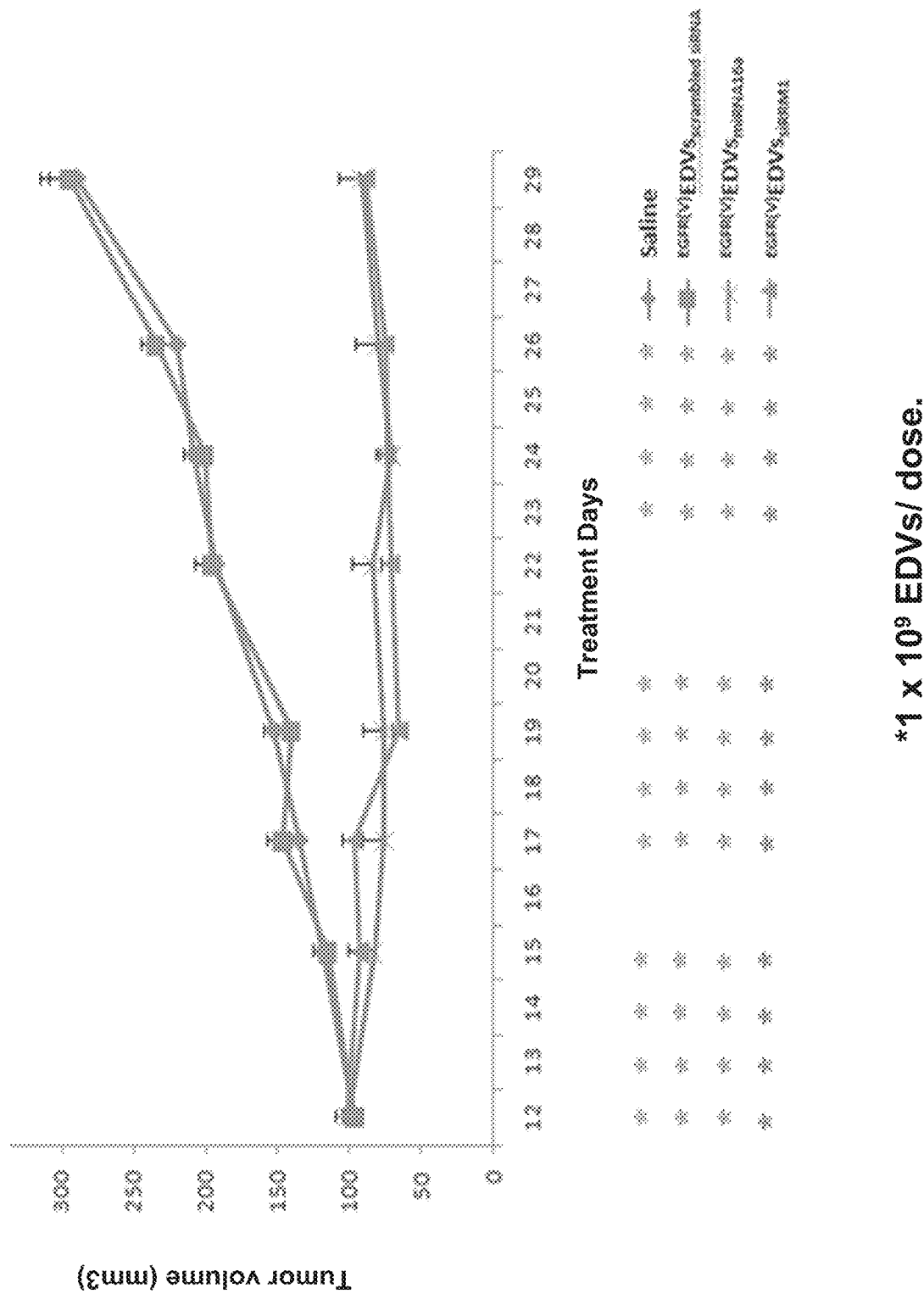
FIG. 14 shows the effect of delivering EGFR-targeted, miRNA16a ($^{EGFR}$EDV$_{miRNA16a}$™), or EGFR-targeted, siRRM1-packaged EDVs ($^{EGFR}$EDV$_{siRRM1}$™), on mesothelioma xenograft tumor growth in Balb/c nu/nu mice. Negative controls were saline or EGFR-targeted EDVs loaded with scrambled siRNA.
Figure 15:
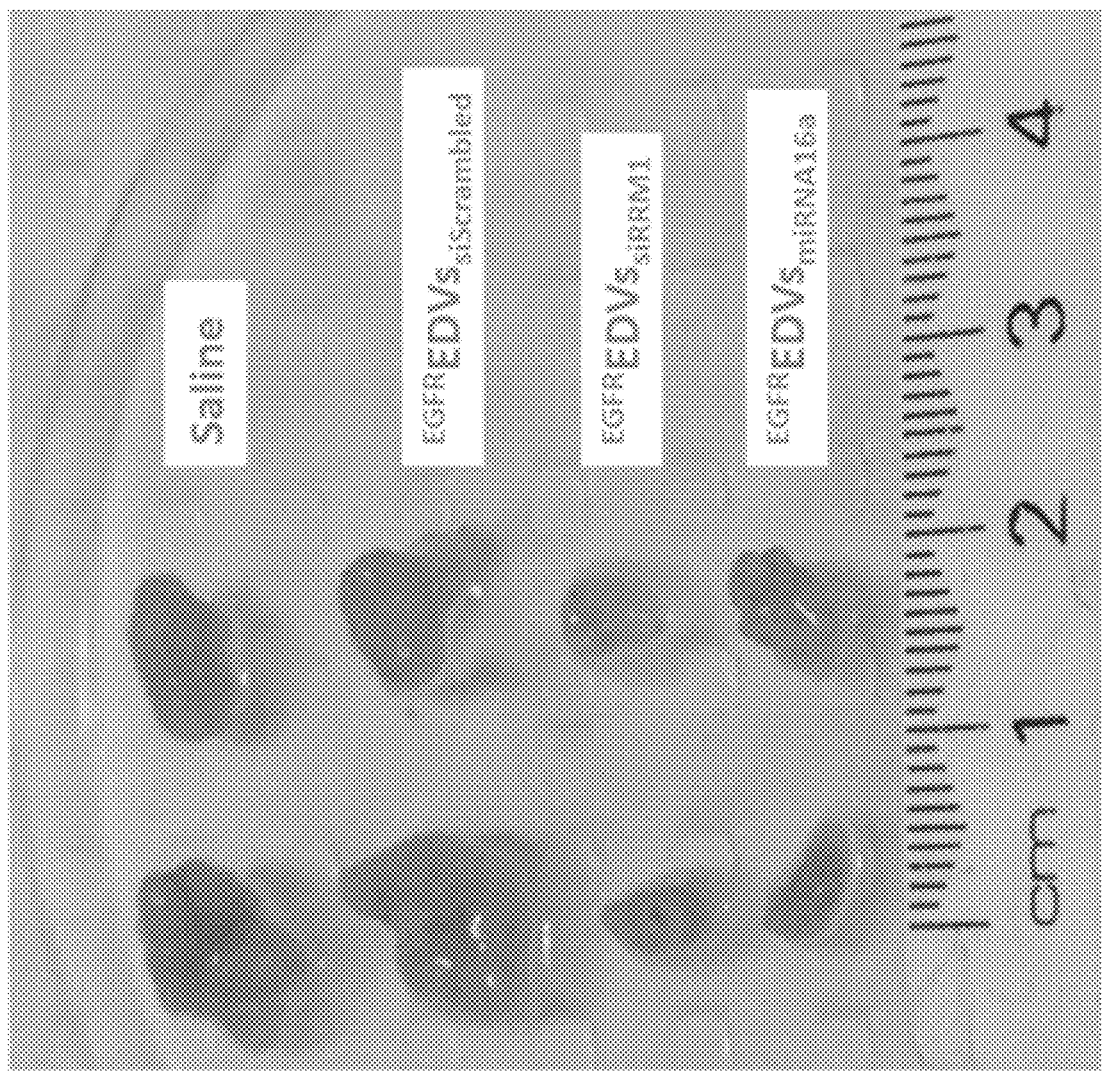
FIG. 15 shows tumors isolated from mesothelioma xenograft Balb/c nu/nu mice treated with EGFR-targeted, miRNA16a ($^{EGFR}$EDV$_{miRNA16a}$™), or EGFR-targeted, siRRM1-packaged EDVs ($^{EGFR}$EDV$_{siRRM1}$™), as compared to saline treated or EGFR-targeted EDVs loaded with scrambled siRNA.
Figures 16A, 16B:
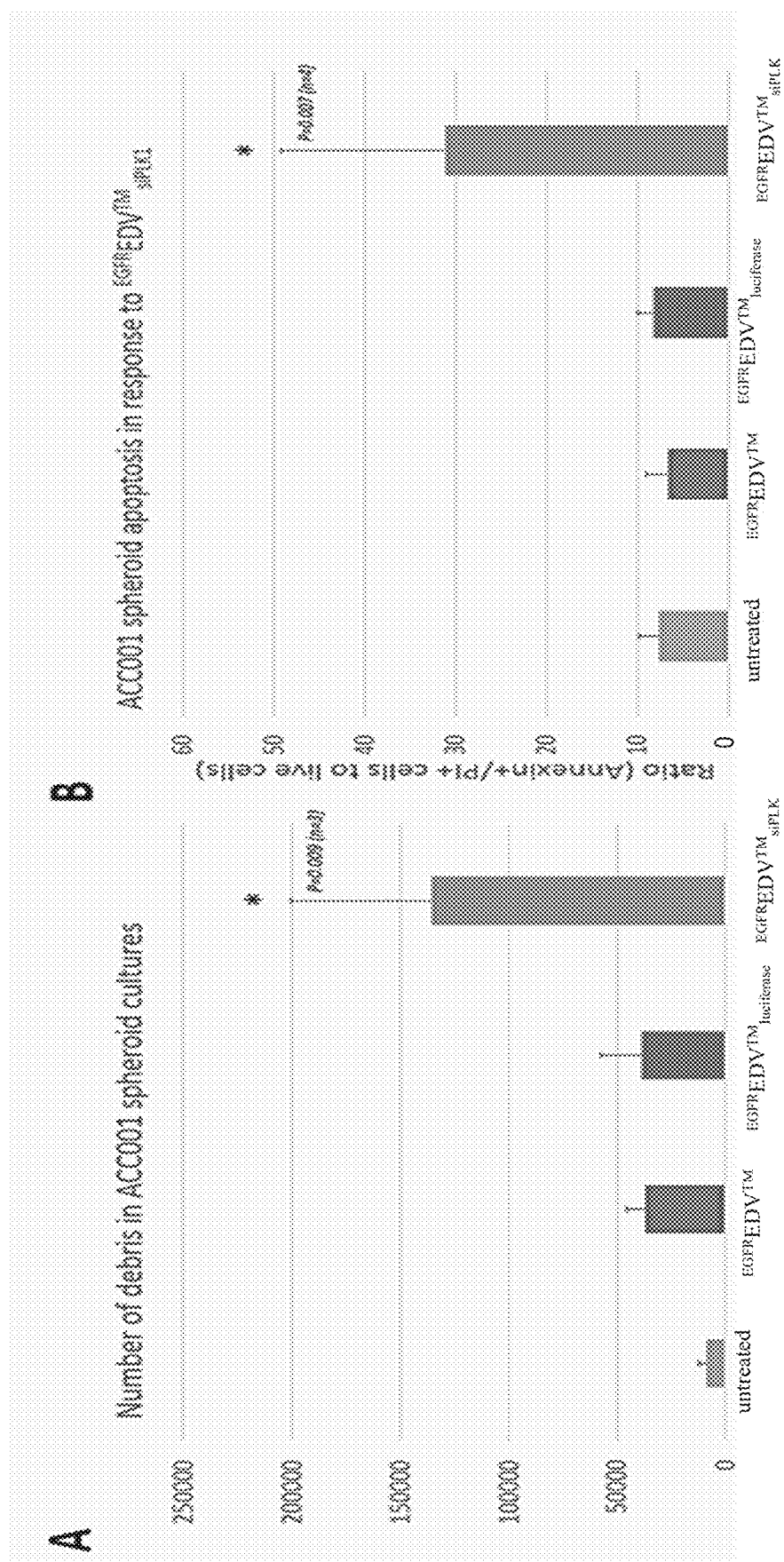
FIGS. 16A and 16B show apoptosis induced in adreno-cortical cancer cells (ACC01) by EGFR-targeted EDVs loaded with siRNA targeting Polo like kinase 1 ($^{EGFR}$EDV™$_{siPLK}$™) and ribonucleotide reductase enzyme 1 ($^{EGFR}$EDV$_{siRRM1}$™) based on measuring the number of cellular debris (FIG. 16A) and the ratio of Annexin5 to Propidium Iodide (PI) positive cells (FIG. 16B). Apoptosis in untreated ACC01 cells, in ACC01 cells treated with EDVs loaded with irrelevant siRNA ($^{EGFR}$EDV™$_{siLuciferase}$™), and unloaded EDVs ($^{EGFR}$EDV™) are included as negative controls.
Figures 17A, 17B, 17C, 17D:
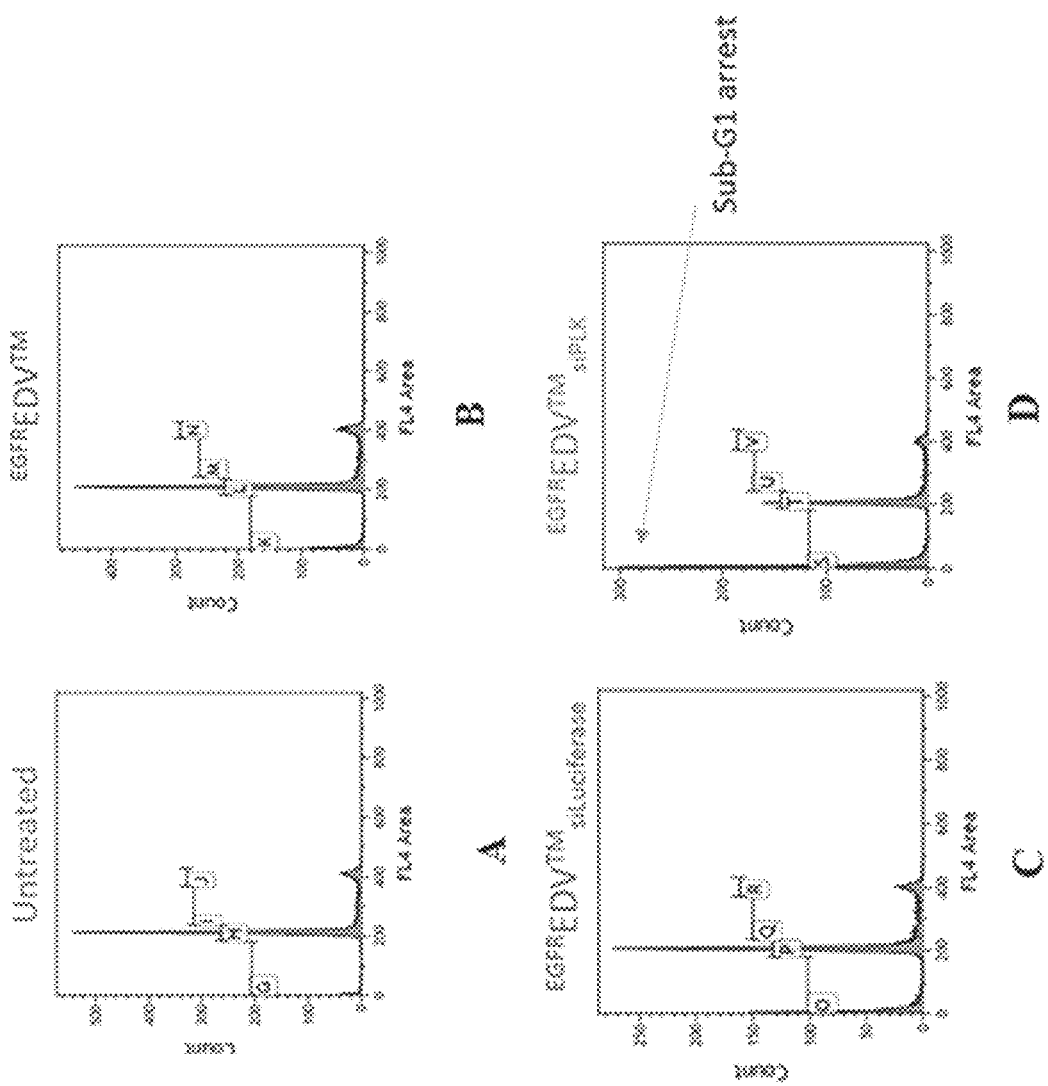
FIGS. 17A-D show sub-G1 arrest (FIG. 17D) induced in adreno-cortical cancer cells (ACC01) by EGFR-targeted EDVs loaded with siRNA targeting Polo like kinase 1 ($^{EGFR}$EDV™$_{siPLK}$™) (FIG. 17D) and ribonucleotide reductase enzyme 1 ($^{EGFR}$EDV$_{siRRM1}$™) based on measuring the number of cellular debris and the ratio of Annexin5 to Propidium Iodide (PI) positive cells. Apoptosis in untreated ACC01 cells (FIG. 17A), in ACC01 cells treated with EDVs loaded with irrelevant siRNA ($^{EGFR}$EDV™$_{siLuciferase}$™) (FIG. 17C), and unloaded EDVs ($^{EGFR}$EDV™) (FIG. 17B) are included as negative controls.

In a mesothelioma (MSTO) xenograft study in Balb/c nu/nu mice, intravenous (IV) treatment with EGFR-targeted, siRRM1-packaged EDVs showed highly significant anti-tumor efficacy as compared to saline or EGFR-targeted, siScrambled-packaged EDVs as shown in FIG. 14. The tumors isolated from mice receiving the siRRM1 packaged EDVs were significantly smaller than tumors from mice receiving negative controls. FIG. 15.

miRNA16a was found to inhibit proliferation of mesothelioma cancer cells. In a mesothelioma (MSTO) xenograft study in Balb/c nu/nu mice, intravenous (IV) treatment with EGFR-targeted, miRNA16a-packaged EDVs showed highly significant anti-tumor efficacy compared to saline or EGFR-targeted, siScrambled-packaged EDVs as shown in FIG. 14. The tumors isolated from mice receiving the miRNA16a packaged EDVs were significantly smaller than tumors from mice receiving negative controls. FIG. 15.

siPLK loaded EDVs targeted to EGFR ($^{EGFR}$EDV™$_{siPLK}$) induced apoptosis in cancer patient-derived tumor Spheroids (ACC001) as shown in FIGS. 16A-16B. EDVs without any payload ($^{EGFR}$EDV™), or EDVs with RNA interference molecules targeting the irrelevant luciferase sequence ($^{EGFR}$EDV™$_{luciferase}$) were used as a negative control. Compared to these negative controls, $^{EGFR}$EDV™$_{siPLK}$ induced apoptosis in the ACC001 spheroids as determined by measurements of cellular debris (FIG. 16A), and measurements of Annexin/propidium iodide (PI) ratio (FIG. 16B). $^{EGFR}$EDV™$_{siPLK}$ treatment also resulted in a significant number of cells in sub-G1 cell cycler arrest as compared to the negative controls as shown in FIGS. 17A-17D. Thus, inhibiting Plk1 expression with siRNA is an effective strategy for inducing apoptosis and cell cycle arrest in ACC001 adreno cortical cancer cells.

Example 11: Delivering Interferon Type I Agonists with EGFR Targeted EDVs Augments Anti-Tumor Efficacy of EDVs Loaded with Cytotoxic Drugs in a Xenograft Model This example showed that using minicells (EDVs) to deliver a chemotherapy agent combined with an interferon type I agonist, was an effective strategy for treating a cancer such as lung cancer xenografts. The interferon type I agonist can be in the same or a different minicell as the chemotherapy agent. In the present example, the chemotherapy agent is the supertoxic drug PNU-159682 and the interferon type I agonist is a 40mer double stranded DNA.

A549 (lung cancer) xenografts in Balb/c nu/nu mice were treated with various EDV combinations by intravenous injection in the tail vein as depicted in FIG. 18. The mice were treated with: (i) solid triangle=$^{EGFR}EDVs_{PNU\text{-}59682}$+$EDVs_{40mer}$, (ii) solid circle=$^{EGFR}EDVs_{PNU\text{-}59682}$, (iii) open square=$^{EGFR}EDVs_{PNU\text{-}159682}$+EDVs, (iv) open triangle=$^{EGFR}EDVs_{PNU\text{-}59682}$+$EDVs_{50mer}$, and (v) solid square=saline. The is a type I interferon agonist.

The mice were treated with these EDVs combinations at day 24, 27, 29, 31, 34, 36, and 38 after the xenograft implantation as indicated with up arrows in FIG. 18. As shown in FIG. 18, all combinations of EDVs tested resulted in stabilizing the tumor growth. In contrast, the saline treated control group exhibited tumor growth up to a volume of 650 mm$^3$ On day 36 and 38, the saline group mice with tumor volume of ~650 mm$^3$ were treated with $^{EGFR}EDVs_{PNU\text{-}59682}$+$EDVs_{50mer}$ as indicated by the down arrows in FIG. 18.

Treating mice having tumors with a large volume of ~650 mm$^3$ with minicells (EDVs) comprising PNU-159682 and EGFR targeting ($^{EGFR}EDVs_{PNU\text{-}59682}$) combined with EDVs comprising 40mer double stranded DNA ($EDVs_{40mer}$) resulted in a dramatic regression of the tumors. Specifically, in just 5 days the tumor volumes decreased from ~650 mm$^3$ to ~250 mm$^3$—or a 62% reduction in size in 5 days. The results are summarized in the table below.

TABLE 12

| Group | Treatment | FIG. | Phase I Results | Phase II Treatment Starting at days 36 and 38 | Results |
|---|---|---|---|---|---|
| 1 | $^{EGFR}EDVs_{PNU\text{-}159682}$ + $EDVs_{40mer}$ | FIG. 18, solid triangle | Tumor growth stabilization | N/A | N/A |
| 2 | $^{EGFR}EDVs_{PNU\text{-}159682}$ | FIG. 18, solid circle | Tumor growth stabilization | N/A | N/A |
| 3 | $^{EGFR}EDVs_{PNU\text{-}159682}$ + EDVs (no payload) | FIG. 18, open square | Tumor growth stabilization | N/A | N/A |
| 4 | $^{EGFR}EDVs_{PNU\text{-}159682}$ + $EDVs_{50mer}$ | FIG. 18, open triangle | Tumor growth stabilization | N/A | N/A |
| 5 | Saline | FIG. 18, solid square | tumor growth up to a volume of ~650 mm$^3$ | Treatment with $^{EGFR}EDVs_{PNU\text{-}159682}$ + $EDVs_{40mer}$ | In 5 days, tumors having a large volume of ~650 mm$^3$ decreased to ~250 mm$^3$ - or a 62% reduction in tumor size in 5 days |

Furthermore, EDVs comprising 40mer double stranded DNA ($EDVs_{40mer}$) in combination with minicells (EDVs) comprising PNU-159682 and EGFR targeting ($^{EGFR}EDVs_{PNU\text{-}59682}$) induced more significant regression of tumors as compared to tumor cells treated with $^{EGFR}EDVs_{PNU\text{-}159682}$ alone in a mouse xenograft model of lung cancer, as shown in FIG. 19. In FIG. 19, Balb/c nu/nu mice were treated with (i) solid circle=$^{EGFR}EDVs_{PNU\text{-}159682}$, (ii) solid triangle=$^{EGFR}EDVs_{PNU\text{-}159682}$+$EDVs_{40}$mer, or (iii) solid square=saline. The results are summarized in the table below.

TABLE 13

| Group | Treatment | FIG. | Results |
|---|---|---|---|
| 1 | $^{EGFR}EDVs_{PNU\text{-}159682}$ | FIG. 19, solid circle | Slight tumor size reduction (from a tumor volume of about 275 mm$^3$ to 260 mm$^3$) |
| 2 | solid triangle = $^{EGFR}EDVs_{PNU\text{-}159682}$ + $EDVs_{40mer}$ | FIG. 19, solid triangle | Significant tumor reduction, from a tumor volume about 275 mm$^3$ to about 175 mm$^3$) |
| 3 | Saline | FIG. 19, solid square | Significant tumor growth. |

In conclusion, a type I IFN agonist packaged in a minicell augments the anti-neoplastic effects of $^{EGFR}EDVs_{PNU\text{-}159682}$ treatment.

Example 12: Clinical Evaluation of $EDVs_{PNU\text{-}59682}$ with Adjuvant Type I IFN Agonists ($EDV_{40mer}$ or $EDVs_{60mer}$) and Type II IFN Agonists (Imukin)

This example showed that type I and type II IFN agonists augment the anti-cancer effect of $^{EGFR}EDVs_{PNU\text{-}159682}$ in human patients suffering from advanced solid tumors.

Remarkably, even in an advanced stage pancreatic cancer patient, this treatment produced a 90% drop in tumor marker levels after only 3 doses and the patient exhibited markedly improved life quality.

Treatment with Minicells comprising drug, type I IFN agonist, and type II IFN agonist: The inventors of the present disclosure performed clinical case studies where subjects received targeted and loaded EDVs in combination with minicells loaded with the type 1 IFN agonists 40mer double stranded DNA ($EDVs_{40mer}$) (type 1 IFN agonist) or 60mer double stranded DNA ($EDVs_{60mer}$) (type 1 IFN agonist).

Three subjects with advanced solid tumors received combination treatment of $^{EGFR(V)}EDVs_{PNU\text{-}59682}$ with adjuvant $EDVs_{40mer}$ (type 1 IFN agonist) as part of the Designer EDV Study (Melbourne, Australia). Two additional patients received loaded and targeted EDVs in combination with $EDVs_{60mer}$ (type 1 IFN agonist) under compassionate use legislation. One compassionate-use patient diagnosed with Stage IV pancreatic cancer received treatment with $^{EGFR(V)}EDVs_{PNU\text{-}59682}$ and $EDVs_{40mer}$ (type 1 IFN agonist) or $EDVs_{60mer}$ (type 1 IFN agonist), and a second compassionate use patient diagnosed with recurrent adreno-cortical cancer received $^{EGFR(V)}EDVs_{PNU}$ and $EDVs_{60mer}$+Imukin (type II IFN).

Clinical Study

Minicells Comprising Drug and Type I IFN Agonist: $^{EGFR(V)}EDVs_{PNU}$ with adjuvant $EDVs_{40mer}$ (type 1 IFN agonist) was evaluated in 3 patients in an open-label, single centre, exploratory Phase 1 study in subjects with advanced solid tumors (Designer EDV Study). To be eligible, patients were to have histological or cytological documentation of advanced solid tumors with evidence of EGFR expression in their tumor tissue to facilitate targeting. Patients must have displayed disease progression during or following the administration of standard 1st, 2nd or 3rd line therapy regimens. The primary end points of the trial were to establish the safety and tolerability of $^{EGFR(V)}EDVs_{PNU\text{-}159682}$ with adjuvant $EDVs_{40mer}$ (type 1 IFN agonist).

This trial was initiated at a single centre in Melbourne, Australia, and was registered with the Australian New Zealand Clinical Trials Registry (number ACTRN 12617000037303).

The 3 patients in the trial received a total of 13 doses of $^{EGFR(V)}EDVs_{PNU\text{-}159682}$ at $2.5\times10^9$ with $EDVs_{40mer}$ (type 1 IFN agonist) at $5\times10^8$. Treatment was administered weekly as a 20-minute IV infusion in cycles consisting of 8 weeks of treatment. At the end of each cycle, patients were to undergo radiological assessment of their tumors.

Available safety data are limited, but the treatment has generally been well tolerated with no unexpected adverse reactions to the IP. As seen with administration of other EDV products, patients generally experienced a transient increase in the inflammatory cytokines IL-6, IL-8 and TNF-α, which returned to baseline between treatments doses. Observed changes in haematology parameters largely mirrored changes seen in previous trials with EDV therapeutics, including mild self-limiting elevation of white blood cells (WBC), elevation of neutrophils 3 hours post-dose, and a concomitant decrease in lymphocytes and monocytes. Parameters returned to normal at the following time point, prior to the next dose. Some subjects experienced a mild reduction in serum phosphate levels, which did not require intervention and returned to baseline between doses.

Two patients experienced related adverse events involving infusion-related reactions, with rigors and fever beginning approximately 1 hour post-dose. These patients were admitted overnight for observation and the events resolved by the following day. One patient was withdrawn from study due to dose limiting toxicity. The second patient continued the study and received additional doses.

Compassionate Use Studies

The first compassionate use case study took place at Royal North Shore Hospital, Sydney. The patient was a 68 year old female who was diagnosed with Stage IV pancreatic cancer. She had Whipple surgery (pancreaticoduodenectomy), with gemcitabine as first line treatment. She also received the FOLFIRINOX treatment regime but developed metastatic liver disease. Her tumor cells were tested in vitro and found to be sensitive to PNU-159682.

The patient received bi-weekly doses of EDV products including PNU-loaded and EGFR-targeted EDVs in combination with different immunomodulatory adjuvants. These were delivered IV as a 20 mL infusion. She received both EGFR(V)-targeted EDVs and ITG(609)-targeted EDVs comprising PNU, and also $EDV_{40mer}$ (type 1 IFN agonist) or $EDVs_{60mer}$ (type 1 IFN agonist) as intended for use in the current protocol. In total, the patient received 45 doses of $^{EGFR(V)}EDVs_{PNU\text{-}159682}$+$EDVs_{40mer}$ (or the related product $EDVs_{60mer}$). Doses of $^{EGFR(V)}EDVs_{PNU\text{-}59682}$ and $^{ITG(609)}EDVs_{PNU\text{-}159682}$ were escalated up to a maximum of $2\times10^9$ and $4\times10^9$ respectively, and $EDV_{40mer/60mer}$ were given at a set dose of $5\times10^8$.

The patient tolerated the treatment very well, with no IP-related serious adverse events. Preliminary results indicate a transient increase in the inflammatory cytokines IL-6, IL-8 and TNF-α post-dose, similar to that seen with administration of other EDV products.

These responses were generally reduced over subsequent doses. The anti-inflammatory cytokine IL-10 also was transiently increased, post-dose. Interestingly, IFN-α was increased as well at various time points throughout the study, which is likely a consequence of stimulation with $EDV_{40mer/60mer}$. No elevation of IFN-γ was detected at 2 hours post-dose.

Remarkably, the levels of the patient's tumor marker (CA 19-9) dropped by more than 90% after the first 3 doses, equivalent to only 10 days of treatment. After 10 doses this had dropped even further, with an almost 95% reduction in tumor marker levels. She also demonstrated significant weight gain, in contrast to the cachexic state experienced by most patients presenting with stage IV pancreatic cancer, and reported a marked improvement in quality of life. The preliminary safety and efficacy results of this case study are thus extremely promising, particularly given the poor prognosis associated with advanced pancreatic cancer.

Minicells Comprising Drug, Type I IFN Agonist, and Type II Agonist:

The second compassionate use case study in an end-stage adreno-cortical cancer patient with a very heavy tumor burden was treated at Royal North Shore Hospital (Sydney.

The patient received 10 bi-weekly doses of $^{EGFR(V)}EDVsP_{NU}\text{-}15_968_2$ (minicell comprising an antineoplastic agent, with doses of the antineoplastic agent ranging from $1\times10^9$ to $4\times10^9$ [EDVs], $EDVs_{60mer}$ (minicell comprising type I IFN agonist, with doses of the type 1 IFN agonist ranging from $5\times10^8$ to $2\times10^9$ [EDVs]), and Imukin (type II IFN, with doses of the type II IFN ranging from 5 μg ($1\times10^5$ IU) to 30 μg ($6\times10^5$ IU)).

The patient tolerated the treatment very well, experiencing only mild elevation of temperature up to 60 minutes post-dose. This is to be expected on administration of EDV products. Unfortunately, the patient had a very high disease burden including high levels of cortisol which is known to be a serious immune system suppressor and the CT scans during week 7 showed progressive disease and hence the patient was taken off the study.

In summary, 5 patients received a total of 69 doses of $^{EGFR(V)}EDVs_{PNU/Dox}$ or $^{EGFR(V)}EDVs_{PNU/PNU}+EDV_{40mer60mer}$, (type I IFN agonist)±Imukin (type II IFN). The treatments were well tolerated, and addition of immunomodulatory adjuvants did not seem to change the safety profile of single agent loaded and targeted EDVs.

Example 13: Addition of IFN-γ (Type II IFN Agonist) Augments the Anti-Tumor Efficacy of Epidermal Growth Factor Receptor Targeted EDVs Loaded with Doxorubicin and Cause Tumor Regression in Xenograft Models of Various Cancers This example showed that using minicells (EDVs) to deliver doxorubicin combined with IFN-γ provides improved anti-tumor effects in mice xenograft models.

Lung Cancer:

To study the anti-tumor effects of combining $^{EGFR}EDVs_{Dox}$ and IFN-γ (type II IFN) in a lung cancer model, A549 (lung cancer) xenografts in Balb/c nu/nu mice were established and divided into four groups receiving different treatment combinations by intravenous tail vein injection. Group 1 received sterile physiological saline (FIG. 20, open diamonds). Group 2 received IFN-γ ($0.5\times10^4$ IU) per dose (FIG. 20, solid triangles). Group 3 received $^{EGFR}EDVs_{Dox}$ (FIG. 20, solid squares). Group 4 received $^{EGFR}EDVs_{Dox}$ and IFN-γ ($0.5\times10^4$ IU) per dose (FIG. 20, solid circles).

Mice treated with $^{EGFR}EDVs_{Dox}$ achieved tumor stabilisation of A549 lung cancer xenografts (FIG. 20, solid squares). In contrast, mice treated with $^{EGFR}EDVs_{Dox}$ and IFN-γ showed highly significant tumor regression by day 43 after a total of 6 doses (FIG. 20, solid circles). Mice treated with IFN-γ alone showed no anti-tumor efficacy (FIG. 20, solid triangles), and the tumors grew as in the saline treated group (FIG. 20, open diamonds).

Thus, combining $^{EGFR}EDVs_{Dox}$ and IFN-γ (type II IFN) resulted in tumor regression in a mouse xenograft model of lung cancer, as summarized in Table 14, below.

Breast Cancer:

To study the anti-tumor effects of combining $^{EGFR}EDVs_{Dox}$ and IFN-γ in a breast cancer model, MDA-MB 468 xenografts in Balb/c nu/nu mice were established and divided into four groups receiving different treatment combinations by intravenous tail vein injection. Group 1 received sterile physiological saline (FIG. 21, open diamonds). Group 2 received IFN-γ ($0.5\times10^4$ IU) per dose (FIG. 21, solid triangles). Group 3 received $^{EGFR}EDVs_{Dox}$ (FIG. 21, solid squares). Group 4 received $^{EGFR}EDVs_{Dox}$ and IFN-γ ($0.5\times10^4$ IU) per dose (FIG. 21, solid circles).

Mice treated with $^{EGFR}EDVs_{Dox}$ achieved tumor stabilisation of MDA-MB 468 breast cancer xenografts, but by –day 25 the tumors began to grow again, likely due to development of resistance to doxorubicin (FIG. 21, solid squares). In contrast, mice treated with $^{EGFR}EDVs_{Dox}$ and IFN-γ showed highly significant tumor regression, and by day 30, after a total of 6 doses, these tumors were more like scar tissue (FIG. 21, solid circles). Mice treated with IFN-γ alone showed no anti-tumor efficacy (FIG. 21, solid triangles), and the tumors grew as in the saline treated group (FIG. 21, open diamonds). In an additional experiment depicted in FIG. 22, mice treated with $^{EGFR}EDVs_{Dox}$ again achieved tumor regression of MDA-MB 468 breast cancer xenografts, but by –day 23 the tumors began to grow again, likely due to development of resistance to doxorubicin (FIG. 22, solid squares).

Figure 22:
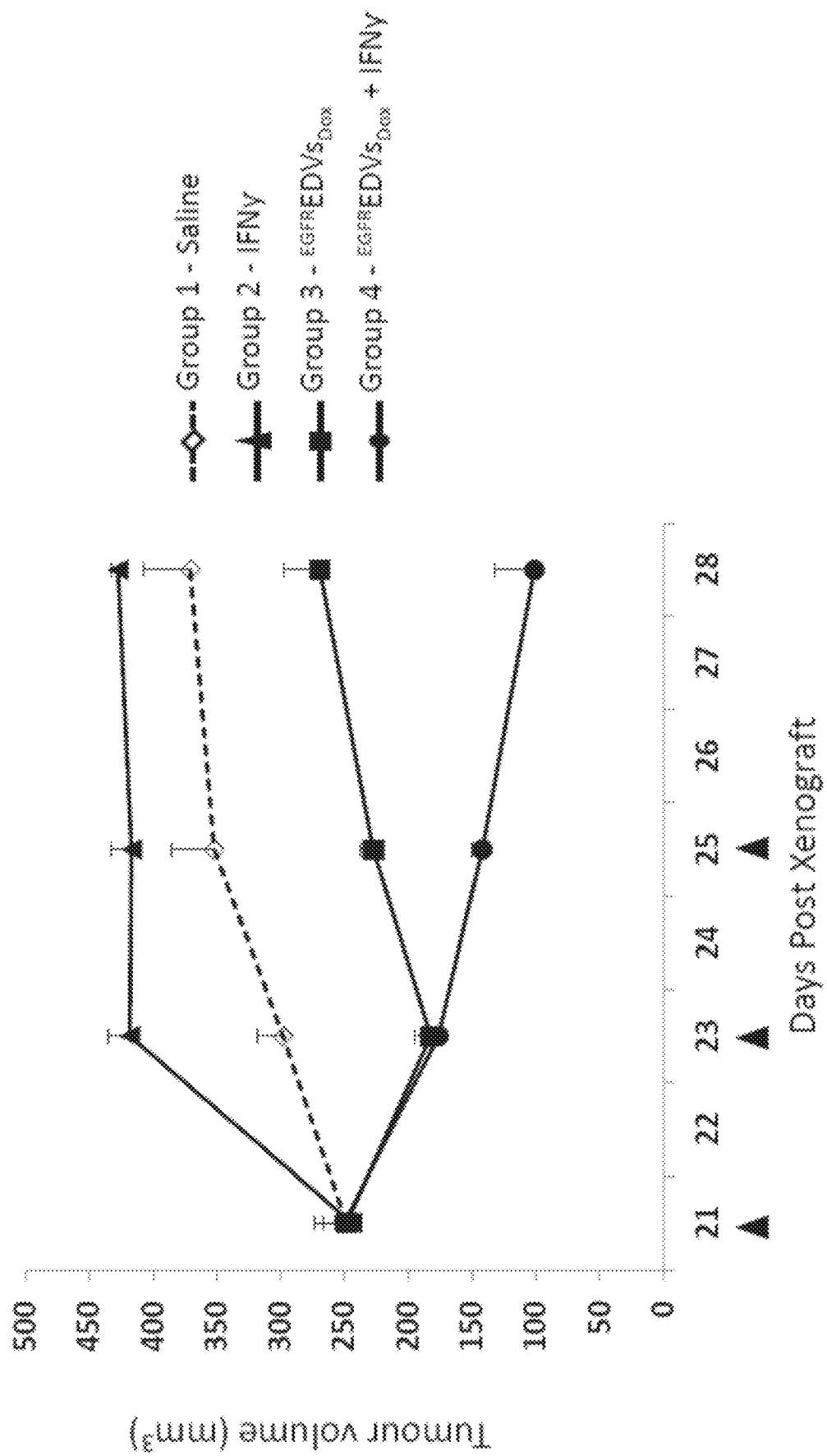
FIG. 22 shows another experiment illustrating the effect on MDA-MB 468 (breast cancer) xenograft tumor growth in Balb/c nu/nu mice treated with saline (negative control), IFN-γ (0.5×104 IU per dose), EGFR-targeted EDVs loaded with doxorubicine ($^{EGFR}$EDVs$_{Dox}$™), and $^{EGFR}$EDVs$_{Dox}$™+IFN-γ. The triangles indicate treatment days.

In contrast, mice treated with $^{EGFR}EDVs_{Dox}$ and IFN-γ showed highly significant tumor regression and by day 28, after a total of 3 doses, these tumors were more like scar tissue (FIG. 22, solid circles). Mice treated with IFN-γ alone showed no anti-tumor efficacy (FIG. 22, solid triangles), and the tumors grew, as in the saline treated group (FIG. 22, open diamonds). Thus, combining $^{EGFR}EDVs_{Dox}$ and IFN-γ (type II IFN) resulted in tumor regression in a mouse xenograft model of breast cancer, as summarized in Table 15, below.

TABLE 14

| Group | Treatment | FIG. | Results |
| --- | --- | --- | --- |
| Group 1 | sterile physiological saline | FIG. 20, open diamonds | no anti-tumor efficacy, and tumors grew |
| Group 2 | IFN-γ ($0.5\times10^4$ IU) per dose | FIG. 20, solid triangles | no anti-tumor efficacy, and tumors grew |
| Group 3 | $^{EGFR}EDVs_{Dox}$ | FIG. 20, solid squares | tumor stabilisation |
| Group 4 | $^{EGFR}EDVs_{Dox}$ and IFN-γ ($0.5\times10^4$ IU) per dose | FIG. 20, solid circles | highly significant tumor regression by day 43 after a total of 6 doses |

TABLE 15

| Group | Treatment | FIG. | Results |
| --- | --- | --- | --- |
| Group 1 | sterile physiological saline | FIG. 21, open diamonds<br>FIG. 22, open diamonds | Exps. #1 and #2: no anti-tumor efficacy, and tumors grew |
| Group 2 | IFN-γ (0.5 × 104 IU) per dose | FIG. 21, solid triangles<br>FIG. 22, solid triangles | Exps. #1 and #2: no anti-tumor efficacy, and tumors grew |
| Group 3 | $^{EGFR}EDVs_{Dox}$ | FIG. 21, solid squares | Exp. #1: tumor stabilisation, but by ~day 25 the tumors began to grow again, likely due to development of resistance to doxorubicin |
| | | FIG. 22, solid squares | Exp. #2: tumor regression, but by ~day 23 the tumors began to grow again, likely due to development of resistance to doxorubicin |
| Group 4 | $^{EGFR}EDVs_{Dox}$ and IFN-γ (0.5 × 104 IU) per dose | FIG. 21, solid circles | Exp #1: highly significant tumor regression, and by day 30, after a total of 6 doses, these tumors were more like scar tissue |
| | | FIG. 22, solid circles | Exp. #2: highly significant tumor regression and by day 28, after a total of 3 doses, these tumors were more like scar tissue |

Lung cancer: To study the anti-tumor effects of combining $^{EGFR}EDVs_{Dox}$ and IFN-γ (type II IFN) in a IFN-γ can overcome drug resistance in a lung cancer xenograft model as summarized in Table 16, below.

TABLE 16

Figure 23:
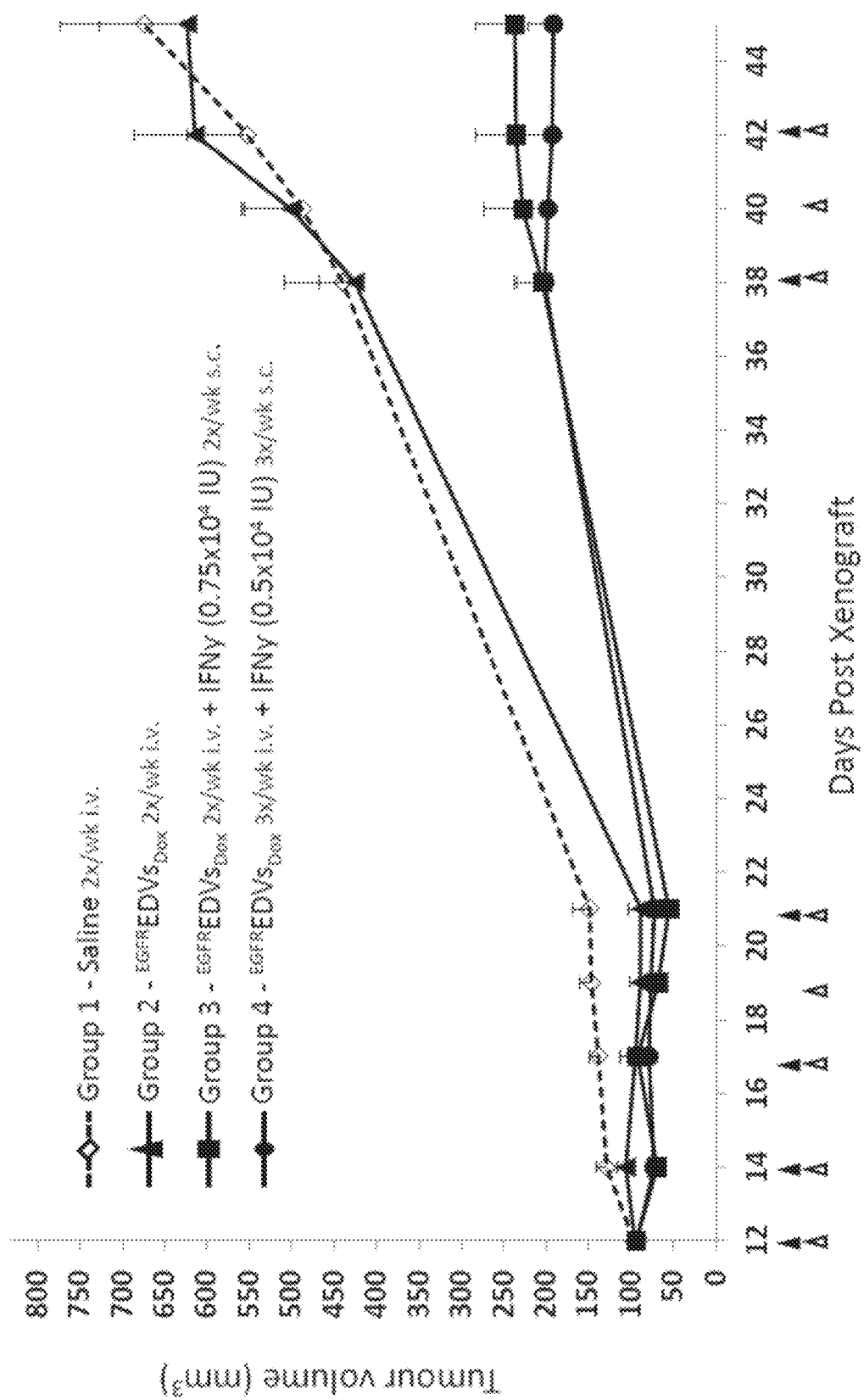
FIG. 23 shows the effect on doxorubicin-resistant A549 xenograft tumor growth in Balb/c nu/nu mice treated with saline (negative control, Group 1), EGFR-targeted EDVs loaded with doxorubicine ($^{EGFR}$EDVs$_{Dox}$™, Group 2), $^{EGFR}$EDVs$_{Dox}$™+IFN-γ (0.75×10$^4$ IU per dose) (Group 3), and $^{EGFR}$EDVs$_{Dox}$™+IFN-γ (0.5×10$^4$ IU per dose) (Group 4). Mice in Groups 1-3 received treatment twice per week indicated by the solid triangles. Mice in Group 4 were treated three times per week as indicated by open triangles.
Figures 24A, 24B, 24C:
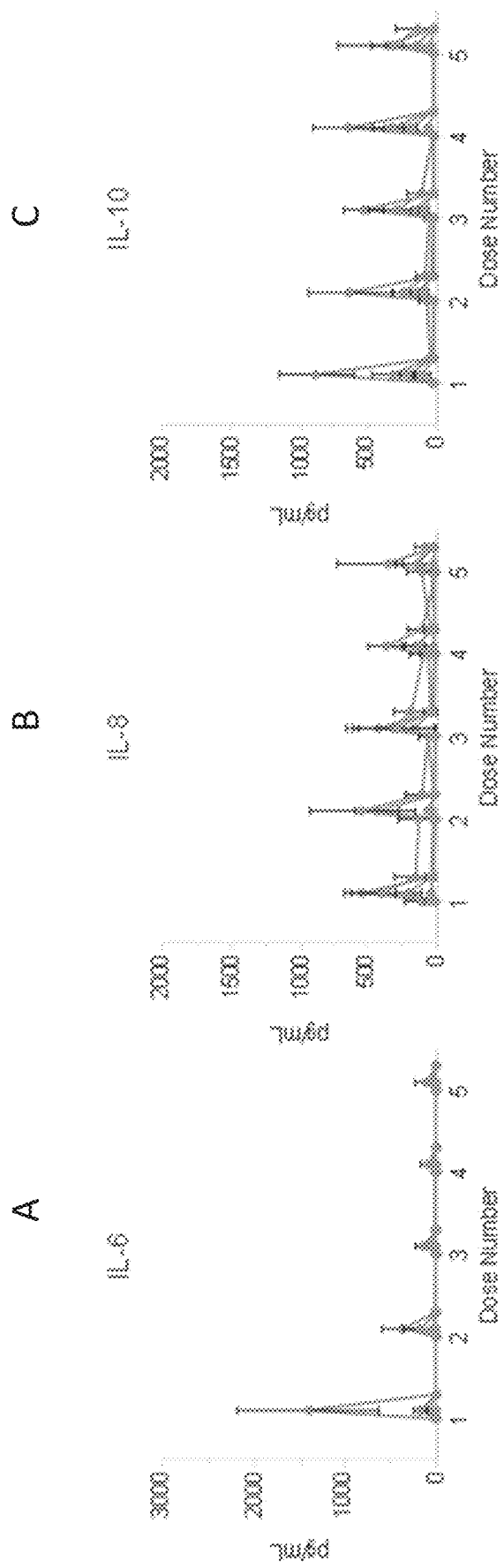
FIGS. 24A-K show a cytokine profile of patients from a First-in-Man clinical study where different dosages of $^{EGFR}$EDVs™ loaded with paclitaxel were administered.
Figures 24D, 24E, 24F:
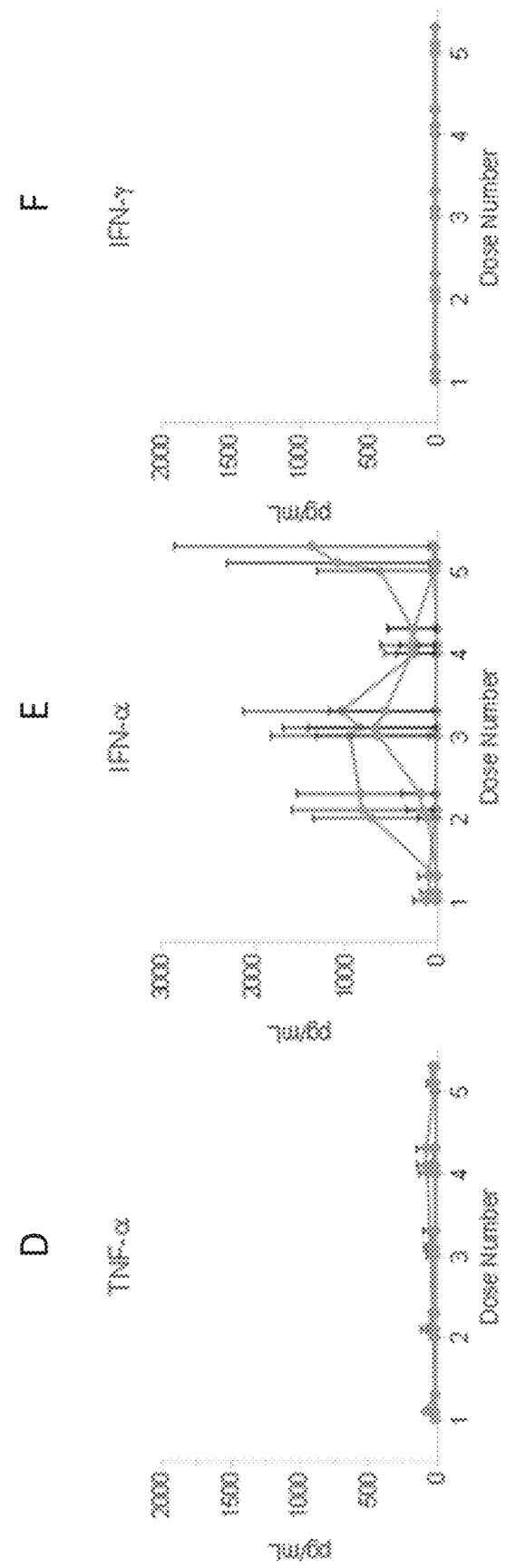
Figures 24G, 24H, 24I:
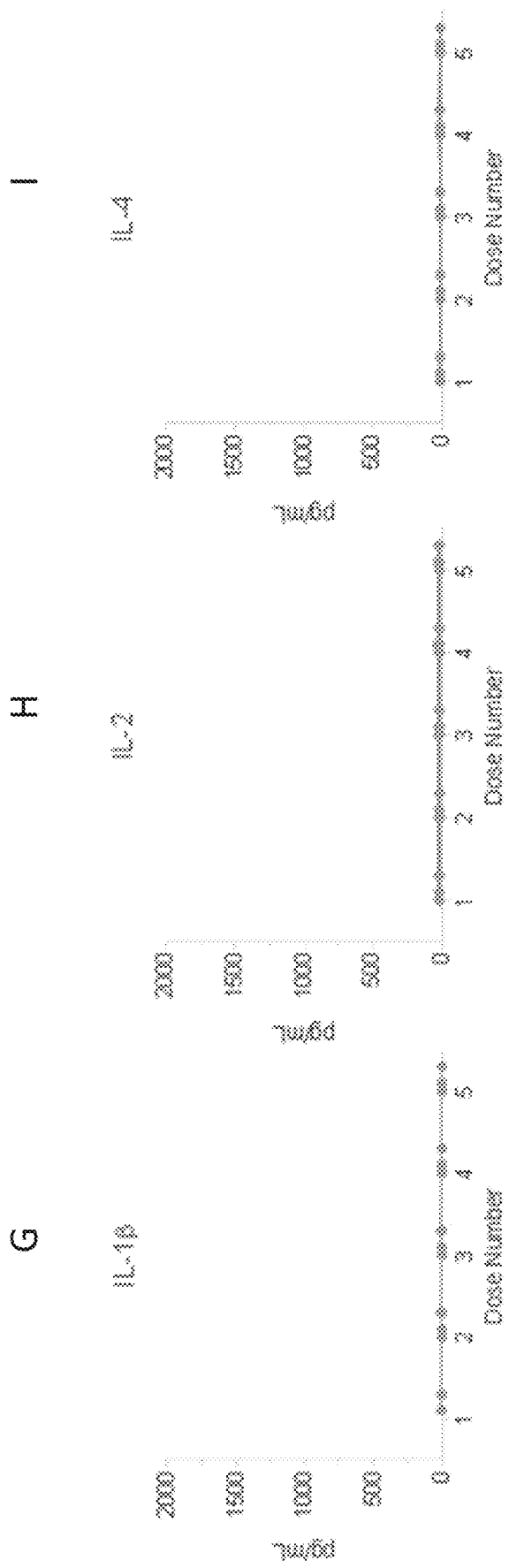
Figures 24J, 24K:
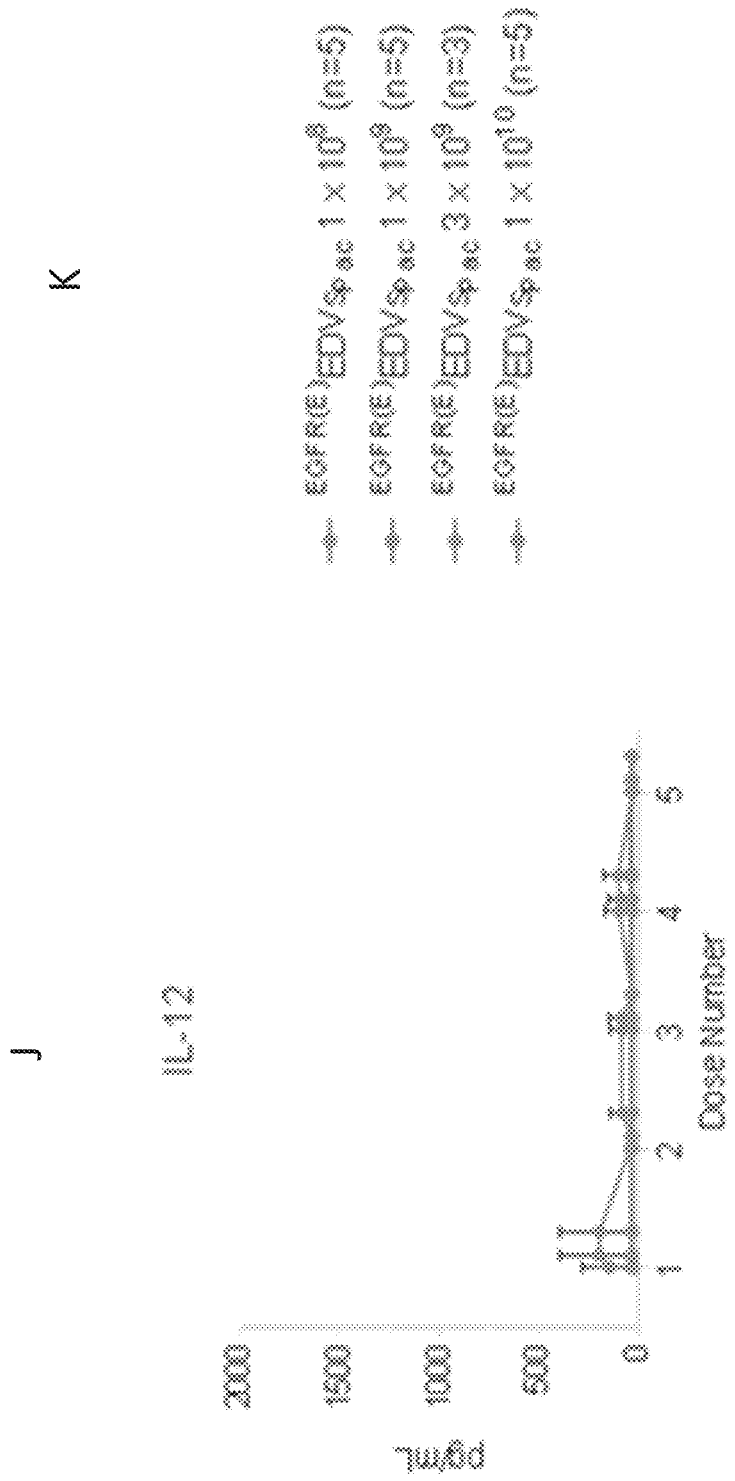
Figures 25A, 25B, 25C:
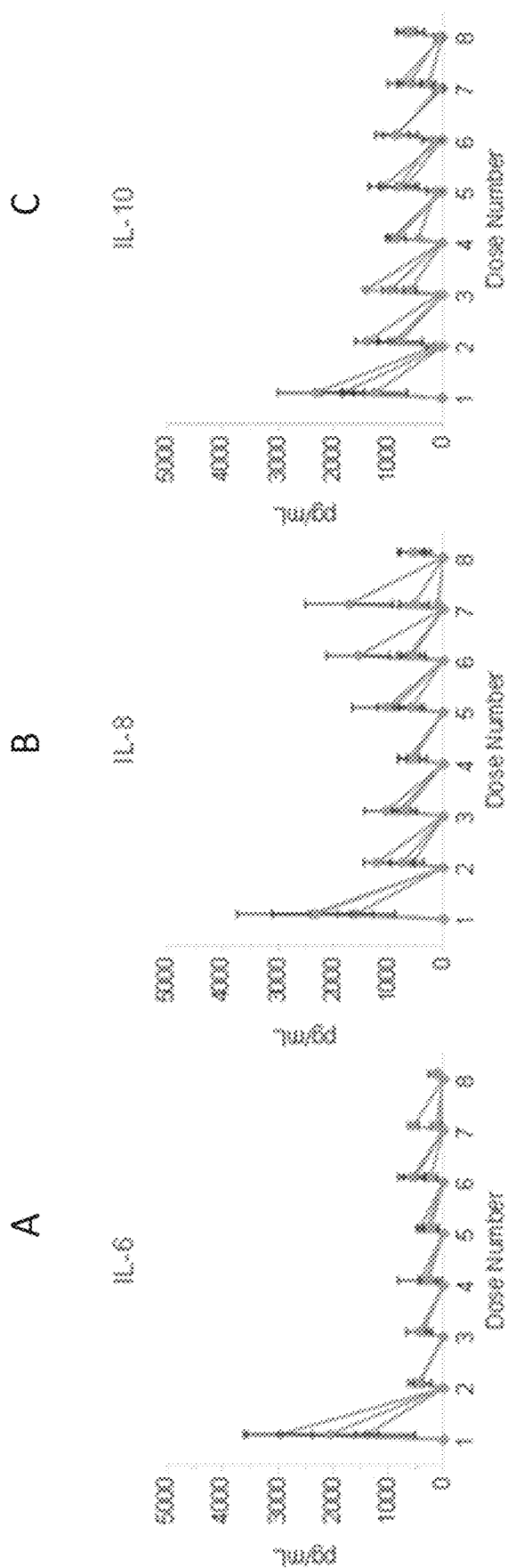
Figures 25G, 25H, 25I:
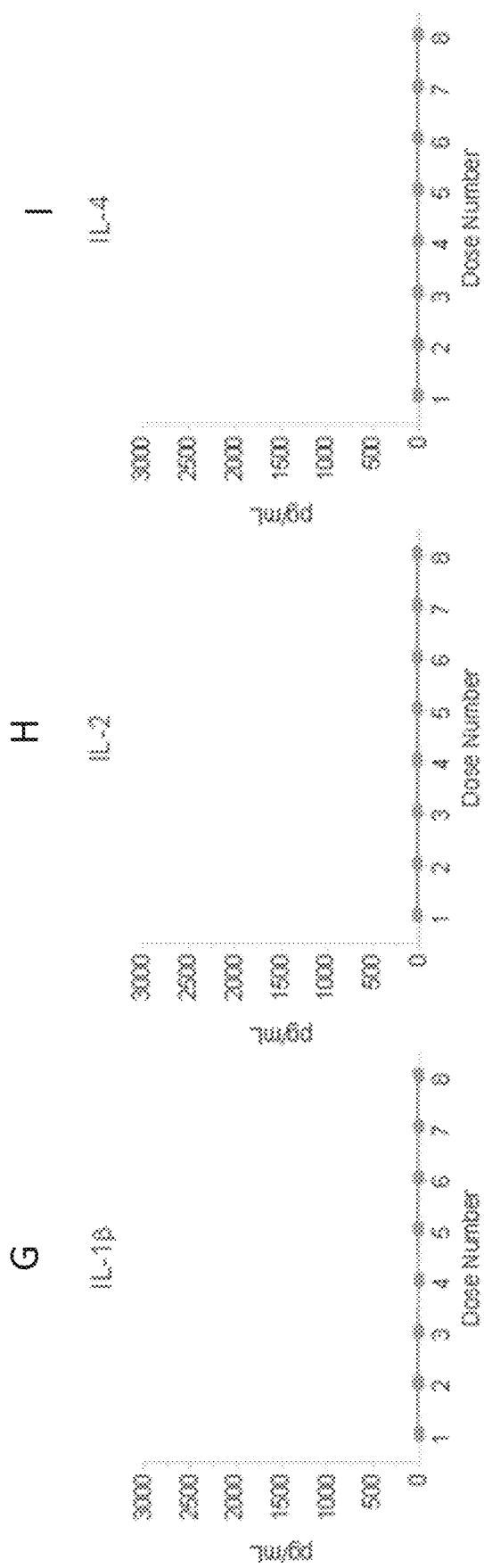
Figures 25J, 25K:
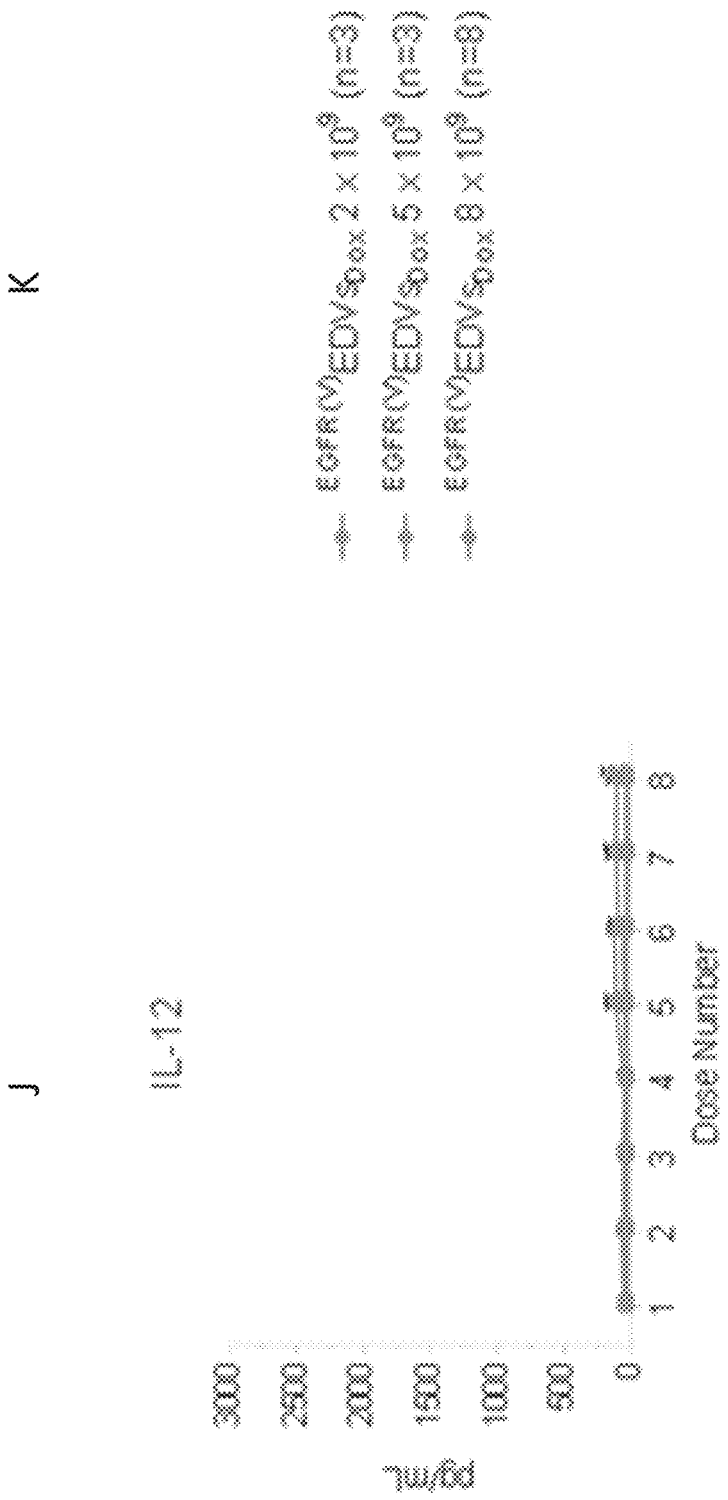

| Group | Treatment | FIG. | Results |
| --- | --- | --- | --- |
| Group 1 | sterile physiological saline 2x per week | FIG. 23, open diamonds | no anti-tumor efficacy, and tumors grew |
| Group 2 | $^{EGFR}EDVs_{Dox}$ | FIG. 23, solid triangles | no anti-tumor efficacy, and tumors grew |
| Group 3 | $^{EGFR}EDVs_{Dox}$ and IFN-γ (0.75 × $10^4$ IU) per dose | FIG. 23, solid squares | tumor stabilisation |
| Group 4 | $^{EGFR}EDVs_{Dox}$ and IFN-γ (0.5 × $10^4$ IU) per dose | FIG. 23, solid circles | tumor stabilisation | doxorubicin-resistant lung cancer model, the A549 lung cancer cell line was initially grown in culture in the presence of doxorubicin (Dox), and a Dox-resistant derivative cell line was established. Then, Dox-resistant A549 xenografts in Balb/c nu/nu mice were established and divided into four groups receiving different treatment combinations by intravenous tail vein injection. Group 1 received sterile physiological saline two times per week (FIG. 23, open diamonds). Group 2 received $^{EGFR}EDVs_{Dox}$ (FIG. 23, solid triangles). Group 3 received $^{EGFR}EDVs_{Dox}$ and IFN-γ (0.75× $10^4$ IU) per dose (FIG. 23, solid squares). Group 4 received $^{EGFR}EDVs_{Dox}$ and IFN-γ (0.5×$10^4$ IU) per dose (FIG. 23, solid circles). As depicted in FIG. 23, group 1, 2, and 3 were the indicated dosages two times per week (indicated by solid triangles on the x axis in FIG. 23); whereas group 4 mice were administered the indicated dosage three times per week (depicted by open triangles on the x-axis in FIG. 23). Mice treated twice or three times a week with $^{EGFR}EDVs_{Dox}$ and IFN-γ (0.5 or 0.75×$10^4$ IU) achieved tumor stabilisation of resistant A549 lung cancer xenografts (FIG. 23). In contrast, mice treated with $^{EGFR}EDVs_{Dox}$ showed no anti-tumor efficacy and the tumors grew as in the saline treated group. This result suggests that the inclusion of IFN-γ (0.5 or 0.75×$10^4$ IU) along with $^{EGFR}EDVs_{Dox}$ in the treatment of tumors normally resistant to the latter alone is essential to achieve tumor stabilisation. Thus, combining $^{EGFR}EDVs_{Dox}$ and Example 14: Treatment of Dogs with Late-Stage Endogenous Tumors with $^{EGFR}EDVs_{PNU}$ or $^{ITG}EDVs_{PNU-159682}$+$EDVs_{40mer}$ (Type 1 IFN Agonist)+Imukin (Type II IFN)

This example showed that delivering the supertoxic drug PNU-159682 and a type I IFN agonist (40mer double stranded DNA) with minicell technology and additionally interferon gamma (Imukin) (type II IFN) was well tolerated in a dog study.

A toxicology study was carried out in dogs with endogenous late-stage cancers. Dogs were companion animals presenting with late stage tumors. Informed consent was obtained from each pet owner.

Thirteen dogs with brain cancer, sarcoma, or melanoma were treated with PNU-loaded EDVs targeted to EGFR or ITG (integrin), in combination with immunomodulatory adjuvants (EDVs$_{60mer/50mer}$ and/or Imukin). Dogs with brain cancer or sarcoma were treated with EGFR-targeted EDVs (n=9), and dogs with melanoma were treated with ITG-targeted EDVs (n=4). A total of 185 weekly or bi-weekly doses were administered in different combinations with or without adjuvants, with up to 73 doses received by a single dog. Doses of EDVs administered were up to 5×$10^9$ PNU-loaded and targeted EDVs, up to 2×$10^9$ EDVs$_{40mer/50mer}$, and Imukin at 25 μg/m² per dose. All combinations were generally well-tolerated, with the most common adverse events being similar to those seen on administration of other EDV products (mild lethargy, fever, nausea, vomiting).

Addition of immunomodulatory adjuvants did not appear to change the general spectrum or increase the frequency of AEs seen with EDV dosing.

Notable effects on haematological parameters included mild transitory reduction of leukocyte subsets at 3 hours post-dose (WBC, neutrophils, lymphocytes, monocytes and eosinophils). Similar changes were seen with or without the addition of immunomodulatory adjuvants. It is of interest to note that in other canine and human clinical studies, neutrophils generally increased rather than decreased at 3 hours post-dose. This mild reduction in neutrophils appears to be specific to treatment of dogs with PNU-loaded EDVs.

Dogs experienced transient elevation of IL-6, IL-8, IL-10, IL-12p40 and TNF-α at 3 hours post-dose. In general, doses comprising immunomodulatory adjuvants resulted in a slightly higher induction of these cytokines than doses comprising PNU-loaded EDVs alone. They also resulted in reduced levels of IL-2 post-dose. These data provide support for the safety and tolerability of immunomodulatory EDV adjuvants used in combination with anti-neoplastic-loaded and targeted EDVs.

The best response observed was stabilized disease in 6 of 7 evaluable animals (85.7%), although 1 dog achieved a near partial response (29.8% reduction in tumor size). One dog demonstrated stabilized disease over the course of the study, receiving 73 doses over more than 11 months of treatment. This dog exhibited loss of vision due to the tumor mass pressing on the optic nerve; however, vision was restored over the course of treatment, demonstrating improvement in clinical symptoms.

Example 15: Targeted and Loaded EDVs do not Activate IFN-γ in Human Clinical Studies This example showed that EDVs packaged with Paclitaxel or Doxorubicin induced a cytokine response in human patients consistent with toll like receptor activation, but this EDV treatment did not induce an interferon type II response.

To gain insight into the pathways activated by administration of targeted and loaded EDVs, a panel of cytokines was evaluated in the First-in-Man (Example 5 above) and recurrent glioblastoma human clinical trials (Example 6 above).

FIGS. 24A-25K shows the cytokine response to $^{EGFR(Erb)}$EDVs$_{Pac}$ treatment in the First in Man study (Example 5), and FIGS. 25A-25K shows the cytokine response to $^{EGFR(V)}$EDVs$_{Dox}$ in the recurrent glioblastoma study. As shown in FIGS. 24A-24K and 25A-25K, IL-6, IL-8, IL-10, and to a lesser extent TNF-α were transiently elevated at 3-4 hours post-dose, and returned to baseline by 24 hours or prior to the next dose for both treatments. The cytokine response to EDVs loaded with Paclitaxel or Doxorubicin is consistent with activation of the toll-like receptor pathway, and in particular TLR4 which is known to be stimulated by bacterial LPS. IL-12 was randomly elevated in 2 patients in the First-in-Man study only (FIGS. 24A-24K), though elevations were not consistent with dosing.

Interestingly the type I interferon IFN-α was elevated at random stages throughout the study in 3/22 patients in the First-in-Man study (see FIGS. 24A-24K), and in 1/14 patients in the recurrent glioblastoma study (see FIGS. 25A-25K). Induction of IFN-α was not consistent with dosing. Interferon pathways are generally activated by viral rather than bacterial stimuli like the TLR pathways, so it is possible that these selected patients had concurrent unreported viral infections during the study (e.g. a cold). However all other cytokines tested, including IFN-γ, were not affected by dosing with targeted and loaded EDVs. This suggests that activation of type II IFN-γ (via addition of Imukin) may be a viable approach for enhancing the efficacy of targeted and loaded EDVs by stimulating different antitumor pathways.

Example 16: Cyto-Immuno-Therapy for Cancer: A Novel Pathway Elicited by Tumor-Targeted, Supertoxic Drug-Packaged Bacterially-Derived Nanocells This example demonstrates that the EDV nanocell targeted to a tumor cell surface receptor functions as a cancer immunotherapy capable of a dual assault on the tumor by delivering the super cytotoxin PNU-159682 (682) in conjunction with activation of the innate and adaptive immune systems.

This example shows targeted EDV nanocells delivering 682 activated M1 macrophages and NK cells which are capable of killing tumor cells within the microenvironment accompanied with a predominantly Th1 cytokine response. This is followed by dendritic cell maturation resulting in antigen presentation and generation of tumor specific CD8$^+$ T-cells. The combination of super cytotoxin delivery and activation of both innate and adaptive antitumor immune responses, results in a potent cancer cyto-immunotherapeutic which has potential in clinical oncology.

This example shows for the first time on the novel cyto-immunotherapy function of the EDV nanocell, where it is not only capable of delivering a cytotoxic drug within tumor cells but at the same time of eliciting an innate and adaptive immune response specifically targeting the tumor. Clinically, in a compassionate use case patient, 682 loaded EDV are shown to overcome drug resistance while stimulating adaptive immunity. Pre-clinical studies demonstrated that the immunotherapeutic pathway resulting from EDV treatment encompasses an approach which addresses all the necessary steps needed to mount an effective antitumor response by the immune system. This example illustrates the ability of the EDV to activate cells of the innate immune system, including macrophages, NK cells and dendritic cells. This is followed by dendritic cell maturation and antigen presentation leading to an adaptive T-cell response in which tumor specific cytotoxic T-cells are produced and results in further recruitment of additional immune cells to the tumor microenvironment. This approach circumvents some of the current pitfalls with immunotherapies by creating an immunogenic tumor microenvironment and also acting on multiple immune cell subsets thereby avoiding primary and/or adaptive resistances that may arise in patients.

Results: M1 Macrophage Polarization and Dendritic Cell Maturation in Response to EDV Treatment:

Due to the fact that the EDV is derived from *Salmonella Typhimurium* bacteria, the outer EDV membrane contains a substantial lipopolysaccharide (LPS) content (MacDiarmid et al., 2007b). The interaction of high doses of LPS with macrophages is well known to result in macrophage activation and M1 polarization. To determine if the EDV was capable of eliciting a similar phenotypic response, RAW264.7 cells were incubated with Ep-EDV-682 and Ep-EDV and examined for changes in macrophage phenotype and cytokine production. Expression of the co-stimulatory CD86 expression is known to be a phenotypic indicator of macrophage polarization as well as a hallmark of the antitumor M1 tumor associated macrophages (TAMs) (Dong et al., 2016).

Figures 27A, 27B, 27C, 27D:
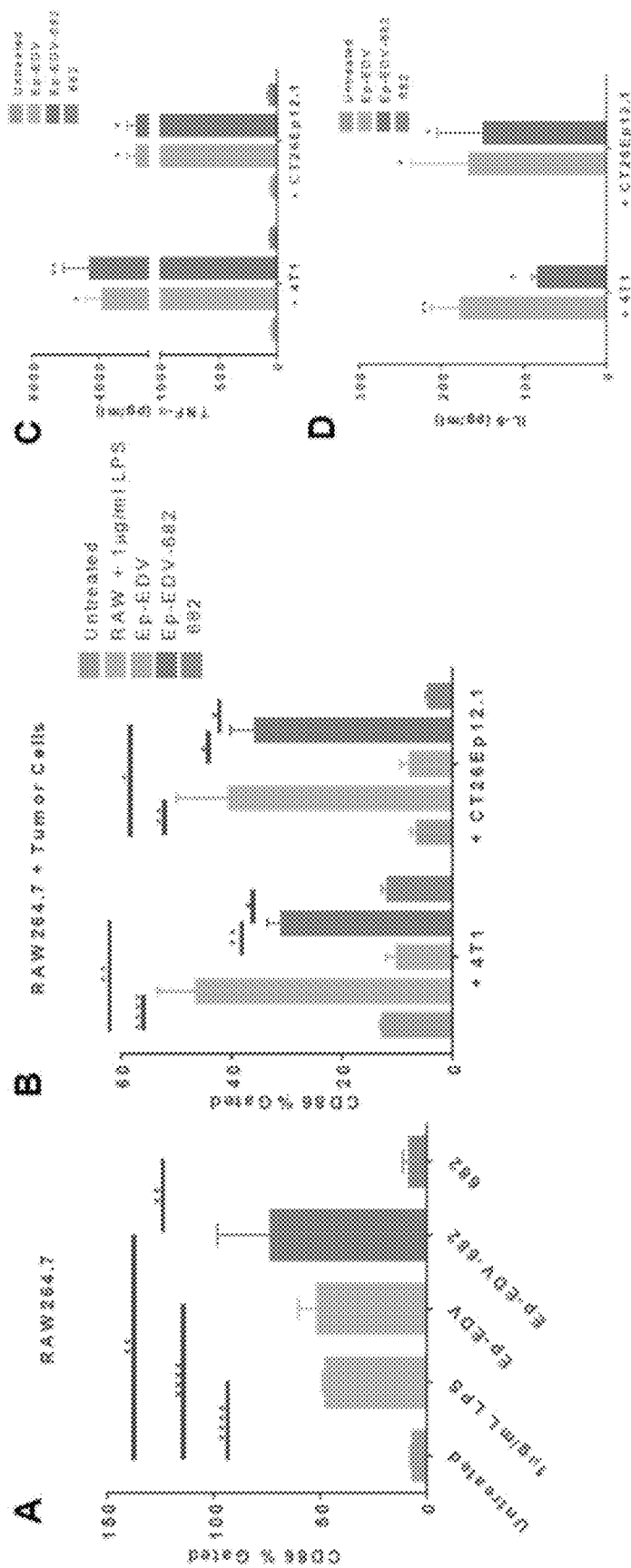
Figures 35A, 35B, 35C:
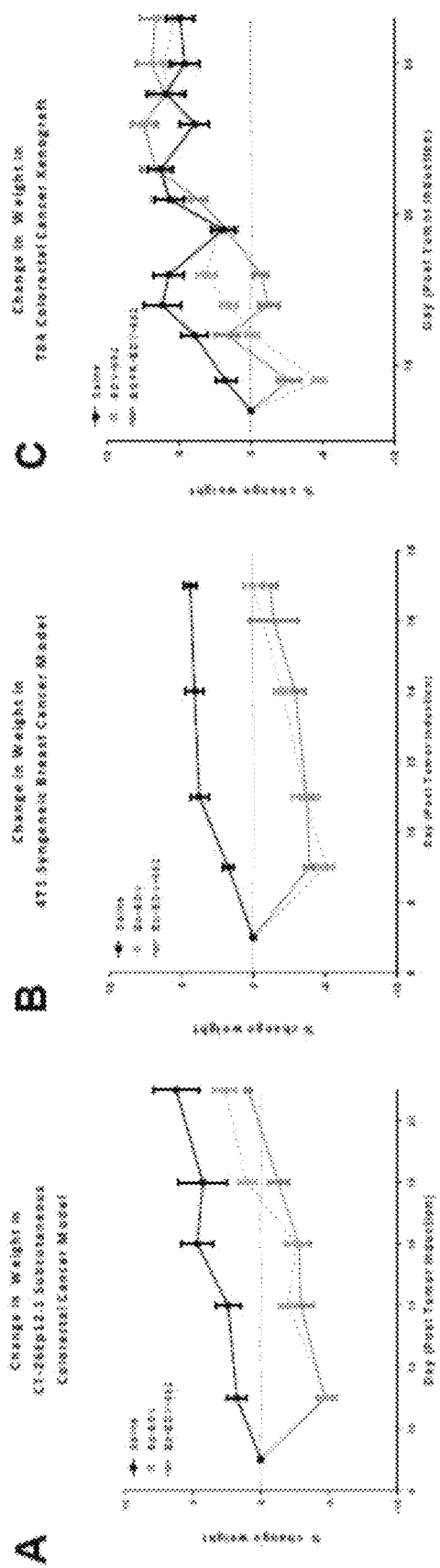
FIGS. 35A-35I shows body weight changes and macrophage activation in response to EDV treatment in Balb/c and Balb/c nude xenografts. % change in body weights of mice bearing (FIG. 35A) CT26Ep12.1 (FIG. 35 B) 4T1 (FIG. 35 C) T84 and (FIG. 35 D) A549/MDR tumors in response to treatment. No more than 5% weight loss is seen with the initial dose, and weights then recover and stabilize with subsequent dosing. Data represents mean±s.e.m. M1/M2 (CD86:CD206) ratio of macrophages in (FIG. 35E) A549/MDR and (FIG. 35F) T84 tumors of EDV treated mice.

Both Ep-EDV-682 and Ep-EDV were capable of eliciting significant increases in the level of CD86 expression, most likely in response to the presence of LPS on the EDV surface, whereas 682 alone did not induce the same response (FIG. 27A). Furthermore, EDV treated RAW cells displayed a significant increase in the pro-inflammatory cytokines TNF-α and IL-6, which have been identified as being responsible for Th1 macrophage polarization (Yuan et al., 2015) (FIGS. 35A and 35B). Interestingly, mouse tumor cells (4T1 and CT26Ep12.1) which had been treated with Ep-EDV-682 followed by co-culture with RAW264.7 cells were also able to generate a significant increase in CD86 expression on the RAW264.7 cells (FIG. 27B) as well as a significant increase in the production of the pro-inflammatory cytokines TNF-α and IL-6. (FIG. 27C-27D). However, Ep-EDV or 682 treatment alone was unable to produce any significant change in CD86 expression, and 682 treatments showed no increase in the production of Th1 cytokines, indicating that cell death in response to EDV loaded 682 was necessary to fully induce subsequent M1 macrophage polarization.

Figures 27E, 27F:
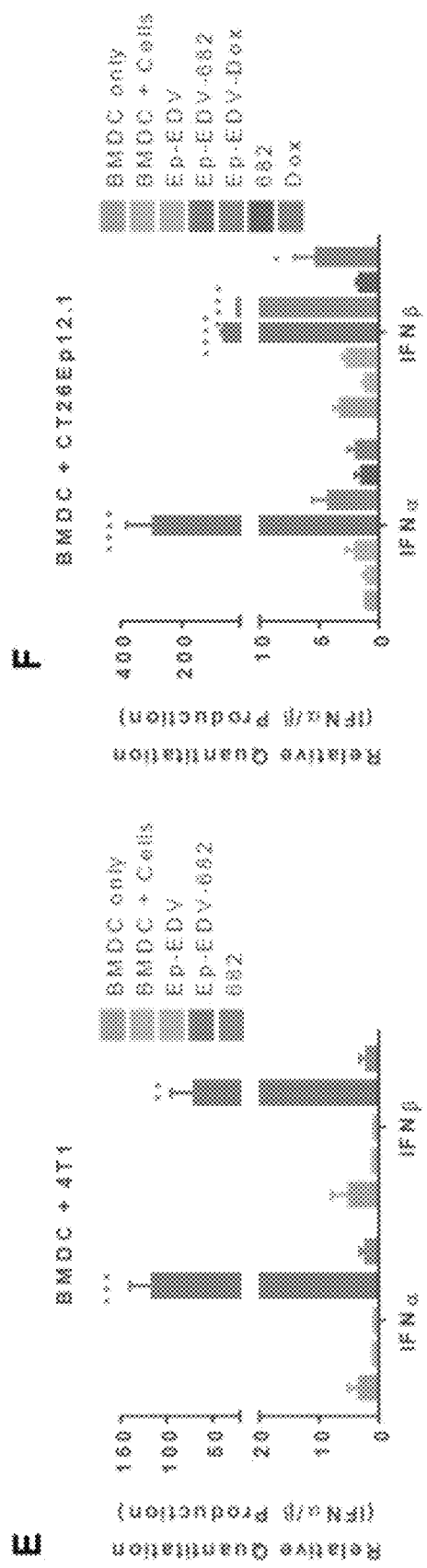
Figures 27G, 27H:
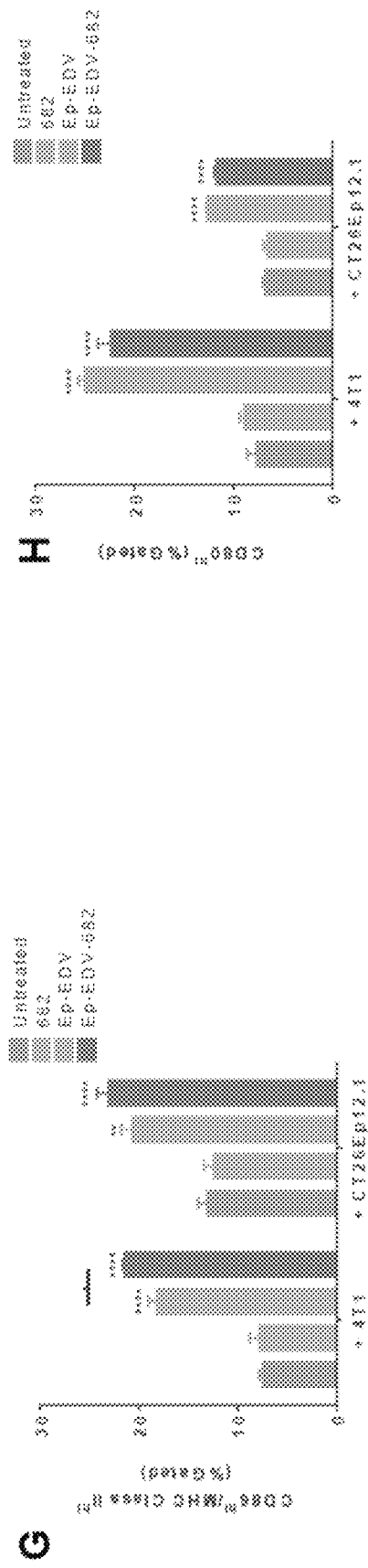

The effect of tumor cell death in response to Ep-EDV, Ep-EDV-682, and 682 treatment on dendritic cell maturation was also examined (FIGS. 27E-27I). Bone marrow derived dendritic cells (BMDC) were co-incubated with treated tumor cells (4T1 and CT26Ep12.1) for 48 h, followed by assessment of the production of the type 1 interferons IFNα and IFNβ. Increases in type 1 interferon production by dendritic cells is well established as a mechanism of dendritic cell maturation and enhanced antigen presentation as well as being vital for their interaction with other immune cell subsets including NK cells and T-cells (Fitzgerald-Bocarsly and Feng, 2007; Simmons et al., 2012). BMDC co-culture with Ep-EDV-682 treated 4T1 cells showed significant increases in both type 1 interferons with ~100 fold increase in IFNα mRNA production and ~70 fold increase in IFNβ mRNA production (FIG. 27E). Similarly, BMDC co-culture with Ep-EDV-682 treated CT26Ep12.1 showed ~300 fold increase in IFNα mRNA production and ~60 fold increase in IFNβ mRNA production (FIG. 27F).

Figures 27J, 27K, 27L:
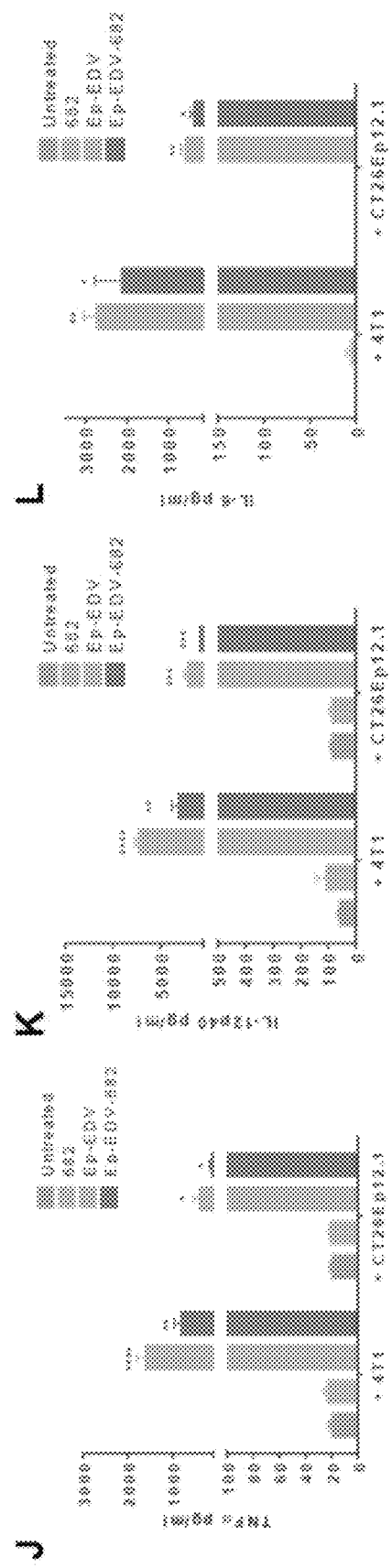
Figure 35D:
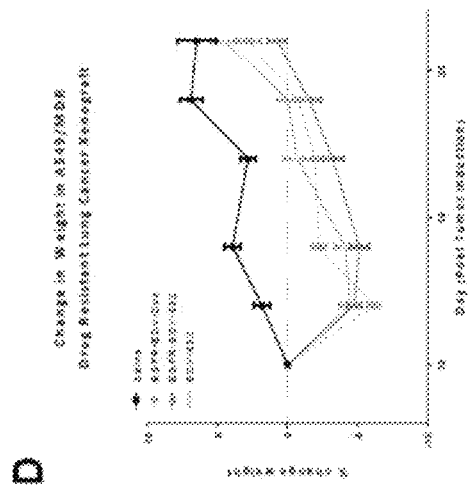
Figure 35E:
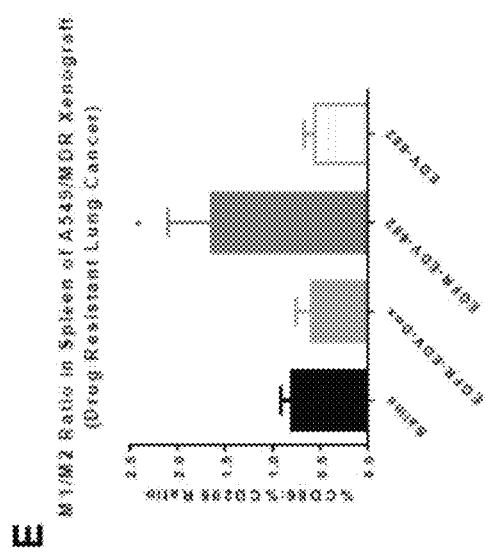

In addition, to assess if differences in the drug loaded into the EDV had any effect on type 1 interferon production, CT26Ep12.1 were treated with Ep-EDV-Dox and showed a significant ~20 fold increase in IFNβ mRNA production, but only a slight, non-significant increase in IFNα mRNA production. Ep-EDV and 682 treatment were unable to elicit increases in type 1 interferon mRNA production in co-cultures with either cell line. However, doxorubicin (Dox) treatment of CT26Ep12.1 did in fact show a significant ~5 fold increase in IFNβ mRNA production (FIG. 27F). Doxorubicin treatment of tumor cells is known to result in immunogenic cell death, and is therefore capable of prompting dendritic cell maturation. However, drug doses well above the IC50 are generally necessary for this type of death to occur with the drug alone (Showalter et al., 2017). Co-incubation of BMDC with EDV and drug treated 4T1 and Ct26Ep12.1 cells resulted in upregulation of CD86, MHC Class II, and CD80 within 24 h (FIGS. 27G-27I) with similar results seen in mouse JAWS II cells (FIGS. 35C-35E). BMDC co-cultured with EDV treated tumor cells also exhibited a profound and significant increase in the production of TNFα, IL-12p40, and IL-6 (FIGS. 27J-27L) Combined, these results indicate that EDVs loaded with 682 are capable of polarizing macrophages towards the M1 antitumor phenotype, as well as promoting dendritic cell maturation, while 682 alone is unable to elicit a similar response.

Example 17: Effective Delivery of the Super Cytotoxin PNU-159682 Generates Tumoricidal CD11b$^+$ Innate Immune Cells Since 682 is a super cytotoxin with IC50s for even drug-resistant cancer cells in the pM range (Quintieri et al., 2005), it is unable to be used clinically due to the severe systemic toxicity associated with such compounds (Staudacher and Brown, 2017). However, when encapsulated in the EDV, super cytotoxins such as 682 can be effectively delivered to the tumor with few side effects as evidenced by minimal weight loss (≤5%), little to no fur ruffling, and no appearance of lethargy or hunched postures in Ep-EDV-682 treated mice which correlates with previous studies involving mice treated with EDVs carrying a variety of therapeutic payloads (MacDiarmid et al., 2009; MacDiarmid et al., 2007a; MacDiarmid et al., 2007b; Sagnella et al., 2018) (FIGS. 35A-35D).

Figures 28A, 28B:
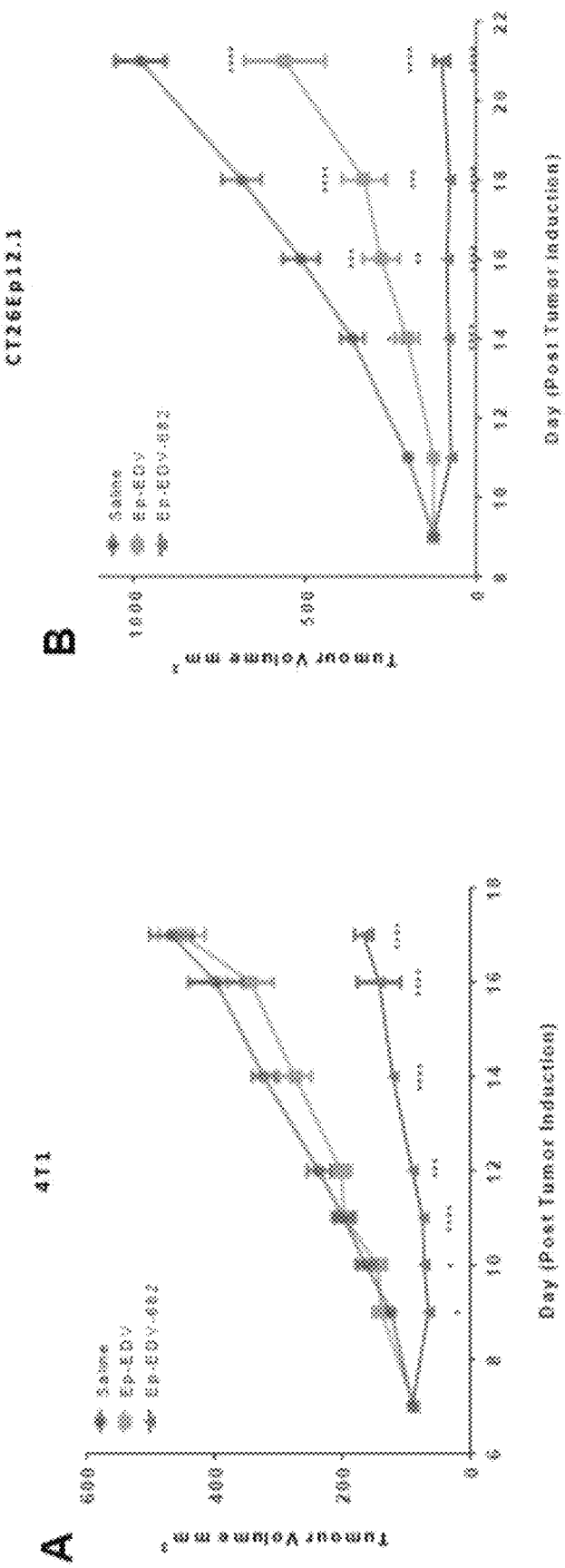
FIGS. 28A-28H shows tumor response and macrophage activation in response to EDV treatment. Tumor growth in response to Ep-EDV and Ep-EDV682 treatment in BALB/c mice bearing (FIG. 28 A) 4T1 or (FIG. 28 B) CT26Ep12.1 tumors. Tumor growth in response to (FIG. 28 C) EDV-682 and EDV-EGFR682 in BALB/C nude mice T84 xenografts and (FIG. 28 D) EDV-682, EDV-EGFRDox, and EDV-EGFR682 in BALB/C nude mice bearing A549/MDR xenografts. Green arrow indicates where EDV-EGFR682 treatment of formally saline treated mice was begun. Data (FIGS. 28A-D) represents mean±s.e.m. and analyzed by a two way ANOVA and Tukey's multiple comparison test (FIG. 28E) xCELLigence RTCA of CD11b$^+$ isolated from 4T1 tumors and co-cultured with 4T1 cells at a 5:1 (E:T) ratio. Plot represents normalized cell index which correlates to cell adhesion and growth/death vs time. CD11b$^+$ cells from 4T1 tumors undergo and initial adhesion and settling phase as indicated by an increase in cell index, followed by growth or death represented by an increasing or decreasing cell index.
Figures 28C, 28D:
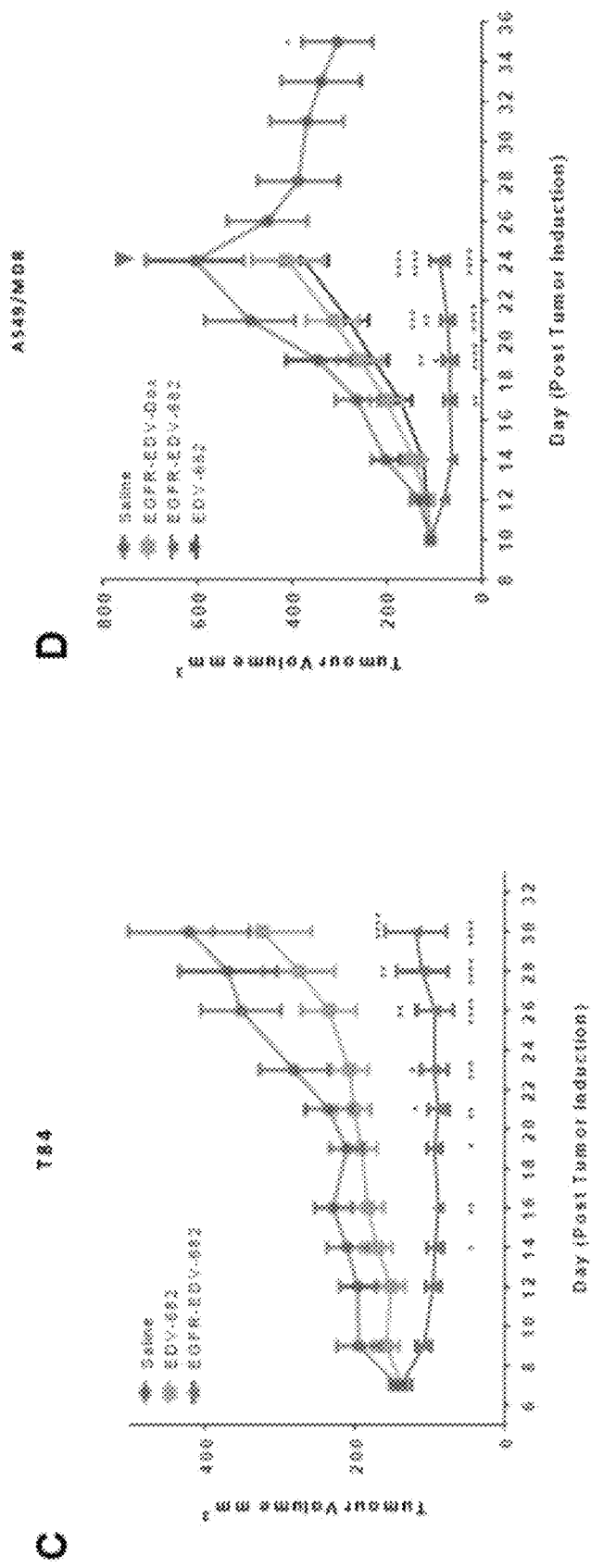

Here, significant tumor regression was seen in Ep-EDV-682 treated BALB/c mice bearing either 4T1 tumors in the mammary fat pad or subcutaneous CT26Ep12.1 tumors (FIGS. 28A-28B). Ep-EDV-682 was also capable of prompting significant tumor reduction in athymic BALB/c nude mice bearing T84 human xenografts and drug resistant A549/MDR xenografts as well as elicit significant tumor reduction in large (~600 mm$^3$) A549/MDR tumors (FIGS. 28C-28D).

Figure 28E:
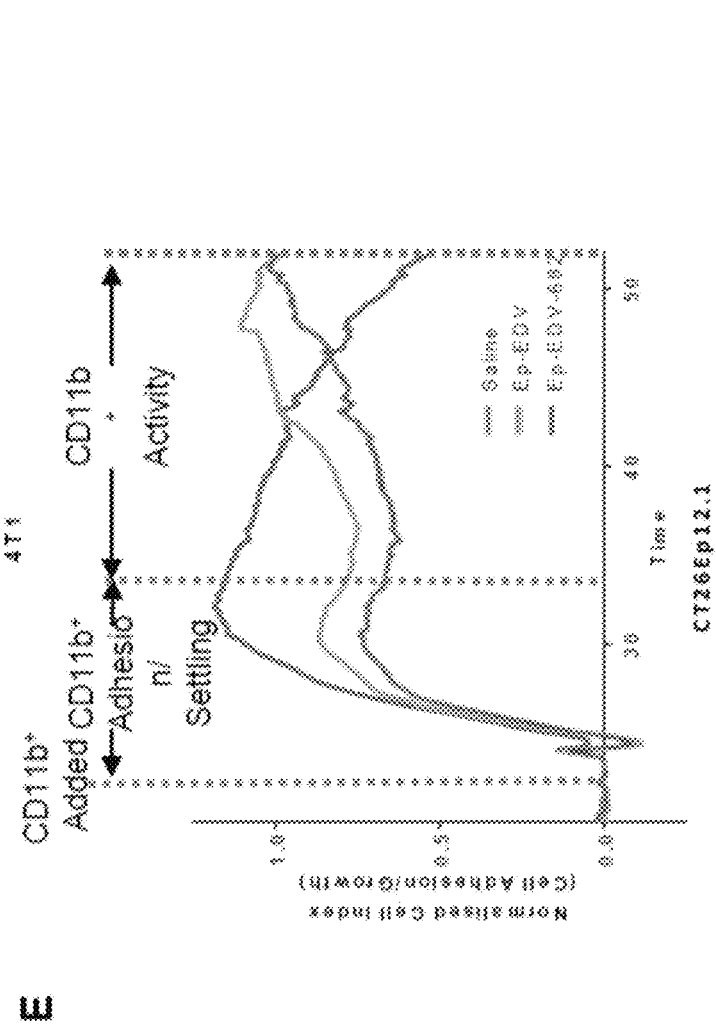
Figure 28F:
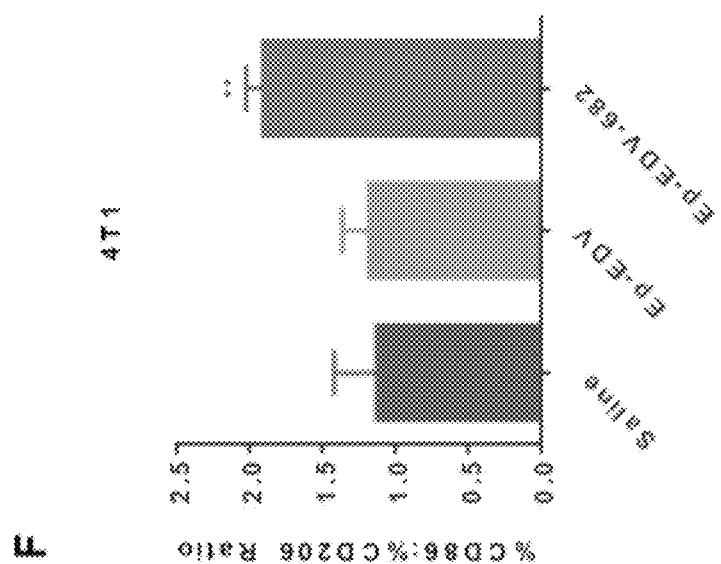
Figure 28G:
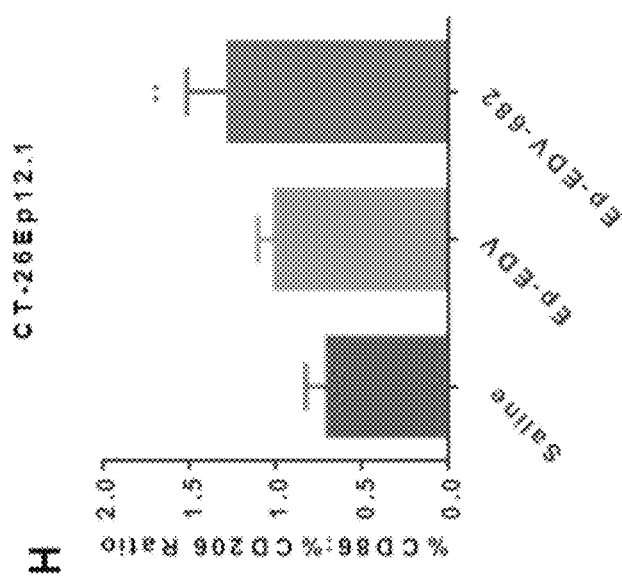

While it has been well established that the EDV can effectively deliver chemotherapeutics to tumors, initial in vitro experiments indicated that the EDV can also behave as an immunotherapeutic in a number of ways including, but not limited to, driving M1 macrophage polarization. To establish if these results extended to in vivo stimulation of the innate immune system within the tumor microenvironment, CD11b$^+$ immune cells were isolated from either 4T1 or CT26Ep12.1 mouse tumors which had been treated with saline, Ep-EDV, or Ep-EDV-682 and co-cultured ex vivo with their corresponding tumor cells in an xCELLigence real time cell analyzer (RTCA) at a 5:1 (Effector:Target) ratio (FIGS. 28E-28G). CD11b$^+$ cells co-cultured with adherent 4T1 cells, showed an initial adhesion and settling phase resulting in an increase in the cell index followed by an active phase in which cell index decreased steadily if the CD11b$^+$ cells were effective in killing the adherent tumor cells or increased if tumor cells were not effectively lysed and continued to grow.

As demonstrated, CD11b$^+$ cells isolated from the tumors of mice which had been treated with Ep-EDV-682 were highly effective at killing 4T1 cells, while those isolated from either Ep-EDV or saline treated tumors did not kill 4T1 tumor cells (FIG. 28E). Phenotyping of macrophages within the 4T1 tumors (CD45$^+$ CD11b$^+$ Ly6G-Ly6C$^+$) showed an increase in the M1/M2 ratio as evidenced by an increase in the ratio of CD86:CD206 expressing macrophages (FIG. 28F). Moreover, CD11b$^+$ from Ep-EDV-682 4T1 tumor bearing mice exhibited a 2-fold increase over saline and Ep-EDV treated mice in the production of macrophage inflammatory protein 1a (CCL3/MIP-1α), when co-cultured ex vivo with 4T1 cells (FIG. 36I). Localized production of MIP-1α has been implicated as a major factor responsible for attracting immune effector cell infiltrates into the tumor microenvironment and potentiating an effector cell mediated antitumor immune response (Allen et al., 2018; Zibert et al., 2004).

Figure 28H:
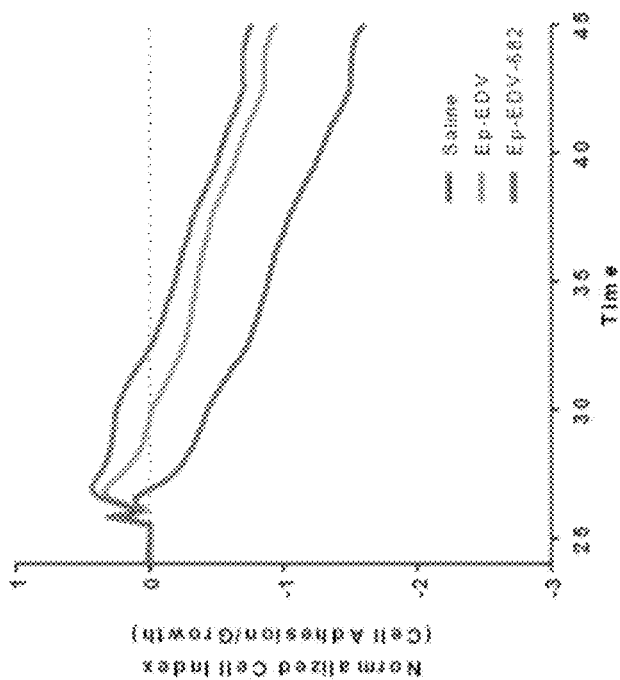

CD11b+ cells co-cultured with adherent CT26Ep12.1 cells similarly exhibited enhanced cytolytic activity of CD11b+ cells isolated from the tumors of mice treated with Ep-EDV-682 (FIG. 28G). Overall, CD11b+ cells from CT26Ep12.1 tumors were more active than those from 4T1 tumors as indicated by the steady decrease in cell index on the xCELLigence RTCA for all three treatment groups. However, cytolysis was more pronounced and began within 1 hr post CD11b+ cell addition in the Ep-EDV-682 treated group falling to 42% viability at 10h post CD11b+ cell addition. In contrast, it took nearly 5h for cytolysis to begin in the Ep-EDV treated samples and 7h for the saline treated group and viability at 10h post CD11b+ cell addition was 76% and 86% respectively. Flow Cytometric analysis of the CD11b+ cells isolated from the CT26Ep12.1 tumors showed a significant increase in the CD86:CD206 ratio (M1/M2 ratio) in the Ep-EDV-682 treated tumors (FIG. 28H).

Figure 35F:
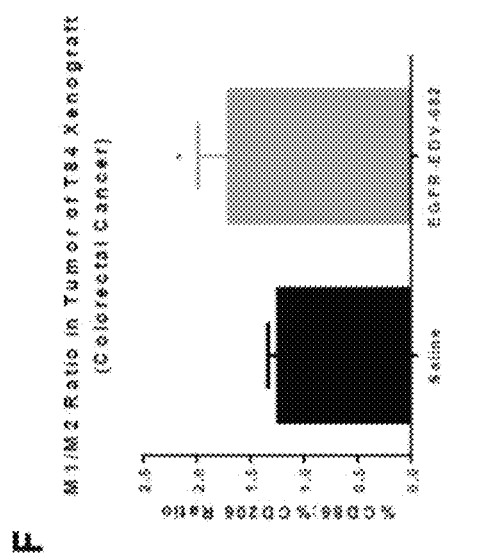

As with the immunocompetent mouse strains, a shift in macrophage polarization was also seen in a drug resistant human lung cancer xenograft (A549/MDR) in athymic nude mice where ~2-3 fold increase in M1/M2 ratio in the spleens of EGFR-EDV-682 treated mice was observed as compared to saline treated mice or mice treated with EDVs that were ineffective at reducing tumor growth (FIG. 35E). Additionally, a small, but significant increase in M1/M2 ratio was also detected in the EGFR-EDV-682 treated T84 tumors (FIG. 35F).

Figure 35G:
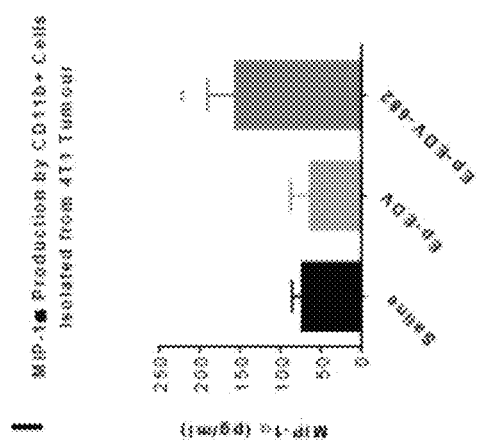
Figure 35H:
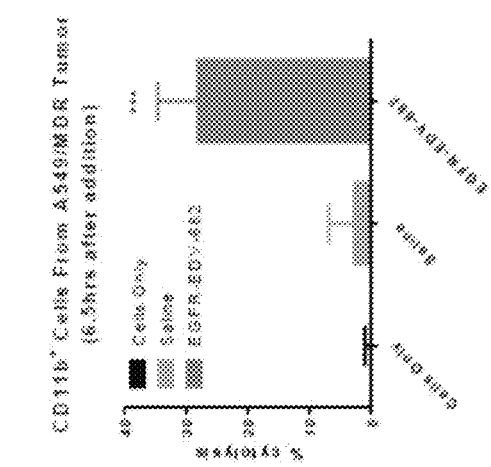
Figure 35I:
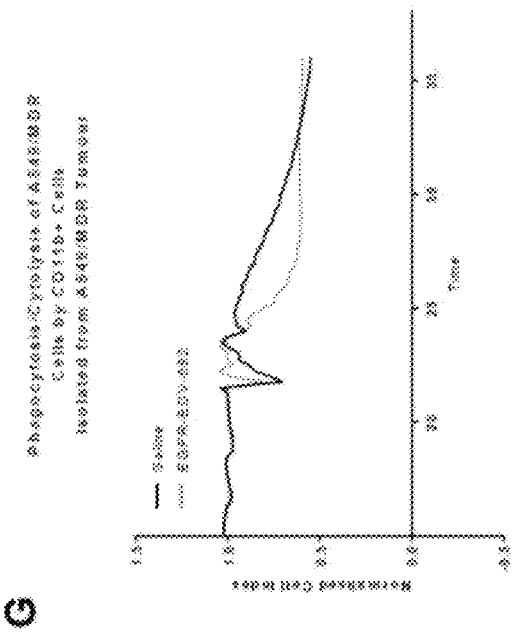

Similar to both immunocompetent mouse cancer models, CD11b+ cells isolated from the tumors of nude mice bearing A549/MDR tumors treated with EGFR-EDV-682 exhibited superior tumor cell cytolysis with 28% cytolysis 6.5h post CD11b+ cell addition to A549/MDR tumor cells as determined by xCELLigence RTCA compared to those treated with saline (FIGS. 35G and 35H).

Example 18: NK Cells Adopt an Antitumor Phenotype In Vivo Following Ep-EDV-682 Treatment The purpose of this example was to determine the impact on NK cell function of bacterial minicells comprising an antineoplastic agent.

To explore the effect of EDVs carrying 682 on NK cell function, NK cells were isolated from spleens of EDV treated and control BALB/c mice bearing either 4T1 or CT26Ep12.1 tumors following 2 weeks treatment with Ep-EDV-682, Ep-EDV or saline. Splenic NK cells were co-cultured in the xCELLigence RTCA with their corresponding tumor cells at an E:T ratio of 20:1 and tumor cell death was analyzed over a 3-4 day period (FIGS. 29A-29D).

Figures 29A, 29B:
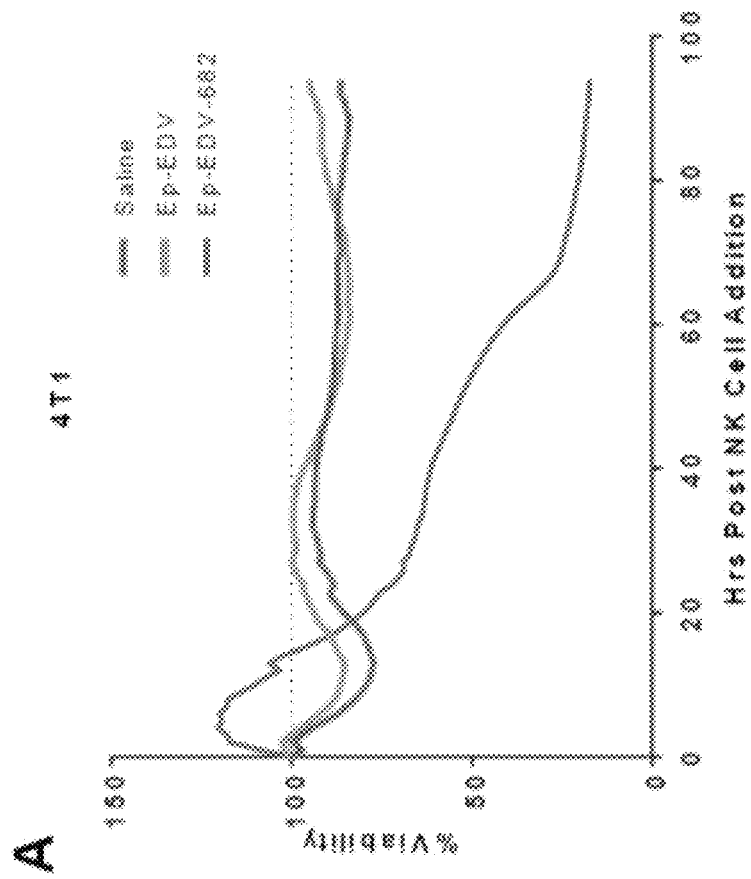
FIGS. 29A-29J shows NK cell response to EDV treatment.
Figures 29C, 29D:
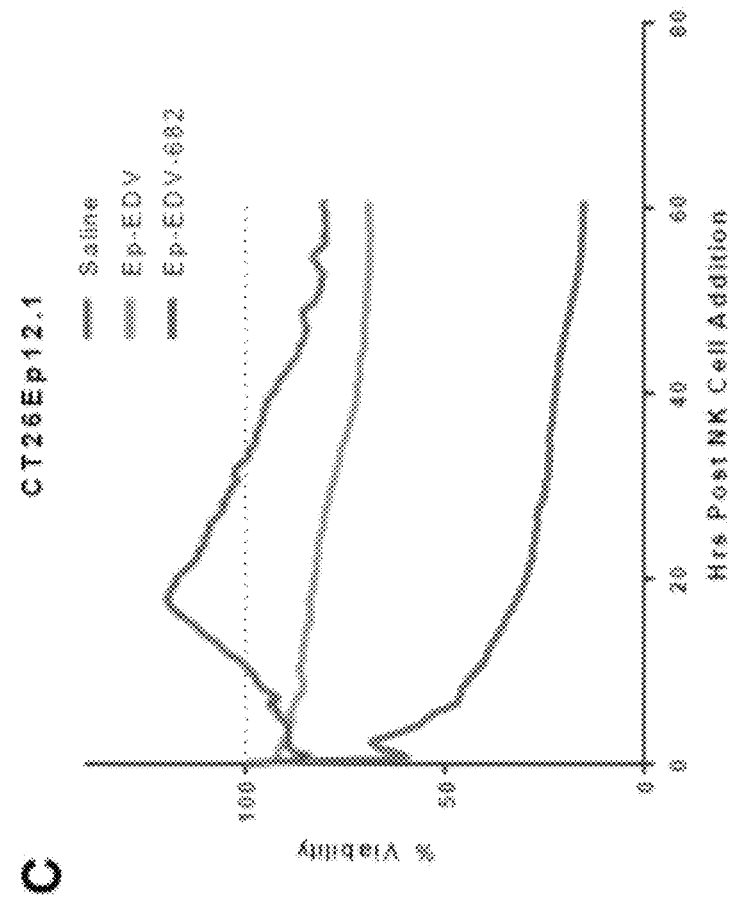

NK cells of Ep-EDV-682 treated mice in both tumor models demonstrated antitumor properties via significant and potent cytolysis of the target tumor cells, while those treated with saline or Ep-EDV showed little to no cytolytic potential towards their target tumor cells. NK cells from mice bearing CT26Ep12.1 displayed rapid cytolysis of target CT26Ep12.1 cells, dropping to nearly 60% target cell viability within the first few hours of co-culture and maintaining only 18% target cell viability after 50 h. NK cells from Ep-EDV treated CT26Ep12.1 had a low level of cytolytic capacity, with 70-80% target cell viability after 50h, while NK cells from saline treated mice showed ~82% target cell viability in the same time period (FIG. 29D). NK cells from Ep-EDV-682 treated mice bearing 4T1 tumors, while still highly active, displayed a more gradual cytolytic profile dropping to ~36% target cell viability after 70h, while NK cells from saline or Ep-EDV treated mice maintained ≥90% target cell viability (FIGS. 29A and 29B). Additionally, NK/4T1 co-cultures with NK cells isolated from mice treated with Ep-EDV-682 exhibited more than a 2-fold increase in the production of both TNFα and RANTES as compared to those from saline treated mice (FIGS. 29F and 29G).

Figure 36A:
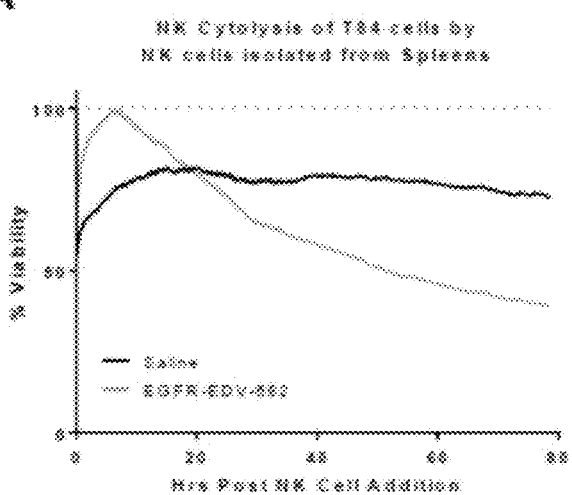
FIGS. 36A-36C shows NK cell response to EDV treatment.
Figure 36B:
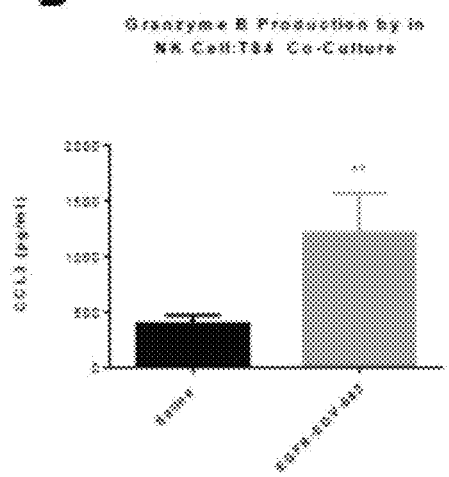
Figure 36C:
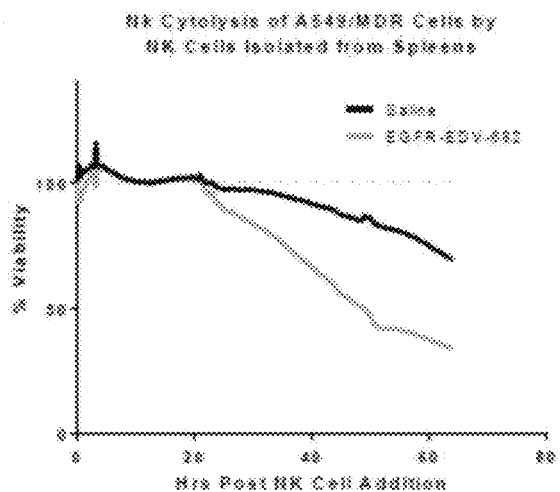

NK cells isolated from the spleens of athymic mice bearing either A549/MDR or T84 tumors demonstrated similar cytolytic profiles to the immunocompetent mouse tumor models (FIGS. 36A and 36C). NK cells of EGFR-EDV-682 treated mice, when co-cultured with their target tumor cells, resulted in under 40% target cell viability in both the A549/MDR and T84 tumors, while the saline controls for both maintained a target cell viability ≥70%. Examination of Granzyme B production in the T84/NK cell co-cultures revealed significantly higher levels of Granzyme B in the co-cultures containing the NK cells from the Ep-EDV-682 treated mice (FIG. 36B).

Figures 29E, 29F, 29G:
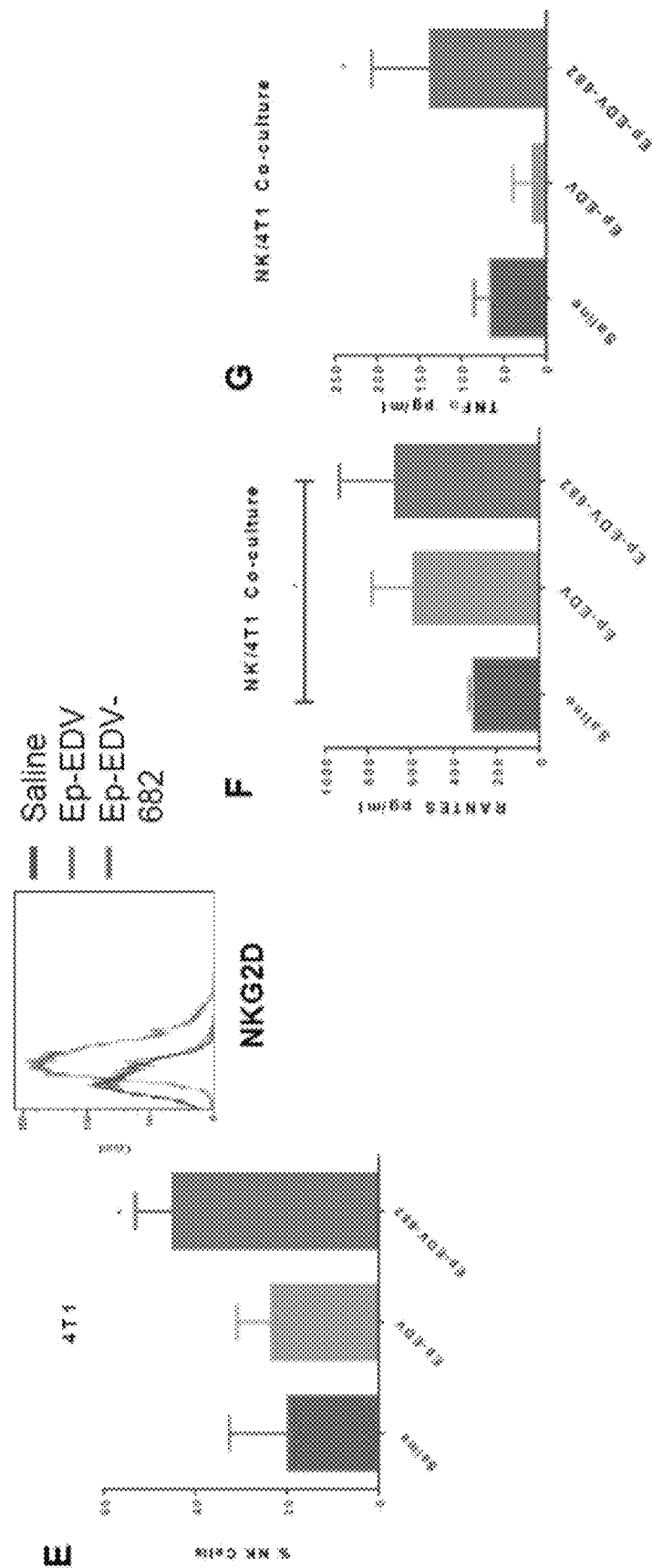
Figures 29H, 29I, 29J:
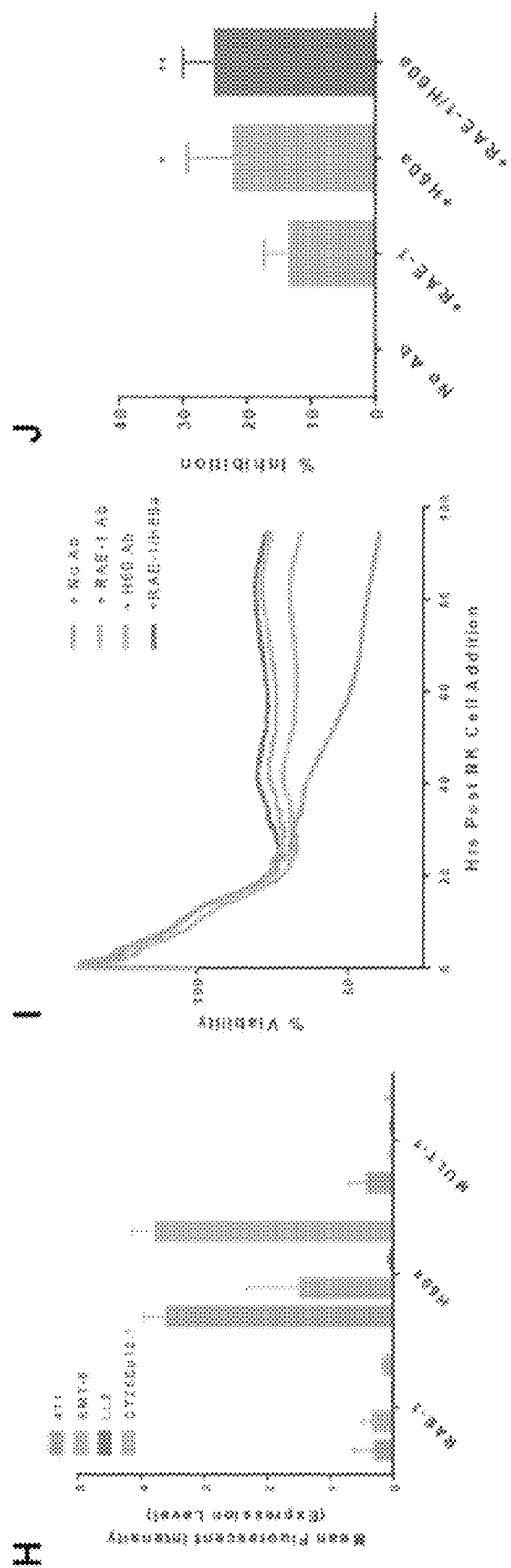

Examination of NK cells within the 4T1 tumors via flow cytometry showed that NK cells (CD45+, CD11b+, DX5+) in the Ep-EDV-682 treated tumors had a significant increase the NKG2D expression, an NK activating receptor known to be important in tumor immunosurveillance (FIG. 29E). Upregulation of NKG2D ligands on the tumor cell surface are sufficient to override NK inhibitory signals thus enabling tumor cell cytolysis (Morvan and Lanier, 2016). Screening of mouse tumor cell lines (including CT26Ep12.1 and 4T1) for the NKG2D binding NK ligands RAE-1, H60a, and MULT-1 showed that both 4T1 and CT26Ep12.1 had the highest level of expression of H60a of the 4 cell lines screened and this was the ligand with the highest overall expression in these two cell lines. Further, the mouse breast cancer cell lines 4T1 and EMT-6 cells showed the highest expression of RAE-1 in all cell lines screened, however, at much lower levels than H60a, while CT26Ep12.1 had only very low levels of this ligand. Finally, with the exception of the 4T1 cells, all other cell lines showed no expression of MULT-1 (FIG. 29H).

To further examine the role of these ligands and the NKG2D receptor in the cytolytic activity of the isolated NK cells, NK cells were isolated from the spleens of Ep-EDV-682 treated mice bearing 4T1 tumors. NK cells were incubated with antibodies designed to block binding of the NKG2D receptor to its particular ligand before co-culture with 4T1 cell in the xCELLigence RTCA system (FIG. 29I). Antibodies to RAE-1 resulted in ~13% inhibition of NK cytolysis of 4T1 cells, while antibodies to H60a resulted in ~21% inhibition, and combination of the two antibodies inhibited ~25% of the cytolytic ability of the NK cells (FIG. 29J).

Example 19: A Predominantly Th1 Cytokine Response within the Tumor Microenvironment is Exhibited Following Ep-EDV-682 Treatment The purpose of this example was to explore the cytokine milieu within the tumor microenvironment following EDV treatment.

Figures 30A, 30B:
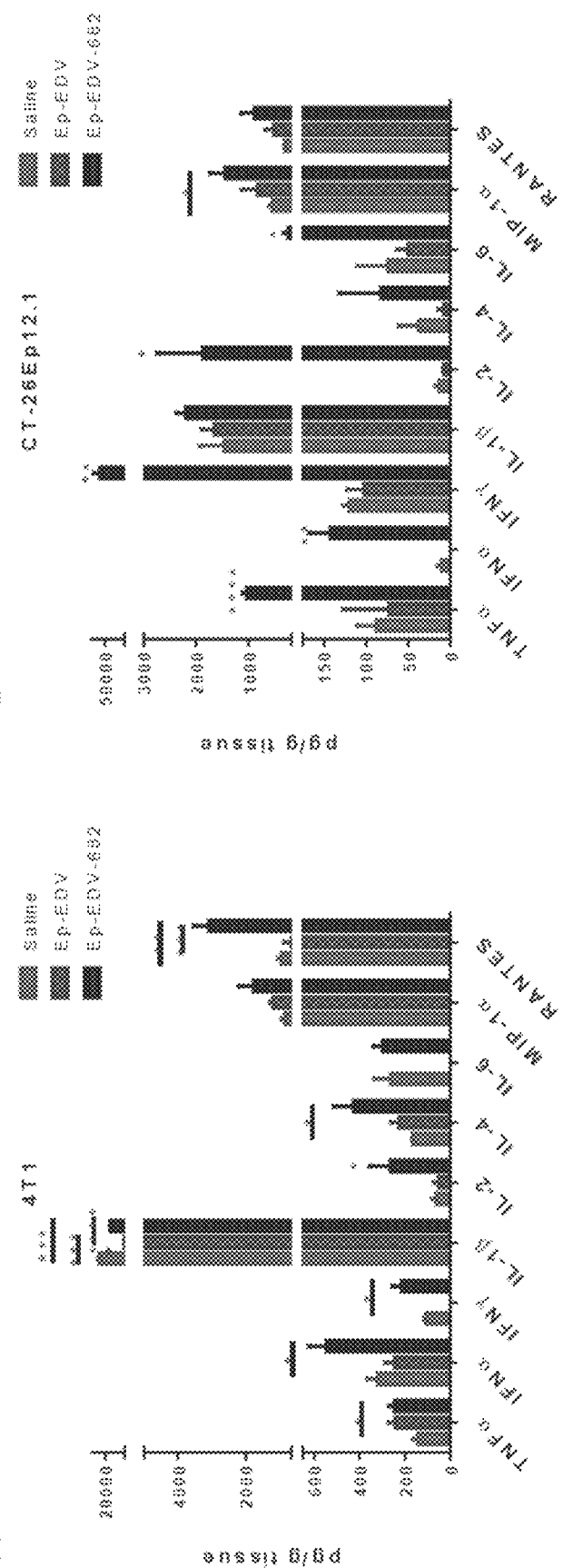
FIGS. 30A-30G shows interstitial tumor cytokine/chemokine production and cytokine production by splenocyte/tumor cell co-cultures in response to EDV treatment. ELISA analysis of interstitial cytokines and chemokines produced in response to Ep-EDV and Ep-EDV682 treatment in BALB/c mice bearing a (FIG. 30A) 4T1 or (FIG. 30B) CT26Ep12.1 tumors. Ep-EDV-682 treatment results in an increase in predominantly Th1 cytokines. Data represents mean±s.e.m. Individual cytokine data analyzed by one way ANOVA and Tukey's multiple comparison test. ELISA analysis of (FIG. 30C) TNFα (FIG. 30D) IL-2 (FIG. 30E) IL-1β (FIG. 30F) IFNγ and (FIG. 30G) IL-10 from the supernatants of co-cultures of splenocytes isolated from saline, Ep-EDV, and Ep-EDV-682 treated mice bearing 4T1 and CT26Ep12.1 tumors with their corresponding tumor cells. Data represents mean±s.e.m. One way ANOVA analysis and Tukey's multiple comparison used to compare groups + or − tumor cells. T-test used to compare individual treatments with and without tumor cells.

4T1 and CT26Ep12.1 tumors were harvested 24h following the final treatment and gently dissociated in a non-enzymatic manner ensuring no lysis of cells so that interstitial tumor cytokine levels could be assessed (FIGS. 30A-30B). Due to the significant differences in tumor sizes, tumors were weighed and measured, and cytokine levels were calculated per gram of tissue to account for these size differences. Both tumors exhibited a significant increase in TNFα within the tumor microenvironment in response to Ep-EDV-682 treatment, although this increase was more pronounced in the CT26Ep12.1 tumors with >10-fold increase following Ep-EDV-682 treatment compared to saline treatment. Similarly, Ep-EDV-682 treatment resulted in a significant increase in the interstitial IFNα concentration in both tumors with ~2 fold increase in IFNα levels in the 4T1 tumors and a 15 fold increase in the CT26Ep12.1 tumors.

The most prominent change in cytokine level with Ep-EDV-682 treatment was seen in the CT26Ep12.1 tumors where a 500 fold increase in IFNγ levels occurred, while a small, but significant 2 fold increase in IFNγ levels occurred in the 4T1 tumors. The IL-1l3 level as a result of Ep-EDV-682 treatment was significantly decreased in 4T1 tumors but showed an increase, albeit not significant, in the CT26Ep12.1 tumors. Significant increases in IL-2 (~4 fold) and IL-4 (~3 fold) occurred in the 4T1 tumors, while there was no significant change in IL-6 levels following Ep-EDV-682 treatment. In the CT26Ep12.1 tumors of Ep-EDV-682 treated mice, IL-2 levels significantly increased more than 150 fold, while a significant 3 fold increase in IL-6 levels and a 2 fold nonsignificant increase in IL-4 was observed. MIP-1α (CCL3) and RANTES (CCL5), which have been shown to be major determinants of infiltration by immune cells such as antigen presenting cells, NK cells, and T-cells, were also examined (Allen et al., 2018). Both the 4T1 and CT26Ep12.1 exhibited increases in the level of the two chemokines in the Ep-EDV-682 treated tumors with a ~3 fold significant increase in MIP-1α levels in the CT26Ep12.1 tumors and RANTES levels in the 4T1 tumors treated with Ep-EDV-682. Furthermore, a 2-2.5 fold increase in RANTES and MIP-1α levels occurred in both the CT-26Ep12.1 and 4T1 Ep-EDV treated tumors respectively, although this was not significant. Generally, Ep-EDV treatment resulted in interstitial tumor cytokine and chemokine levels similar to the saline treated group.

Figures 30C, 30D:
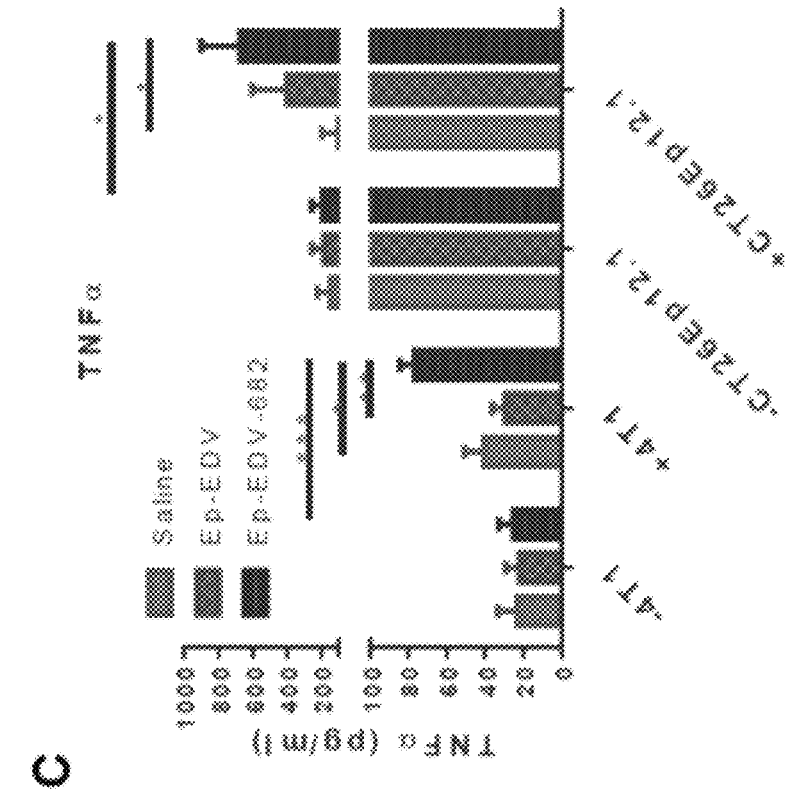
Figures 30E, 30F:
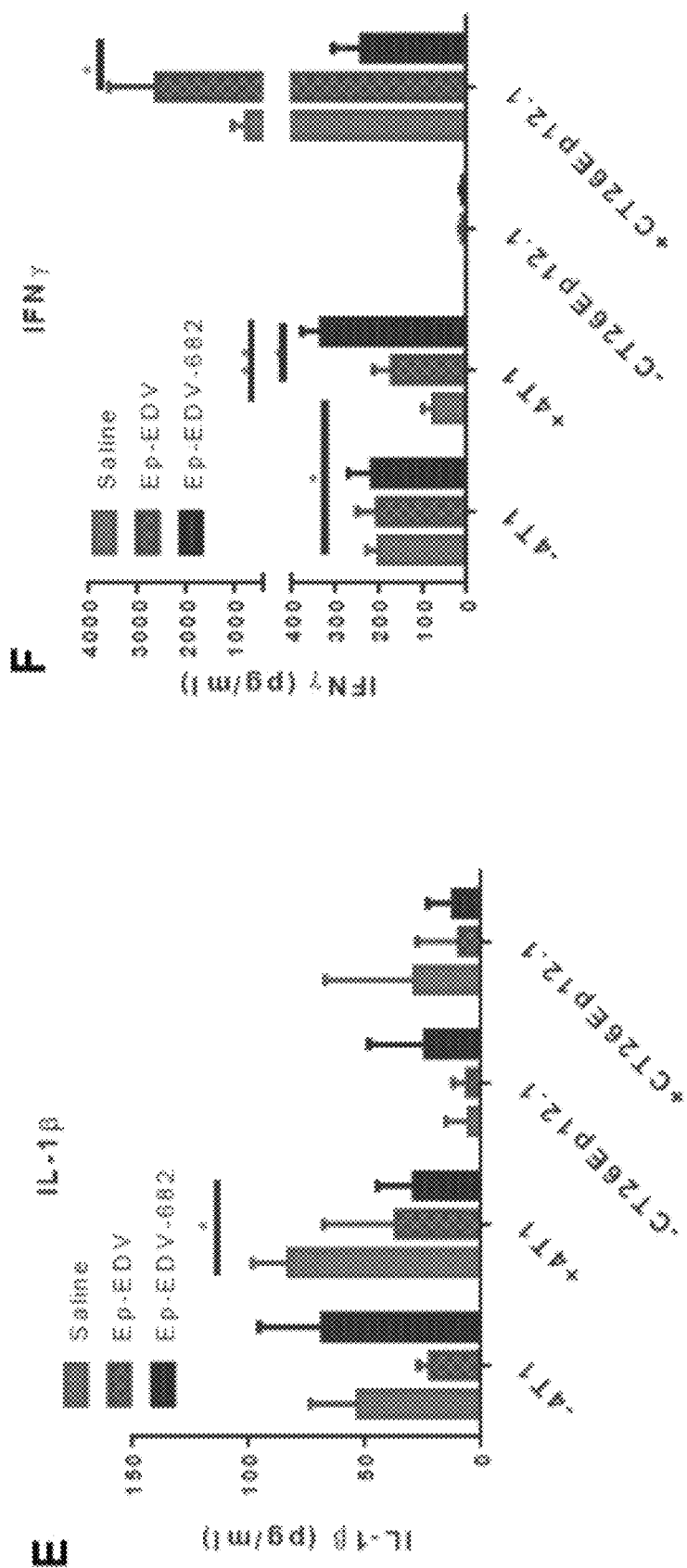
Figure 30G:
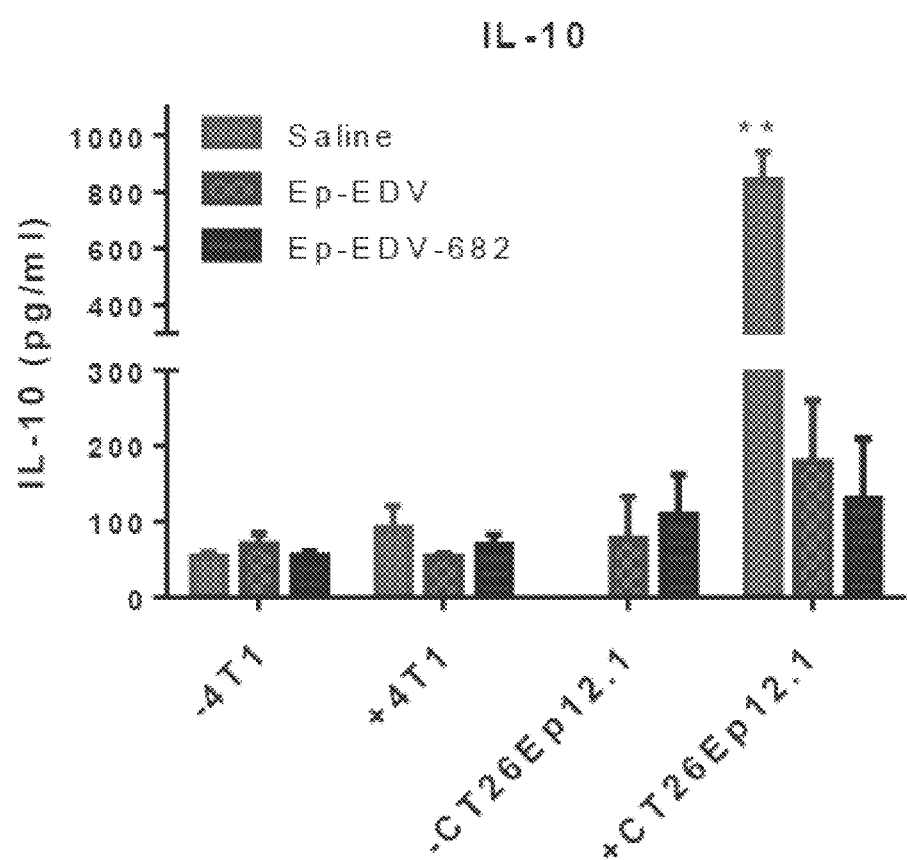

In addition to examination of the interstitial tumor cytokines, cytokine production (TNFα, IFNγ, IL-1l3, IL-2, and IL-10) by splenocytes from treated animals was assessed. Splenocytes were cultured alone or co-cultured with dispersed tumor cells from their corresponding mouse. Systemic treatment with saline, Ep-EDV, and Ep-EDV-682 had no significant effect on cytokine production by splenocytes from either the 4T1 or Ct26Ep12.1 tumor model (FIGS. 30C-30G). However, when splenocytes were cultured with their corresponding treated tumor, this was no longer the case. TNFα production significantly increased in the co-cultures from mice treated with Ep-EDV-682 as compared to splenocytes only as well as the co-cultures from saline and Ep-EDV treated mice from both tumor models (FIG. 30C). In the 4T1 model, IL-2 production significantly increased in the co-cultures from the Ep-EDV-682 treated mice as compared to the saline treated mice (FIG. 30D). Moreover, there was a significant decrease in IL-2 production when the splenocytes from saline treated mice were co-cultured with their corresponding tumor cells. IL-2 production increased significantly in all co-cultures as compared to the splenocytes alone isolated from mice bearing CT26Ep12.1 tumors. The only significant change in IL-10 production occurred in co-cultures from the 4T1 model in which samples from saline treated mice exhibited a significant increase as compared to Ep-EDV-682 treated mice corresponding to the difference seen in vivo (FIG. 30E). IFNγ production significantly decreased between splenocytes alone and co-cultures isolated from saline treated mice bearing 4T1 tumors and significantly greater in the Ep-EDV-682 treated splenocyte/tumor cell co-cultures than those from saline or Ep-EDV treated 4T1 tumor bearing mice (FIG. 30F). In the CT26Ep12.1 tumor model, IFNγ production decreased in the Ep-EDV-682 treated splenocyte/tumor cell co-cultures as compared to the saline and Ep-EDV co-cultures, however this was only significant for Ep-EDV. Finally, IL-10 production significantly increased in the saline treated splenocyte/tumor cell co-cultures from the CT26Ep12.1 treated mice as compared splenocytes alone and the EDV treatment groups (FIG. 30G).

Example 20: Ep-EDV-682 Treatment Lead to the Production of Tumor Specific CD8+ T-Cells Initial in vitro experiments indicated that EDV treatment can result in dendritic cell maturation either via direct interaction or as a result of cell death in response to a targeted EDV loaded with an effective chemotherapeutic. Thus, this experiment aimed to examine if this result could translate to DC maturation and antigen presentation in vivo resulting in the production of tumor specific $CD8^+$ cytotoxic T-cells.

Following 2 weeks treatment, spleens were removed from 4T1 or CT26Ep12.1 tumor bearing mice which had been treated with saline, Ep-EDV, or Ep-EDV-682 and the $CD8^+$ T-cells were isolated. $CD8^+$ T-cells were then added to the corresponding tumor cells and examined for their ability to specifically recognize and kill those cells using the xCEL-Ligence RTCA (FIGS. 31A and 31C). $CD8^+$ T-cells isolated from mice bearing 4T1 and treated with saline or Ep-EDV exhibited no cytotoxicity towards 4T1 cells, while $CD8^+$ T-cells isolated from the mice treated with Ep-EDV-682 induced 50% cytolysis of the target cells after 30h (FIG. 31B).

Figure 31D:
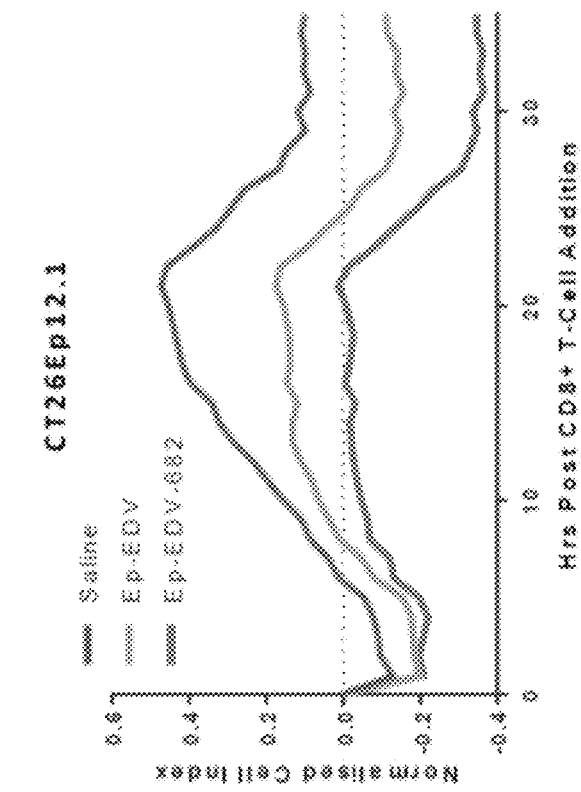
Figures 31E, 31F, 31G, 31H:
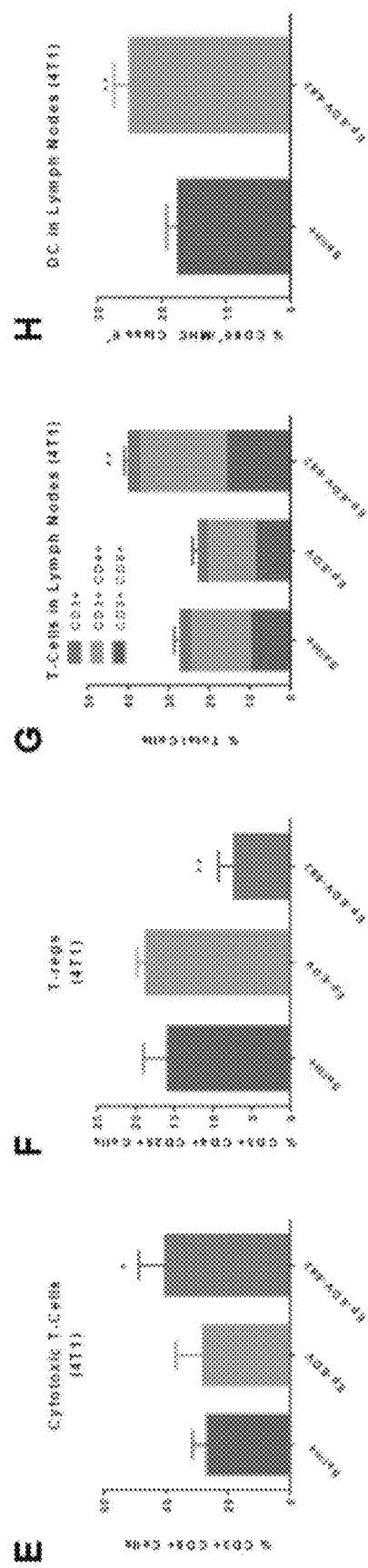
Figure 31I:
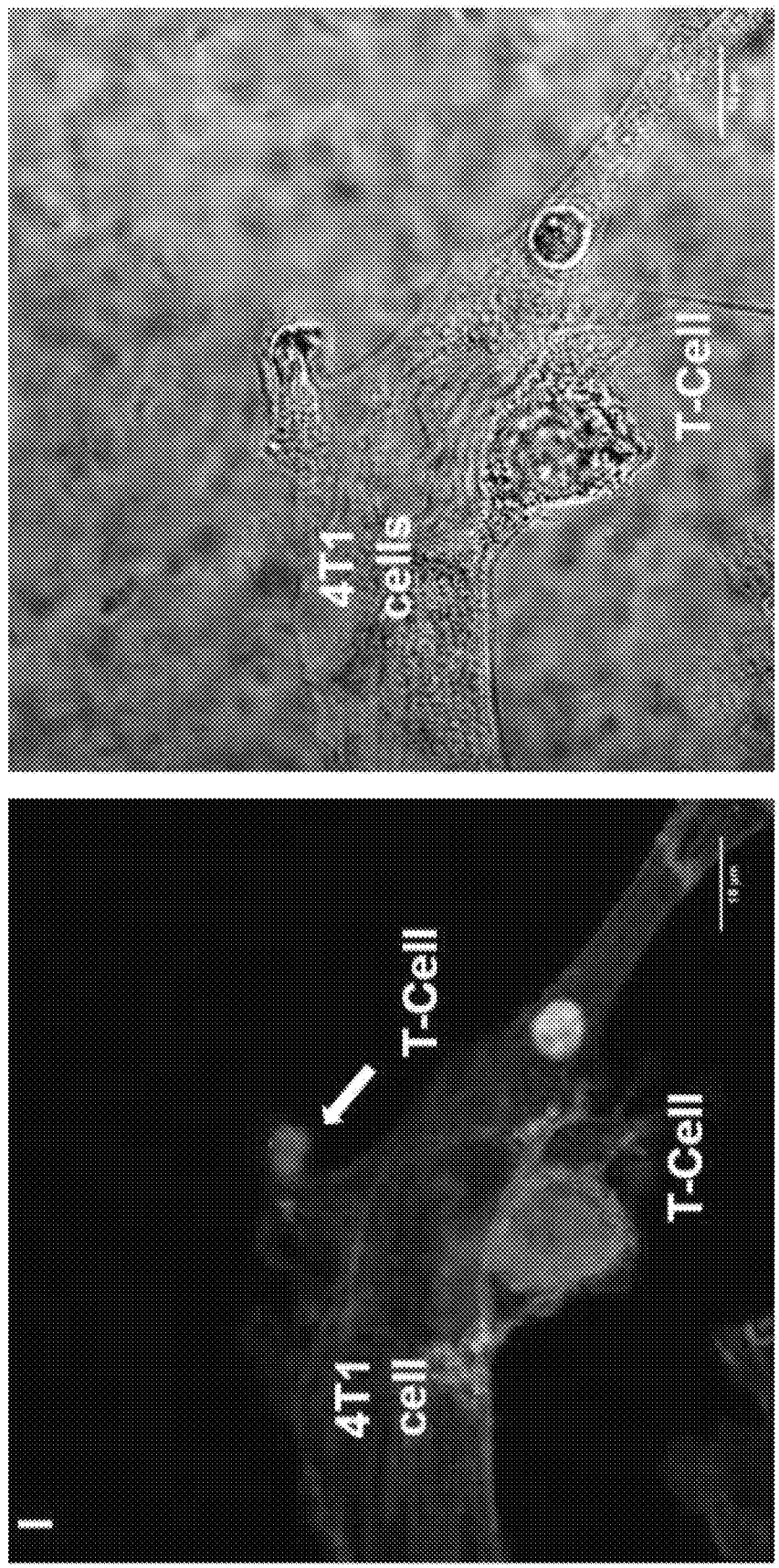

$CD8^+$ T-cells isolated from mice bearing CT26Ep12.1 and treated with Ep-EDV-682 were highly effective in killing the target CT26Ep12.1 cells, with 81% cytotoxicity seen 20h after the addition of the effector cells to the target cells (FIG. 31D). Interestingly, even the Ep-EDV treatment was able to elicit the production of tumor specific $CD8^+$ T-cells in the CT26Ep12.1 model, with 40% cytotoxicity apparent after 20h, while the $CD8^+$ T-cells from the saline treated mice showed no specificity towards the CT26Ep12.1 cells. Flow analysis of CD8+ T-cells within the 4T1 tumors showed a small, but significant increase in the percentage of CD8+ T-cells within the tumors ($CD45^+$, $CD3^+$, $CD8^+$) of Ep-EDV-682 treated mice (FIG. 31E). Additionally, a significant 2 fold decrease was seen in the percentage of regulatory T-cells ($CD45^+$, $CD3^+$, $CD4^+$, $CD25^+$) within the tumors of Ep-EDV-682 treated mice (FIG. 31F). T-cell numbers in the tumor draining lymph nodes of 4T1 tumor bearing mice were also examined via flow. A significant increase in overall T-cell numbers (CD3+) as well as a significant increase in both CD4+ and CD8+ T-cells numbers were seen in the lymph nodes of Ep-EDV-682 treated mice as compared to both the saline and Ep-EDV treated mice (FIG. 31G). A significant increase in mature dendritic cells in the lymph nodes of Ep-EDV-682 treated mice bearing 4T1 tumors was also detected (FIG. 31H). Visualization of the interaction between isolated $CD8^+$ T-cells from Ep-EDV-682 treated mice with 4T1 cells shows that these T-cells are capable of attaching to and expelling perforin (green) into the tumor cell (FIG. 31I).

Example 21: Patient Response to EGFR-EDV-682 in a Case of Stage IV Pancreatic Ductal Adenocarcinoma This experiment pertains to the clinical observation of a compassionate case usage of EGFR-EDV-682 treatment in a patient (CEB) with stage IV pancreatic ductal adenocarcinoma (PDAC).

Diagnostic evaluation of CEB included computerised axial tomography (CT) of the abdomen (May 2017) which revealed multiple low density liver lesions. The tumours were not avid on positron emission tomography (PET). Standard biochemistry and haematology tests were generally unremarkable. Serum CA19-9 and C-reactive (CRP) protein were also assessed. Low serum levels of CA 19-9, a carbohydrate antigen that is expressed on some gastrointestinal malignancies, particularly pancreatic cancers, have been shown to be a prognostic indicator of overall survival and response to therapy. Similarly, elevated CRP levels have also been shown to be significantly associated with poor clinical outcomes (Szkandera et al., 2014). Even after gemcitabine and FOLFIRINOX, CEB presented with a CA19-9 level of >120,000kU/L, 3,000 times higher than normal, and a considerable elevated CRP level of 64 mg/L.

Figure 37A:
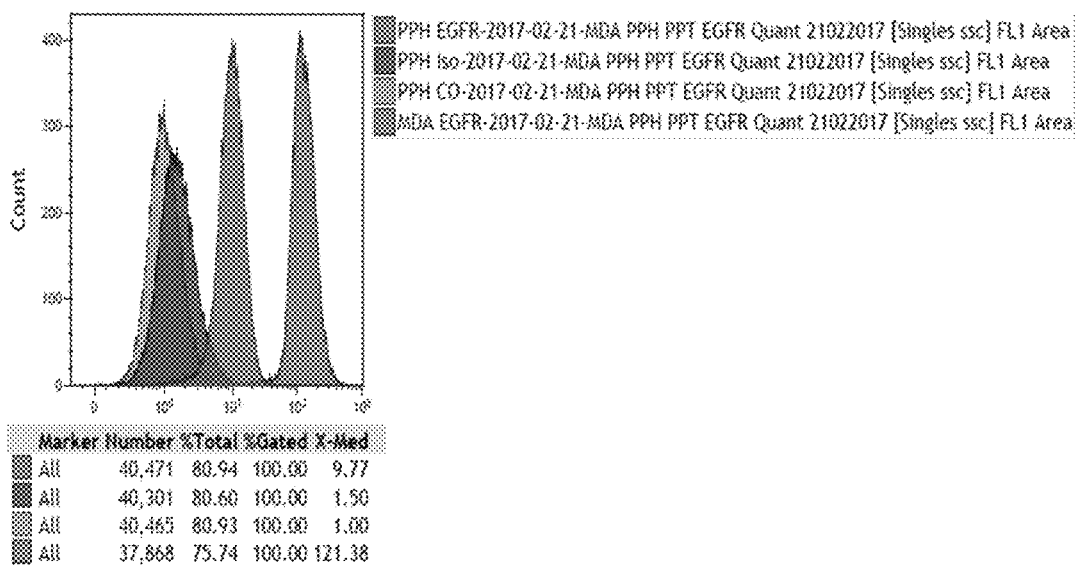
FIGS. 37A-37C shows receptor expression and drug sensitivity screening of patient derived pancreatic ductal adenocarcinoma cells.
Figure 37B:
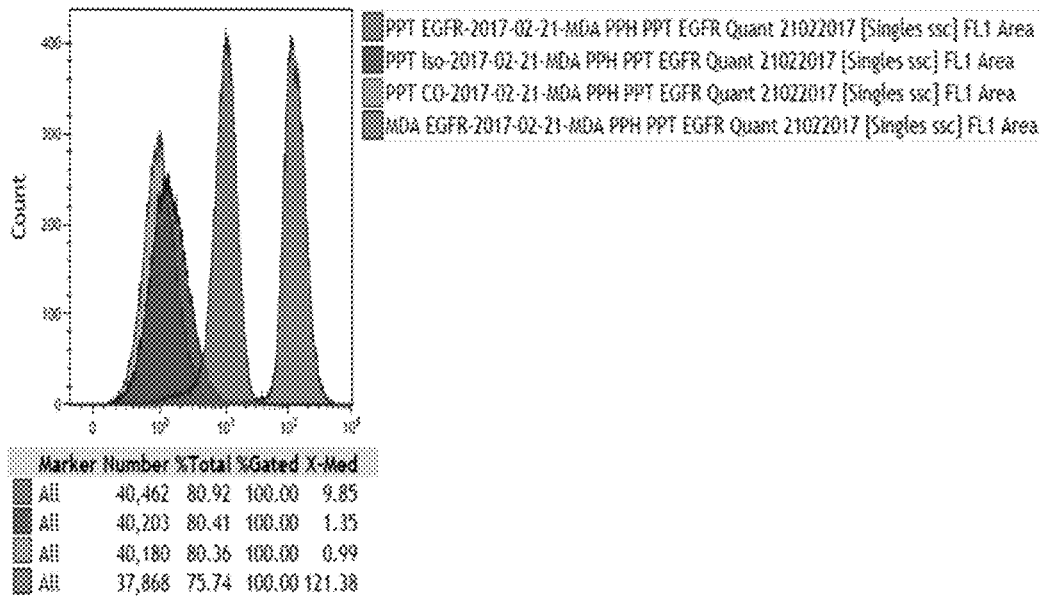
Figure 37C:
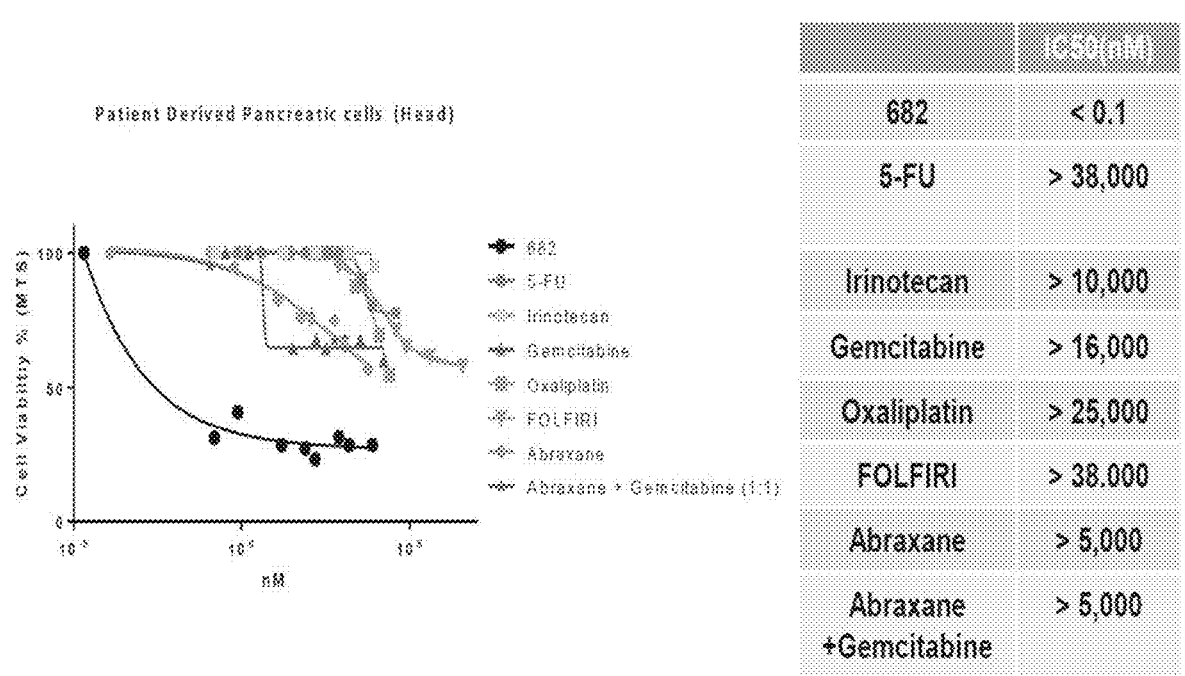

PDAC cells obtained from resected tumor tissue from both the head and tail of the pancreas were examined for drug sensitivity. Both the head and tail PDAC cells exhibited low sensitivity with partial to no response to first and second line drugs (FIG. 37A). In contrast, both displayed extreme sensitivity to 682, with IC50's in the pM range (FIG. 37A). Further, epidermal growth factor receptor (EGFR) was found to be overexpressed with >200,000 copies per cell by flow cytometry (FIGS. 37A-37C) and therefore, an ideal receptor for targeting EDVs loaded with 682 for treatment.

Figures 32A, 32B:
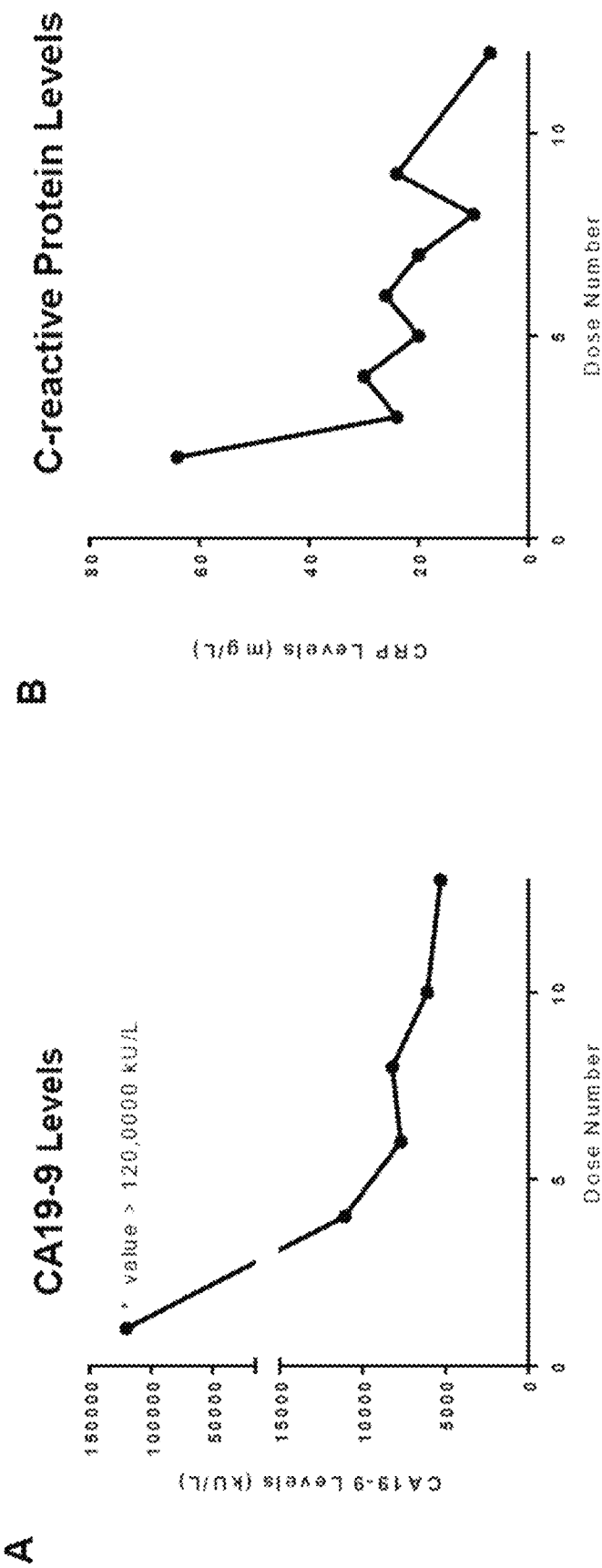
FIGS. 32A-32G shows Prognostic Indicators and Immunophenotyping of patient peripheral blood mononuclear cells (PBMCs) reveals evidence of enhanced antigen presentation by dendritic cells and monocytes and elevated cytotoxic CD8+ T cell content at dose 12. Prognostic indicators (FIG. 32A) CA19-9 and (FIG. 32B) C-reactive protein serum levels. Analysis of PBMC with Duraclone immunophenotyping panels for (FIG. 32C) Monocytes and (FIG. 32D) intermediate (CD14+CD16++) antigen presenting monocyte subtype. Expressed as % Leukocytes. Dendritic cell subtypes including (FIG. 32E) myeloid dendritic (Clec9A+) cells (mDC) that drive the CD8+ Effector T cell response and (FIG. 32F) Plasmacytoid dendritic and myeloid dendritic (professional antigen presenting DC). Expressed as % DC or % mDC as indicated.

CEB tolerated the EDVs carrying 682 and targeted to EGFR (E-EDV-D682) very well and reported a dramatic increase in well-being throughout the cycle. Her ECOG performance status fell from 2 to 0 during that time. There was a transient rise in TNFα and IL-6 at 3 hours post dose which was highest post dose 1 and was much lower in subsequent doses, possibly indicative of a tolerance build up. There were no changes in haematological parameters, and white cell count (WCC) remained normal throughout the cycle. Biochemistry results were unremarkable, even after 14 doses. Of note was the CA19-9 marker which steadily fell from >120,000 kU/1 to 5,310 kU/ml at, and the CRP levels which feel from 64 mg/L to 7 mg/L at dose 13 (FIGS. 32A and 32B).

Figures 32C, 32D, 32E:
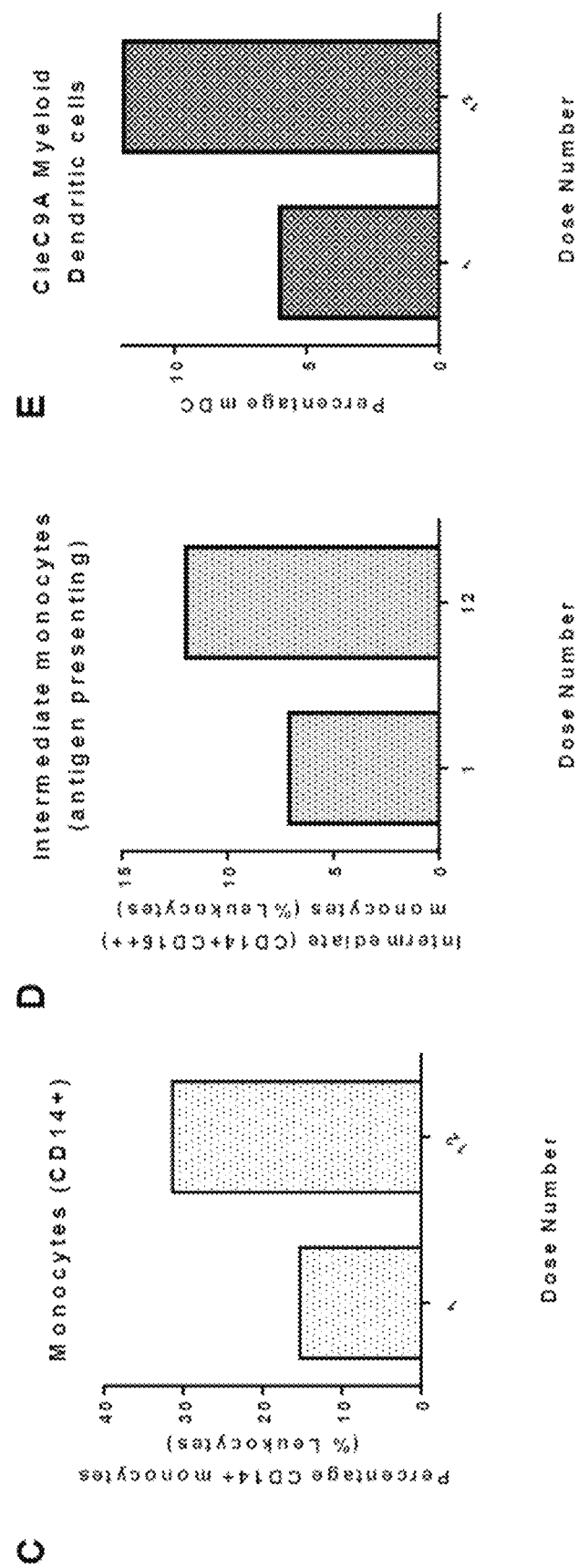
Figure 38:
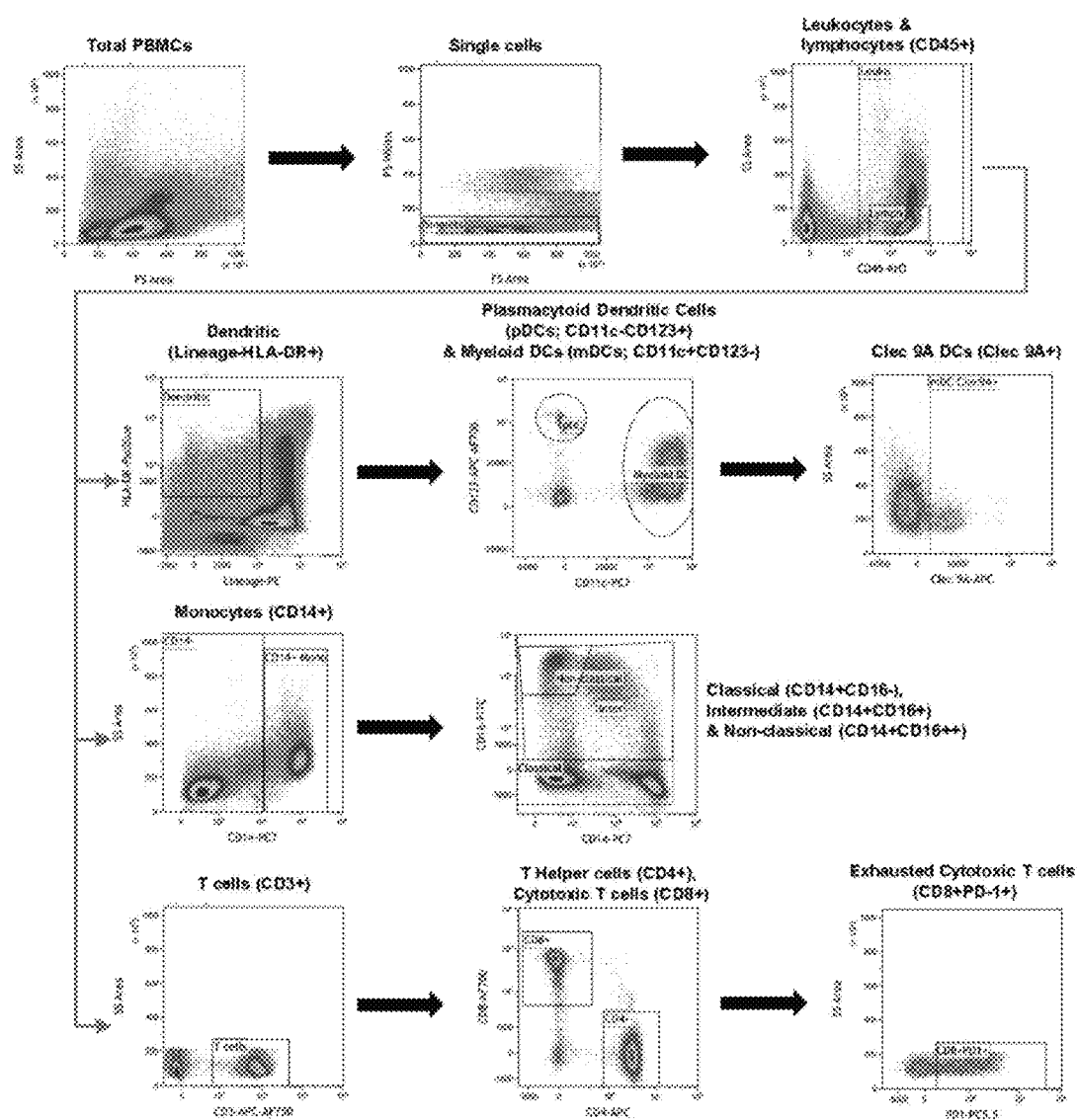
FIG. 38 shows single cells from the total PBMC pool (FSC v SSC) were gated based on forward scatter width (FSC-W) versus forward scatter area (FSC-A) then analysed for CD45 staining (CD45+ gate on FSC v CS45+). Cell viability was 96% (Count and viability kit #C00162, Beckman Coulter, data not shown) with dead cells excluded based on a FSC threshold discriminator of 80. Total dendritic cells (DCs) were gated on Leukocytes (CD45+) and defined as HLA-DR+ and Lineage– (#B53351, Beckman Coulter). The lineage negative marker was comprised of a pool of antibodies conjugated with the same fluorophore (PE) raised against CD3, CD14, CD19, CD20 and CD56 used to negatively select for T cells, Monocytes, B cells, and NK cells, respectively. The remaining cells that were HLA-DR+ were gated as dendritic and subdivided into plasmacytoid DCs (CD11c-CD123+) or antigen presenting myeloid DCs (CD11c+CD123-). The myeloid DCs (mDC) were divided into the three major subsets, CD1c+ mDC1, CD141+ mDC2 (Clec9A+ shown here) and CD16+ mDCs. CD14+ expression defined the monocytes (#B93604, Beckman Coulter) that were gated on leukocytes, then subdivided into classical (CD14+CD16-), intermediate (CD14+CD16+) and non-classical (CD14+CD16++). T cells (#B53328, Beckman Coulter) were CD3+ and gated on lymphocytes (CD45+ SSC low). CD3+ T cell subsets, T helper (CD4+) and cytotoxic T (CD8+) were then defined. The PD1+CD8+ cytotoxic T cell gate was plotted against SSC and gated on CD8+ T cells. All FSC and SSC axes are linear while fluorescence channel axes (all CD markers) are logarithmic or bi-exponential ('logicle', Kaluza software, Beckman Coulter).

Post dose 12, immunophenotyping of major immune cell subsets from peripheral blood mononuclear cells (PBMCs) revealed changes within multiple cell types that may support a favorable anti-tumor response (Gating strategy—FIG. 38). Total CD14+ monocytes, the precursors for macrophages and dendritic cells, were increased from 15.28% to 31.39% at D12 (105% increase) when compared with the screen dose (D1) (FIG. 32C), including the intermediate (CD14+ CD16++) monocyte subset (69% increase; FIG. 32D). The intermediate monocytes demonstrate the highest capacity to present antigen to T cells, with superior antigen-specific induction of IL-12 and IFN-γ (Ziegler-Heitbrock and Hofer, 2013).

Figure 32F:
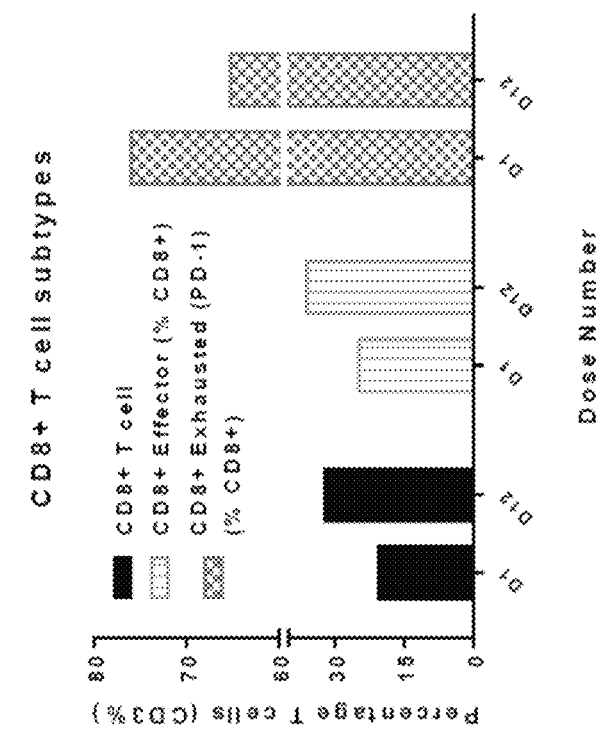
Figure 32G:
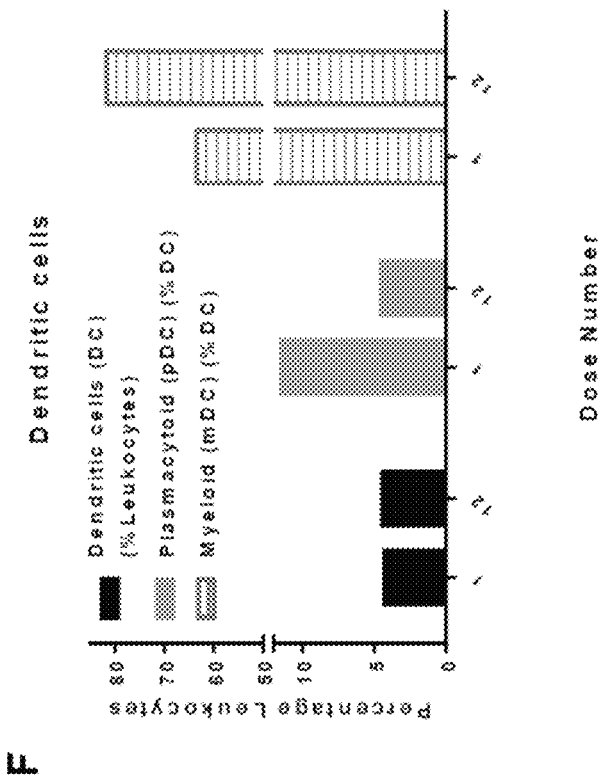
Figure 34A:
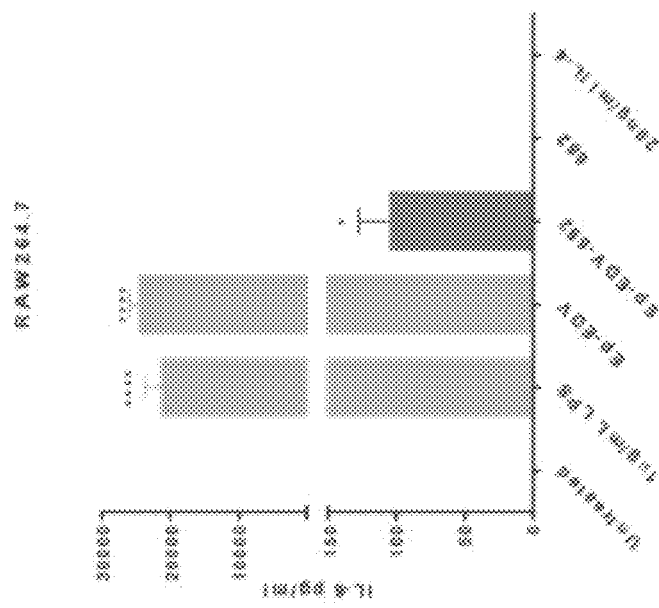
FIGS. 34A-34E shows RAW264.7 and JAWS II cell activation in response to EDV treatment.
Figure 34B:
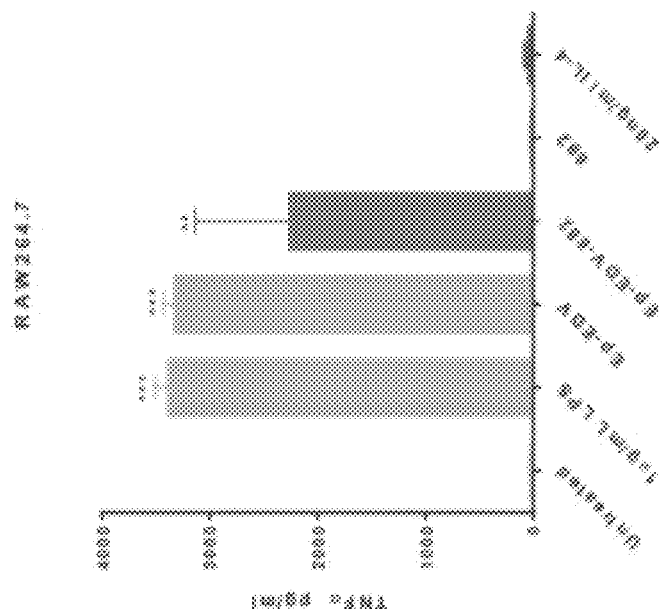
Figure 34C:
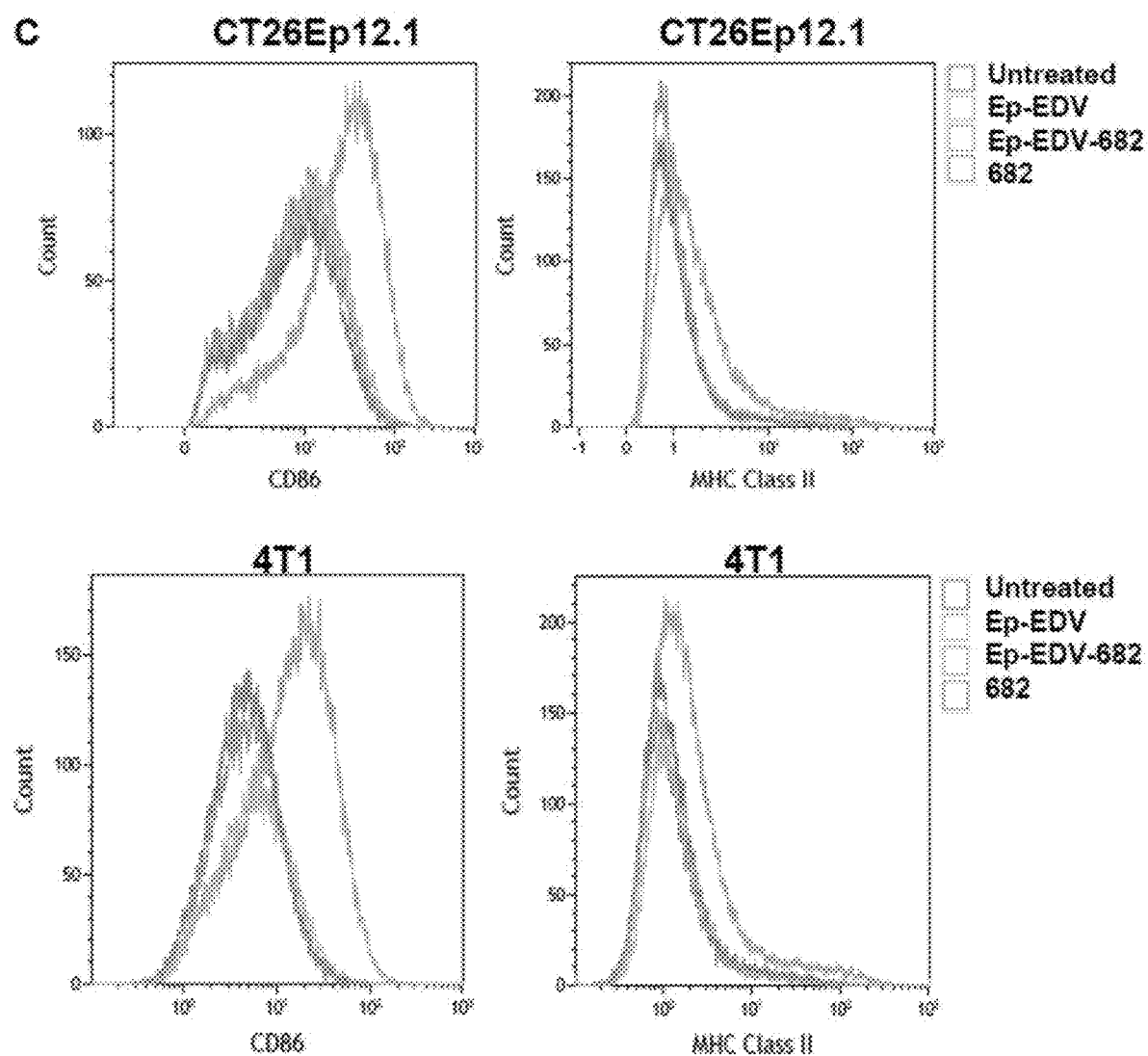
Figures 34D, 34E:
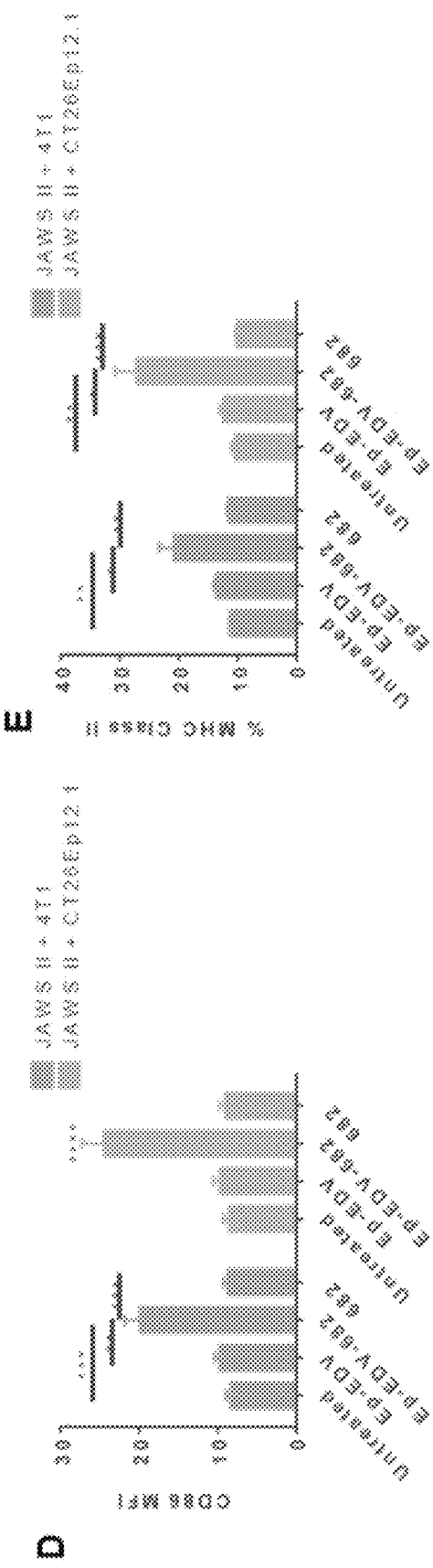

A 28% increase in the myeloid dendritic cells (mDC) and a 60% decrease in the plasmacytoid DC (pDC) were also observed (FIG. 32F). Clec9A+ myeloid dendritic cells (mDCs) which are responsible for driving a CD8+ effector T response also increased (98% at D12) (FIG. 32E). This increase was in concordance with increases in the totalcytotoxic CD8+ T cells (60%), including effector CD8+ T cells (50% increase) at D12 (FIG. 32G). The effector CD8+ T cell pool are CD8+ T cells that have recently interacted with antigen presented by monocytes, macrophages or dendritic cells and contain tumour and/or EDV antigen-specific T cells. Cytotoxic CD8+ T cells expressing the exhausted programmed death-1 (PD-1+) phenotype, indicative of prolonged cell activation and susceptibility to PD-1 ligation by tumour cells expressing PD-L1, were decreased at D12 by 17% compared to D1. This process commonly occurs within the tumour and tumour-draining lymph nodes. The results observed in this case study follow a similar trend to those observed in the pre-clinical mouse models.

Discussion:

This data demonstrates the ability of targeted EDVs loaded with the super-cytotoxin 682 to not only effectively deliver this drug to the tumor site, but also behave as an immunotherapeutic by stimulating multiple immune cell subsets. The ability of Ep-EDV-682 treatment to push immune cell subsets including macrophages, NK cells and CD8$^+$ T-cells towards an antitumor phenotype capable of effectively eliminating tumor cells has been demonstrated. When combined with the effectiveness of the drug, this results in a dual assault on the tumor.

Following intravenous administration, the EDV extravasates to the tumor via its leaky vasculature where ≥30% of the administered dose of targeted EDVs carrying their toxic payload deposit directly into the tumor microenvironment within a 2 hr period (MacDiarmid et al., 2007b). EpCAM targeted EDVs bind to surface expressed EpCAM on the tumor cells (4T1 and CT26Ep12.1 in this case), and are then internalized effectively delivering their payload (682) directly within the tumor cells. 682 is a highly potent super cytotoxin resulting in rapid apoptosis within 24h of being delivered to the tumor cells (FIG. 33A). The apoptotic cells and DAMP signals produced by Ep-EDV-682 treatment can then interact with innate immune cells such as tumor associated macrophages (TAMs) and stimulate upregulation of CD86 and the production of Th1 proinflammatory cytokines such as TNFα and IL-6 (FIG. 33B).

Furthermore, the EDV itself can also interact directly with TAMs producing a similar M1 polarization, albeit this would be expected to occur at very low levels in the current system. Here, the ability of Ep-EDV-682 treatment to shift the M1:M2 balance within the tumor microenvironment in 4 different tumor models has been demonstrated. Despite differences in the degree of this shift in the different tumor models, it was shown that the increase in M1 polarization translated to increased tumor cell lysis by TAMs isolated from the tumors of mice which had been treated with Ep-EDV-682. In addition to the phenotypic shifts to M1, TAMs from tumors of Ep-EDV-682 treated mice also secreted an increased amount of MIP-1α (FIG. 33C), a chemokine which has been established to play a role in promoting immune cell recruitment, and in particular tumor infiltration by NK cells, CD4$^+$ T-cells and CD8$^+$ T-cells (Allen et al., 2018).

EDV treatment allows for in vivo priming and maturation of DCs within the tumor microenvironment in response to dying tumor cells (FIG. 33D). During the maturation process, the DCs migrate to the tumor draining lymph nodes for antigen presentation to T-cells thereby increasing production of CD4$^+$ T-helper cells and tumor specific CD8$^+$ CTL initiating an adaptive immune response to the tumor (FIG. 33E).

In conjunction with enhancing macrophage and DC antitumor functions, EDV treatment is capable of eliciting NK cell activation leading to increased cytotoxicity (FIG. 33F). Upregulation of the NKG2D receptor was observed on NK cells within the tumors of mice treated with Ep-EDV-682, and this receptor was demonstrated to contribute significantly to the cytolytic ability of NK cells isolated from Ep-EDV-682 treated mice. Moreover, immature, intermediate and mature mouse NK cells express both the CCR1 and CCR5 chemokine receptors that can bind the chemokines MIP1α and RANTES, both of which are upregulated in Ep-EDV-682 treated tumors as well as by macrophages and NK cells from Ep-EDV-682 treated mice (Bernardini et al., 2016).

Chemokines, such as MIP1α and RANTES, are responsible for the further recruitment of helper and effector immune cells including NK cells, macrophages, and T-cells to the tumor microenvironment (FIG. 33G) (Allen et al., 2018; Bernardini et al., 2016; Zibert et al., 2004). Following the initial innate immune response due to EDV treatment which encompasses macrophages, NK cells, and DCs, an adaptive immune response is mounted in which tumor specific CTLs and T-helper cells are produced and then recruited to the tumor site (FIG. 33H). Tumor specific CTLs then target and lyse tumor cells further contributing to the overriding antitumor environment which has been created by the other immune cell subsets in combination with the targeted, drug loaded EDVs. Targeted, drug loaded EDV treatment elicits a mainly Th1 response as evidenced by the increase of Th1 cytokines (TNFα, IFNα, IFNγ, IL-2, and IL-6) within the tumor microenvironment. As previously mentioned, innate immune cell subsets, when activated, become a primary source of one or more of these particular cytokines. T-cells are similarly capable of producing all of the aforementioned cytokines (Belardelli and Ferrantini, 2002; Lee and Margolin, 2011). Release of these cytokines by either innate immune cells or T-cells are responsible for co-stimulation, activation, growth, and increased antigen presentation of additional immune cells creating a feedback loop which further enhances the antitumor activity of the immune system FIG. 33I) (Lee and Margolin, 2011).

Methods and Materials

EnGeneIC Dream Vector (EDV):

EDV were produced and purified from a *Salmonella enterica* serovar *Typhimurium* (S. *Typhimurium*) minCDE- strain as previously described (MacDiarmid et al., 2007b). Drug loading, antibody targeting, lyophilization, and dose preparation have been previously described (MacDiarmid et al., 2007b; Sagnella et al., 2018). EDV preparations were subject to strict quality control in which EDV size and number were assessed using dynamic light scattering using a Zetasizer Nano Series and NanoSight LM20 (Malvern Instrument). Endotoxin levels were assessed using an Endosafe portable test system (Charles River). Drug was extracted from EDV™ preparations and quantified via HPLC as previously described (MacDiarmid et al., 2007b).

Flow Cytometry:

All flow cytometry was performed on a Beckman Coulter Gallios 6C and analyzed using Kaluza software (Beckman Coulter).

Cell Culture:

RAW264.7 cells (ATCC) were grown to ~70% confluence in Dulbecco's Modified Eagle Media (DMEM) (Sigma) containing 10% FCS and passaged using a cell scraper. Mouse tumor cell lines (4T1 and CT26) were grown in monolayers in RPMI-1640 media (Sigma) containing 10% FCS and passaged 2-3 times per week using phosphate buffered saline (PBS)/Trypsin EDTA. All cells were maintained in culture at 37° C. in a humidified atmosphere containing 5% $CO_2$ and routinely screened and found to be free of mycoplasma. EpCAM expression and receptor number in the mouse cell lines were quantified using flow cytometry with APC anti-mouse CD326 (Biolegend) using Quantum Simply Cellular anti-Rat IgG microspheres (Bangs Laboratory). As CT26 were shown to be negative for EpCAM, cells were transfected with a pcDNA3. 1+C DYK containing the mouse EpCAM ORF clone (NM_008532.2) (Genescript) using Lipofectamine 2000 (Thermo Fisher). G418 selection was used to obtain pure populations of EpCAM expressing CT26 clones, and cells were screened as described above for EpCAM expression. Clones were examined for growth rate, drug sensitivity and in vivo tumorgenicity, and one that possessed high EpCAM expression with the above 3 parameters being similar to the parental CT26 cell line was selected for all subsequent studies (CT26Ep12.1).

Bone Marrow Derived DCs (BMDC):

Bone marrow was isolated from the femurs and tibias of Balb/c mice. Following red blood cell lysis and washing, cells were resuspended in AIMV+5% FBS+2-mercaptoethanol+penicillin/streptomycin+20 ng/ml GM-CSF (Miltenyi Biotec) and grown for 7 days.

Treatment of RAW264.7 Cells with EDVs:

RAW264.7 cells were seeded in 6-well plates at $3 \times 10^5$ cells per well and incubated overnight. Media was then replaced with fresh media containing one of the following: 1 μg/mL LPS (Sigma); 100 pmol PNU-159682 (Najing Levena); Ep-EDV-682 (500:1 and 1000:1 EDV: cells), Ep-EDV (5000:1 EDV:cells), or left untreated. Cells were harvested 6h and 24h post treatment using a cell scraper and samples were stained with DAPI (Sigma), anti-CD45 Brilliant Violet 510 (BioLegend), anti-CD86 APC-Cy7 (BioLegend), and anti-CD206 AF488 (R&D Systems) and assessed by flow cytometry.

Macrophage and DC/Tumor Cell Co-Cultures:

CT26Ep12.1 and 4T1 cells were harvested with Versene (Gibco) and cells were collected in 1 mL Eppendorf tubes. Cells were resuspended in 1 mL DMEM (Sigma) supplemented with 10% FBS (Bovogen) containing: Ep-EDV (1000:1 and 5000:1—EDV:cells); Ep-EDV-682 (500:1 and 1000:1—EDV:cells); Ep-EDV-Dox (10,000:1—EDV:cell), 100 pmol PNU-159682, 5 μM Doxorubicin, or media alone. Drug and EDV amounts were established via MTS and XCELLigence real time experiments such that chosen concentrations resulted in the initiation of cell death within the first 24h post treatment. Cells were then washed thoroughly with PBS to remove any non-adherent EDV or excess drug. Treated tumor cells were cultured overnight with either RAW264.7 or BMDC at a 1:1 ratio of tumor cells: RAW264.7/BMDC/JAWS II. Supernatants were collected for ELISA analysis. RAW264.7/tumor cell co-cultures were collected using a cell scraper and samples were stained with DAPI (Sigma), anti-CD45 Brilliant Violet 510 (BioLegend), anti-CD86 APC-Cy7, and anti-CD206 AF488 and assessed by flow cytometry. JAWS II/tumor cell and BMDC/tumor cell co-cultures were collected with versene and stained with DAPI (Sigma), CD11b AF488 (Abcam), CD11c PE (Molecular Probes), anti-CD45 Brilliant Violet 510 or PECy5 (BioLegend), anti-CD86 APC-Cy7, MHC Class II PECy5 (Thermo Fisher), MHC Class II Brilliant Violet 421 (BioLegend), 7-AAD (BioLegend), and/or CD80 PE (Thermo Fisher) and assessed by flow cytometry. RNA was extracted from BMDC/tumor cell co-cultures using an RNAeasy Plus Mini Kit (Qiagen) according to the manufacturer's protocol. Briefly, cells were lysed and homogenized in RLT buffer, and passed through a gDNA eliminator spin column. 70% ethanol was added to the flow through and samples were then passed through an RNeasy spin column, washed and eluted in RNase-free water. RNA concentration was determined on an Eppendorf biophotometer plus. The RNA was used to reverse transcribe cDNA using a SuperScript-™VILO™cDNA Synthesis Kit (Thermo Fisher) according to the manufacturer's protocol. The transcribed cDNA was diluted 1:2 for qPCR. Each qPCR reaction contained 5 uL TaqMan fast advanced master mix (Thermo Fisher), 0.5 uL 20× Taqman primer/probe mix (IFN(Mm03030145_gH, IFNb1 Mm00439552_s1, GAPDH Mm99999915_g1; Thermo Fisher) and 2.5 uL of water. 8 µL of the mix plus 2 µL of cDNA was added into 96 well plate. qPCR was performed using an Applied Biosystems Real-Time PCR System. Data was exported to excel and the relative quantitation was calculated from the ΔΔCt.

In Vivo Tumor Models:

All animal work was performed in accordance with the EnGeneIC animal ethics guidelines under AEC 1/2016, AEC 14/2016, AEC 15/2011, and AEC 11/2017. For the 4T1 and CT26Ep12.1 model, female BALB/c mice were obtained from Animal Resources Centre at 6-8 weeks of age. For T84 and A549/MDR models BALB/c Fox1$^{nu}$/ARC were obtained from Animal Resources Centre at 5-7 weeks of age.

After at least 1 week of observation, mice were injected with $5\times10^4$ 4T1 cells per 50 µl PBS into the 3rd mammary fat pad on the right hand side or $2\times10^5$ CT26Ep12.1 per 100 µl PBS subcutaneously into the right flank of BALB/c mice. For human xenografts, $5\times10^6$ A549/MDR or $1\times10^7$ T84 per 100 µl PBS/Matrigel (Sigma) was subcutaneously injected into the right flank. Treatment was commenced on day 7 post tumor induction for the 4T1 model, when the average tumor size was ~90 mm$^3$, and on day 9 for the CT26Ep12.1 model when the average tumor size was ~125 mm$^3$ Mice were treated via i.v, tail vein injection three times weekly for 2 weeks with one of the following treatments: Saline, $1\times10^9$ EpCAM targeted EDVs (Ep-EDV), or $1\times10^9$ EpCAM targeted EDVs loaded with PNU-159682 (Ep-EDV-682). Tumors were measured 3 times/week and tumor volume was calculated as t/6(Length×Width×Height). At the end of the 2 week period, mice were humanely euthanized and tumors and spleens collected for ex vivo analysis. Treatment of A549/MDR and T84 tumors was commenced when tumors reached 100-120 mm$^3$ and 120-150 mm$^3$ respectively. Mice were treated with Saline, $1\times10^9$ EGFR targeted EDVs loaded with Doxorubicin (EGFR-EDV-Dox), $1\times10^9$ EGFR targeted EDVs loaded with PNU-159682 (EGFR-EDV-682), or $1\times10^9$ non-targeted EDVs loaded with PNU-159682 (EDV-682).

Figures 39A, 39B, 39C:
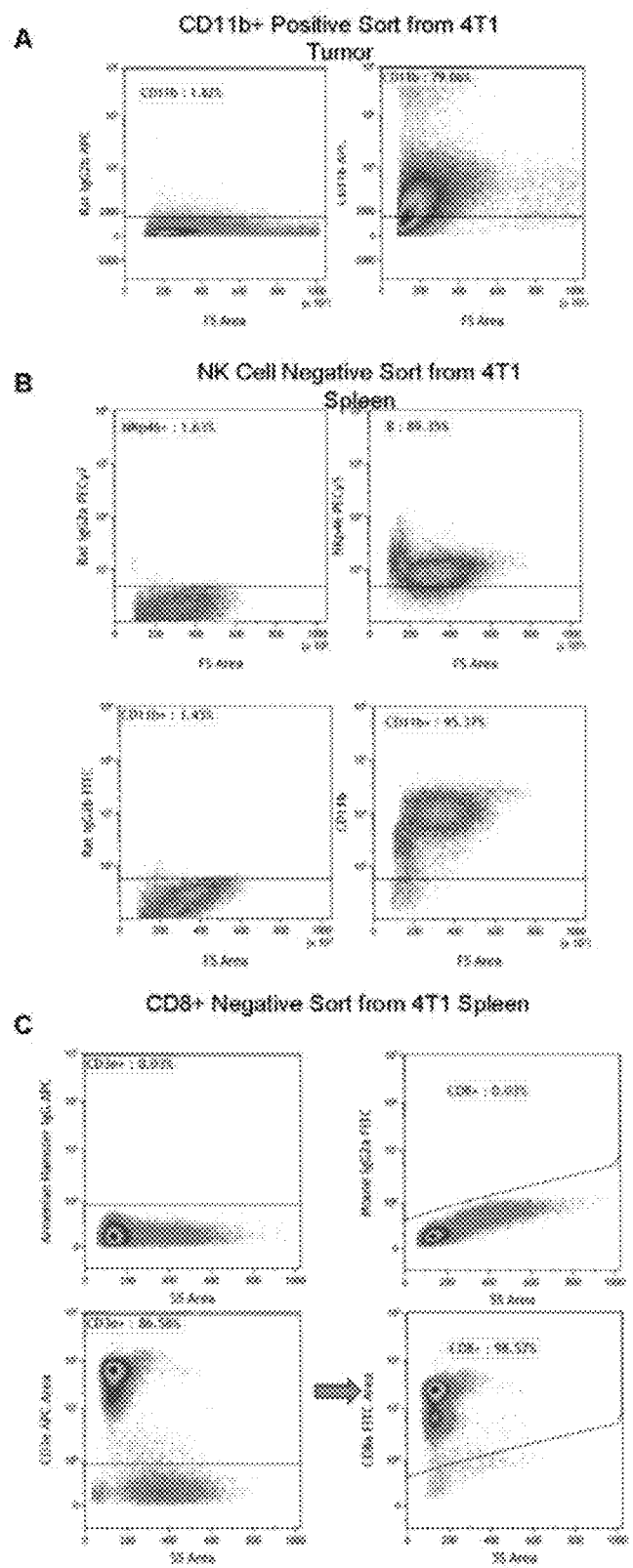
FIGS. 39A-39C shows Flow Cytometric analysis showing purity of cell isolations used for xCelligence RTCA experiments.

Isolation of CD11b$^+$ Cells from 4T1 and CT26Ep12.1 Tumors:

Tumors were dissected, weighed, and enzymatically digested using a Tissue Dissociation Kit (Miltenyi Biotec) at 37° C. according to the manufacturer's instructions, using the GentleMACS™ Dissociator. Following dissociation, red blood cells were removed using RBC lysis buffer (Sigma). After washing, cells were passed through a 70 µm cell strainer to remove any clumps. CD11b$^+$ cells were purified by positive selection using CD11b MACS beads (Miltenyi Biotec) on LS column on the MACS separator (Miltenyi Biotec). The purity of the isolated CD11b$^+$ cell population was assessed by flow-cytometry with an APC anti-mouse CD11b (Biolegend) and shown to be ~80% pure (FIG. 39A).

Isolation of NK and CD8 from Spleens:

Spleens were homogenized using a Dounce homogenizer and filtered through 70pM mesh strainers to obtain single cell suspension followed by erythrocyte lysis using RBC lysis buffer. Splenocytes were then washed and a cell count performed before progressing to NK or CD8+ T-cell isolation. NK cells and CD8+ T cells were isolated from dissociated spleen cells by negative selection using either the NK Cell Isolation II kit (Miltenyi Biotec) or the CD8a+ T Cell Isolation Kit (Miltenyi Biotec), according to the manufacturer's instructions. Cells were separated by using an LS column on the MACS separator (Miltenyi Biotec). NK cell and CD8+ T-cell preparations were assessed by flow-cytometry and NK cell purity was consistently greater that 90% (FIG. 39B) while CD8+ T-cell purity was consistently greater than 86% (FIG. 39C). NK cells were rested overnight in RPMI-1640 media supplemented with 10% FBS at 37° C. prior to the NK cell-mediated cytolysis assay. CD8+ T-cells were added to tumor cells immediately following isolation to assess CD8+ T-cell cytolysis.

XCELLigence Monitored CD11b+, CD8+, and NK Cell Cytolysis of Tumor Cells:

Cell growth characteristics and tumor cell death were monitored in real time by the xCELLigence DP system. To do so, circular electrodes covering the base of the tissue culture wells detect changes in electrical impedance and convert the impedance values to a Cell Index (CI). Cell Index measurements directly correspond to the strength of cell adhesion and cell number. Target cells (4T1, CT26Ep12.1, A549/MDR, or T84) were seeded into an E-Plate 16. Cells were allowed to attach and proliferate till they had reached their logarithmic growth phase. The effector cells (CD11b+ cells, NK cells, or CD8+ T-cells) were added to the target cells at the following effector-to-target cell ratios: 5:1 (CD11b+: tumor cell), 20:1 (NK cell: mouse tumor cell), 10:1 (NK:human tumor cell), and 30:1 (CD8+ T-cell: tumor cell). After addition of effector cells, the system took regular measurements (every 5 or 15 min) for 3-4 days to monitor immune cell-mediated killing of tumor cells.

NK Cell Mediated Cytolysis Inhibition:

Mouse tumor cell lines were initially screened for NK cell ligand expression via flow cytometry with anti-Rae-1α/β/γ-PE (Miltenyi Biotec), anti-H60a-PE (Miltenyi Biotec), and anti-MULT-1 PE (R&D Systems). For NK cell-mediated cytolysis inhibition based on these ligand expression levels, the effector NK cells were added to target cells in the presence of 3 µg/ml of blocking mAb to the following NK cell ligands: anti-RAE-1αβγ (R&D Systems) or anti-H60 (R&D Systems) separately and as mixture. xCELLigence data was transformed in Excel and exported to Prism (GraphPad Software) for graphing and statistical analysis.

Tumor/Spleen Flow Cytometry:

Tumors and spleens were dissociated as described above. Following red blood cell lysis, cells were incubated with Fc block 1:10 in MACS buffer (Miltenyi Biotec) for 10 min. After the 10 min incubation, cells were washed once and incubated with a primary antibody panel in MACS buffer for 15 min on ice in the dark. Cells were washed 2 times and then resuspended in MACS buffer for flow cytometric analysis. The following antibodies were used in T-cell, NK cell, and macrophage staining panels: anti-CD45 PECy7 (BioLegend), anti-CD45 BV510 (Biolegend), anti-CD3e APC-eFluor780 (eBioscience), anti-CD3 APC (Molecular Probes), anti-CD4 PE-TR (Abcam), anti-CD8a FITC (eBioscience), anti-CD8 BV510 (BioLegend), anti-CD25 PE (Abcam), anti-CD314 (NKG2D) PE-eFluor610 (eBioscience), anti-CD335 (NKp46) PECy7 (BioLegend), anti-CD27 BV421 (BioLegend), ant-CD183 (CXCR3) BV510 (BioLegend), anti-NKG2A/C/E FITC (eBioscience), anti-CD11b APC (BD Pharmingen), anti-Ly6C FITC (BioLegend), anti-Ly6G BV510 (BioLegend), anti-F4/80 PE Dazzle594 (BioLegend), anti-CD206 PECy7 (BioLegend), and anti-CD86 APC-Cy7 (BioLegend). Single stained controls and/or versacomp (Beckman Coulter) beads were used for fluorescence compensation. DAPI (Sigma), propidium iodide (Sigma), DRAQ5 (Thermo Fisher), or Live/Dead Yellow (Thermo Fisher) were used for live cell detection. Unstained and isotype controls were employed to determine autofluorescence levels and confirm antibody specificity.

Cytokine and Chemokine Detection (Tumor and Splenocytes):

To measure the interstitial cytokine and chemokine levels in the mouse tumors, tumors were carefully dissected removing all skin, placed into serum free media, and weighed. Tumors were then gently broken up using Eppendorf micropestles (Sigma), ensuring no large pieces were visible. The cell suspension was centrifuged and the supernatant collected and stored at −80° C. until analysis. For splenocyte/tumor cell co-cultures, spleens were dissociated and tumors were enzymatically digested as previously described. Splenocytes and tumors from the same mouse were then placed into tissue culture plates at a ratio of 10:1 (Splenocytes:tumor cells) and cultured for up to 72 h. Supernatant was collected at 24, 48 and 72 h and stored at −80° C. until analysis. Tumor and splenocyte supernatant was analyzed for mouse IL-1β, TNF-α, IL-2, IL-4, IL-6, IFNα, IFNγ, RANTES and MIP-1α according the manufacturer's instructions. The IFNα kit was obtained from PBL Assay Science, while IL-1β, TNF-α, IL-2, IL-4, IL-6, IFNγ, RANTES (CCL5) and MIP-1α (CCL3) duoset kits were obtained from R&D systems. Each ELISA was developed using the 3,3',5,5'-tetramethylbenzidine (Sigma) substrate. Microwell plates were read in a Biotek uQuant plate reader at 450 nm with 540 nm as the reference wavelength. KC junior software was used to fit 4 parameter logistic curves to the standards and interpolate the samples. The minimum detectable concentration (MDC) of each assay was calculated by multiplying the s.d. of the response by 10 and dividing by the slope of the standard curve at the inflection point.

Confocal Microscopy:

4T1 cells were seeded on Lab-Tek chamber slides (Sigma) and left to attach and grow for 24 h. Isolated $CD8^+$ T-cells were added to the 4T1 cells and left for 8 h, at which time, cells were fixed in 4% paraformaldehyde. Cells were washed and permeabilized with 0.5% triton-x-100 in PBS (PBST). Cells were blocked with 3% BSA for 30 min followed by incubation with the primary anti-perforin antibody (Abcam) diluted in PBST. After washing, cells were incubated with the secondary goat anti-rat IgG Alexafluor 488 (Abcam), followed by incubation with AlexaFluor 568 Phalloidin (Thermo Fisher). Cells were mounted with Prolong Diamond Antifade with DAPI (Thermo Fisher) and sealed with nail polish prior to imaging. Images were acquired on a Zeiss LSM 780, and images were merged and processed in Image J.

Case Presentation of Stage IV Pancreatic Ductal Adenocarcinoma:

A 67-year old Caucasian woman, CEB, whose primary symptom was jaundice, had previously undergone a complete Whipple procedure for pancreatic ductal adenocarcinoma (PDAC), to remove the pancreas, the gallbladder, the duodenum, the spleen and a portion of the stomach and surrounding lymph nodes. She had tumours in both the head and tail of the pancreas and her disease was diagnosed as Stage IV. She was treated with gemcitabine followed by FOLFIRINOX at another institution but had developed extensive metastatic disease in the liver on treatment. At the conclusion of her chemotherapy, sixteen months after her Whipple procedure, she had exhausted all treatment options, her weight was down from 62 kg to 45 kg, and she sought experimental EDV treatment which could be administered under the Australian Therapeutic Goods Administration (TGA) compassionate use scheme, and had been previously tested in a Phase I trial for mesothelioma (van Zandwijk et al., 2017) and recurrent glioblastoma (Whittle et al., 2015). CEB was dosed twice weekly for 7 weeks in her first cycle in the oncology ward at Royal North Shore Hospital, Sydney. However, because of her weakened state, and to potentially build tolerance to the lipopolysaccharide inherent in the EDV, doses were slowly escalated within the cycle (Table 17, below).

TABLE 17

| Week | Dose | EDV concentration |
|---|---|---|
| 1 | 1, 2 | $0.75 \times 10^8$ |
| 2 | 3, 4 | $1.0 \times 10^9$ |
| 3 | 5, 6 | $1.25 \times 10^9$ |
| 4 | 7, 8 | $1.5 \times 10^9$ |
| 5 | 9, 10 | $2.0 \times 10^9$ |
| 6 | 11, 12 | $2.0 \times 10^9$ |
| 7 | 13, 14 | $2.5 \times 10^9$ |

The dosed was administered over 20 min via a 20 ml niki pump and premedications were given prior to dosing as before (van Zandwijk et al., 2017). Serum biochemistry, haematology and cytokine expression was evaluated pre and 3 hours post each dose. CA19-9 and C-reactive protein levels were monitored at least bi-weekly. Peripheral Blood mononuclear cells (PBMCs) were examined by flow cytometry prior to dosing and at the end of the cycle for changes in anti-tumour immune cell numbers. Tumour tissue was obtained from the original surgical resection and PDAC cells were cultured and tested for drug sensitivity and surface receptors expression.

Statistics:

All statistical analysis was performed using the GraphPad Prism software package. Data is represented as mean±standard deviation (SD) or standard error of the mean (SEM). Statistical significance between 2 groups was determined by a student's t-test. Statistical significance between groups of 3 or more was determined by a one way ANOVA, followed by the Tukey's multiple comparison test. Significance for tumor regression studies was determined by a two way ANOVA followed by the Tukey's multiple comparison test. For all tests, p values were as follows: * $p \leq 0.05$,  $p \leq 0.01$, * $p \leq 0.001$, and **** $p \leq 0.0001$.

Example 22: $EDV_{\alpha GC}$ Treatment of JAWSII Cells and the Subsequent Surface Presentation of αGC Through CD1d Ligand This example contrasts EDV-delivery of αGC and free αGC against cancer cells.

Cells used: Mouse immature monocytes JAWSII (ATCC® CRL-11904™).

Preparation Perfecta3D 96-Well Hanging Drop Plate:

The upper and lower side tray reservoirs of the 3D hanging drop plates were filled with melted 1% agarose using a P1000 pipette (1 g agarose dissolve in 100 ml of water, dissolved in microwave and allowed to cool to ~50° C.). The plates were allowed to dry and settle at room temperature for at least 30 min. The outside wells of the hanging drop plate were then filled with 50 µl of sterile cell culture media (without cells)/well.

Treatment of JAWSII Spheroids with $EDV_{\alpha GC}$:

JAWSII cells were treated with 1000 ng/ml αGC (positive control); empty minicells and minicells$_{\alpha GC}$ compared to untreated cells and collected at 8h, 16h, 24h and 48h post-treatment (FIG. 46A-46D).

Dissociation of JAWSII Cells into Single-Cell Suspensions:

JAWSII cells were grown as semi-suspension cultures in T25 or T75 flasks. The culture media was carefully collected into a sterile 50 ml tube by pipetting using a pipette-aid and the culture surface of the flask was washed 2× with 5 ml of sterile PBS, and collected in the same sterile 50 ml tube after each wash. The adherent cells were collected by the addition of 5 ml of 0.25% trypsion/EDTA and incubated at 37° C. for 3 min or until all the cells were lifted from the surface of the flask. The lifted cells were carefully broken up into single cells by gentle pipetting using a pipette-aid and transferred into the sample sterile 50 ml tube used in previous steps. The cell suspension was then centrifuged at 300 g for 7 min and the supernatant was carefully decanted. The cell pellet was dissociated by flicking the bottom of the tube with a finger and resuspended in 5 ml of pre-warmed JAWSII culture media. The cell suspension was further dissociated into single cells by careful pipetting using a pipette-aid. To determine the cell number, 10 µl of the cell suspension was mixed with 10l of trypan blue solution and analysed using an EVE automated cell counter.

Initial Treatment Preparation:

6 hanging drop suspension samples were used for each treatment group per time point. $5\times10^4$ JAWSII cells and $5\times10^8$ minicells (1:1000 minicell to cell ratio) were used for each treatment sample and cultured in JAWSII cell culture media in a total volume of 50 µl. Extra untreated samples were prepared for isotype controls. The appropriate amount of minicells were pelleted by centrifugation at 12,000 g for 7 min and the supernatant was carefully removed by pipetting. Appropriate amount of live JAWS cells (based on the cell count from the previous section) were added to the pelleted minicells. The minicells were then dissociated into single-minicells-cell suspensions by gentle pipetting. The final volume of each sample was then made up by the addition of sterile culture media. For the untreated and αGC treated samples, $5\times10^4$ JAWSII cells were used for each sample and cultured in JAWSII cell culture media in a total volume of 50 µl. Appropriate amount of live JAWSII cells were transferred into Eppendorf tubes. The final volume of each sample was then made up by the addition of sterile culture media. 1000 ng/mL of αGC was added directly into the cell suspension for the JAWSII cells treated with 1000 ng/ml αGC (positive control) treatment group. The samples were then carefully seeded into each well of the hanging drop plates at 50 µl of treatment suspension/well and incubated at 37° C. at 5% $CO_2$ until collection.

Staining the Treated JAWSII Cells with Anti-Alpha GalCer:mCD1d Complex Monoclonal Antibody:

The entire content of each hanging drop well was carefully collected using a P200 pipette and transferred into an Eppendorf tube. A total of 6 samples were collected for each treatment group into 1 tube. 1:1000 PE conjugated anti-mouse alpha GalCer:mCD1d complex monoclonal antibody and 1:1000 PE conjugated mouse IgG1 isotype control were added into appropriate samples and mixed by gentle vortexing. GalCer:mCD1d monoclonal antibody binds to the cell surface exposed portion of the GalCer:CD1d complex. The samples were then incubated at room temperature for 20 min in the dark. Samples were then pelleted by centrifugation at 350 g for 5 min. The supernatant was removed by careful pipetting and the pellets were re-suspended and washed once in 500 µL FACS buffer. The cells were then collected by centrifugation at 350 g for 5 min, resuspended in 250 µL FACS buffer and transferred into FACS tubes. 1 µL of DAPI was added into each sample and mixed by gently swirling of the tubes. The samples were then analyzed using a Gallios flow cytometer.

Results:

Flow cytometry data (FIGS. 45A-45E) showed a clear shift after staining with anti-GalCer:mCD1d for JAWSII cells treated with minicells$_{\alpha-GC}$ and with free α-GC compared to JAWSII cells treated with minicells alone and untreated. This positive staining, confirms the successful delivery of α-GC by minicells to JAWSII cells and subsequent antigen presentation on the cell surface by the CD1d molecule which presents glycolipids on the cell surface. Presentation of α-GC is a crucial step which leads to receptor recognition by invariant NKT cells triggering off a type II IFN cascade essential in anti-tumor activity.

Example 23: In Vivo Studies Using Combination Treatment of $^{Ep}$Minicell$_{Dox}$ and Minicell$_{\alpha-GC}$ in a Syngeneic Mouse Model ($^{Ep}$CT26 Murine Colon Cancer in Balb/c Mice)

This example illustrates the efficacy of minicell contained therapeutic and minicell contained interferon type II agonist against tumors. This result demonstrates that compositions lacking interferon type I agonists can be used to effectively treat tumors.

Mice and Treatments (Experiments 1-3):

Balb/c mice, female, 6-7 weeks old were obtained from the Animal Resources Company in Western Australia. The mice were acclimatized for one week before the experiments commenced. CT26 cells (mouse colon cancer) were stably transformed with a plasmid expressing EpCAM antigen and a stable clone (Epclone 12.1) was established. This clone expressed EpCAM on the surface of the cells. All animal experiments were performed in compliance with National Health and Medical Research Council, Australia guidelines for the care and use of laboratory animals, and with EnGeneIC Animal Ethics Committee approval.

CT26 (Epclone 12. 1) isografts were established by injecting $2\times10^5$ cells per 100 l PBS subcutaneously on the left flank of each mouse. The tumors grew to the ~125 mm$^3$ starting volume within 8 days post implantation. The mice were randomly distributed into groups with 8 mice for each treatment group. Tumors were treated with $^{Ep}$minicell$_{Dox}$, minicell$_{\alpha-GC}$ and $^{Ep}$minicell$_{Dox}$+ minicell$_{\alpha-GC}$ (combination) compared to saline treatment alone.

Dosing was carried out 3× per week for 2 weeks. $^{EP}$minicell$_{Dox}$ was dosed at $1\times10^9$ minicells per dose in single and in combination treatments. minicell$_{\alpha-GC}$ was dosed at $1\times10^7$ in experiments 1 (FIG. 40) and 3 (FIG. 42) and $1\times10^8$ in experiment 2 (FIG. 40); where the saline group was also challenged when the tumor volume reached 800 mm$^3$.

Results:

All 3 experiments showed a marked halt in tumor progression for combination treatment groups receiving $^{Ep}$minicell$_{Dox}$+ minicell$_{\alpha-GC}$ compared to saline and $^{Ep}$minicell$_{Dox}$ treatments. This result supports the theory of an immune adjuvant effect by the addition of minicell$_{\alpha-GC}$ treatment to $^{Ep}$minicell$_{Dox}$. Treatment with minicell$_{\alpha-GC}$ alone also showed a halt in tumor progression for all 3 experiments, though not to the extent of the combination treatment, as best seen in experiment 2.

Figure 41:
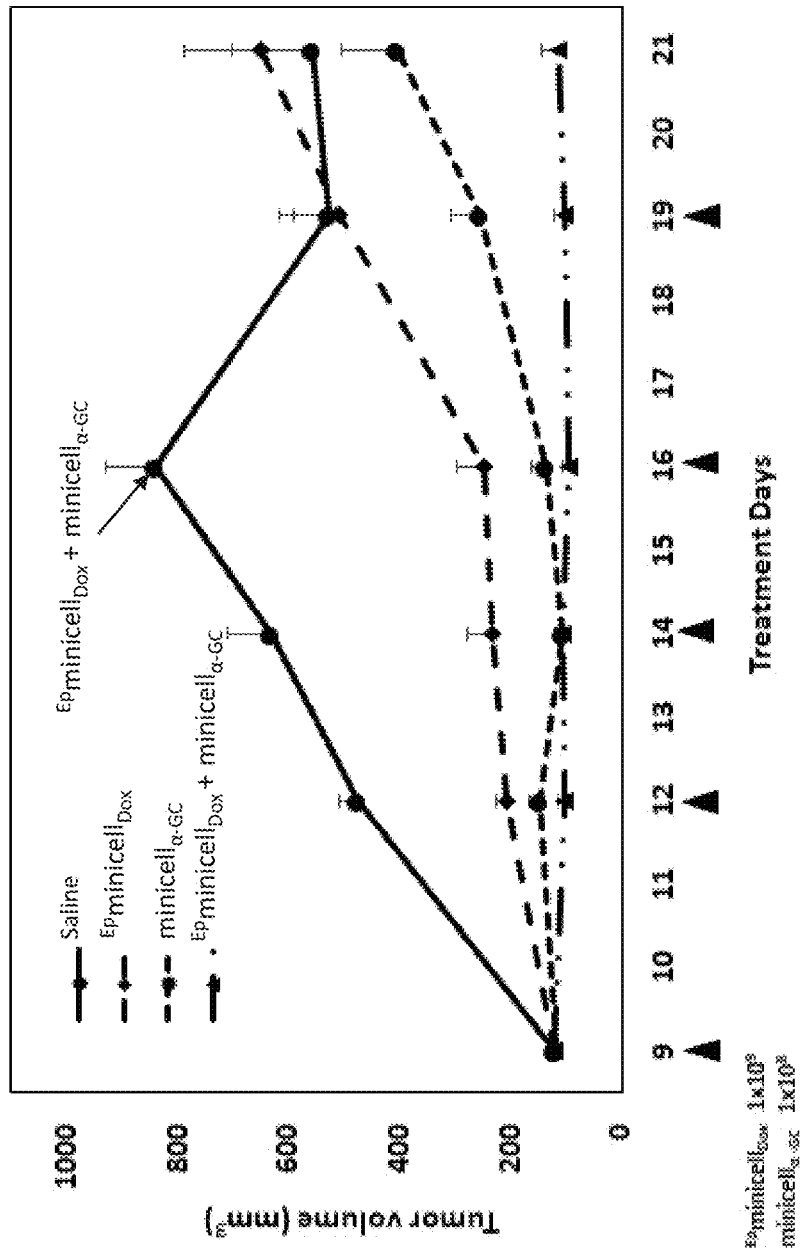
FIG. 41 shows combination treatment of $^{EP}$minicell$_{Dox}$ and minicell$_{\alpha\text{-}GC}$ is effective in reducing large tumors in Balb/c mice bearing CT26 isograft.

In experiment 2, saline treated control tumors demonstrated dramatic tumor regression following a treatment change to drug and α-GC EDV mediated combination therapy (FIG. 41). Tumours that had reached 800 mm$^3$ dropped to below 600 mm$^3$ in 3 days before the experiment was terminated.

Dose Evaluation of Different Sized Tumors; Mice and Treatments (Experiment 4):

CT26 (Ep clone 12.1) isograft was established by injecting subcutaneously $2\times10^5$ cells/100 l PBS into the left flank of female, 6-7 weeks old Balb/c mice. The tumours were grown to ~200-250 $mm^3$ or 600-800 $mm^3$ before treatments commenced. The mice were randomised into 6 groups, 3 mice per group. Mice received one dose only. Treatment groups included; Saline (FIG. 43C), $^{EP}$minicell$_{D}$ox ($1\times10^9$) (FIG. 43F), minicell$_{\alpha\text{-}GC}$ ($1\times10^6$) (FIG. 43E), minicell$_{\alpha\text{-}GC}$ ($1\times10^7$) (FIG. 43D), $^{EP}$minicell$_{Dox}$ $1\times10^9$+ minicell$_{\alpha\text{-}GC}$ ($1\times10^6$) (FIG. 43B), $^{EP}$minicell$_{Dox}$ ($1\times10^9$)+ minicell$_{\alpha\text{-}GC}$ ($1\times10^7$) (FIGS. 43A-43F).

Mice were sacrificed at 24 hrs post treatment for 200-250 $mm^3$ (FIG. 43) tumors and at 16 hrs and 24 hrs for 600-800 $mm^3$ tumors (FIGS. 44A-44B).

Results:

The effect of minicell$_{\alpha\text{-}GC}$ dosing, alone and in combination, in CT26 syngeneic tumor bearing Balb/c mice was further investigated by treating different sized tumors with a single dose as described above. Interestingly it was found that in both, mice carrying tumors of 200-250 $mm^3$ as well as 400-600 $mm^3$, the tumours developed a marked necrosis (black color) within 24 hours of dosing. This effect was more pronounced in the larger tumours and not seen in the control groups.

In sum, this data shows that a combination of minicell contained therapeutic and a interferon type II agonist against demonstrates efficacy against tumors. This result demonstrates that compositions lacking interferon type I agonists can be used to effectively treat tumors It will be apparent to those skilled in the art that various modifications and variations can be made in the methods and compositions of the present invention without departing from the spirit or scope of the invention. Thus, it is intended that the present invention cover the modifications and variations of this invention, provided they come within the scope of the appended claims and their equivalents.

CITED PUBLICATIONS

Ablasser et al., *Nat. Immunol.*, 10 (10):1065-72 (2009).
Ablasser et al., *Nature*, 498:380-384 (2013a).
Ablasser et al., *Nature*, 503:530-534 (2013b).
Adamus et al., *Contemp. Oncol (Ponzn)*, 22(1A):56-60 (March 2018).
Aduro Biotech Inc. (2016), Novartis Pharmaceuticals. *Study of the Safety and Efficacy of MIW815 (ADU-S100) in Patients with Advanced/Metastatic Solid Tumors or Lymphomas*. 2020. ClinicalTrials.gov [Internet]. Bethesda (Md.): National Library of Medicine (US). Identifier: NCT02675439. Available from: https://ClinicalTrials.gov/show/NCT02675439. (cited 1 Jul. 2016).
Ahmadzadehfar et al., "Radioembolization of liver tumors with yttrium-90 microspheres," *Semin Nucl Med.* 2010; 40(2):105-121.
Ahmadzadehfar et al., "Therapeutic response and side effects of repeated radioligand therapy with 177Lu-PSMA-DKFZ-617 of castrate-resistant metastatic prostate cancer," *Oncotarget.* 2016; 7(11):12477-12488.
Alexopoulou et al., *Nature*, 413: 732-738 (2001).
Alzahrani A S, AlShaikh O, Tuli M, Al-Sugair A, Alamawi R, Al-Rasheed M M. Diagnostic value of recombinant human thyrotropin-stimulated 123I whole-body scintigraphy in the follow-up of patients with differentiated thyroid cancer. *Clin Nucl Med.* 2012; 37(3):229-234.
Andersson L, Blomberg L, Flegel M, Lepsa L, Nilsson B, Verlander M. Large-scale synthesis of peptides. Pept Sci. 2000; 55:227-250.
Anguille et al., *Pharmacological Reviews* 67, 731-753 (2015).
Barber et al., *Curr. Opin. Immunol.*, 23(1): 10-20 (2011).
Belardelli et al., *TRENDS in Immunology* 23, 201-208 (2002).
Bernardini et al., *Frontiers in immunology* 7, 402 (2016).
Birkholz et al. (2015), J Biol Chem. *The Alpha and Omega of Galactyosylceramides in T Cell Immune Function*. NIH.gov [Internet]. Bethesda (Md.): United States National Library of Medicine (United States). Identifier: PMC4505449. Available from: https://www.ncbi.nlm.nih.gov/pmc/articles/PMC4505449/.
Bobanga et al., *Oncoimmunology* 7, e1393598.
Bredel, *Brain Res. Rev.*, 35: 161 (2001).
Britton et al., *Genes Dev.*, 12: 1254-9 (1998).
Brody et al., *J. Clin. Oncol.*, 28:4324-4332 (2010).
Burckstummer et al., *Nat. Immunol.*, 10:266-272 (2009).
Burger M, Hartmann T, Krome M, Rawluk J, Tamamura H, Fujii N, Kipps T J, Burger J A. Small peptide inhibitors of the CXCR4 chemokine receptor (CD184) antagonize the activation, migration, and antiapoptotic responses of CXCL12 in chronic lymphocytic leukemia B cells. Blood. 2005; 106:1824-1830.
Caplen, N. J., *Expert Opin. Biol. Ther.*, 3: 575-86 (2003).
Caplen and Mousses, *Ann. NY Acad. Sci.*, 1002: 56-62 (2003).
Caravella and Lugovskoy, *Curr. Opin. Chem. Biol.*, 14: 520-28 (2010).
Carreno et al., *Clin Transl. Immunology*, 5(4): e69 (2016).
Caskey et al., *J. Exp. Med.*, 208:2357-2366 (2011).
Cauwels et al. *Cancer research* 78, 463-474 (2018).
Chatalic K L S, Kwekkeboom D J, de Jong M. Radiopeptides for imaging and therapy: a radiant future. J Nucl Med. 2015; 56:1809-1812.
Chen et al., *Int. J. Cancer*, 93: 107 (2001).
Chikuma et al., *Cancer Sci.*, 108: 574-580 (2017).
Chiu et al., *Cell*, 138:576-591 (2009).
Chu et al., *PLoS Biology*, 4: 1122-36 (2006).
Civril et al., *Nature*, 498:332-337 (2013).
Clark-Curtiss and Curtiss, *Methods Enzymol.*, 101: 347-362 (1983).
Colonna et al., *Nat. Immunol.*, 5:1219-1226 (2004).
Corrales et al., *Cell Rep.*, 11:1018-1030 (2015).
Cory et al., *Cancer Commun.*, 3(7): 207-12 (1991).
D'Aloia et al., *Cell death & disease* 9, 282 (2018).
D'Angiolella et al., *Cell*, 149:1023-34 (2012).
Da Silva et al., *Breast Cancer Res.*, 12: R46 (1-13) (2010).
Debinski et al., *J. Neurooncol.*, 48: 103-11 (2000).
Debinski and Gibo, *Mol. Med.*, 6: 440-49 (2000).
de Boer et al., *J. Bacteriol.*, 174(1): 63-70 (1992).
Deutscher S L. Phage display in molecular imaging and diagnosis of cancer. Chem Rev. 2010; 110:3196-3211.
Dine et al., *Asia-Pacific journal of oncology nursing* 4, 127-135 (2017).
Dobbs et al., *Cell Host Microbe*, 18(2): 15-24 (2015).
Dong et al., *International journal of molecular sciences* 17, 320 (2016).
Dowling et al., *PLoS One*, 8:e58164 (2013).
Dredge et al., *Cancer immunology, immunotherapy*: CII 51, 521-531 (2002).
Duan et al., *Mol. Cancer Ther.*, 3: 833-8 (2004).
Duxbury et al., *Ann. Surg.*, 240: 667-74 (2004).
Dynavax Technologies Corporation (2016). Study of SD-101 in Combination with Localized Low-dose Radiation in Patients with Untreated Low-grade B-cell Lymphoma. 2016. ClinicalTrials.gov [Internet]. Bethesda (Md.): National Library of Medicine (US). Identifier: NCT02266147. Available from: https://ClinicalTrials.gov/show/NCT02266147. (cited 1 Jul. 2016).
Emens et al., *European journal of cancer* 81, 116-129 (2017).
Erathodiyil N, Ying J Y. Functionalization of inorganic nanoparticles for bioimaging applications. Acc Chem Res. 2011; 44:925-935. [PubMed: 21648430].
Fang et al., *Seminars in immunology* 31, 37-54 (2017).
Farkona, et al., *BMC medicine* 14, 73 (2016).
Ferlazzo et al. *The Journal of Immunology* 172, 1333-1339 (2004).
Fernandes-Alnemri et al., *Nature*, 458:509-513 (2009).
Field et al., *Proc. NatlAcad. Sci. USA*, 58: 1004-1010 (1967).
Fitzgerald-Bocarsly et al., *Biochimie* 89, 843-855 (2007).
Fu et al., *Sci. Transl. Med.*, 7(283):283ra252 (2015).
Fukuda, *Curr. Protocols Molec. Biol.* (Suppl. 26), 17.5.1-17.5.8 (1994).
Gao et al., *Nat Biotechnol.*, 22(8): 969-976 (2004).
Gao et al., *Science*, 341:903-906 (2013a).
Gao et al., *Cell*, 153:1094-1107 (2013b).
Gerard S K, Cavalieri R R. I-123 diagnostic thyroid tumor whole-body scanning with imaging at 6, 24, and 48 hours. Clin Nucl Med. 2002; 27(1):1-8.
Ghosh A, Heston W D W. Tumor target prostate specific membrane antigen (PSMA) and its regulation in prostate cancer. J Cell Biochem. 2004; 91(3):528-539.
Gitlin et al., *Proc. NatlAcad. Sci. USA*, 103: 8459-8464 (2006).
Goh and Sorkin, *Cold Spring Harb. Perspect. Biol.*, 5: a017459 (2013).
Gray B P, Brown K C. Combinatorial peptide libraries: mining for cell-binding peptides. Chem Rev. 2013; 114: 1020-1081.
Gregory et al., *Methods in Molecular Biology*, 342: 33-47 (2006).
Gupta et al., "Abstract CT091: Safety and pharmacodynamic activity of MEDI9197, a TLR 7/8 agonist, administered intratumorally in subjects with solid tumors," Cancer Research, AACR Annual Meeting 2017; Apr. 1-5, 2017 (Published July 2017)).
Hansen et al., *EMBO J.*, 33(15): 1654-66 (2014).
Harry, E. J., *Mol. Microbiol.*, 40(4): 795-803 (2001).
Hershey, J. *Allergy Clin. Immunol.*, 111: 677-90 (2003).
Hiraga et al., *J. Bacteriol.*, 171: 1496-1505 (1989).
Hobbs et al., *Proc. Natl. Acad. Sci. USA*, 95(8): 4607-4612 (1998).
Holman B L, Tumeh SS. Single-photon emission computed tomog-iraphy (SPECT): applications and potential. JAMA. 1990; 263(4):561-564.
Hornung et al., *Nature*, 458:514-518 (2009).
Hu & Lutkenhaus, *Mol. Microbio.*, 34(1): 82-90 (1999).
Iftode et al., *Crit. Rev. Biochem. Mol. Biol.*, 34: 141-80 (1999).
Igarashi H, Fujimori N, Ito T, Nakamura T, Oono T, Nakamura K, Suzuki K, Jensen R T, Takayanagi R. Vasoactive intestinal peptide (VIP) and VIP receptors—elucidation of structure and function for therapeutic applications. Int J Clin Med. 2011; 2:500-508.
Immune Design (2016), Merck Sharp & Dohme Corp. Study of Intratumoral G100 with or without Pembrolizumab in Patients with Follicular Non-Hodgkin's Lymphoma. 2017. ClinicalTrials.gov [Internet]. Bethesda (Md.): National Library of Medicine (US). Identifier: NCT02501473. Available from: https://ClinicalTrials.gov/show/NCT02501473. (cited 1 Jul. 2016).
Jarboe et al., *Cancer Res.*, 67: 7983-86 (2007).
Jenkins et al., *British journal of cancer* 118, 9-16 (2018).
Jung et al., *Translational oncology* 11, 686-690 (2018).
Kao et al., *Am. J. Respir. Crit. Care Med.*, 191(12): 1467-1469 (2015).
Kao et al., *American Journal of Respiratory and Critical Care Medicine* 191, 1467-1469 (2015).
Kawai and Akira, *Nat. Immunol.*, 11:373-384 (2010).
Khalil et al., *Proc Nat'l Acad. USA*, 106: 11667-72 (2009).
Kim et al., *Proc. Natl. Acad. Sci. USA*, 107:15181-15186 (2010).
Kota et al., *Cell*, 137: 1005-17 (2009).
Kramer-Marek G, Capala J. The role of nuclear medicine in modern therapy of cancer. Tumour Biol. 2012; 33(3):629-640.
Kranzusch et al., *Cell Rep.*, 3:1362-1368 (2013).
Krieg et al., *Nature*, 374: 546-549 (1995).
Kwekkeboom D J, de Herder W W, Kam B L, et al. Treatment with the radiolabeled somatostatin analog [177 Lu-DOTA 0, Tyr3]octreotate: toxicity, efficacy, and survival. J Clin Oncol. 2008; 26(13):2124-2130.
Landskron et al., *Journal of immunology research* 2014, 149185 (2014).
Lee et al., *Cancers* 3, 3856-3893 (2011).
Lemmon and Schlessinger, *Cell*, 141(7): 1117-134 (2010).
Leung and Amarasinghe, *Curr. Opin. Struct. Biol.*, 36:133-141 (2016).
Li et al., *Science*, 341:1390-1394 (2013b).
Liu et al., *Science*, 347(6227): aaa2630 (2015).
Lu et al., *Structure*, 18:1032-1043 (2010).
Ma et al., *Mol. Microbiol.*, 54: 99-108 (2004).
MacDiarmid et al., *PLoS One*, 11(4) (2016).
MacDiarmid et al. *Nature biotechnology* 27, 643-651 (2009).
MacDiarmid et al., *Cell cycle* 6, 2099-2105 (2007a).
MacDiarmid et al., *Cancer cell* 11, 431-445 (2007b).
Majkowska et al., "Complexes of low energy beta emitters 47Sc and 177Lu with zoledronic acid for bone pain therapy," Appl Radiat Isot. 2009; 67(1):11-13.
Mankan et al., *EMBO J.*, 33:2937-2946 (2014).
McWhirter et al., *J. Exp. Med.*, 206:1899-1911 (2009).
Marq et al., *J. Biol. Chem.*, 286:6108-6116 (2011).
Matsuno M, Matsui T, Iwasaki A, Arakawa Y. Role of acetylcholine and gastrin-releasing peptide (GRP) in gastrin secretion. J Gastroenterol. 1997; 32:579-586.
MedImmune LLC (2016). A Study of MEDI9197 Administered in Subjects with a Solid Tumor Cancer. 2018. ClinicalTrials.gov [Internet]. Bethesda (Md.): National Library of Medicine (US). Identifier: NCT02556463. Available from: https://ClinicalTrials.gov/show/NCT02556463. (cited 1 Jul. 2016).
Mellman et al., *Nature* 480, 480-489 (2011).
Merrifield R. Solid-phase peptide synthesis. Adv Enzymol Relat Areas Mol Biol. 2006; 32:221-296.
Meulen and Brady, *Hum. Vaccin. Immunother.*, 13(1):15-16 (2017).
Mhawech-Fauceglia P, Zhang S, Terracciano L, et al. Prostate-specific membrane antigen (PSMA) protein expression in normal and neoplastic tissues and its sensitivity and specificity in prostate adenocarcinoma: an immunohistochemical study using mutiple tumour tissue microarray technique. *Histopathology.* 2007; 50(4):472-483.
Morvan et al., *Nature reviews Cancer* 16, 7-19 (2016).
Muller et al., *Frontiers in immunology* 8, 304 (2017).

Müller C, Zhernosekov K, Kister U, et al. A unique matched quadru-iplet of terbium radioisotopes for PET and SPECT and for alpha- and beta-radionuclide therapy: an in vivo proof-of-concept study with a new receptor-targeted folate derivative. J Nucl Med. 2012; 53(12):1951-1959.

NHMRC Clinical Trials Centre, University of Sydney Australian New Zealand Clinical Trials Registry: Sydney (NSW): (2017)—Identifier ACTRN12617000037303 A Phase 1 Study of Anti-Human EGFR (Vectibix Sequence) Targeted EDVs Carrying the Cytotoxic Drug PNU-159682 (EGFR(V)-EDV-PNU) with Concurrent Non-Targeted EDVs Carrying an Immunomodulatory Adjuvant (EDV-40mer) in Subjects with Advanced Solid Tumours who have No Curative Treatment Options 2017 Jan. 10; https://www.anzctr.org.au/ACTRN12617000037303.aspx.

Nielsen et al, Biochim. Biophys. Acta., 1591(1-3), 109-118 (2002).

Nieth et al., FEBS Lett., 545: 144-50 (2003).

Oh and Park, Advanced Drug Delivery Rev., 61: 850-62 (2009).

Ohki-Hamazaki H, Iwabuchi M, Maekawa F. Development and function of bombesin-like peptides and their receptors. Int J Dev Biol. 2005; 49:293-300.

Oiseth et al., Journal of Cancer Metastasis and Treatment 3, 250 (2017).

Okada et al., J. Bacteriol., 176: 917-22 (1994).

Okano et al., J. Am. Chem. Soc., 128: 7136-37 (2006).

Oncovir Inc. (2016), National Institutes of Health, Icahn School of Medicine at Mount Sinai, Bay Hematology Oncology, Emory University, University of Pittsburgh, National Cancer Institute. In Situ, Autologous Therapeutic Vaccination Against Solid Cancers with Intratumoral Hiltonol®. 2018. ClinicalTrials.gov [Internet]. Bethesda (Md.): National Library of Medicine (US). Identifier: NCT02423863. Available from: https://ClinicalTrials.gov/show/NCT02423863. (cited 1 Jul. 2016).

Oritz-Zapater et al., Nature Medicine, 18(1):83-90 (2011).

Orzalli et al., Proc. Natl. Acad. Sci. USA, 109: E3008-E3017 (2012).

Park et al., Breast Cancer Res., 4(3): 95-99 (2002).

Palmedo H. Radionuclide therapy of bone metastases. In: Biersack H J, Freeman LM, editors. Clinical Nuclear Medicine. Berlin, Heidelberg: Springer Berlin Heidelberg; 2007:433-442.

Pillai et al., "Production logistics of 177Lu for radionuclide therapy," Appl Radiat Isot. 2003; 59(2-3):109-118.

Quintieri et al., Clinical Cancer Research 11, 1608-1617 (2005).

Raskin & de Boer, J. Bacteriol., 181: 6419-6424 (1999).

Reeve and Cornett, J. Virol., 15: 1308-16 (1975).

Reid et al., Annals of oncology: official journal of the European Society for Medical Oncology 24, 3128-3135 (2013).

Rezvani et al., Molecular therapy: the journal of the American Society of Gene Therapy 25, 1769-1781 (2017).

Rice et al., Semin. Nucl. Med., 41: 265-282 (2011).

Ruoslahti E. RGD and other recognition sequences for integrins. Annu Rev Cell Dev Biol. 1996; 12:697-715.

Sagnella et al., Molecular cancer therapeutics 17, 1012-1023 (2018).

Santoni M, Scarpelli M, Mazzucchelli R, et al. Targeting prostate-specific membrane antigen for personalized therapies in prostate cancer: morphologic and molecular backgrounds and future promises. J Biol Regul Homeost Agents. 2014; 28(4):555-563.

Sawa-Wejksza et al., Archivum immunologiae et therapiae experimentalis 66, 97-111 (2018).

Sazar, "Activating the Natural Host Defense; Hiltonol (Poly-ICLC) and Malignant Brain Tumors, Oncovir, Inc., www.oncovir.com/id2 (accessed Jul. 11, 2018).

Sharma et al. Cell 168, 707-723 (2017).

Sharpe, Immunological reviews 276, 5-8 (2017).

Showalter, Cytokine 97, 123-132 (2017).

Silver D A, Pellicer I, Fair W R, Heston W D, Cordon-Cardo C. Prostate-specific membrane antigen expression in normal and malignant human tissues. Clin Cancer Res. 1997; 3(1):81-85.

Simmons et al. The Journal of Immunology 188, 3116-3126 (2012).

Singh M, Mukhopadhyay K. Alpha-melanocyte stimulating hormone: an emerging anti-inflammatory antimicrobial peptide. Biomed Res Int. 2014; 2014:874610.

Sioud, M., Trends Pharmacol. Sci., 25: 22-8 (2004).

Schoggins et al., Nature, 505:691-695 (2014).

Solomon et al., PLos One, 10: 1-17 (2015).

Staudacher et al., British journal of cancer 117, 1736-1742 (2017).

Strand, F L. Neuropeptides: Regulators of Physiological Processes. MIT press; 1999.

Stewart and D'Ari, J. Bacteriol., 174: 4513-6 (1992).

Sun et al., Science, 339(6121):786-791 (2013).

Sun et al., Biochem. Biophys. Res. Commun., 280: 788 (2001).

Sun X, Li Y, Liu T, Li Z, Zhang X, Chen X. Peptide based imaging agents for cancer detection. Adv Drug Deliv Rev. 110-111: 38-51 (2017).

Szkandera et al., British journal of cancer 110, 183-188 (2014).

Takahashi H, Emoto K, Dubey M, Castner D G, Grainger D W. Imaging surface immobilization chemistry: correlation with cell patterning on non-adhesive hydrogel thin films. Adv Funct Mater. 2008; 18:2079-2088.

Takaoka et al., Nature, 448:501-505 (2007).

Takeshita et al., Molec. Ther., 18: 181-87 (2010).

Tanpure et al., Bioorg. Med. Chem., 21: 8019-32 (2013).

Tatemoto, K. Neuropeptide Y: history and overview, Neuropeptide Y and Related Peptides. Springer; 2004. p. 1-21.

Teunissen et al., "Endocrine tumours of the gastrointestinal tract. Peptide receptor radionuclide therapy," Best Pract Res Clin Gastroenterol. 2005; 19(4):595-616.

Tyler-McMahon B M, Boules M, Richelson E. Neurotensin: peptide for the next millennium. Regul Pept. 2000; 93:125-136.

Unterholzner et al., Nat. Immunol., 11:997-1004 (2010).

Unterholzner et al., Immunobiology, 128(11): 1312-21 (2013).

van Zandwijk et al., Lancet Oncol., 18(10): 1386-1396 (2017).

van Zandwijk et al., The Lancet Oncology 18, 1386-1396 (2017).

Ventola, Pharmacy and Therapeutics 42, 452-463 (2017).

Wallace et al., Springer seminars in immunopathology 27, 49-64 (2005).

Walrand S, Hesse M, Renaud L, Jamar F. The impact of image recon-istruction bias on PET/CT $^{90}$Y dosimetry after radioembolization. J Nucl Med. 2015; 56(3):494-495.

Wang et al., Nat. Struct. Mol. Biol., 17:781-787 (2010).

Wang et al., Immunity, 41(6): 919-33 (2014).

Weckbecker G, Lewis I, Albert R, Schmid H A, Hoyer D, Bruns C. Opportunities in somatostatin research: biological, chemical and therapeutic aspects. Nat Rev Drug Discov. 2003; 2:999-1017.
White & McCubrey, *Leukemia,* 15: 1011-1021 (2001).
Whittle et al., *J. Clin. Neurosci.,* 22(12): 1889-1894 (2015).
Whittle et al., *Journal of clinical neuroscience: official journal of the Neurosurgical Society of Australasia* 22, 1889-1894 (2015).
Wu et al., *Science,* 339:826-830 (2013).
Wykosky et al., *Clin Cancer Res.,* 14: 199-208 (2008).
Xia et al., *Nat. Immunol.,* 16:366-375 (2015).
Yague et al., *Gene Ther.,* 11: 1170-74 (2004).
Yang W, Luo D, Wang S, Wang R, Chen R, Liu Y, Zhu T, Ma X, Liu R, Xu G. TMTP1, a novel tumor-homing peptide specifically targeting metastasis. Clin Cancer Res. 2008; 14:5494-5502.
Yang et al., *Nat. Immunol.,* 11:487-494 (2010).
Yi et al., *PLoS One,* 8(10):e77846 (2013).
Yuan et al., *Scientific reports* 5, 14273 (2015).
Zhang et al., *J. Immunol.,* 186:4541-4545 (2011a).
Zhang et al., *Nat. Immunol.,* 12:959-965 (2011b).
Zhang et al., *Cell Rep.,* 6:421-430 (2014).
Zibert et al., *Human Gene Therapy* 15, 21-34 (2004).
Ziegler-Heitbrock et al., *Frontiers in immunology* 4, 23 (2013).
Zitvogel et al., *Nature reviews Immunology* 15, 405-414 (2015).
U.S. Pat. No. 8,591,862.
U.S. Pat. No. 7,183,105.
U.S. 2008/0051469.
WO 2000/067776.
WO 2003/033519.
WO 2004/113507.
WO 2005/056749.
WO 2005/079854.
WO 2009/027830.

What is claimed is:

1. A composition comprising:
(a) a therapeutically effective dose of purified, intact bacterially derived minicells comprising at least one anti-neoplastic agent, wherein the anti-neoplastic agent comprises nemorubicin, PNU-159682, idarubicin, daunorubicin, caminomycin, and/or and
(b) an interferon type I agonist, an interferon type II agonist, or a combination of an interferon type I agonist and an interferon type II agonist,
wherein the interferon type I agonist is an oligonucleotide, wherein the oligonucleotide is double stranded DNA or DNA-RNA hybrids and comprises a sequence of at least about 40 nucleotides, and
wherein the interferon type II agonist is selected from the group consisting of C-glycosidific form of α-galactosylceramide (α-C-GalCer), α-galactosylceramide (α-GalCer), 12 carbon acyl form of galactosylceramide (β-GalCer), β-D-glucopyranosylceramide (β-GlcCer), 1,2-Diacyl-3-0-galactosyl-sn-glycerol (BbGL-II), diacylglycerol containing glycolipids (Glc-DAG-s2), ganglioside (GD3), gangliotriaosylceramide (Gg3Cer), glycosylphosphatidylinositol (GPI), α-glucuronosylceramide (GSL-1 or GSL-4), isoglobotrihexosylceramide (iGb3), lipophosphoglycan(LPG), lyosphosphatidylcholine (LPC), a-galactosylceramide analog (OCH), threitolceramide, and a combination thereof.

2. The composition of claim 1, wherein element (b) of the composition comprises:
(i) a therapeutically effective dose of purified, intact bacterially derived minicells comprising an interferon type I agonist; or
(ii) a therapeutically effective dose of purified, intact bacterially derived minicells comprising an interferon type II agonist; or
(iii) a combination of:
(1) a therapeutically effective dose of purified, intact bacterially derived minicells comprising an interferon type I agonist; and
(2) a therapeutically effective dose of purified, intact bacterially derived minicells comprising an interferon type II agonist.

3. The composition of claim 1, wherein:
(a) the anti-neoplastic agent and the interferon type I agonist, the interferon type II agonist, or the combination of an interferon type I agonist and an interferon type II agonist, are packaged within two or more purified, intact bacterially derived minicells; or
(b) the anti-neoplastic agent and the interferon type I agonist, the interferon type II agonist, or the combination of an interferon type I agonist and an interferon type II agonist are packaged within three separate populations of purified, intact bacterially derived minicells.

4. The composition of claim 1 comprising the anti-neoplastic agent, the interferon type I agonist, and the interferon type II agonist, wherein:
(a) the anti-neoplastic agent, the interferon type I agonist, and the interferon type II agonist are comprised within the same minicell;
(b) the anti-neoplastic agent and the interferon type I agonist are comprised within a first minicell, and the interferon type II agonist is comprised within a second minicell;
(c) the anti-neoplastic agent and the interferon type II agonist are comprised within a first minicell, and the interferon type I agonist is comprised within a second minicell;
(d) the anti-neoplastic agent is comprised within a first minicell, and the interferon type I agonist and the interferon type II agonist are comprised within a second minicell; or
(e) the anti-neoplastic agent is comprised within a first minicell, the interferon type I agonist is comprised within a second minicell, and the interferon type II agonist is comprised within a third minicell.

5. The composition of claim 1, wherein the composition does not comprise an interferon type I agonist.

6. The composition of claim 1, wherein:
the anti-neoplastic agent is PNU-159682.

7. The composition of claim 1, wherein:
(a) the oligonucleotide comprises a sequence of at least about 50 nucleotides or at least about 60 nucleotides.

8. The composition of claim 1, wherein the interferon type I agonist is an oligonucleotide selected from the group consisting of double stranded Z-DNA and B-DNA.

9. The composition of claim 1, wherein: the interferon type II agonist is α-galactosylceramide (α-GalCer).

10. The composition of claim 1, further comprising:
(a) a bispecific ligand bound to the minicells comprising the anti-neoplastic agent; and/or
(b) a bispecific ligand bound to the minicells comprising the type I interferon agonist; and/or
(c) a bispecific ligand bound to the minicells comprising the type II interferon agonist.

11. The composition according to claim 10, wherein the bispecific ligand:
 (a) comprises a first arm that carries specificity for a minicell surface structure and a second arm that carries specificity for a non-phagocytotic mammalian cell surface receptor; and/or
 (b) comprises a first arm that carries specificity for a minicell surface structure and a second arm that carries specificity for a non-phagocytotic mammalian cell surface receptor and wherein the minicell surface structure is an O-polysaccharide component of a lipopolysaccharide on the minicell surface; and/or
 (c) comprises a first arm that carries specificity for a minicell surface structure and a second arm that carries specificity for a non-phagocytotic mammalian cell surface receptor wherein the non-phagocytotic mammalian cell surface receptor is capable of activating receptor-mediated endocytosis of the minicell; and/or
 (d) comprises a bispecific antibody or antibody fragment; and/or
 (e) comprises a bispecific antibody or antibody fragment and wherein the antibody or antibody fragment comprises a first multivalent arm that carries specificity for a bacterially derived minicell surface structure and a second multivalent arm that carries specificity for a cancer cell surface receptor, wherein the cancer cell surface receptor is capable of activating receptor-mediated endocytosis of the minicell.

12. The composition of claim 1, wherein the composition comprises fewer than about 1 contaminating parent bacterial cell per $10^7$ minicells, fewer than about 1 contaminating parent bacterial cell per $10^8$ minicells, fewer than about 1 contaminating parent bacterial cell per $10^9$ minicells, fewer than about 1 contaminating parent bacterial cell per $10^{10}$ minicells, or fewer than about 1 contaminating parent bacterial cell per $10^{11}$ minicells.

13. The composition of claim 1, further comprising a pharmaceutically acceptable carrier.

14. The composition of claim 1, wherein the minicells are approximately 400 nm in diameter.

15. The composition of claim 1, wherein the composition is free of parent bacterial cell contamination removable through 200 nm filtration.

16. The composition of claim 1, wherein the composition comprises the following amount of minicells or killed bacterial cells:
 (a) at least about $10^9$;
 (b) at least about $1 \times 10^9$;
 (c) at least about $2 \times 10^9$;
 (d) at least about $5 \times 10^9$;
 (e) at least $8 \times 10^9$;
 (f) no more than about $10^{11}$;
 (g) no more than about $1 \times 10^{11}$;
 (h) no more than about $9 \times 10^{10}$; or
 (i) no more than about $8 \times 10^{10}$.

17. The composition of claim 1, comprising the antineoplastic agent, the interferon type I agonist, and interferon gamma.

* * * * *